United States Patent
Springer et al.

(10) Patent No.: US 9,540,372 B2
(45) Date of Patent: *Jan. 10, 2017

(54) PYRIDO[2,3-B]PYRAZIN-8-SUBSTITUTED COMPOUNDS AND THEIR USE

(71) Applicants: INSTITUTE OF CANCER RESEARCH: ROYAL CANCER HOSPITAL (THE), London (GB); CANCER RESEARCH TECHNOLOGY LIMITED, London (GB)

(72) Inventors: Caroline Joy Springer, Sutton (GB); Dan Niculescu-Duvaz, Sutton (GB); Ion Niculescu-Duvaz, Sutton (GB); Richard Marais, London (GB); Bartholomeus Marinus Josephus Marie Suijkerbuijk, Sutton (GB); Alfonso Zambon, Sutton (GB); Arnaud Nourry, Le Mans (FR); Delphine Menard, Sutton (GB)

(73) Assignees: INSTITUTE OF CANCER RESEARCH: ROYAL CANCER HOSPITAL (THE), London (GB); CANCER RESEARCH TECHNOLOGY LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,199

(22) Filed: Sep. 14, 2015

(65) Prior Publication Data

US 2016/0002230 A1 Jan. 7, 2016

Related U.S. Application Data

(63) Continuation of application No. 14/543,379, filed on Nov. 17, 2014, now Pat. No. 9,155,737, which is a continuation of application No. 14/035,133, filed on Sep. 24, 2013, now Pat. No. 8,912,191, which is a continuation of application No. 13/459,120, filed on Apr. 28, 2012, now Pat. No. 8,546,387, which is a continuation of application No. 12/808,249, filed as application No. PCT/GB2008/004208 on Dec. 19, 2008, now Pat. No. 8,198,279.

(60) Provisional application No. 61/015,019, filed on Dec. 19, 2007.

(51) Int. Cl.
C07D 471/04 (2006.01)
A61K 31/4985 (2006.01)

(52) U.S. Cl.
CPC ......... *C07D 471/04* (2013.01); *A61K 31/4985* (2013.01)

(58) Field of Classification Search
None
See application file for complete search history.

(56) References Cited

U.S. PATENT DOCUMENTS

| 4,082,845 A | 4/1978 | Saari et al. |
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,521,073 A | 5/1996 | Davis et al. |
| 5,877,020 A | 3/1999 | Alitalo et al. |
| 5,879,672 A | 3/1999 | Davis et al. |
| 5,882,864 A | 3/1999 | An et al. |
| 6,030,831 A | 2/2000 | Godowski et al. |
| 6,218,529 B1 | 4/2001 | An et al. |
| 6,258,809 B1 | 7/2001 | Rajagopalan et al. |
| 6,492,529 B1 | 12/2002 | Kapadia et al. |
| 7,625,922 B2 | 12/2009 | Niculescu-Duvaz et al. |
| 7,951,819 B2 | 5/2011 | Niculescu-Duvaz et al. |
| 8,198,279 B2 | 6/2012 | Springer et al. |
| 8,383,816 B2 | 2/2013 | Niculescu-Duvaz et al. |
| 8,546,387 B2 | 10/2013 | Springer et al. |
| 8,815,896 B2 | 8/2014 | Springer et al. |

(Continued)

FOREIGN PATENT DOCUMENTS

| CN | 101084217 A | 12/2007 |
| EP | 1724268 A1 | 11/2006 |

(Continued)

OTHER PUBLICATIONS

Abasolo et al.,"Kinetic study on the anelation of heterocycles. 2. pyrido[2,3-b]pyrazine and pyrido[3,4-b]pyrazine derivatives synthesized by the Hinsberg reaction," J Heterocyclic Chem. 27(2):157-162 (1990).

Adams et al., "Roles of ephrinB ligands and EphB receptors in cardiovascular development: demarcation of arterial/venous domains, vascular morphogenesis, and sprouting angiogenesis," Genes Dev. 13(3):295-306 (1999).

(Continued)

*Primary Examiner* — Samantha Shterengarts
(74) *Attorney, Agent, or Firm* — Clark & Elbing LLP

(57) ABSTRACT

The present invention pertains generally to the field of therapeutic compounds for treating proliferative disorders, cancer, etc., and more specifically to certain pyrido[2,3-b]pyrazin-8-substituted compounds, as described herein, which, inter alia, inhibit RAF (e.g.,B-RAF) activity. The present invention also pertains to pharmaceutical compositions comprising such compounds, and the use of such compounds and compositions, both in vitro and in vivo, to inhibit RAF (e.g., BRAF) activity, to inhibit receptor tyrosine kinase (RTK) activity, to inhibit cell proliferation, and in the treatment of diseases and disorders that are ameliorated by the inhibition of RAF, RTK, etc., proliferative disorders such as cancer (e.g., colorectal cancer, melanoma), etc.

37 Claims, 5 Drawing Sheets

(56) References Cited

U.S. PATENT DOCUMENTS

| | | |
|---|---|---|
| 8,912,191 B2 | 12/2014 | Springer et al. |
| 9,120,789 B2 | 9/2015 | Springer et al. |
| 9,155,737 B2 | 10/2015 | Springer et al. |
| 2004/0082583 A1 | 4/2004 | Cheung et al. |
| 2007/0287838 A1 | 12/2007 | Niculescu-Duvaz et al. |
| 2008/0113967 A1 | 5/2008 | Flynn et al. |
| 2009/0325945 A1 | 12/2009 | Niculescu-Duvaz et al. |
| 2010/0298320 A1 | 11/2010 | Springer et al. |
| 2011/0053946 A1 | 3/2011 | Niculescu-Duvaz et al. |
| 2012/0238568 A1 | 9/2012 | Springer et al. |
| 2012/0283288 A1 | 11/2012 | Springer et al. |
| 2014/0121212 A1 | 5/2014 | Springer et al. |
| 2014/0357663 A1 | 12/2014 | Springer et al. |
| 2015/0182526 A1 | 7/2015 | Springer et al. |
| 2016/0002230 A1 | 1/2016 | Springer et al. |
| 2016/0030405 A1 | 2/2016 | Springer et al. |

FOREIGN PATENT DOCUMENTS

| | | |
|---|---|---|
| JP | S5665863 A | 6/1981 |
| JP | S5738777 A | 3/1982 |
| NZ | 555005 A | 10/2010 |
| WO | WO-98/13350 A1 | 4/1998 |
| WO | WO-99/16438 A1 | 4/1999 |
| WO | WO-99/21859 A1 | 5/1999 |
| WO | WO-00/35436 A2 | 6/2000 |
| WO | WO-00/40235 A2 | 7/2000 |
| WO | WO-00/45435 A1 | 8/2000 |
| WO | WO-01/05392 A2 | 1/2001 |
| WO | WO-01/36383 A1 | 5/2001 |
| WO | WO-01/46196 A1 | 6/2001 |
| WO | WO-02/102367 A1 | 12/2002 |
| WO | WO-03/056036 A2 | 7/2003 |
| WO | WO-2004/014300 A2 | 2/2004 |
| WO | WO-2004/083458 A1 | 9/2004 |
| WO | WO-2004/110452 A1 | 12/2004 |
| WO | WO-2006/003378 A1 | 1/2006 |
| WO | WO-2006/024834 A1 | 3/2006 |
| WO | WO-2006/040568 A1 | 4/2006 |
| WO | WO-2006/043090 A1 | 4/2006 |
| WO | WO-2006/067466 A2 | 6/2006 |
| WO | WO-2007/059202 A2 | 5/2007 |
| WO | WO-2007/064872 A2 | 6/2007 |
| WO | WO-2007/067444 A1 | 6/2007 |
| WO | WO-2007/076092 A2 | 7/2007 |
| WO | WO-2007/125330 A1 | 11/2007 |
| WO | WO-2008/009700 A1 | 1/2008 |
| WO | WO-2008/044688 A1 | 4/2008 |
| WO | WO-2009/007934 A2 | 1/2009 |
| WO | WO-2009/077766 A1 | 6/2009 |
| WO | WO-2009/130487 A1 | 10/2009 |
| WO | WO-2010/038085 A2 | 4/2010 |
| WO | WO-2010/038086 A2 | 4/2010 |
| WO | WO-2010/067130 A1 | 6/2010 |
| WO | WO-2010/067131 A1 | 6/2010 |
| WO | WO-2010/112936 A1 | 10/2010 |
| WO | WO-2011/004276 A1 | 1/2011 |
| WO | WO-2011/028540 A1 | 3/2011 |
| WO | WO-2011/048111 A1 | 4/2011 |
| WO | WO-2011/070368 A1 | 6/2011 |
| WO | WO-2011/070369 A1 | 6/2011 |
| WO | WO-2011/092469 A1 | 8/2011 |
| WO | WO-2011/121366 A1 | 10/2011 |
| WO | WO-2011/124923 A2 | 10/2011 |
| WO | WO-2011/124930 A1 | 10/2011 |
| WO | WO-2011/158039 A1 | 12/2011 |
| WO | WO-2011/158042 A2 | 12/2011 |
| WO | WO-2011/158044 A2 | 12/2011 |
| WO | WO-2012/008564 A1 | 1/2012 |
| WO | WO-2012/052753 A1 | 4/2012 |
| WO | WO-2012/149547 A1 | 11/2012 |
| WO | WO-2012/177725 A1 | 12/2012 |
| WO | WO-2013/001372 A2 | 1/2013 |
| WO | WO-2013/033133 A1 | 3/2013 |
| WO | WO-2013/050756 A1 | 4/2013 |
| WO | WO-2013/050757 A1 | 4/2013 |
| WO | WO-2014/027209 A1 | 2/2014 |
| WO | WO-2014/033446 A1 | 3/2014 |
| WO | WO-2014/033447 A2 | 3/2014 |
| WO | WO-2014/033448 A1 | 3/2014 |
| WO | WO-2014/033449 A1 | 3/2014 |
| WO | WO-2014/076484 A1 | 5/2014 |
| WO | WO-2014/140582 A1 | 9/2014 |
| WO | WO-2014/140597 A1 | 9/2014 |
| WO | WO-2014/162121 A1 | 10/2014 |
| WO | WO-2014/162122 A1 | 10/2014 |
| WO | WO-2014/162126 A1 | 10/2014 |
| WO | WO-2015/075483 A1 | 5/2015 |
| WO | WO-2015/092423 A1 | 6/2015 |
| WO | WO-2015/121444 A1 | 8/2015 |
| WO | WO-2015/121660 A1 | 8/2015 |
| WO | WO-2016/051186 A1 | 4/2016 |
| WO | WO-2016/051187 A1 | 4/2016 |
| WO | WO-2016/051188 A1 | 4/2016 |

OTHER PUBLICATIONS

Akula et al.,"Raf promotes human herpesvirus-8 (HHV-8/KSHV) infection," Oncogene. 23(30):5227-5241 (2004).
Alon et al., "Vascular endothelial growth factor acts as a survival factor for newly formed retinal vessles and has implications for retinopathy of prematurity," Nat. Med. 1(10):1024-1028 (1995).
Ananthanarayanan et al., "Reaction of azides in presence of aluminium chloride," Indian J Chem. 27B:156-7 (1988).
Anastasaki et al., "Continual low-level MEK inhibition ameliorates cardio-facio-cutaneous phenotypes in zebrafish," Dis Model Mech. 5(4):546-552 (2012).
Angerer et al., "Demonstration of tissue-specific gene expression by in situ hybridization," Methods Enzymol. 152:649-61 (1987).
Antony et al.,"C-RAF Mutations confer resistance to RAF inhibitors," Cancer Res. 73(15):4840-4851 (2013).
Arcaini et al., "The BRAF V600E mutation in hairy cell leukemia and other mature B-cell neoplasms," Blood. 119(1):188-191 (2012) (5 pages).
Asrih et al., "Role of mitogen-activated protein kinase pathways in multifactorial adverse cardiac remodeling associated with metabolic syndrome," Mediators Inflamm. 2013:367245 (2013) (12 pages).
Auvray et al., "Preparation and nucleophilic substitution of (E)-1-bromo-2-phenylsulfonyl-2-alkenes and 3-acetoxy-2-phenylsulfonyl-1-alkenes," Tetrahedron. 44(19):6095-106 (1988).
Avenoza et al., "New efficient synthesis of 4-amino-3-arylphenols," Synthesis. 671-674 (1995).
Badalian-Very et al., "Recent advances in the understanding of Langerhans cell histiocytosis," Br J Haematol. 156(2): 163-172 (2012).
Ballesteros et al., "Study of the catalytic properties of tris (3,6-dioxaheptyl) amine (tda-1) in heteroaromatic nucleophilic substitution of chloropyridines and their n-oxides," Tetrahedron. 43(11):2557-64 (1987).
Bart et al., "Development of novel, highly potent inhibitors of V-RAF murine sarcoma viral oncogene homologue B1 (BRAF): increasing cellular potency through optimization of a distal heteroaromatic group," J Med Chem. 53:2741-56 (2010).
Bates et al., "A new synthesis of pyrazinol[2,3-c]isoquinolines," Aust J Chem. 43(1): 179-184 (1990).
Belgore et al., "Localisation of members of the vascular endothelial growth factor (VEGF) family and their receptors in human atherosclerotic arteries," J Clin Pathol. 57(3): 266-272 (2004).
Benn et al., "Hepatitis B virus HBx protein activates Ras-GTP complex formation and establishes a Ras, Raf, MAP kinase signaling cascade," Proc Natl Acad Sci USA. 91(22): 10350-10354 (1994).
Berge et al., "Pharmaceutical salts," J Pharm Sci. 66(1):1-19 (1977).
Bergman et al., "Synthesis of pyridopyrazino[2,3-b]indoles and 10H-indolo[3,2-g]pteridins," Recl Tray Chim Pays-Bas. 115(1): 31-36 (1996).
Berry et al., "TNF-alpha in asthma," Curr Opin Pharmacol. 7(3): 279-282 (2007).

(56) References Cited

OTHER PUBLICATIONS

Bhatt et al., "Preparation of N'-2-phenyl-4-quinolinoyl-N3-aryl thioureas," J Instit Chem (India). 52:113-4 (1980).
Bianchi et al., "Compounds with antiulcer and antisecretory activity," Eur J Med Chem. 16(4):321-6 (1981).
Borthakur et al., "New direct synthesis of thioamides from carboxylic acids," Tetrahedron Letters. 36(37):6745-6 (1995).
Bos, "Ras oncogenes in human cancer: a review," Cancer Res. 49(17):4682-9 (1989).
Broekhof et al., "Novel applications of alpha-aminosubstituted diphenylphosphine oxides. The conversion of aldehydes into alpha-aminomethylketones," Tetrahedron Lett. 22(29):2799-802 (1981).
Brooks et al., "Integrin alpha v beta 3 antagonists promote tumor regression by inducing apoptosis of angiogenic blood vessels," Cell. 79(7): 1157-64 (1994).
Brose et al., "BRAF and RAS mutations in human lung cancer and melanoma," Cancer Res. 62(23):6997-7000 (2002).
Bruckner et al.,"Tyrosine phosphorylation of transmembrane ligands for Eph receptors," Science. 275(5306):1640-3 (1997).
Bruder et al., "Serum-, TPA-, and Ras-induced expression from Ap-1/Ets-driven promoters requires Raf-1 kinase," Genes Dev. 6(4):545-56 (1992).
Byeon et al., "The role of Src kinase in macrophage-mediated inflammatory responses," Mediators Inflamm. 2012:512926 (2012) (19 pages).
Calhoun et al., "BRAF and FBXW7 (CDC4, FBW7, AGO, SEL10) mutations in distinct subsets of pancreatic cancer: potential therapeutic targets," Am J Pathol. 163(4): 1255-1260 (2003).
Cantrell, "GTPases and T cell activation," Immunol Rev. 192:122-30 (2003).
Chan et al., "Regulation of antigen receptor signal transduction by protein tyrosine kinases," Curr Opin Immunol. 8(3):394-401 (1996).
Chapman et al., "Improved survival with vemurafenib in melanoma with BRAF V600E mutation," N Engl J Med. 364(26): 2507-2516 (2011).
Ciampi et al., "Oncogenic AKAP9-BRAF fusion is a novel mechanism of MAPK pathway activation in thyroid cancer," J Clin Invest. 115(1): 94-101 (2005).
Clare et al., "Protease inhibitors: synthesis of a series of bacterial collagenase inhibitors of the sulfonyl amino acyl hydroxamate type," J Med Chem. 44(13):2253-8 (2001).
Clark-Lewis et al., "Quinoxaline derivatives. Part IV. Dihydro-oxo-1 : 4 : 5-triazanaphthalenecarboxyureides and related spiroHydantoins," J Chem Soc. 430-439 (1957).
Cohen et al., "Lack of BRAF mutation in primary uveal melanoma," Invest Ophthalmol Vis Sci. 44(7):2876-8 (2003).
Colville-Nash et al., "Angiogenesis and rheumatoid arthritis: pathogenic and therapeutic implications," Ann Rheum Dis. 51(7):919-25 (1992).
Comins et al., "Grignard addition to 1-acyl salts of chiral 4-alkoxypyridines. A new enantioselective preparation of 2-alkyl-2,3-dihydro-4-pyridones," Tetrahedron Lett. 35(40):7343-6 (1994).
Cooper, "Membrane-associated tyrosine kinases as molecular switches," Semin Cell Biol. 5(6):377-87 (1994).
Corcoran et al., "BRAF gene amplification can promote acquired resistance to MEK inhibitors in cancer cells harboring the BRAF V600E mutation," Sci Signal. 3(149):ra84 (2010) (10 pages).
Correia, "Reaction of phenylglyoxal with aniline under acidic conditions," J Org Chem 43(17):3394-6 (1978).
Coulthard et al., "p38(MAPK): stress responses from molecular mechanisms to therapeutics," Trends Mol Med. 15(8): 369-379 (2009).
Courtneidge et al., "The Src family of protein tyrosine kinases: regulation and functions," Dev Suppl. 57-64 (1993).
Cowely et al., "Activation of MAP kinase kinase is necessary and sufficient for PC12 differentiation and for transformation of NIH 3T3 cells," Cell. 77(6):841-52 (1994).
Cuadrado et al., "Mechanisms and functions of p38 MAPK signalling," Biochem J. 429(3): 403-417 (2010).
Cushman et al., "19F NMR studies on the mechanism of riboflavin synthase. Synthesis of 6-(Trifluoromethyl)-7-oxo-8-(D-ribityl-)lumazine and 6-(Trifluoromethyl)-7-methyl-8- (D-ribityl-)lumazine," J Org Chem. 57(21): 5630-5643 (1992).
Damodar Reddy et al., 2001, "Role of MAP kinase pathways in primitive neuroectodermal tumors," Anticancer Res. 21(4A): 2733-2738 (2001).
Davies et al., "Mutations of the BRAF gene in human cancer," Nature. 417(6892):949-54 (2002).
Davis et al., "Isolation of angiopoietin-1, a ligand for the TIE2 receptor, by secretion-trap expression cloning," Cell. 87(7):1161-9 (1996).
Davis et al., "Raf and mitogen-activated protein kinase regulate stellate cell collagen gene expression," J Biol Chem. 271(19): 11039-11042 (1996) (5 pages).
Denekamp, "Review article: angiogenesis, neovascular proliferation and vascular pathophysiology as targets for cancer therapy," Br J Radiol. 66(783):181-96 (1993).
Dettner et al., "Chemical defense of giant springtail Tetrodontophora bielanensis (Waga) (Insecta: Collembola)," J Chem Ecol. 22(5): 1051-1074 (1996).
Dhomen et al., "Oncogenic Braf induces melanocyte senescence and melanoma in mice," Cancer Cell. 15(4): 294-303 (2009).
Dickson et al., "Raf functions downstream of Ras1 in the Sevenless signal transduction pathway," Nature. 360(6404):600-3 (1992).
Downward, "Targeting RAS signalling pathways in cancer therapy," Nat Rev Cancer. 3(1):11-22 (2003).
Dubey et al., "Structure and reactions of monoanils obtained from 2,3-pyridinediamines," Indian J Chem. 40B(5): 361-367 (2001).
DuBois, "Amination of aryl sulfamate esters. A convenient general synthesis of aliphatic sulfamides," J Org Chem. 45:5373-5 (1980).
Ellis et al., "VEGF-targeted therapy: mechanisms of anti-tumour activity," Nat Rev Cancer. 8(8):579-591 (2008).
Falchook et al., "RAF inhibitor dabrafenib (GSK2118436) is active in melanoma brain metastases, multiple BRAF genotypes and diverse cancers" NIH Public Access Author Manuscript 20 pages Jul. 24, 2014, published in final edited form as "Dabrafenib in patients with melanoma, untreated brain metastases, and other solid tumours: a phase 1 dose-escalation trial," Lancet. 379(9829):1893-1901 (2012).
Fernandez-Medarde et al., "Ras in cancer and developmental diseases," Genes Cancer. 2(3): 344-358 (2011).
Fidler et al., "The implications of angiogenesis for the biology and therapy of cancer metastasis," Cell. 79(2):185-8 (1994).
Flaherty et al., "Inhibition of mutated, activated BRAF in metastatic melanoma," N Engl J Med. 363(9): 809-819 (2010).
Folkman et al., "Angiogenesis," J Biol Chem. 267(16):10931-4 (1992).
Folkman, "Angiogenesis and angiogenesis inhibition: An overview," EXS. 79:1-8 (1997).
Folkman, "Angiogenesis in cancer, vascular, rheumatoid and other disease," Nat Med. 1(1):27-31 (1995).
Folkman, "The role of angiogenesis in tumor growth," Semin Cancer Biol. 3(2):65-71 (1992).
Fourrey et al., "Preparation of stable 1,4-dihydropyrazines," J Chem Soc., Perkins Transactions 1: Org. and Bio. Chem. 8:1841-3 (1987).
Friedlander et al., "Definition of two angiogenic pathways by distinct alpha v integrins," Science. 270(5241):1500-2 (1995).
Fujita et al., "ERK and p38 mediate high-glucose-induced hypertrophy and TGF-beta expression in renal tubular cells," Am J Physiol Renal Physiol. 286(1): F120-6 (2004).
Fukuda et al., "Epstein-Barr virus latent membrane protein 2A mediates transformation through constitutive activation of the Ras/PI3-K/Akt Pathway," J Virol. 81(17): 9299-9306 (2007).
Gale et al., "Growth factors acting via endothelial cell-specific receptor tyrosine kinases: VEGFs, angiopoietins, and ephrins in vascular development," Genes Dev. 13(9):1055-66 (1999).
Galons, "Cyclisation indolique selon Bischler en presence d'acides de Lewis," J Heterocyclic Chemistry. 18:561-63 (1981).
Garnett et al., "Guilty as charged: B-RAF is a human oncogene," Cancer Cell. 6(4):313-9 (2004).
Gaudi et al., "Molecular bases of cutaneous and uveal melanomas," Patholog Res Int. 2011:159421 (2011) (8 pages).

(56) References Cited

OTHER PUBLICATIONS

Genot et al.,"Ras regulation and function in lymphocytes," Curr Opin Immunol. 12(3):289-94 (2000).
Geppert et al., "Lipopolysaccharide signals activation of tumor necrosis factor biosynthesis through the ras/raf-1/MEK/MAPk pathway," Mol Med. 1(1): 93-103 (1994).
Giannotti et al., "New dibenzothiadiazepine derivatives with antidepressant activities," J Med Chem 34(4):1356-62 (1991).
Giardina et al., "Replacement of the quinoline system in 2-phenyl-4-quinolinecarboxamide NK-3 receptor antagonists," Farmaco. 54(6):364-74 (1999).
Girotti et al., "Inhibiting EGF receptor or SRC family kinase signaling overcomes BRAF inhibitor resistance in melanoma," Cancer Discov. 3(2): 158-167 (2013).
Glinka, "Synthesis and structure of new hetercyclic systems containing the sulfamide group," Pol J Chem. 65:2053-5 (1991).
Golub et al., "Molecular classification of cancer: class discovery and class prediction by gene expression monitoring," Science. 286(5439):531-7 (1999).
Gorden et al., "Analysis of BRAF and N-RAS mutations in metastatic melanoma tissues," Cancer Res. 63(14):3955-7 (2003).
Graf et al., "Mitogen-activated protein kinase activation is involved in platelet-derived growth factor-directed migration by vascular smooth muscle cells," Hypertension. 29(1 Pt. 2): 334-339 (1997).
Gray-Schopfer et al., "Melanoma biology and new targeted therapy," Nature. 445(7130):851-7 (2007).
Greger et al., "Combinations of BRAF, MEK, and Pl3K/mTOR inhibitors overcome acquired resistance to the BRAF inhibitor GSK2118436 dabrafenib, mediated by NRAS or MEK mutations," Mol Cancer Ther. 11(4): 909-920 (2012).
Grosios et al., "Angiogenesis inhibition by the novel VEGF receptor tyrosine kinase inhibitor, PTK787/ZK222584, causes significant anti-arthritic effects in models of rheumatoid arthritis," Inflamm Res. 53(4): 133-142 (2004).
Guarna et al., "Synthesis of a new enantiopure bicyclic gamma/delta-amino acid (BTKa) derived from tartaric acid and alpha-amino acetophenone," Tetrahedron. 58(49):9865-70 (2002).
Haase et al., "A role for mitogen-activated protein kinase activation by integrins in the pathogenesis of psoriasis," J Clin Invest. 108(4): 527-536 (2001).
Haesslein et al., "Recent advances in cyclin-dependent kinase inhibition. Purine-based derivatives as anti-cancer agents. Roles and perspectives for the future," Curr Top Med Chem. 2(9):1037-50 (2002).
Hammond et al., "Structure-activity relationships in a series of NPY Y5 antagonists: 3-amido-9-ethylcarbazoles, core-modified analogues and amide isosteres," Bioorg Med Chem Lett. 13(12):1989-92 (2003).
Haroche et al., "High prevalence of BRAF V600E mutations in Erdheim-Chester disease but not in other non-Langerhans cell histiocytoses," Blood. 120(3): 2700-2703 (2012) (5 pages).
Heidorn et al., "Kinase-dead BRAF and oncogenic RAS cooperate to drive tumor progression through CRAF," Cell. 140(2): 209-221 (2010).
Helbling et al., "The receptor tyrosine kinase EphB4 and ephrin-B ligands restrict angiogenic growth of embryonic veins in Xenopus laevis," Development. 127(2):269-78 (2000).
Hirayama et al., "Design, synthesis and biological activity of YM-60828 derivatives: potent and orally-bioavailable factor Xa inhibitors based on naphthoanilide and naphthalensulfonanilide templates," Bioorg Med Chem. 10(8):2597-610 (2002).
Holland et al., "Bidirectional signalling through the EPH-family receptor Nuk and its transmembrane ligands," Nature. 383(6602):722-5 (1996).
Hu et al., "Mutation that blocks ATP binding creates a pseudokinase stabilizing the scaffolding function of kinase suppressor of Ras, CRAF and BRAF," Proc Natl Acad Sci USA. 108(15): 60676072 (2011) (9 pages).

Hwang et al., "Over-expression of c-raf-1 proto-oncogene in liver cirrhosis and hepatocellular carcinoma," Hepatol Res. 29(2): 113-121 (2004).
Ingber et al., "Synthetic analogues of fumagillin that inhibit angiogenesis and suppress tumour growth," Nature. 348(6301):555-7 (1990).
Inoue et al., "Vascular endothelial growth factor (VEGF) expression in human coronary atherosclerotic lesions: possible pathophysiological significance of VEGF in progression of atherosclerosis," Circulation. 98(20): 2108-2116 (1998).
International Preliminary Report on Patentability for International Application No. PCT/GB2005/004081, issued Apr. 24, 2007 (8 pages).
International Preliminary Report on Patentability for International Application No. PCT/GB2007/001534, issued Oct. 28, 2008 (10 pages).
International Preliminary Report on Patentability for International Application No. PCT/GB2008/004208, issued Jun. 22, 2010 (6 pages).
International Preliminary Report on Patentability for International Application No. PCT/GB2009/001077, issued Oct. 26, 2010 (6 pages).
International Preliminary Report on Patentability for International Application No. PCT/GB2011/000106, issued Aug. 7, 2012 (7 pages).
International Search Report and Written Opinion for International Application No. PCT/GB2005/004081, mailed Feb. 2, 2006 (12 pages).
International Search Report and Written Opinion for International Application No. PCT/GB2008/004208, mailed Mar. 5, 2009 (7 pages).
International Search Report and Written Opinion for International Application No. PCT/GB2009/001077, mailed Sep. 21, 2009 (8 pages).
International Search Report and Written Opinion for International Application No. PCT/GB2011/000106, mailed Mar. 18, 2011 (10 pages).
International Search Report and Written Opinion for International Application No. PCT/GB2014/053489, mailed Jan. 15, 2015 (11 pages).
International Search Report and Written Opinion for International Application No. PCT/GB2014/053490, mailed Jan. 26, 2015 (10 pages).
International Search Report for International Application No. PCT/GB2007/001534, mailed Sep. 6, 2007 (4 pages).
Ishii et al., "First synthesis and reactivities of isolable dithiiranes and their 1-oxides," Bulletin of the Chemical Society of Japan. 70:509-23 (1997).
Itaya et al., "Syntheses of the marine ascidian purine aplidiamine and its 9-beta-d-ribofuranoside," Tetrahedron Lett. 39:4695-6 (1998).
Jaffee et al., "Inhibition of MAP kinase kinase (MEK) results in an anti-inflammatory response in vivo," Biochem Biophys Res Commun. 268(2): 647-651 (2000).
Janvier et al., "Ammonium chloride-promoted four-component synthesis of pyrrolo[3,4-b]pyridin-5- one," J Am Chem Soc. 124(11):2560-7 (2002).
Jessen et al., "MEK inhibition exhibits efficacy in human and mouse neurofibromatosis tumors," J Clin Invest 123(1): 340-347 (2013).
Ji et al., "ERK MAP kinase activation in superficial spinal cord neurons induces prodynorphin and NK-1 upregulation and contributes to persistent inflammatory pain hypersensitivity," J Neurosci. 22(2): 478-85 (2002).
Jo et al., "MEK inhibitor, U0126, attenuates cisplatin-induced renal injury by decreasing inflammation and apoptosis," Kidney Int. 67(2): 458-466 (2005).
Johnson et al., "Preparation and reactions of sulfonimidoyl chlorides," J Org Chem. 44(13):2055-61 (1979).
Johnson et al., "The role of MKK1/2 kinase activity in human cytomegalovirus infection," J Gen Virol. 82(Pt 3): 493-497 (2001).
Jursic, "Synthetic application of micellar catalysis. williamson's synthesis of ethers," Tetrahedron. 44(21):6677-80 (1988).

(56) References Cited

OTHER PUBLICATIONS

Kahlon et al., "Angiogenesis in atherosclerosis," Can J Cardiol. 8(1):60-4 (1992).
Kam et al.,"TNF-alpha antagonists for the treatment of Crohn's disease," Expert Opin Pharmacother. 1(4): 615-622 (2000).
Karim et al.,"Impaired inflammatory pain and thermal hyperalgesia in mice expressing neuron-specific dominant negative mitogen activated protein kinase kinase (MEK)," Mol Pain. 2:2 (2006) (10 pages).
Keffer et al., "Transgenic mice expressing human tumour necrosis factor: a predictive genetic model of arthritis," EMBO J. 10(13): 4025-4031 (1991).
Kolch et al., "Raf-1 protein kinase is required for growth of induced NIH/3T3 cells," Nature. 349(6308):426-8 (1991).
Kotoula et al., "Mutational analysis of the BRAF, RAS and EGFR genes in human adrenocortical carcinomas," Endocr Relat Cancer. 16(2): 565-572 (2009).
Lala et al., "Role of nitric oxide in tumor progression: lessons from experimental tumors," Cancer Metastasis Rev. 17(1):91-106 (1998).
Leese et al., "Polyazanaphthalenes. Part I. Some derivatives of 1:4:5-triazanaphthalene and quinoxaline," J Chem Soc. 303-309 (1955).
Lemonnier et al., "Role of N-cadherin and protein kinase C in osteoblast gene activation induced by the S252W fibroblast growth factor receptor 2 mutation in Apert craniosynostosis," J Bone Miner Res. 16(5):832-45 (2001).
Li et al., "Activation of NF-kappaB via a Src-dependent Ras-MAPK-pp90rsk pathway is required for Pseudomonas aeruginosa-induced mucin overproduction in epithelial cells," Proc Natl Acad Sci USA. 95(10): 5718-5723 (1998).
Lin et al., "VEGF and its receptor-2 involved in neuropathic pain transmission mediated by P2X2(/)3 receptor of primary sensory neurons," Brain Res Bull. 83(5):284-291 (2010).
Lindauer et al., "Dasatinib," Recent Results Cancer Res. 184: 83-102 (2010).
Link et al., "Phosphodiesterase 4 inhibition but not beta-adrenergic stimulation suppresses tumor necrosis factor-alpha release in peripheral blood mononuclear cells in septic shock," Crit Care. 12(6):R159 (2008) (9 pages).
Liu et al., "Effects of overexpression of ephrin-B2 on tumour growth in human colorectal cancer," Br J Cancer. 90(8):1620-6 (2004).
Long et al., "Prognostic and clinicopathologic associations of oncogenic BRAF in metastatic melanoma," J Clin Oncol. 29(10): 1239-1246 (2011).
Lorenz et al., "Cardiac hypertrophy: targeting Raf/MEK/ERK1/2-signaling," Int J Biochem Cell Biol. 41(12): 2351-2355 (2009).
Lowenberg et al.,"Specific inhibition of c-Raf activity by semapimod induces clinical remission in severe Crohn's disease," J Immunol. 175(4): 2293-2300 (2005).
Lozinskii et al., "Alkylthio derivatives of the aminoketene S,N-Acetals of heterocyclic beta-dicarbonyl compounds: one stage synthesis and properties," Chemistry of Heterocyclic Compounds. 38(9):1077-80 (2002).
Luo et al., "Coxsackievirus B3 replication is reduced by inhibition of the extracellular signal-regulated kinase (ERK) signaling pathway," J Virol. 76(7): 3365-3373 (2002).
Ma et al., "The ERK/MAPK pathway, as a target for the treatment of neuropathic pain," Expert Opin Ther Targets. 9(4):699-713 (2005).
Maddahi et al.,"Cerebral ischemia induces microvascular pro-inflammatory cytokine expression via the MEK/ERK pathway," J Neuroinflammation. 7:14 (2010) (13 pages).
Mammas et al., "Involvement of the ras genes in female genital tract cancer," Int J Oncol. 26(5):1241-1255 (2005).
Mansour et al., "Transformation of mammalian cells by constitutively active MAP kinase kinase," Science. 265(5174):966-70 (1994).

Marais et al., "Differential regulation of Raf-1, A-Raf, and B-Raf by oncogenic ras and tyrosine kinases," J Biol Chem. 272(7):4378-83 (1997).
Martich et al., "Detection of interleukin 8 and tumor necrosis factor in normal humans after intravenous endotoxin: the effect of antiinflammatory agents," J Exp Med. 173(4):1021-1024 (1991).
Martin et al., "Update on lymphocyte specific kinase inhibitors: a patent survey," Expert Opin Ther Pat. 20(11): 1573-1593 (2010).
Mashelkar et al., "Synthesis of some novel 4-substituted coumarins having potential biological activity (Part II)," Indian J Chem. 45B(4): 967-971 (2006).
Mataloni et al., "Synthesis of secondary amines by reduction of alpha-amidoalkylphenyl sulfones with sodium acetoxyborohydride," Synlett. 8:1129-32 (2003).
McCann et al.,"Apremilast, a novel PDE4 inhibitor, inhibits spontaneous production of tumour necrosis factor-alpha from human rheumatoid synovial cells and ameliorates experimental arthritis," Arthritis Res Ther. 12(3): R107 (2010) (11 pages).
McKay et al., "Complexity in KSR function revealed by Raf inhibitor and KSR structure studies," Small GTPases. 2(5):276-281 (2011) (7 pages).
McKillop et al., "Applications of ethyl carboethoxyformimidate to heterocyclic synthesis: preparation of condensed pyrazinones and 1,4-oxazinones," Synthesis. 3:301-304 (1997).
McMahon, "VEGF receptor signalling in tumor angiogenesis," Oncologist. 5(suppl I):3-10 (2000).
Mei et al., "Distribution, levels and phosphorylation of Raf-1 in Alzheimer's disease," J Neurochem. 99(5): 1377-1388 (2006).
Menard et al., "Novel potent BRAF inhibitors: toward 1 nM compounds through optimization of the central phenyl ring," J Med Chem. 52(13): 3881-3891 (2009).
Mercer et al., "Emerging role of MAP kinase pathways as therapeutic targets in COPD," Int J Chron Obstruct Pulmon Dis. 1(2):137-150 (2006).
Messinger et al., "Synthesis of alpha-amino- and alpha-amidosulfones. 5. Sulfones as chemical transport forms of substances with germicidae effect," Arch Pharm (Weinheim). 307(8):653-5 (1974). (in German with partial English language translation).
Metzner et al., "Fibroblast growth factor receptors as therapeutic targets in human melanoma: synergism with BRAF inhibition," J Invest Dermatol. 131(10): 2087-2095 (2011).
Meyers et al., "FGFR2 exon IIIa and IIIc mutations in Crouzon, Jackson-Weiss, and Pfeiffer syndromes: evidence for missense changes, insertions, and a deletion due to alternative RNA splicing," Am J Hum Genet. 58(3):491-8 (1996).
Milella et al., "Therapeutic targeting of the MEK/MAPK signal transduction module in acute myeloid leukemia," J Clin Invest. 108(6): 851-859 (2001).
Mineo et al., "Prognostic impact of VEGF, CD31, CD34, and CD105 expression and tumour vessel invasion after radical surgery for IB-IIA non-small cell lung cancer," J Clin Pathol. 57(6):591-7 (2004).
Miura et al., "Simvastatin suppresses coronary artery endothelial tube formation by disrupting Ras/Raf/ERK signaling," Atherosclerosis. 175(2): 235-243 (2004).
Mohanta et al., "1-(methyldithiocarbony)imidazole: a useful thiocarbonyl transfer reagent for synthesis of substituted thioureas," Tetrahedron. 56(4):629-37 (2000).
Montagut et al., "Elevated CRAF as a potential mechanism of acquired resistance to BRAF inhibition in melanoma," Cancer Res. 68(12): 4853-4861 (2008) (16 pages).
Moore et al., "ROMP-generated oligomeric sulfonyl chlorides as versatile soluble scavenging agents," Org Lett. 5(2):105-7 (2003).
Mukherjee et al., "Raf-1 expression may influence progression to androgen insensitive prostate cancer," Prostate. 64(1):101-107 (2005).
Mukhopadhyay et al., "Role of TNFalpha in pulmonary pathophysiology," Respir Res. 7:125 (2006) (9 pages).
Mustonen et al., "Endothelial receptor tyrosine kinases involved in angiogenesis," J Cell Biol. 129(4):895-8 (1995).

(56) References Cited

OTHER PUBLICATIONS

Nakamoto et al., "Diverse roles for the Eph family of receptor tyrosine kinases in carcinogenesis," Miscrosc Res Tech. 59(1):58-67 (2002).
Nakamura et al., "Novel strategies for the treatment of inflammatory bowel disease: Selective inhibition of cytokines and adhesion molecules," World J Gastroenterol. 12(29): 4628-4635 (2006).
Nazarian et al., "Melanomas acquire resistance to B-RAF(V600E) inhibition by RTK or N-RAS upregulation," Nature. 468(7326): 973-977 (2010) (7 pages).
O'Reilly et al., "Angiostatin: A novel angiogenesis inhibitor that mediates the suppression of metastases by a Lewis lung carcinoma," Cell. 79(2):315-28 (1994).
Oeztuerk-Winder et al., "The many faces of p38 mitogen-activated protein kinase in progenitor/stem cell differentiation," Biochem J. 445(1): 1-10 (2012).
Orre et al., "VEGF, VEGFR-1, VEGFR-2, microvessel density and endothelial cell proliferation in tumours of the ovary," Int J Cancer. 84(2):101-8 (1999).
Ozawa et al., "Growth factors and their receptors in pancreatic cancer," Teratog Carcinog Mutagen. 21(1):27-44 (2001).
Pabst et al., "Analysis of K-ras mutations in pancreatic tissue after fine needle aspirates," Anticancer Res. 19(4A):2481-3 (1999).
Palanisamy et al., "Rearrangements of the RAF kinase pathway in prostate cancer, gastric cancer and melanoma," Nat. Med. 16(7): 793-798 (2010) (7 pages).
Parlow et al., "Synthesis and crystal structures of substituted benzenes and benzoquinones as tissue factor VIIa inhibitors," J Med Chem. 46(20):4297-312 (2003).
Partanen et al., "A novel endothelial cell surface receptor tyrosine kinase with extracellular epidermal growth factor homology domains," Mol Cell Biol. 12(4):1698-707 (1992).
Partanen et al., "Functions of Tie1 and Tie2 receptor tyrosine kinases in vascular development," Curr Top Microbiol Immunol. 237:159-72 (1999).
Patani et al., "Bioisosterism: a rational approach to drug design," Chem Rev. 96(8):3147-76 (1996).
Paulson et al., "Receptor tyrosine kinases and the regulation of hematopoiesis," Semin Immunol. 7(4):267-77 (1995).
Payne et al., "Human papillomavirus type 6b virus-like particles are able to activate the Ras-MAP kinase pathway and induce cell proliferation," J Virol. 75(9): 4150-4157 (2001).
Peacock et al., "A novel angiogenesis inhibitor suppresses rat adjuvant arthritis," Cell Immunol. 160(2):178-84 (1995).
Peacock et al., "Angiogenesis inhibition suppresses collagen arthritis," J Exp Med. 175(4):1135-8 (1992).
Pelletier et al., "In vivo selective inhibition of mitogen-activated protein kinase kinase 1/2 in rabbit experimental osteoarthritis is associated with a reduction in the development of structural changes," Arthritis Rheum. 48(6): 1582-1593 (2003).
Peters, "Vascular endothelial growth factor and the angiopoietins working together to build a better blood vessel," Circ Res. 83(3):342-3 (1998).
Petrovan et al., "DNA vaccination against VEGF receptor 2 reduces atherosclerosis in LDL receptor-deficient mice," Arterioscler Thromb Vasc Biol. 27(5): 1095-1100 (2007) (11 pages).
Pinedo et al., "Translational research: the role of VEGF in tumor angiogenesis," The Oncologist. 5:1-2 (2000).
Planz et al., "MEK-specific inhibitor U0126 blocks spread of Borna disease virus in cultured cells," J Virol. 75(10): 4871-4877 (2001).
Pleschka et al., "Influenza virus propagation is impaired by inhibition of the Raf/MEK/ERK signalling cascade," Nat Cell Biol. 3(3): 301-305 (2001) (7 pages).
Plomp et al., "Pfeiffer syndrome type 2: further delineation and review of the literature," Am J Med Genet. 75(3):245-51 (1998).
Poulikakos et al., "RAF inhibitor resistance is mediated by dimerization of aberrantly spliced BRAF(V600E)," Nature. 480(7377): 387-390 (2011) (5 pages).
Poulikakos et al., "RAF inhibitors transactivate RAF dimers and ERK signalling in cells with wild-type BRAF," Nature. 464(7287): 427-430 (2010) (5 pages).
Powers et al., "Fibroblast growth factors, their receptors and signalling," Endocr Relat Cancer. 7(3):165-97 (2000).
Prakash et al., "A convenient synthesis of alpha-anilinoacetophenones using hypervalent iodine," Indian Journal of Chemistry, Section B: Organic Chemistry Including Medicinal Chemistry. 31:349-50 (1992).
Prix et al., "Diagnostic biochip array for fast and sensitive detection of K-ras mutations in stool," Clin Chem. 48(3):428-35 (2002).
Rajagopalan et al., "Tumorgenesis: RAF/RAS oncogenes and mismatch-repairs status," Nature. 418(6901):934 (2002).
Ramadas et al., "LAC sulfur assisted synthesis of symmetrical thioureas," Synth Comm. 27(23):2255-60 (1997).
Reck et al., "Novel N-linked aminopiperidine inhibitors of bacterial topoisomerase type II: broad-spectrum antibacterial agents with reduced hERG activity," J Med Chem. 54(22): 7834-7847 (2011).
Remli et al., "Reaction of o-arylenediamines with ethyl 3-fluoro 2-ketoesters synthesis of quinoxaline derivatives," J Fluorine Chem. 44:15-23 (1989).
Riva et al., "Differential c-myc, c-jun, c-raf and p53 expression in squamous cell carcinoma of the head and neck: implication in drug and radioresistance," Eur J Cancer B Oral Oncol. 31 B(6): 384-391 (1995).
Rotsos et al., "Cystoid macular edema," Clin Ophthalmol. 2(4): 919-930 (2008).
Rubinstein et al., "Incidence of the V600K mutation among melanoma patients with BRAF mutations, and potential therapeutic response to the specific BRAF inhibitor PLX4032," J Transl Med. 8: 67 (2010) (3 pages).
Rudy et al., "Zweikernige Alloxan-Abkömmlinge von 2.3-Diaminopyridinen," Chemische Berichte. 71:1323-1332 (1938) (Abstract Included) (11 pages).
Salama et al., "BRAF in Melanoma: Current strategies and future directions," Clin Cancer Res. 19(16): 4326-4334 (2013).
Sarkis et al., "Synthesis and spectroscopic properties of some new N,N'-disubstituted thioureas of potential biological interest," J Heterocyclic Chemistry. 22:137-40 (1985).
Schindler et al., "Analysis of BRAF V600E mutation in 1,320 nervous system tumors reveals high mutation frequencies in pleomorphic xanthoastrocytoma, ganglioglioma and extra-cerebellar pilocytic astrocytoma," Acta Neuropathol. 121(3): 397-405 (2011).
Schreck et al., "Raf kinases: Oncogenesis and drug discovery," Int J Cancer. 119(10): 2261-2271 (2006).
Search Report for British Application No. GB 0423554.5, dated Feb. 23, 2005 (1 page).
Search Report for British Application No. GB 0608268.9, dated Aug. 9, 2006 (1 page).
Search Report for British Application No. GB 0807609.3, dated Aug. 21, 2008 (2 pages).
Search Report for United Kingdom Application No. GB 1320729.5, dated May 20, 2014 (2 pages).
Search Report for United Kingdom Application No. GB 1320732.9, dated May 19, 2014 (2 pages).
Seki et al., "Reaction products of dialkyl acetylenedicarboxylates with 2,3-diaminopyridine," J Heterocyclic Chem. 32(3): 1071-1073 (1995).
Shakhov et al., "Kappa B-type enhancers are involved in lipopolysaccharide-mediated transcriptional activation of the tumor necrosis factor alpha gene in primary macrophages," J Exp Med. 171(1): 35-47 (1990).
Shapira et al., "Protection against endotoxic shock and lipopolysaccharide-induced local inflammation by tetracycline: correlation with inhibition of cytokine secretion," Infect Immun. 64(3): 825-828 (1996).
Shaw et al., "The preparation of 2,6-diaminopyrazine, 2,6-diazidopyrazine and some of their derivatives," J Heterocycl Chem. 17(1): 11-6 (1980).
Sherman et al., "Synthesis of unsymmetrical and regio-defined 2,3,6-quinoxaline and 2,3,7-pyridopyrazine derivatives," Tetrahedron Lett. 48(51):8943-8946 (2007).

(56) References Cited

OTHER PUBLICATIONS

Shi et al., "Melanoma whole-exome sequencing identifies (V600E)B-RAF amplification-mediated acquired B-RAF inhibitor resistance," Nat Commun. 3: 724 (2012) (8 pages).
Shibuya, "Vascular endothelial growth factor and its receptor system: physiological functions in angiogenesis and pathological roles in various diseases," J Biochem. 153(1):13-19 (2013).
Shiina et al., "A new method for the synthesis of carboxamides and peptides using 1,1'-carbonyldioxydi[2(1H)-pyridone] (CDOP) in the absence of basic promoters," Tetrahedron Letters. 44:1951-55 (2003).
Shin et al., "Expression of EphrinB2 identifies a stable genetic difference between arterial and venous vascular smooth muscle as well as endothelial cells, and marks subsets of microvessels at sites of adult neovascularization," Dev Biol. 230(2):139-50 (2001).
Sievert et al.,"Paradoxical activation and RAF inhibitor resistance of BRAF protein kinase fusions characterizing pediatric astrocytomas," Proc Natl Acad Sci USA. 110(15): 5957-5962 (2013) (9 pages).
Singer et al., "Mutations in BRAF and KRAS characterize the development of low-grade ovarian serous carcinoma," J Natl Cancer Inst. 95(6):484-6 (2003).
Smalley et al.,"CRAF inhibition induces apoptosis in melanoma cells with non-V600E BRAF mutations," Oncogene. 28(1): 85-94 (2009).
Smith et al.,"Vascular endothelial growth factor receptors VEGFR-2 and VEGFR-3 are localized primarily to the vasculature in human primary solid cancers," Clin Cancer Res. 16(14): 3548-3561 (2010).
Solit et al., "BRAF mutation predicts sensitivity to MEK inhibition," Nature. 439(7074):358-62 (2006).
Song et al., "Activation of ERK/CREB pathway in spinal cord contributes to chronic constrictive injury-induced neuropathic pain in rats," Acta Pharmacol Sin. 26(7): 789-98 (2005).
Sosman et al., "Survival in BRAF V600-mutant advanced melanoma treated with vemurafenib," N Engl J Med. 366(8):707-714 (2012).
Srinivas et al., "A highly convenient, efficient, and selective process for preparation of esters and amides from carboxylic acids using Fe(3+)-K-10- montmorillonite clay," J Org Chem. 68(3):1165-7 (2003).
Srivastava et al., "Synthesis and antithyroid activity of some benzimidazolyl and benzenesulphonyl thiocarbamides" Current Science. 50(7):305-7 (1981).
Straussman et al., "Tumour micro-environment elicits innate resistance to RAF inhibitors through HGF secretion," Nature. 487(7408): 500-504 (2012) (7 pages).
Suijkerbuijk et al., "Development of novel, highly potent inhibitors of V-RAF murine sarcoma viral oncogene homologue B1 (BRAF): increasing cellular potency through optimization of a distal heteroaromatic group," J Med Chem. 53(7):2741-56 (2010).
Sullivan et al., "BRAF in melanoma: pathogenesis, diagnosis, inhibition, and resistance," J Skin Cancer. 2011:423239 (2011) (8 pages).
Suri et al., "Requisite role of angiopoietin-1, a ligand for TIE2 receptor, during embryonic angiogenesis," Cell. 87(7):1171-80 (1996).
Tam et al., "Blockade of VEGFR2 and not VEGFR1 can limit diet-induced fat tissue expansion: role of local versus bone marrow-derived endothelial cells," PLoS One. 4(3):e4974 (2009) (6 pages).
Tang et al., "Coexpression of transcripts encoding EPHB receptor protein tyrosine kinases and their ephrin-B ligands in human small cell lung carcinoma," Clin Cancer Res. 5(2):455-60 (1999).
Tang et al., "High-level expression of EPHB6, EFNB2, and EFNB3 is associated with low tumor stage and high TrkA expression in human neuroblastomas," Clin Cancer Res. 5(6):1491-6 (1999).
Tanga et al., "Syntheses of two potential food mutagens," J Heterocycl Chem. 40(4):569-73 (2003).
Taraboletti et al., "Inhibition of angiogenesis and murine hemangioma growth by batimastat, a synthetic inhibitor of matrix metalloproteinases," J Natl Cancer Inst. 87(4):293-8 (1995).
Temple et al., "New anticancer agents: alterations of the carbamate group of ethyl (5-amino-1,2-dihydro-3-phenylpyrido[3,4-b]pyrazin-7-yl)car bamates," J Med Chem. 32(10):2363-7 (1989).
Terao et al., "Synthesis of .alpha.-thio, .alpha.-sulfinyl, and .alpha.-sulfonyl-substituted nitrosamines," Chem Pharm Bull. 25(11):2964-8 (1977).
Thalhamer et al., "MAPKs and their relevance to arthritis and inflammation," Rheumatology (Oxford). 47(4):409-414 (2008).
Thornber, "Isosterism and molecular modification in drug design," Chem Soc Rev. 8(4):563-80 (1979).
Uchida et al., "Studies on 2(1H)-quinolinone derivatives as gastric antiulcer active agents. 2-(4-chlorobenzoylamino)-3-[2(1H)-quinolinon-4-yl]propionic acid and related compounds," Chem Pharm Bull (Tokyo). 33(9):3775-86 (1985).
Vergani et al., "Identification of MET and SRC activation in melanoma cell lines showing primary resistance to PLX4032," Neoplasia. 13(12):1132-1142 (2011) (14 pages).
Villanueva et al., "Acquired resistance to BRAF inhibitors mediated by a RAF kinase switch in melanoma can be overcome by cotargeting MEK and IGF-1 R/PI3K," Cancer Cell. 18(6):683-695 (2010) (34 pages).
Wan et al., "Mechanism of activation of the RAF-ERK signaling pathway by oncogenic mutations of B-RAF," Cell. 116(6):855-67 (2004).
Wang et al., "Antisense targeting of basic fibroblast growth factor and fibroblast growth factor receptor-1 in human melanomas blocks intratumoral angiogenesis and tumor growth," Nature. 3(8): 887-893 (1997).
Wang et al., "Inhibition of MEK/ERK 1/2 pathway reduces pro-inflammatory cytokine interleukin-1 expression in focal cerebral ischemia," Brain Res. 996(1):55-66 (2004).
Wang et al., "Molecular distinction and angiogenic interaction between embryonic arteries and veins revealed by ephrin-B2 and its receptor Eph-B4", Cell. 93(5):741-53 (1998).
Wang et al., "Significant neuroprotection against ischemic brain injury by inhibition of the MEK1 protein kinase in mice: exploration of potential mechanism associated with apoptosis," J Pharmacol Exp Ther. 304(1): 172-178 (2003).
Ward et al., "Targeting oncogenic Ras signaling in hematologic malignancies," Blood. 120(17): 3397-3406 (2012).
Wellbrock et al., "The RAF proteins take centre stage," Nat Rev Mol Cell Biol. 5(11):875-85 (2004).
Wellbrock et al., "V599EB-RAF is an oncogene in melanocytes," Cancer Res. 64(7): 2338-2342 (2004) (6 pages).
Whittaker et al., "A novel, selective and efficacious nanomolar pyridopyrazinone inhibitor of V600EBRAF," Cancer Res. 70(20): 8036-8044 (2010) (13 pages).
Wilks, "Structure and function of the protein tyrosine kinases," Prog Growth Factor Res. 2(2):97-111 (1990).
Wilson et al., "Widespread potential for growth-factor-driven resistance to anticancer kinase inhibitors," Nature. 487(7408): 505-509 (2012) (6 pages).
Xing, "Molecular pathogenesis and mechanisms of thyroid cancer," Nat Rev Cancer. 13(3)184-199 (2013).
Yancopoulos et al., "Vasculogenesis, angiogenesis and growth factors: ephrins enter the fray at the border," Cell. 93(5):661-4 (1998).
Yang et al., "Regulation of human immunodeficiency virus type 1 infectivity by the ERK mitogen-activated protein kinase signaling pathway," J Virol. 73(4):3460-3466 (1999).
Yao et al., "Lipopolysaccharide induction of the tumor necrosis factor-alpha promoter in human monocytic cells. Regulation by Egr-1, c-Jun and NF-kappaB transcription factors," J Biol Chem. 272(28): 17795-17801 (1997).
Yeatman, "A renaissance for SRC," Nat Rev Cancer. 4(6):470-480 (2004).
Young et al., "Ras signaling and therapies," Adv Cancer Res. 102:1-17 (2009).
Yu et al., "Loss of fibroblast growth factor receptor 2 ligand-binding specificity in Apert syndrome," Proc Natl Acad Sci U.S.A. 97(26):14536-41 (2000).
Zejc et al., "Synthesis and anticonvulsant properties of some arylsuccinate methylpyridylimides", Pol J Pharmacol Pharm. 42(1):69-77 (1990).

(56) References Cited

OTHER PUBLICATIONS

Zhang et al., "Activation of the Ras/Raf/MEK pathway facilitates hepatitis C virus replication via attenuation of the interferon-JAK-STAT pathway," J Virol. 86(3): 1544-1554 (2012).

Zhang et al., "Targeting Src family kinases in anti-cancer therapies: turning promise into triumph," Trends Pharmacol Sci. 33(3): 122-128 (2012).

Zhou et al.,"Synthesis and SAR of 5-, 6-, 7- and 8-aza analogues of 3-aryl-4-hydroxyquinolin-2(1H)-one as NMDA/glycine site antagonists," Bioorg Med Chem. 9(8):2061-71 (2001).

Ziegler et al.,"Some 9-Aza-alloxazines," J Am Chem Soc. 71:1891-1893 (1949).

Zouki et al.,"Peroxynitrite induces integrin-dependent adhesion of human neutrophils to endothelial cells via activation of the Raf-1/MEK/Erk pathway," FASEB J. 15(1):25-27 (2001).

Bekerman et al., "Comparative kinetic studies on the synthesis of quinoxalinone derivatives and pyrido[2,3-b]pyrazinone derivatives by the hinsberg reaction," J Heterocyclic Chem. 29:129-33 (1992).

Chapman et al., "Initial genome sequencing and analysis of multiple myeloma," Nature 471(7339):467-72 (2011).

International Preliminary Report on Patentability for International Application No. PCT/GB2014/053489, issued May 31, 2016 (6 pages).

International Preliminary Report on Patentability for International Application No. PCT/GB2014/053490, issued May 31, 2016 (7 pages).

Zambon et al., "Novel hinge binder improves activity and pharmacokinetic properties of BRAF inhibitors," J Med Chem. 53(15):5639-55 (2010).

A375M non-established intraperitoneal

- Controls
- AA-018 5 mg/kg

A375M non-established intraperitoneal

- Controls
- AA-018 10 mg/kg

A375M non-established intraperitoneal

A375M non-established intraperitoneal

A375M non-established oral

A375M established intraperitoneal

A375M established oral

A375M oral established

A375M established oral

Days from inoculation of cells

- ◆ Controls
- × AA-067 10 mg/kg

A375M established oral

Days from inoculation of cells

- ◆ Controls
- ▨ AA-017 20 mg/kg

PYRIDO[2,3-B]PYRAZIN-8-SUBSTITUTED COMPOUNDS AND THEIR USE

RELATED APPLICATION

This application is related to U.S. provisional patent application No. 61/015,019 filed 19 Dec. 2007, the contents of which are incorporated herein by reference in their entirety.

TECHNICAL FIELD

The present invention pertains generally to the field of therapeutic compounds for treating proliferative disorders, cancer, etc., and more specifically to certain pyrido[2,3-b]pyrazin-8-substituted compounds, as described herein, which, inter alia, inhibit RAF (e.g., B-RAF) activity. The present invention also pertains to pharmaceutical compositions comprising such compounds, and the use of such compounds and compositions, both in vitro and in vivo, to inhibit RAF (e.g., BRAF) activity, to inhibit receptor tyrosine kinase (RTK) activity, to inhibit cell proliferation, and in the treatment of diseases and disorders that are ameliorated by the inhibition of RAF, RTK, etc., proliferative disorders such as cancer (e.g., colorectal cancer, melanoma), etc.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

RAF, Proliferative Disorders, and Cancer

Mutations in genes that directly or indirectly control cell growth and differentiation are generally considered to be the main cause of cancer. Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation.

RAF is key downstream target for the ras GTPase and mediates the activation of the MAP kinase cascade consisting of raf-MEK-ERK. Activated ERK is a kinase that subsequently targets a number of proteins responsible for mediating, amongst other things, the growth, survival and transcriptional functions of the pathway. These include the transcription factors ELK1, C-JUN, the Ets family (including Ets 1, 2, and 7), and the FOS family. The ras-raf-MEK-ERK signal transduction pathway is activated in response to many cell stimuli including growth factors such as EGF, PDGF, KGF etc. Because the pathway is a major target for growth factor action, the activity of raf-MEK-ERK has been found to be upregulated in many factor dependent tumours. The observation that about 20% of all tumours have undergone an activating mutation in one of the ras proteins indicates that the pathway is more broadly important in tumorigenesis. There is growing evidence that activating mutations in other components of the pathway also occur in human tumours. This is true for RAF.

The RAF oncogene family includes three highly conserved genes termed A-RAF, B-RAF and C-RAF (also called Raf-1). RAF genes encode protein kinases that are thought to play important regulatory roles in signal transduction processes that regulate cell proliferation. RAF genes code for highly conserved serine-threonine-specific protein kinases, which are recruited to the plasma membrane following direct binding to the Ras small Guanine-nucleotide binding proteins and this is the initiating event in RAF activation. RAF proteins are part of a signal transduction pathway believed to consist of receptor tyrosine kinases, p21 Ras, RAF protein kinases, Mek1 (ERK activator or MAPKK) kinases and ERK (MAPK) kinases, which ultimately phosphorylate several cellular substrates, including transcription factors. Signaling through this pathway can mediate differentiation, proliferation or oncogenic transformation in different cellular contexts. Thus, RAF kinases are believed to play a fundamental role in the normal cellular signal transduction pathway, coupling a multitude of growth factors to their net effect, cellular proliferation. Because RAF proteins are direct downstream effectors of ras protein function, therapies directed against RAF kinases are believed to be useful in treatment of ras-dependent tumors.

The RAF kinases are differentially regulated and expressed; C-RAF is the most thoroughly characterized and is expressed in all organs and in all cell lines that have been examined. A-RAF and B-RAF also appear to be ubiquitous, but are most highly expressed in urogenital and brain tissues, respectively. Because B-RAF is highly expressed in neural tissues it was once thought to be limited to these tissues but it has since been found to be more widely expressed. Although all RAF proteins can bind to active Ras, B-raf is most strongly activated by oncogenic Ras, and may be the primary target of oncogenic Ras in transformed cells.

Recent evidence indicates that mutational activation of B-RAF is found in a number of different tumours including more than 65% of malignant melanomas, more than 10% of colorectal cancers (Davies, H., et al., 2002, Nature, Vol. 417, pp. 949-954; Rajagopalan, H. et al., 2002, Nature, Vol. 418, p. 934), ovarian cancers (Singer, G., et al., 2003, J. Natl. Cancer Inst., Vol. 95, pp. 484-486) and papillary thyroid cancers (Brose, M., et al., 2002, *Cancer Res.*, Vol. 62, pp. 6997-7000; Cohen, Y., et al., 2003, *Invest. Ophthalmol. Vis. Sci.*, Vol. 44, pp. 2876-2878). A range of different B-RAF mutations have been identified in different tumours with the most common being a V600E mutation in the so-called activation loop of the kinase domain (Davies, H., et al., 2002, *Nature*, Vol. 417, pp. 949-954).

Other mutations of B-RAF found associated with human cancers may not necessarily activate B-RAF directly but do upregulate the activity of the ras-raf-MEK-ERK pathway by mechanisms which are not fully understood but may involve cross-talk with other RAF isoforms, such as A-RAF (Wan, P., et al., 2004, *Cell, Vol.* 116, pp. 855-867). In such cases, inhibition of RAF activity would remain a beneficial aim in cancer treatment.

In addition to link between B-RAF and certain cancers, there is a significant amount of evidence to indicate a more broad inhibition of RAF activity could be beneficial as an antitumour therapy. Blocking the pathway at the level of B-RAF would be effective at counteracting the upregulation of this pathway caused by tumourigenic ras mutations and also in tumours responding to growth factor action via this pathway. Genetic evidence in *Drosophila* and *C. elegans* indicates that RAF homologues are essential for ras dependent actions on differentiation (Dickson, B., et al., 1993, *Nature*, Vol. 360, pp. 600-603). Introduction of constitutively active MEK into NIH3T3 cells can have a transforming action whilst expression of dominant negative MEK proteins can suppress the tumourigenicity of ras transformed cell lines (Mansour, S. J., et al., 1994, *Science*, Vol. 265, pp. 966-970; Cowely, S., et al., 1994, *Cell*, Vol. 77, pp. 841-852). Expression of a dominant negative raf protein has also been found to inhibit ras dependent signalling as has suppression of raf expression using an antisense oligonucleotide construct (Koch, W., et al., 1991, *Nature*, Vol. 349, pp. 426-428; Bruder, T. T., et al., 1992, *Genes and Development*, Vol. 6, pp. 545-556).

This and other evidence suggests that inhibition of RAF (e.g., B-RAF) activity would be beneficial in the treatment of cancer, and that inhibition of RAF (e.g., B-RAF) activity could be particularly beneficial in those cancers containing a constitutively activated B-raf mutation.

The raf-MEK-ERK pathway functions downstream of many receptors and stimuli indicating a broad role in regulation of cell function. For this reason inhibitors of RAF may find utility in other disease conditions that are associated with upregulation of signalling via this pathway. The raf-MEK-ERK pathway is also an important component of the normal response of non-transformed cells to growth factor action. Therefore inhibitors of RAF may be of use in diseases where there is inappropriate or excessive proliferation of normal tissues. These include, but are not limited to glomerulonephritis and psoriasis. The cellular signalling pathway of which RAF is a part has also been implicated in inflammatory disorders characterized by T-cell proliferation (T-cell activation and growth), such as tissue graft rejection, endotoxin shock, and glomerular nephritis.

RAF (e.g., B-RAF) has been shown to be a valid therapeutic target in hyperproliferative disorders such as cancer. Activated versions of RAF (e.g., B-RAF) are able to transform mammalian cells, allowing them to take on the characteristics of cancer cells and the growth of these cells becomes dependent on the mutant RAF (e.g., B-RAF) protein. Inhibition of RAF (e.g., B-RAF) activity in human cancer cell lines that express the mutant forms of RAF (e.g., B-RAF) blocks their growth and ultimately induces their death.

Angiogenesis

Chronic proliferative diseases are often accompanied by profound angiogenesis, which can contribute to or maintain an inflammatory and/or proliferative state, or which leads to tissue destruction through the invasive proliferation of blood vessels. (Folkman, 1997, *EXS*, Vol. 79, pp. 1-81; Folkman, 1995, *Nature Medicine*, Vol. 1, pp. 27-31; Folkman and Shing, 1992, *J. Biol. Chem.*, Vol. 267, p. 10931.)

Angiogenesis is generally used to describe the development of new or replacement blood vessels, or neovascularisation. It is a necessary and physiological normal process by which the vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, 1992, *Ann. Rhum. Dis.*, Vol. 51, p. 919). In diabetes (and in many different eye diseases), new vessels invade the macula or retina or other ocular structures, and may cause blindness (Brooks et al., 1994, *Cell*, Vol. 79, p. 1157). The process of atherosclerosis has been linked to angiogenesis (Kahlon et al., 1992, *Can. J. Cardiol.*, Vol. 8, p. 60). Tumor growth and metastasis have been found to be angiogenesis-dependent (Folkman, 1992, *Cancer Biol.*, Vol. 3, p. 65; Denekamp, 1993, *Br. J. Rad.*, Vol. 66, p. 181; Fidler and Ellis, 1994, *Cell*, Vol. 79, p. 185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly et al., 1994, *Cell*, Vol. 79, p. 315; Ingber et al., 1990, *Nature*, Vol. 348, p. 555), ocular diseases (Friedlander et al., 1995, *Science*, Vol. 270, p. 1500), arthritis (Peacock et al., 1992, *J. Exp. Med.*, Vol. 175, p. 1135; Peacock et al., 1995, *Cell. Immun.*, Vol. 160, p. 178) and hemangioma (Taraboletti et al., 1995, *J. Natl. Cancer Inst.*, Vol. 87, p. 293).

RTKs

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

FGFR

The fibroblast growth factor (FGF) family of signaling polypeptides regulates a diverse array of physiologic functions including mitogenesis, wound healing, cell differentiation and angiogenesis, and development. Both normal and malignant cell growth as well as proliferation are affected by changes in local concentration of these extracellular signaling molecules, which act as autocrine as well as paracrine factors. Autocrine FGF signaling may be particularly important in the progression of steroid hormone-dependent cancers and to a hormone independentstate (Powers et al., 2000, *Endocr. Relat. Cancer*, Vol. 7, pp. 165-197).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Ozawa et al., 2001, *Teratog. Carcinog. Mutagen.*, Vol. 21, pp. 27-44).

The two prototypic members are acidic fibroblast growth factor (aFGF orFGF1) and basic fibroblast growth factors (bFGF or FGF2), and to date, at least twenty distinct FGF family members have been identified. The cellular response to FGFs is transmitted via four types of high affinity transmembrane tyrosine-kinase fibroblast growth factor receptors numbered 1 to 4 (FGFR-1 to FGFR-4). Upon ligand binding, the receptors dimerize and auto- or trans-phosphorylate specific cytoplasmic tyrosine residues to transmit an intracellular signal that ultimately reaches nuclear transcription factor effectors.

Disruption of the FGFR-1 pathway should affect tumor cell proliferation since this kinase is activated in many tumor types in addition to proliferating endothelial cells. The over-expression and activation of FGFR-1 in tumor-associated vasculature has suggested a role for these molecules in tumor angiogenesis.

FGFR-2 has high affinity for the acidic and/or basic fibroblast growth factors, as well as the keratinocyte growth factor ligands. FGFR-2 also propagates the potent osteogenic effects of FGFs during osteoblast growth and differentiation. Mutations in FGFR-2, leading to complex functional alterations, were shown to induce abnormal ossification of cranial sutures(craniosynostosis), implying a major role of FGFR signaling in intramembranous bone formation. For example, in Apert (AP) syndrome, characterized by premature cranial suture ossification, most cases are associated with point mutations engendering gain-of-function in FGFR-2 (Lemonnier et al., 2001, *J. Bone Miner. Res.*, Vol. 16, pp. 832-845).

Several severe abnormalities in human skeletal development, including Apert, Crouzon, Jackson-Weiss, Beare-Stevenson cutis gyrata, and Pfeiffer syndromes are associated with the occurrence of mutations in FGFR-2. Most, if not all, cases of Pfeiffer Syndrome (PS) are also caused by de novo mutation of the FGFR-2 gene (Meyers et al., 1996, *Am. J. Hum. Genet.*, Vol. 58, pp. 491-498; Plomp et al., 1998, *Am. J. Med. Genet.*, Vol. 75, 245-251), and it was recently shown that mutations in FGFR-2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of FGFR-2 (Yu et al., 2000, *Proc. Natl. Acad. Sci. U.S.A.*, Vol. 97, pp. 14536-14541).

Activating mutations of the FGFR-3 receptor tyrosine kinase such as chromosomal translocations or point mutations produce deregulated, constitutively active, FGFR-3 receptors which have been involved in multiple myeloma and in bladder and cervix carcinomas (Powers, C. J., et al., 2000, *Endocr. Rel. Cancer*, Vol. 7, p. 165). Accordingly, FGFR-3 inhibition would be useful in the treatment of multiple myeloma, bladder and cervix carcinomas.

VEGFR

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al., 2000, *The Oncologist*, Vol. 5 (90001), pp. 1-2). VEGFR(s) are protein tyrosine kinases (PTKs). PTKs catalyze the phosphorylation of specific tyrosyl residues in proteins involved in the regulation of cell growth and differentiation. (Wilks, A. F., 1990, *Progress in Growth Factor Research*, Vol. 2, pp. 97-111; Courtneidge, S. A., 1993, *Dev. Supp.l*, pp. 57-64; Cooper, J. A., 1994, *Semin. Cell Biol.*, Vol. 5(6), pp. 377-387; Paulson, R. F., 1995, *Semin. Immunol.*, Vol. 7(4), pp. 267-277; Chan, A. C., 1996, *Curr. Opin. Immunol.*, Vol. 8(3), pp. 394-401).

Three PTK receptors for VEGF have been identified: VEGFR-1 (Flt-1), VEGFR-2 (Flk-1 or KDR), and VEGFR-3 (Flt-4). These receptors are involved in angiogenesis and participate in signal transduction (Mustonen, T., et al., 1995, *J. Cell Biol.*, Vol. 129, pp. 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with itsextracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G., 2000, *The Oncologist*, Vol. 5(90001), pp. 3-10).

Inhibition at the kinase domain binding site of VEGFR-2 would block phosphorylation of tyrosine residues and serve to disrupt initiation of angiogenesis.

TIE

Angiopoieten 1 (Ang1), a ligand for the endothelium-specific receptor tyrosine kinase TIE-2 is a novel angiogenic factor (Davis et al., 1996, *Cell*, Vol. 87, pp. 1161-1169; Partanen et al., 1992, *Mol. Cell Biol.*, Vol. 12, pp. 1698-1707; U.S. Pat. Nos. 5,521,073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of anEGF-like domain and an immunoglobulin (IG) like domain, which consists of extracellular folding units, stabilized by intra-chain disulfide bonds (Partanen et al., 1999, *Curr. Topics Microbiol. Immunol.*, Vol. 237, pp. 159-172). Unlike VEGF, which functions during the early stages of vascular development, Ang1 and its receptor TIE-2 function in the later stages of vascular development, i.e., during vascular remodelling (remodelling refers to formation of a vascular lumen) and maturation (Yancopoulos et al., 1998, *Cell*, Vol. 93, pp. 661-664; Peters, K. G., 1998, *Circ. Res.*, Vol. 83(3), pp. 342-343; Suri et al., 1996, *Cell*, Vol. 87, pp. 1171-1180).

Consequently, inhibition of TIE-2 would be expected to serve to disrupt remodelling and maturation of new vasculature initiated by angiogenesis thereby disrupting the angiogenic process.

Eph

The largest subfamily of receptor tyrosine kinases (RTKs), the Eph family, and their ligands (ephrins), play important roles in physiologic and pathologic vascular processes. Both the Ephs (receptors) and ephrins (ligands) are divided into two groups, A and B subfamilies (Eph Nomenclature Committee, 1997). The binding of ephrin ligands to Eph receptors is dependent on cell-cell interactions. The interactions of ephrins and Ephs have recently been shown to function via bi-directional signalling. The ephrins binding to Eph receptors initiate phosphorylation at specific tyrosine residues in the cytoplasmic domain of the Eph receptors. In response to Eph receptor binding, the ephrin ligand also undergoes tyrosine phosphorylation, so-called 'reverse' signalling (Holland, S. J., et al., 1996, *Nature*, Vol. 383, pp. 722-725; Bruckner et al., 1997, *Science*, Vol. 275, pp. 1640-1643).

Eph RTKs and their ephrin ligands play important roles in embryonic vascular development. Disruption of specific Eph receptors and ligands (including ephrin-B2) leads to defective vessel remodelling, organisation, and sprouting resulting in embryonic death (Wang, H. U., et al., 1998, *Cell*, Vol. 93, pp. 741-753; Adams, R. H., et al., 1999, *Genes Dev*, Vol. 13, pp. 295-306; Gale and Yancopoulos, 1999, *Genes Dev*, Vol. 13, pp. 1055-1066; Helbling, P. M., et al., 2000, *Development*, Vol. 127, pp. 269-278). Coordinated expression of the Eph/ephrin system determines the phenotype of embryonic vascular structures: ephrin-B2 is present on arterial endothelial cells (ECs), whereas EphB4 is present on venous ECs (Gale and Yancopoulos, 1999, *Genes Dev*, Vol. 13, pp. 1055-1066; Shin, D., et al., 2001, *Dev Biol*, Vol. 230, pp. 139-150). Recently, specific Ephs and ephrins have been implicated in tumour growth and angiogenesis.

The Ephs and ephrins have been found to be overexpressed in many human tumours. In particular, the role of EphB2 has been identified in small cell lung carcinoma (Tang, X. X., et al., 1999, *Clin Cancer Res*, Vol. 5, pp. 455-460), human neuroblastomas (Tang, X. X., et al., 1999, *Clin Cancer Res*, Vol. 5, pp. 1491-1496) and colorectal cancers (Liu, W., et al., 2004, *Brit. J. Canc.*, Vol. 90, pp. 1620-1626), and higher expression levels of Ephs and ephrins, including EphB2, have been found to correlate with more aggressive and metastatic tumours (Nakamoto, M. and Bergemann, A. D., 2002, *Microsc. Res Tech*, Vol. 59, pp. 58-67).

Consequently, inhibition of EphB2 would be expected to serve to disrupt angiogenesis, and in particular in certain tumours where over-expression occurs.

The inventors have discovered compounds that, e.g., inhibit RAF (e.g., B-RAF) activity and/or are useful in the treatment of, e.g., proliferative disorders, cancer, etc.

SUMMARY OF THE INVENTION

One aspect of the invention pertains to certain pyrido[2,3-b]pyrazin-8-substituted compounds compounds (referred to herein as "PDP8 compounds"), as described herein.

Another aspect of the invention pertains to a composition (e.g., a pharmaceutical composition) comprising a PDP8 compound, as described herein, and a pharmaceutically acceptable carrier or diluent.

Another aspect of the invention pertains to method of preparing a composition (e.g., a pharmaceutical composition) comprising the step of admixing a PDP8 compound, as described herein, and a pharmaceutically acceptable carrier or diluent.

Another aspect of the present invention pertains to a method of inhibiting RAF (e.g., B-RAF) activity in a cell, in vitro or in vivo, comprising contacting the cell with an effective amount of a PDP8 compound, as described herein.

Another aspect of the present invention pertains to a method of inhibiting receptor tyrosine kinase (RTK) activity, such as FGFR, Tie, VEGFR and/or Eph activity, for example, FGFR-1, FGFR-2, FGFR-3, Tie2, VEGFR-2 and/or EphB2 activity, in a cell, in vitro or in vivo, comprising contacting the cell with an effective amount of a PDP8 compound, as described herein.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a PDP8 compound, as described herein.

Another aspect of the present invention pertains to a method of treatment comprising administering to a subject in need of treatment a therapeutically-effective amount of a PDP8 compound, as described herein, preferably in the form of a pharmaceutical composition.

Another aspect of the present invention pertains to a PDP8 compound, as described herein, for use in a method of treatment of the human or animal body by therapy.

Another aspect of the present invention pertains to a PDP8 compound, as described herein, for the use in a method of treatment of the human or animal body by therapy wherein said compound is used in combination with other pharmaceutically active substances Another aspect of the present invention pertains to use of a PDP8 compound, as described herein, in the manufacture of a medicament for use in treatment.

In one embodiment, the treatment is treatment of a disease or disorder (e.g., cancer) that is characterised by the up-regulation and/or activation of RAF (e.g., B-RAF), and/or is ameliorated by the inhibition of RAF (e.g., B-RAF).

In one embodiment, the treatment is treatment of a disease or disorder (e.g., cancer) that is characterised by the up-regulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of a disease or disorder that is characterised by inappropriate, excessive, and/or undesirable angiogenesis.

In one embodiment, the treatment is treatment of a proliferative disorder.

In one embodiment, the treatment is treatment of cancer.

In one embodiment, the treatment is treatment of melanoma.

In one embodiment, the treatment is treatment of colorectal cancer.

Another aspect of the present invention pertains to a kit comprising (a) a PDP8 compound, as described herein, preferably provided as a pharmaceutical composition and in a suitable container and/or with suitable packaging; and (b) instructions for use, for example, written instructions on how to administer the compound.

Another aspect of the present invention pertains to a PDP8 compound obtainable by a method of synthesis as described herein, or a method comprising a method of synthesis as described herein.

Another aspect of the present invention pertains to a PDP8 compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

Figure 1:
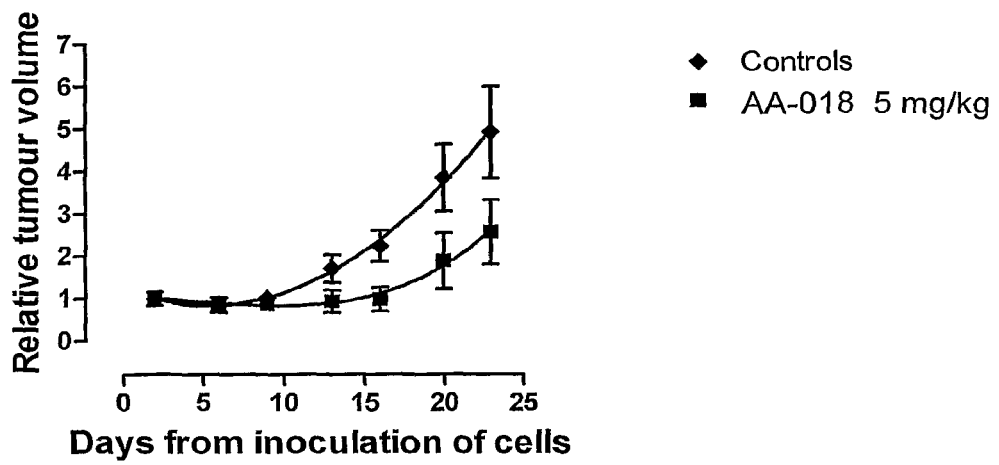
FIG. 1 is a graph of relative tumour volume as a function of days from inoculation for In Vivo Study 1 (AA-018) (non-established) (5 mg/kg/day) (intraperitoneally).

One aspect of the present invention pertains to compounds selected from compounds of the following formula and pharmaceutically acceptable salts, hydrates, and solvates thereof (for convenience, collectively referred to herein as "pyrido[2,3-b]pyrazin-8-substituted compounds" and "PDP8 compounds"):

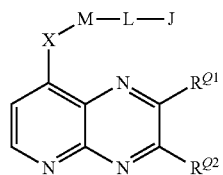

wherein:
—$R^{Q1}$ is independently —H, —$R^1$, —$R^{1X}$, —Cl, —OH, —$OR^1$, —$OR^{1X}$, —SH, —$SR^1$, —$NH_2$, —$NHR^1$, —$NR^1_2$, or —$NR^{RA}R^{RB}$;

wherein:
each —$R^1$ is independently saturated aliphatic $C_{1-6}$alkyl, and is unsubstituted or substituted, for example, with one or more groups selected from —OH, —$OR^{11}$, —$NH_2$, —$NHR^{11}$, and —$NR^{11}_2$, wherein each —$R^{11}$ is independently saturated aliphatic $C_{1-3}$alkyl;

each —$R^{1X}$ is independently saturated aliphatic $C_{1-4}$alkyl substituted with one or more groups selected from —F, —Cl, —Br, and —I; and —$NR^{RA}R^{RB}$ is independently azetidino, pyrrolidino, piperidino, piperazino, morpholino, azepino, or diazepino, and is optionally substituted with one or more groups selected from saturated aliphatic $C_{1-4}$alkyl;

—$R^{Q2}$ is independently —H, —$R^2$, —$R^{2X}$, —Cl, —OH, —$OR^2$, —$OR^{2X}$, —SH, —$SR^2$, —$NH_2$, —$NHR^2$, —$NR^2_2$, or —$NR^{RC}R^{RD}$;

wherein:
each —$R^2$ is independently saturated aliphatic $C_{1-6}$alkyl, and is unsubstituted or substituted, for example, with one or more groups selected from —OH, —$OR^{22}$, —$NH_2$, —$NHR^{22}$, and —$NR^{22}_2$, wherein each —$R^{22}$ is independently saturated aliphatic $C_{1-3}$alkyl; each —$R^{2X}$ is independently saturated aliphatic $C_{1-4}$alkyl substituted with one or more groups selected from —F, —Cl, —Br, and —I; and —$NR^{RC}R^{RD}$ is independently azetidino, pyrrolidino, piperidino, piperazino, morpholino, azepino, or diazepino, and is optionally substituted with one or more groups selected from saturated aliphatic $C_{1-4}$alkyl;

—X— is independently —O—, —S—, —S(=O)—, or —$S(=O)_2$—;

-M- is independently selected from:

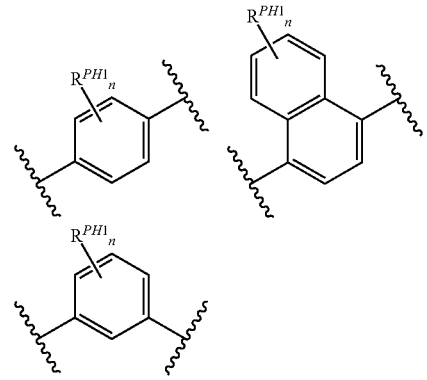

wherein:
each n is independently 0, 1 or 2; and
each $R^{PH1}$ is independently —F, —Cl, —Br, —I, —$R^3$, —$R^{3Y}$, —$CF_3$, —OH, —$OR^3$, —$OCF_3$, —$NH_2$, —$NHR^3$, —$NR^3_2$, —CN, —SH, or —$SR^3$;

wherein each —$R^3$ is independently saturated aliphatic $C_{1-4}$alkyl, and each —$R^{3Y}$ is independently aliphatic $C_{2-6}$alkenyl or aliphatic $C_{2-6}$alkynyl;

J-L- is independently selected from:
J-$NR^{N1}$—C(=Y)—$NR^{N1}$—,
J-$CH_2$—$NR^{N1}$—C(=Y)—$NR^{N1}$—,
J-$NR^{N1}$—C(=Y)—$NR^{N1}$—$CH_2$—,
J-$NR^{N1}$—C(=Y)—, J-CH$_2$—NR$^{N1}$—C(=Y)—,
J-NR$^{N1}$—C(=Y)—CH$_2$—,
J-CH$_2$—NR$^{N1}$—C(=Y)—CH$_2$—,
J-CH$_2$—CH$_2$—NR$^{N1}$—C(=Y)—,
J-NR$^{N1}$—C(=Y)—CH$_2$—CH$_2$—,
J-NR$^{N1}$—C(=Y)—CH$_2$—NR$^{N1}$—,
J-NR$^{N1}$—CH$_2$—NR$^{N1}$—C(=Y)—,
J-C(=Y)—NR$^{N1}$—,
J-CH$_2$—C(=Y)—NR$^{N1}$—,
J-C(=Y)—NR$^{N1}$—CH$_2$—,
J-CH$_2$—C(=Y)—NR$^{N1}$—CH$_2$—,
J-CH$_2$—CH$_2$—C(=Y)—NR$^{N1}$—,
J-C(=Y)—NR$^{N1}$—CH$_2$—CH$_2$—,
J-NR$^{N1}$—CH$_2$—C(=Y)—NR$^{N1}$—,
J-C(=Y)—NR$^{N1}$—CH$_2$—NR$^{N1}$—,
J-C(=Y)—CH$_2$—NR$^{N1}$—,
J-C(=Y)—CH$_2$—NR$^{N1}$—CH$_2$—,
J-C(=Y)—CH$_2$—CH$_2$—NR$^{N1}$—,
J-CH$_2$—C(=Y)—CH$_2$—NR$^{N1}$—,
J-NR$^{N1}$—CH$_2$—C(=Y)—,
J-NR$^{N1}$—CH$_2$—C(=Y)—CH$_2$—,
J-NR$^{N1}$—CH$_2$—CH$_2$—C(=Y)—,
J-CH$_2$—NR$^{N1}$—CH$_2$—C(=Y)—,
J-NR$^{N1}$—S(=O)$_2$—NR$^{N1}$—,
J-NR$^{N1}$—S(=O)$_2$—NR$^{N1}$—CH$_2$—,
J-CH$_2$—NR$^{N1}$—S(=O)$_2$—NR$^{N1}$—,
J-NR$^{N1}$—S(=O)$_2$—,
J-NR$^{N1}$—S(=O)$_2$—CH$_2$—,
J-CH$_2$—NR$^{N1}$—S(=O)$_2$—,
J-CH$_2$—NR$^{N1}$—S(=O)$_2$—CH$_2$—,
J-CH$_2$—CH$_2$—NR$^{N1}$—S(=O)$_2$—,
J-NR$^{N1}$—S(=O)$_2$—CH$_2$—CH$_2$—,
J-NR$^{N1}$—S(=O)$_2$—CH$_2$—NR$^{N1}$—,
J-NR$^{N1}$—CH$_2$—NR$^{N1}$—S(=O)$_2$—,
J-S(=O)$_2$—NR$^{N1}$—,
J-S(=O)$_2$—NR$^{N1}$—CH$_2$—,
J-CH$_2$—S(=O)$_2$—NR$^{N1}$—,
J-CH$_2$—S(=O)$_2$—NR$^{N1}$—CH$_2$—,
J-CH$_2$—CH$_2$—S(=O)$_2$—NR$^{N1}$—,
J-S(=O)$_2$—NR$^{N1}$—CH$_2$—CH$_2$—,
J-S(=O)$_2$—NR$^{N1}$—CH$_2$—NR$^{N1}$—, and
J-NR$^{N1}$—CH$_2$—S(=O)$_2$—NR$^{N1}$—;
wherein:
each —R$^{N1}$ is independently —H or saturated aliphatic C$_{1-4}$alkyl; and
each =Y is independently =O or =S; and
-J is independently phenyl or C$_{5-6}$heteroaryl, and is optionally substituted, for example, with one or more substituents selected from:
—F, —Cl, —Br, —I, —CF$_3$, —OCF$_3$,
—R$^4$, —R$^{4S}$, —R$^{4A}$, —R$^{4B}$, —R$^{4C}$, -L$^4$-R$^{4C}$, —Ar, -L$^4$-Ar,
—OH, —OR$^4$, -L$^4$-OH, -L$^4$-OR$^4$, —O-L$^4$-OH, —O-L$^4$-OR$^4$,
—OR$^{4C}$, —O-L$^4$-R$^{4C}$, —OAr, —O-L$^4$-Ar,
—SH, —SR$^4$, —CN, —NO$_2$,
—NH$_2$, —NHR$^{4SS}$, —R$^N$,
-L$^4$-NH$_2$, -L$^4$-NHR$^{4SS}$, -L$^4$-R$^N$,
—O-L$^4$-NH$_2$, —O-L$^4$-NHR$^{4SS}$, —O-L$^4$-R$^N$,
—NH-L$^4$-NH$_2$, —NH-L$^4$-NHR$^{4SS}$, —NH-L$^4$-R$^N$,
—NR$^4$-L$^4$-NH$_2$, —NR$^4$-L$^4$-NHR$^{4SS}$, —NR$^4$-L$^4$-R$^N$,
wherein:
each —R$^4$ is independently saturated aliphatic C$_{1-6}$alkyl;
each —R$^{4S}$ is independently saturated aliphatic C$_{1-6}$alkyl substituted with one or more groups selected from —OH, —OR$^{4SS}$, —C(=O)OH, —C(=O)OR$^{4SS}$,
—NH$_2$, —NHR$^{4SS}$, —N(R$^{4SS}$)$_2$, —R$^N$, —C(=O)NH$_2$, —C(=O)NHR$^{4SS}$, —C(=O)N(R$^{4SS}$)$_2$, and —C(=O)R$^N$;
each —R$^{4A}$ is independently aliphatic C$_{2-6}$alkenyl;
each —R$^{4B}$ is independently aliphatic C$_{2-6}$alkynyl;
each —R$^{4C}$ is independently optionally substituted saturated C$_{3-6}$cycloalkyl, for example, saturated C$_{3-6}$cycloalkyl optionally substituted with one or more substituents selected from —F, —R$^5$, —OH, —OR$^5$, —CF$_3$, and —OCF$_3$,
each -L$^4$- is independently saturated aliphatic C$_{1-4}$alkylene;
each —Ar is optionally substituted phenyl or C$_{5-6}$heteroaryl, for example, phenyl or C$_{5-6}$heteroaryl optionally substituted with one or more substituents selected from —F, —Cl, —Br, —I, —R$^5$, —OH, —OR$^5$, —CF$_3$, —OCF$_3$, and —S(=O)$_2$R$^5$;
each —R$^{4SS}$ is independently saturated aliphatic C$_{1-4}$alkyl;
each —R$^N$ is independently azetidino, pyrrolidino, piperidino, piperazino, morpholino, azepino, or diazepino, and is optionally substituted with one or more groups selected from saturated aliphatic C$_{1-4}$alkyl; and
each —R$^5$ is independently saturated aliphatic C$_{1-4}$alkyl.

In one embodiment, the compound is selected from compounds of the following formula, and pharmaceutically acceptable salts, hydrates, and solvates thereof:

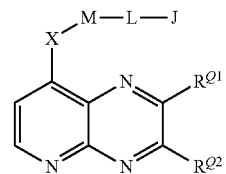

wherein:
—R$^{Q1}$ is independently —H, —R$^1$, —Cl, —OH, —OR$^1$, —SH, —SR$^1$, —NH$_2$, —NHR$^1$, —NR$^1_2$, or —NR$^{RA}$R$^{RB}$;
wherein:
each —R$^1$ is independently saturated aliphatic C$_{1-6}$alkyl, and is unsubstituted or substituted, for example, with one or more groups selected from —OH, —OR$^{11}$, —NH$_2$, —NHR$^{11}$, and —NR$^{11}_2$, wherein each —R$^{11}$ is independently saturated aliphatic C$_{1-3}$alkyl; and
—NR$^{RA}$R$^{RB}$ is independently piperidino, piperazino, or morpholino, and is optionally substituted with one or more groups selected from saturated aliphatic C$_{1-4}$alkyl;
—R$^{Q2}$ is independently —H, —R$^2$, —Cl, —OH, —OR$^2$, —SH, —SR$^2$, —NH$_2$, —NHR$^2$, —NR$^2_2$, or —NR$^R_c$R$^{RD}$;
wherein:
each —R$^2$ is independently saturated aliphatic C$_{1-6}$alkyl, and is unsubstituted or substituted, for example, with one or more groups selected from —OH, —OR$^{22}$, —NH$_2$, —NHR$^{22}$, and —NR$^{22}_2$, wherein each —R$^{22}$ is independently saturated aliphatic C$_{1-3}$alkyl; and
—NR$^{RC}$R$^{RD}$ is independently piperidino, piperazino, or morpholino, and is optionally substituted with one or more groups selected from saturated aliphatic C$_{1-4}$alkyl;
—X— is independently —O— or —S—;

-M- is independently selected from:

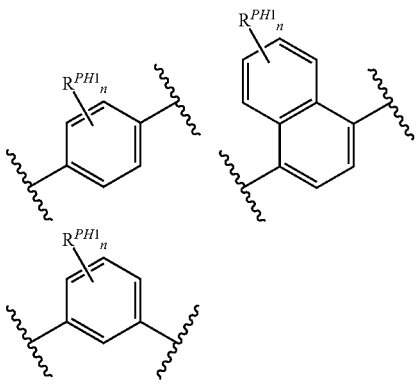

wherein:
each n is independently 0, 1 or 2; and
each $R^{PH1}$ is independently —F, —Cl, —Br, —I, —$R^3$, —OH, —$OR^3$, —SH, or —$SR^3$;
wherein each —$R^3$ is independently saturated aliphatic $C_{1-4}$alkyl;
-L- is independently selected from:

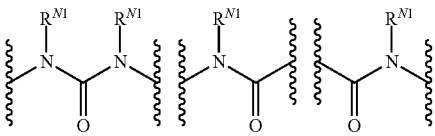

wherein:
each —$R^{N1}$ is independently —H or saturated aliphatic $C_{1-4}$alkyl; and
-J is independently phenyl or $C_{5-6}$heteroaryl, and is optionally substituted, for example, with one or more substituents selected from —F, —Cl, —Br, —I, —$R^4$, —OH, —$OR^4$, —$CF_3$, —$OCF_3$, and -Ph, wherein each —$R^4$ is independently saturated aliphatic $C_{1-4}$alkyl; and each -Ph denotes optionally substituted phenyl, for example, phenyl optionally substituted with one or more substituents selected from —F, —Cl, —Br, —I, —$R^5$, —OH, —$OR^5$, —$CF_3$, —$OCF_3$, wherein each —$R^5$ is independently saturated aliphatic $C_{1-4}$alkyl.

The Group —$R^{Q1}$

In one embodiment, —$R^{Q1}$ is independently —H, —$R^1$, —$R^{1X}$, —Cl, —OH, —$OR^1$, —$OR^{1X}$, —SH, —$SR^1$, —$NH_2$, —$NHR^1$, —$NR^1_2$, or —$NR^{RA}R^{RB}$.

In one embodiment, —$R^{Q1}$ is independently —$R^1$, —$R^{1X}$, —Cl, —OH, —$OR^1$, —$OR^{1X}$, —SH, —$SR^1$, —$NH_2$, —$NHR^1$, —$NR^1_2$, or —$NR^{RA}R^{RB}$.

In one embodiment, —$R^{Q1}$ is independently —H, —$R^1$, —$R^{1X}$, —Cl, —$OR^1$, —$OR^{1X}$, —SH, —$SR^1$, —$NH_2$, —$NHR^1$, —$NR^1_2$, or —$NR^{RA}R^{RB}$.

In one embodiment, —$R^{Q1}$ is independently —$R^1$, —$R^{1X}$, —Cl, —$OR^1$, —$OR^{1X}$, —SH, —$SR^1$, —$NH_2$, —$NHR^1$, —$NR^1_2$, or —$NR^{RA}R^{RB}$.

In one embodiment, —$R^{Q1}$ is independently —H, —$R^1$, —Cl, —OH, —$OR^1$, —SH, —$SR^1$, —$NH_2$, —$NHR^1$, —$NR^1_2$, or —$NR^{RA}R^{RB}$.

In one embodiment, —$R^{Q1}$ is independently —$R^1$, —Cl, —OH, —$OR^1$, —SH, —$SR^1$, —$NH_2$, —$NHR^1$, —$NR^1_2$, or —$NR^{RA}R^{RB}$.

In one embodiment, —$R^{Q1}$ is independently —H, —$R^1$, —Cl, —$OR^1$, —SH, —$SR^1$, —$NH_2$, —$NHR^1$, —$NR^1_2$, or —$NR^{RA}R^{RB}$.

In one embodiment, —$R^{Q1}$ is independently —$R^1$, —Cl, —$OR^1$, —SH, —$SR^1$, —$NH_2$, —$NHR^1$, —$NR^1_2$, or —$NR^{RA}R^{RB}$.

In one embodiment, —$R^{Q1}$ is independently —H, —OH, -Me, —$CF_3$, —$CH_2Br$, —$NH_2$, —NHMe, —$NMe_2$, morpholino, or piperazino, or N-methyl-piperazino.

In one embodiment, —$R^{Q1}$ is independently —OH, -Me, —$CF_3$, —$CH_2Br$, —$NH_2$, —NHMe, —$NMe_2$, morpholino, or piperazino, or N-methyl-piperazino.

In one embodiment, —$R^{Q1}$ is independently —H, -Me, —$CF_3$, —$CH_2Br$, —$NH_2$, —NHMe, —$NMe_2$, morpholino, or piperazino, or N-methyl-piperazino.

In one embodiment, —$R^{Q1}$ is independently -Me, —$CF_3$, —$CH_2Br$, —$NH_2$, —NHMe, —$NMe_2$, morpholino, or piperazino, or N-methyl-piperazino.

In one embodiment, —$R^{Q1}$ is independently —H, —OH, -Me, —$NH_2$, —NHMe, morpholino, or piperazino, or N-methyl-piperazino.

In one embodiment, —$R^{Q1}$ is independently —OH, -Me, —$NH_2$, —NHMe, morpholino, or piperazino, or N-methyl-piperazino.

In one embodiment, —$R^{Q1}$ is independently —H, -Me, —$NH_2$, —NHMe, morpholino, or piperazino, or N-methyl-piperazino.

In one embodiment, —$R^{Q1}$ is independently -Me, —$NH_2$, —NHMe, morpholino, or piperazino, or N-methyl-piperazino.

In one embodiment, —$R^{Q1}$ is —OH. In this case, tautomerisation is possible, and the two equivalent tautomers are shown below.

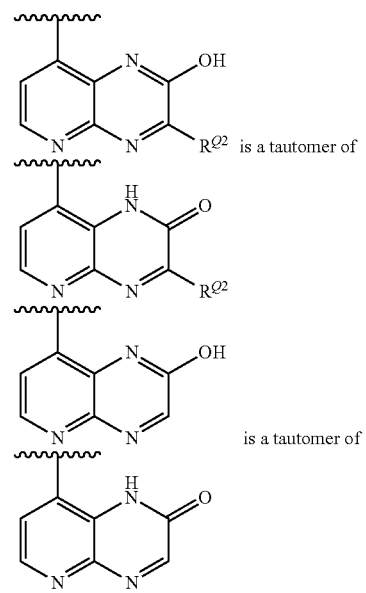

The Group —$R^{Q2}$

In one embodiment, —$R^{Q2}$ is independently —H, —$R^2$, —$R^{2X}$, —Cl, —OH, —$OR^2$, —$OR^{2X}$, —SH, —$SR^2$, —$NH_2$, —$NHR^2$, —$NR^2_2$, or —$NR^{RC}R^{RD}$.

In one embodiment, —$R^{Q2}$ is independently —$R^2$, —$R^{2X}$, —Cl, —OH, —$OR^2$, —$OR^{2X}$, —SH, —$SR^2$, —$NH_2$, —$NHR^2$, —$NR^2_2$, or —$NR^{RC}R^{RD}$.

In one embodiment, —R$^{Q2}$ is independently —H, —R$^2$, —R$^{2X}$, —Cl, —OR$^2$, —OR$^{2X}$, —SH, —SR$^2$, —NH$_2$, —NHR$^2$, —NR$^2_2$, or —NR$^{RC}$R$^{RD}$.

In one embodiment, —R$^{Q2}$ is independently —R$^2$, —R$^{2X}$, —Cl, —OR$^2$, —OR$^{2X}$, —SH, —SR$^2$, —NH$_2$, —NHR$^2$, —NR$^2_2$, or —NR$^{RC}$R$^{RD}$.

In one embodiment, —R$^{Q2}$ is independently —H, —R$^2$, —Cl, —OH, —OR$^2$, —SH, —SR$^2$, —NH$_2$, —NHR$^2$, —NR$^2_2$, or —NR$^{RC}$R$^{RD}$.

In one embodiment, —R$^{Q2}$ is independently —R$^2$, —Cl, —OH, —OR$^2$, —SH, —SR$^2$, —NH$_2$, —NHR$^2$, —NR$^2_2$, or —NR$^{RC}$R$^{RD}$.

In one embodiment, —R$^{Q2}$ is independently —H, —R$^2$, —Cl, —OR$^2$, —SH, —SR$^2$, —NH$_2$, —NHR$^2$, —NR$^2_2$, or —NR$^{RC}$R$^{RD}$.

In one embodiment, —R$^{Q2}$ is independently —R$^2$, —Cl, —OR$^2$, —SH, —SR$^2$, —NH$_2$, —NHR$^2$, —NR$^2_2$, or —NR$^{RC}$R$^{RD}$.

In one embodiment, —R$^{Q2}$ is independently —H, —OH, -Me, —CF$_3$, —CH$_2$Br, —NH$_2$, —NHMe, —NMe$_2$, morpholino, or piperazino, or N-methyl-piperazino.

In one embodiment, —R$^{Q2}$ is independently —OH, -Me, —CF$_3$, —CH$_2$Br, —NH$_2$, —NHMe, —NMe$_2$, morpholino, or piperazino, or N-methyl-piperazino.

In one embodiment, —R$^{Q2}$ is independently —H, -Me, —CF$_3$, —CH$_2$Br, —NH$_2$, —NHMe, —NMe$_2$, morpholino, or piperazino, or N-methyl-piperazino.

In one embodiment, —R$^{Q2}$ is independently -Me, —CF$_3$, —CH$_2$Br, —NH$_2$, —NHMe, —NMe$_2$, morpholino, or piperazino, or N-methyl-piperazino.

In one embodiment, —R$^{Q2}$ is independently —H, —OH, -Me, —NH$_2$, —NHMe, morpholino, or piperazino, or N-methyl-piperazino.

In one embodiment, —R$^{Q2}$ is independently —OH, -Me, —NH$_2$, —NHMe, morpholino, or piperazino, or N-methyl-piperazino.

In one embodiment, —R$^{Q2}$ is independently —H, -Me, —NH$_2$, —NHMe, morpholino, or piperazino, or N-methyl-piperazino.

In one embodiment, —R$^{Q2}$ is independently -Me, —NH$_2$, —NHMe, morpholino, or piperazino, or N-methyl-piperazino.

In one embodiment, —R$^{Q2}$ is —OH. In this case, tautomerisation is possible, and the two equivalent tautomers are shown below.

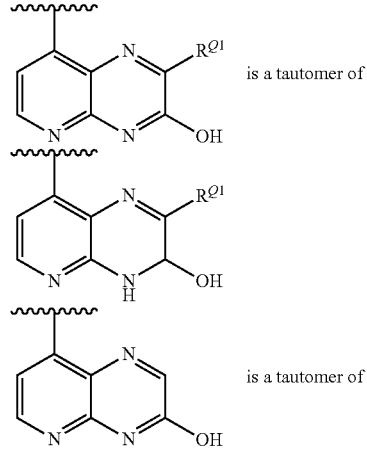

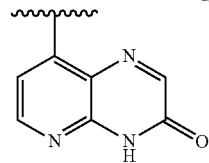

Some Combinations of the Groups —R$^{Q1}$ and —R$^{Q2}$: Both are not —H

In one embodiment:
either:
—R$^{Q1}$ is independently —H, —R$^1$, —R$^{1X}$, —Cl, —OH, —OR$^1$, —OR$^{1X}$, —SH, —SR$^1$, —NH$_2$, —NHR$^1$, —NR$^1_2$, or —NR$^{RA}$R$^{RB}$; and
—R$^{Q2}$ is independently —R$^2$, —R$^{2X}$, —Cl, —OH, —OR$^2$, —OR$^{2X}$, —SH, —SR$^2$, —NH$_2$, —NHR$^2$, —NR$^2_2$, or —NR$^{RC}$R$^{RD}$; or:
—R$^{Q1}$ is independently —R$^1$, —R$^{1X}$, —Cl, —OH, —OR$^1$, —OR$^{1X}$, —SH, —SR$^1$, —NH$_2$, —NHR$^1$, —NR$^1_2$, or —NR$^{RA}$R$^{RB}$; and
—R$^{Q2}$ is independently —H, —R$^2$, —R$^{2X}$, —Cl, —OH, —OR$^2$, —OR$^{2X}$, —SH, —SR$^2$, —NH$_2$, —NHR$^2$, —NR$^2_2$, or —NR$^{RC}$R$^{RD}$.

In one embodiment:
either:
—R$^{Q1}$ is independently —H, —OH, -Me, —CF$_3$, —CH$_2$Br, —NH$_2$, —NHMe, —NMe$_2$, morpholino, or piperazino, or N-methyl-piperazino; and
—R$^{Q2}$ is independently —OH, -Me, —CF$_3$, —CH$_2$Br, —NH$_2$, —NHMe, —NMe$_2$, morpholino, or piperazino, or N-methyl-piperazino; or:
—R$^{Q1}$ is independently —OH, -Me, —CF$_3$, —CH$_2$Br, —NH$_2$, —NHMe, —NMe$_2$, morpholino, or piperazino, or N-methyl-piperazino; and
—R$^{Q2}$ is independently —H, —OH, -Me, —CF$_3$, —CH$_2$Br, —NH$_2$, —NHMe, —NMe$_2$, morpholino, or piperazino, or N-methyl-piperazino.

Some Combinations of the Groups —R$^{Q1}$ and —R$^{Q2}$: Exactly One is —OH

In one embodiment:
either:
—R$^{Q1}$ is independently —OH; and
—R$^{Q2}$ is independently —H, —R$^2$, —R$^{2X}$, —Cl, —OR$^2$, —OR$^{2X}$, —SH, —SR$^2$, —NH$_2$, —NHR$^2$, —NR$^2_2$, or —NR$^{RC}$R$^{RD}$; or:
—R$^{Q1}$ is independently —H, —R$^1$, —R$^{1X}$, —Cl, —OR$^1$, —OR$^{1X}$, —SH, —SR$^1$, —NH$_2$, —NHR$^1$, —NR$^1_2$, or —NR$^{RA}$R$^{RB}$; and
—R$^{Q2}$ is independently —OH.

In one embodiment:
—R$^{Q1}$ is independently —OH; and
—R$^{Q2}$ is independently —H, —R$^2$, —R$^{2X}$, —Cl, —OR$^2$, —OR$^{2X}$, —SH, —SR$^2$, —NH$_2$, —NHR$^2$, —NR$^2_2$, or —NR$^{RC}$R$^{RD}$.

In one embodiment:
—R$^{Q1}$ is independently —H, —R$^1$, —R$^{1X}$, —Cl, —OR$^1$, —OR$^{1X}$, —SH, —SR$^1$, —NH$_2$, —NHR$^1$, —NR$^1_2$, or —NR$^{RA}$R$^{RB}$; and
—R$^{Q2}$ is independently —OH.

In one embodiment:
either:
—R$^{Q1}$ is independently —OH; and
—R$^{Q2}$ is independently —H, -Me, —CF$_3$, —CH$_2$Br, —NH$_2$, —NHMe, —NMe$_2$, morpholino, or piperazino, or N-methyl-piperazino; or:

—$R^{Q1}$ is independently —H, -Me, —$CF_3$, —$CH_2Br$, —$NH_2$, —NHMe, —$NMe_2$, morpholino, or piperazino, or N-methyl-piperazino; and
—$R^{Q2}$ is independently —OH.

In one embodiment:
—$R^{Q1}$ is independently —OH; and
—$R^{Q2}$ is independently —H, -Me, —$CF_3$, —$CH_2Br$, —$NH_2$, —NHMe, —$NMe_2$, morpholino, or piperazino, or N-methyl-piperazino.

In one embodiment:
—$R^{Q1}$ is independently —H, -Me, —$CF_3$, —$CH_2Br$, —$NH_2$, —NHMe, —$NMe_2$, morpholino, or piperazino, or N-methyl-piperazino; and
—$R^{Q2}$ is independently —OH.

In one embodiment:
either:
—$R^{Q1}$ is —OH, and
—$R^{Q2}$ is independently —H, -Me, —$NH_2$, —NHMe, morpholino, or piperazino, or N-methyl-piperazino. or:
—$R^{Q1}$ is independently —H, -Me, —$NH_2$, —NHMe, morpholino, or piperazino, or N-methyl-piperazino, and
—$R^{Q2}$ is —OH.

In one embodiment:
—$R^{Q1}$ is —OH, and
—$R^{Q2}$ is independently —H, -Me, —$NH_2$, —NHMe, morpholino, or piperazino, or N-methyl-piperazino.

In one embodiment,
—$R^{Q1}$ is independently —H, -Me, —$NH_2$, —NHMe, morpholino, or piperazino, or N-methyl-piperazino, and
—$R^{Q2}$ is —OH.

In one embodiment:
either:
—$R^{Q1}$ is -Me or —$NH_2$, and
—$R^{Q2}$ is —OH; or:
—$R^{Q1}$ is —OH, and
—$R^{Q2}$ is -Me or —$NH_2$.

In one embodiment:
—$R^{Q1}$ is -Me or —$NH_2$, and
—$R^{Q2}$ is —OH.

In one embodiment:
—$R^{Q1}$ is —OH, and
—$R^{Q2}$ is -Me or —$NH_2$.

In one embodiment:
either:
—$R^{Q1}$ is —OH, and
—$R^{Q2}$ is —H; or:
—$R^{Q1}$ is —H, and
—$R^{Q2}$ is —OH.

In one embodiment:
—$R^{Q1}$ is —OH, and
—$R^{Q2}$ is —H.

In one embodiment:
—$R^{Q1}$ is —H, and
—$R^{Q2}$ is —OH.

Some Combinations of the Groups —$R^{Q1}$ and —$R^{Q2}$: Both are —OH

In one embodiment:
—$R^{Q1}$ is —OH and
—$R^{Q2}$ is —OH.

In this case, tautomerisation is possible, and the two equivalent tautomers are shown below.

is a tautomer of

Some Combinations of the Groups —$R^{Q1}$ and —$R^{Q2}$: Neither is —OH

In one embodiment:
—$R^{Q1}$ is independently —H, —$R^1$, —$R^{1X}$, —Cl, —$OR^1$, —$OR^{1X}$, —SH, —$SR^1$, —$NH_2$, —$NHR^1$, —$NR^1_2$, or —$NR^{RA}R^{RB}$; and
—$R^{Q2}$ is independently —H, —$R^2$, —$R^{2X}$, —Cl, —$OR^2$, —$OR^{2X}$, —SH, —$SR^2$, —$NH_2$, —$NHR^2$, —$NR^2_2$, or —$NR^{RC}R^{RD}$.

In one embodiment:
—$R^{Q1}$ is independently —H, —$R^1$, —Cl, —$OR^1$, —SH, —$SR^1$, —$NH_2$, —$NHR^1$, —$NR^1_2$, or —$NR^{RA}R^{RB}$; and
—$R^{Q2}$ is independently —H, —$R^2$, —Cl, —$OR^2$, —SH, —$SR^2$, —$NH_2$, —$NHR^2$, —$NR^2_2$, or —$NR^{RC}R^{RD}$.

In one embodiment:
—$R^{Q1}$ is independently —H, -Me, —$NH_2$, —NHMe, morpholino, or piperazino, or N-methyl-piperazino; and
—$R^{Q2}$ is independently —H, -Me, —$NH_2$, —NHMe, morpholino, or piperazino, or N-methyl-piperazino.

In one embodiment:
—$R^{Q1}$ is independently —H; and
—$R^{Q2}$ is independently —H, -Me, —$NH_2$, —NHMe, morpholino, or piperazino, or N-methyl-piperazino.

Some Combinations of the Groups —$R^{Q1}$ and —$R^{Q2}$: Neither is —OH and Both are not —H In one embodiment:
either:
—$R^{Q1}$ is independently —H, —$R^1$, —$R^{1X}$, —Cl, —$OR^1$, —$OR^{1X}$, —SH, —$SR^1$, —$NH_2$, —$NHR^1$, —$NR^1_2$, or —$NR^{RA}R^{RB}$; and
—$R^{Q2}$ is independently —$R^2$, —$R^{2X}$, —Cl, —$OR^2$, —$OR^{2X}$, —SH, —$SR^2$, —$NH_2$, —$NHR^2$, —$NR^2_2$, or —$NR^{RC}R^{RD}$; or:
—$R^{Q1}$ is independently —$R^1$, —$R^{1X}$, —Cl, —$OR^1$, —$OR^{1X}$, —SH, —$SR^1$, —$NH_2$, —$NHR^1$, —$NR^1_2$, or —$NR^{RA}R^{RB}$; and
—$R^{Q2}$ is independently —H, —$R^2$, —$R^{2X}$, —Cl, —$OR^2$, —$OR^{2X}$, —SH, —$SR^2$, —$NH_2$, —$NHR^2$, —$NR^2_2$, or —$NR^{RC}R^{RD}$.

In one embodiment:
—$R^{Q1}$ is independently —H, —$R^1$, —$R^{1X}$, —Cl, —$OR^1$, —$OR^{1X}$, —SH, —$SR^1$, —$NH_2$, —$NHR^1$, —$NR^1_2$, or —$NR^{RA}R^{RB}$; and
—$R^{Q2}$ is independently —$R^2$, —$R^{2X}$, —Cl, —$OR^2$, —$OR^{2X}$, —SH, —$SR^2$, —$NH_2$, —$NHR^2$, —$NR^2_2$, or —$NR^{RC}R^{RD}$.

In one embodiment:
—$R^{Q1}$ is independently —$R^1$, —$R^{1X}$, —Cl, —$OR^1$, —$OR^{1X}$, —SH, —$SR^1$, —$NH_2$, —$NHR^1$, —$NR^1_2$, or —$NR^{RA}R^{RB}$; and —$R^{Q2}$ is independently —H, —$R^2$, —$R^{2X}$, —Cl, —$OR^2$, —$OR^{2X}$, —SH, —$SR^2$, —$NH_2$, —$NHR^2$, —$NR^2{}_2$, or —$NR^{RC}R^{RD}$.

In one embodiment:
either:
—$R^{Q1}$ is independently —H, —$R^1$, —Cl, —$OR^1$, —SH, —$SR^1$, —$NH_2$, —$NHR^1$, —$NR^1{}_2$, or —$NR^{RA}R^{RB}$; and
—$R^{Q2}$ is independently —$R^2$, —Cl, —$OR^2$, —SH, —$SR^2$, —$NH_2$, —$NHR^2$, —$NR^2{}_2$, or —$NR^{RC}R^{RD}$; or:
—$R^{Q1}$ is independently —$R^1$, —Cl, —$OR^1$, —SH, —$SR^1$, —$NH_2$, —$NHR^1$, —$NR^1{}_2$, or —$NR^{RA}R^{RB}$; and
—$R^{Q2}$ is independently —H, —$R^2$, —Cl, —$OR^2$, —SH, —$SR^2$, —$NH_2$, —$NHR^2$, —$NR^2{}_2$, or —$NR^{RC}R^{RD}$.

In one embodiment:
—$R^{Q1}$ is independently —H, —$R^1$, —Cl, —$OR^1$, —SH, —$SR^1$, —$NH_2$, —$NHR^1$, —$NR^1{}_2$, or —$NR^{RA}R^{RB}$; and
—$R^{Q2}$ is independently —$R^2$, —Cl, —$OR^2$, —SH, —$SR^2$, —$NH_2$, —$NHR^2$, —$NR^2{}_2$, or —$NR^{RC}R^{RD}$.

In one embodiment:
—$R^{Q1}$ is independently —$R^1$, —Cl, —$OR^1$, —SH, —$SR^1$, —$NH_2$, —$NHR^1$, —$NR^1{}_2$, or —$NR^{RA}R^{RB}$; and
—$R^{Q2}$ is independently —H, —$R^2$, —Cl, —$OR^2$, —SH, —$SR^2$, —$NH_2$, —$NHR^2$, —$NR^2{}_2$, or —$NR^{RC}R^{RD}$.

In one embodiment:
either:
—$R^{Q1}$ is independently —H, -Me, —$NH_2$, —NHMe, morpholino, or piperazino, or N-methyl-piperazino; and
—$R^{Q2}$ is independently -Me, —$NH_2$, —NHMe, morpholino, or piperazino, or N-methyl-piperazino; or:
—$R^{Q1}$ is independently -Me, —$NH_2$, —NHMe, morpholino, or piperazino, or N-methyl-piperazino; and
—$R^{Q2}$ is independently —H, -Me, —$NH_2$, —NHMe, morpholino, or piperazino, or N-methyl-piperazino.

The Groups —$R^1$ and —$R^2$

In one embodiment, each —$R^1$, if present, is independently saturated aliphatic $C_{1-6}$alkyl, and is unsubstituted or substituted, for example, with one or more groups selected from —OH, —$OR^{11}$, —$NH_2$, —$NHR^{11}$, and —$NR^{11}{}_2$, wherein each —$R^{11}$ is independently saturated aliphatic $C_{1-3}$alkyl.

In one embodiment, each —$R^{11}$, if present, is independently -Me or -Et.

In one embodiment, each —$R^1$, if present, is independently saturated aliphatic $C_{1-6}$alkyl, and is unsubstituted.

In one embodiment, each —$R^1$, if present, is independently saturated aliphatic $C_{1-4}$alkyl, and is unsubstituted.

In one embodiment, each —$R^2$, if present, is independently saturated aliphatic $C_{1-6}$alkyl, and is unsubstituted or substituted, for example, with one or more groups selected from —OH, —$OR^{22}$, —$NH_2$, —$NHR^{22}$, and —$NR^{22}{}_2$, wherein each —$R^{22}$ is independently saturated aliphatic $C_{1-3}$alkyl.

In one embodiment, each —$R^{22}$, if present, is independently -Me or -Et.

In one embodiment, each —$R^2$, if present, is independently saturated aliphatic $C_{1-6}$alkyl, and is unsubstituted.

In one embodiment, each —$R^2$, if present, is independently saturated aliphatic $C_{1-4}$alkyl, and is unsubstituted.

The Groups —$R^{1X}$ and —$R^{2X}$

In one embodiment, each —$R^{1X}$, if present, is independently saturated aliphatic $C_{1-4}$alkyl substituted with one or more groups selected from —F, —Cl, —Br, and —I.

In one embodiment, each —$R^{1X}$, if present, is independently saturated aliphatic $C_{1-4}$alkyl substituted with one or more groups selected from —F or —Cl.

In one embodiment, each —$R^{1X}$, if present, is independently —$CF_3$ or —$CH_2Br$.

In one embodiment, each —$R^{1X}$, if present, is independently —$CF_3$.

In one embodiment, each —$R^{2X}$, if present, is independently saturated aliphatic $C_{1-4}$alkyl substituted with one or more groups selected from —F, —Cl, —Br, and —I.

In one embodiment, each —$R^{2X}$, if present, is independently saturated aliphatic $C_{1-4}$alkyl substituted with one or more groups selected from —F or —Cl.

In one embodiment, each —$R^{2X}$, if present, is independently —$CF_3$ or —$CH_2Br$.

In one embodiment, each —$R^{2X}$, if present, is independently —$CF_3$.

The Groups —$NR^{RA}R^{RB}$ and —$NR^{RC}R^{RD}$

In one embodiment:
—$NR^{RA}R^{RB}$, if present, is independently azetidino, pyrrolidino, piperidino, piperazino, morpholino, azepino, or diazepino, and is optionally substituted with one or more groups selected from saturated aliphatic $C_{1-4}$alkyl; and
—$NR^{RC}R^{RD}$, if present, is independently azetidino, pyrrolidino, piperidino, piperazino, morpholino, azepino, or diazepino, and is optionally substituted with one or more groups selected from saturated aliphatic $C_{1-4}$alkyl.

In one embodiment:
—$NR^{RA}R^{RB}$, if present, is independently piperidino, piperazino, or morpholino, and is optionally substituted with one or more groups selected from saturated aliphatic $C_{1-4}$alkyl; and
—$NR^{RC}R^{RD}$, if present, is independently piperidino, piperazino, or morpholino, and is optionally substituted with one or more groups selected from saturated aliphatic $C_{1-4}$alkyl.

The Group —X—

In one embodiment, —X— is independently —O—, —S—, —S(=O)—, or —$S(=O)_2$—.

In one embodiment, —X— is independently —O— or —S—.

In one embodiment, —X— is independently —O—.

In one embodiment, —X— is independently —S—.

The Group -M-

In one embodiment, -M- is independently selected from:

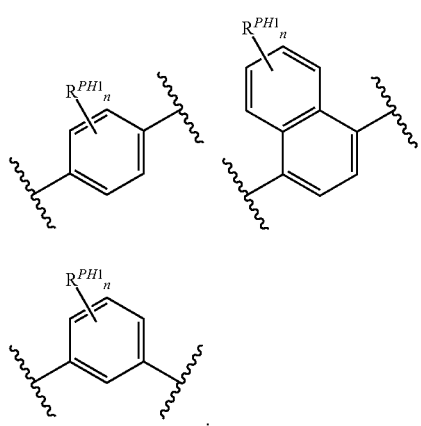

In one embodiment, -M- is independently:

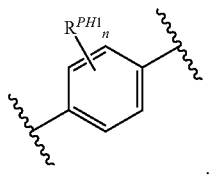

In one embodiment, -M- is independently:

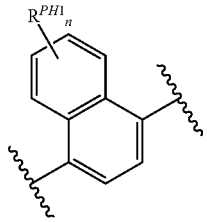

In one embodiment, -M- is independently:

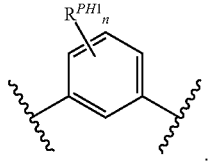

In one embodiment, n is independently 0, 1 or 2.
In one embodiment, n is independently 0 or 1.
In one embodiment, n is independently 0.
In one embodiment, n is independently 1.
In one embodiment, -M- is independently:

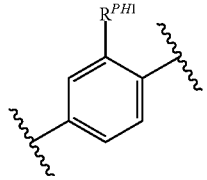

In one embodiment, -M- is independently:

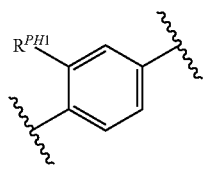

In one embodiment, -M- is independently:

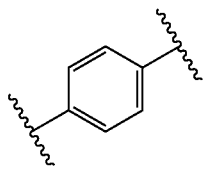

In one embodiment, -M- is independently:

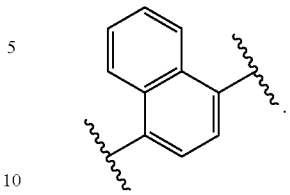

In one embodiment, each —$R^{PH1}$, if present, is independently —F, —Cl, —Br, —I, —$R^3$, —$R^{3Y}$, —$CF_3$, —OH, —$OR^3$, —$OCF_3$, —$NH_2$, —$NHR^3$, —$NR^3_2$, —CN, —SH, or —$SR^3$; wherein each —$R^3$ is independently saturated aliphatic $C_{1-4}$alkyl, and each —$R^{3Y}$ is independently aliphatic $C_{2-6}$alkenyl or aliphatic $C_{2-6}$alkynyl.

In one embodiment, each —$R^{PH1}$, if present, is independently —F, —Cl, —Br, —I, —$R^3$, —OH, —$OR^3$, —SH, or —$SR^3$; wherein each —$R^3$ is independently saturated aliphatic $C_{1-4}$alkyl.

In one embodiment, each —$R^{PH1}$, if present, is independently —F or —$SR^3$.

In one embodiment, each —$R^{PH1}$, if present, is independently —F or —SMe.

In one embodiment, each —$R^{PH1}$, if present, is independently —F.

In one embodiment, each —$R^{PH1}$, if present, is independently —$SR^3$.

In one embodiment, each —$R^{PH1}$, if present, is independently —SMe.

In one embodiment, -M- is independently:

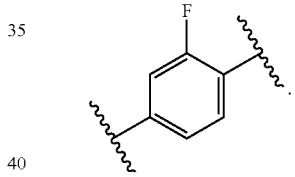

In one embodiment, -M- is independently:

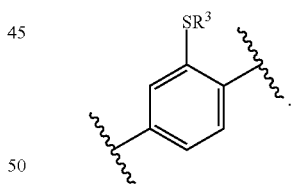

In one embodiment, -M- is independently:

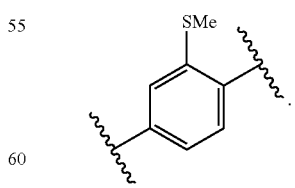

The Group -L-
In one embodiment, J-L- is independently selected from:
J-$NR^{N1}$—C(=Y)—$NR^{N1}$—,
J-$NR^{N1}$—C(=Y)—, and
J-C(=Y)—$NR^{N1}$—.

In one embodiment, =Y is independently =O.
In one embodiment, =Y is independently =S.
In one embodiment, -L- is independently selected from:

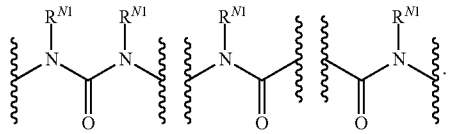

In one embodiment, -L- is independently:

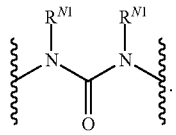

In one embodiment, -L- is independently:

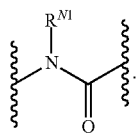

In one embodiment, -L- is independently:

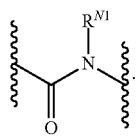

In one embodiment, each —$R^{N1}$, if present, is independently —H or saturated aliphatic $C_{1-4}$alkyl.
In one embodiment, each —$R^{N1}$, if present, is independently —H.

The Group -J

In one embodiment, -J is independently phenyl or $C_{5-6}$heteroaryl, and is optionally substituted.
In one embodiment, -J is independently phenyl, pyrazolyl, or pyridyl, and is optionally substituted.
In one embodiment, -J is independently phenyl or pyrazolyl, and is optionally substituted.
In one embodiment, -J is independently phenyl, and is optionally substituted.
In one embodiment, -J is independently pyrazolyl, and is optionally substituted.
In one embodiment, -J is independently 1H-pyrazol-5-yl, and is optionally substituted.
In one embodiment, -J is independently pyridyl, and is optionally substituted.
In one embodiment, -J is independently pyrid-3-yl, and is optionally substituted.

The Group -J: Optional Substituents

In one embodiment, -J is optionally substituted with one or more substituents selected from:
—F, —Cl, —Br, —I, —$CF_3$, —$OCF_3$,
—$R^4$, —$R^{4S}$, —$R^{4A}$, —$R^{4B}$, —$R^{4C}$, -$L^4$-$R^{4C}$, —Ar, -$L^4$-Ar,
—OH, —$OR^4$, -$L^4$-OH, -$L^4$-$OR^4$, —O-$L^4$-OH, —O-$L^4$-$OR^4$,
—$OR^{4C}$, —O-$L^4$-$R^{4C}$, —OAr, —O-$L^4$-Ar,
—SH, —$SR^4$, —CN, —$NO_2$,
—$NH_2$, —$NHR^{4SS}$, —$R^N$,
-$L^4$-$NH_2$, -$L^4$-$NHR^{4SS}$, -$L^4$-$R^N$,
—O-$L^4$-$NH_2$, —O-$L^4$-$NHR^{4SS}$, —O-$L^4$-$R^N$,
—NH-$L^4$-$NH_2$, —NH-$L^4$-$NHR^{4SS}$, —NH-$L^4$-$R^N$,
—$NR^4$-$L^4$-$NH_2$, —$NR^4$-$L^4$-$NHR^{4SS}$, —$NR^4$-$L^4$-$R^N$, In one embodiment, -J is optionally substituted with one or more substituents selected from:
—F, —Cl, —Br, —I, —$CF_3$, —$OCF_3$,
—$R^4$, —$R^{4S}$, —$R^{4A}$, —$R^{4B}$, —$R^{4C}$, -$L^4$-$R^{4C}$, —Ar, -$L^4$-Ar,
—OH, —$OR^4$, -$L^4$-OH, -$L^4$-$OR^4$, —O-$L^4$-OH, —O-$L^4$-$OR^4$,
—$OR^{4C}$, —O-$L^4$-$R^{4C}$, —OAr, —O-$L^4$-Ar,
—$NH_2$, —$NHR^{4SS}$, —$R^N$,
-$L^4$-$NH_2$, -$L^4$-$NHR^{4SS}$, -$L^4$-$R^N$,
—O-$L^4$-$NH_2$, —O-$L^4$-$NHR^{4SS}$, —O-$L^4$-$R^N$,
—NH-$L^4$-$NH_2$, —NH-$L^4$-$NHR^{4SS}$, —NH-$L^4$-$R^N$,
—$NR^4$-$L^4$-$NH_2$, —$NR^4$-$L^4$-$NHR^{4SS}$, and —$NR^4$-$L^4$-$R^N$.

In one embodiment, -J is optionally substituted with one or more substituents selected from —F, —Cl, —Br, —I, —$R^4$, —Ar, -$L^4$-Ar, —OH, —$OR^4$, —$CF_3$, —$OCF_3$, —OAr, —O-$L^4$-Ar.

In one embodiment, each —Ar, if present, is independently optionally substituted phenyl or pyridyl, for example, phenyl or pyridyl optionally substituted with one or more substituents selected from —F, —Cl, —Br, —I, —$R^5$, —OH, —$OR^5$, —$CF_3$, —$OCF_3$, and —S($=$O)$_2R^5$.

In one embodiment, -J is optionally substituted with one or more substituents selected from —F, —Cl, —Br, —I, —$R^4$, —OH, —$OR^4$, —$CF_3$, —$OCF_3$, and -Ph, wherein each —$R^4$ is independently saturated aliphatic $C_{1-4}$alkyl; and each -Ph denotes optionally substituted phenyl, for example, phenyl optionally substituted with one or more substituents selected from —F, —Cl, —Br, —I, —$R^5$, —OH, —$OR^5$, —$CF_3$, and —$OCF_3$, wherein each —$R^5$ is independently saturated aliphatic $C_{1-4}$alkyl.

The Group -J: Substituted Pyrazolyl

In one embodiment, -J is independently pyrazolyl, and is optionally substituted.
In one embodiment, -J is independently 1H-pyrazol-5-yl, and is optionally substituted.
In one embodiment, -J is independently:

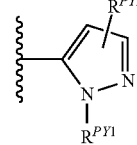

wherein:
—$R^{PY1}$ is independently selected from —$R^4$, —$R^{4S}$, —$R^{4A}$, —$R^{4B}$, —$R^{4C}$, -$L^4$-$R^{4C}$, —Ar, and -$L^4$-Ar; and
—$R^{PY2}$ is independently —F, —Cl, —Br, —I, —$R^4$, —OH, —$OR^4$, —$CF_3$, —$OCF_3$, and —Ar.

In one embodiment, —$R^{PY1}$ is independently —Ar.
In one embodiment, —$R^{PY1}$ is independently phenyl or $C_{5-6}$heteroaryl, and is optionally substituted, for example, with one or more substituents selected from —F, —Cl, —Br, —I, —$R^5$, —OH, —$OR^5$, —$CF_3$, —$OCF_3$, and —S($=$O)$_2R^5$.

In one embodiment, —$R^{PY1}$ is independently phenyl or pyridyl, and is optionally substituted, for example, with one or more substituents selected from —F, —Cl, —Br, —I, —$R^5$, —OH, —$OR^5$, —$CF_3$, —$OCF_3$, and —S($=$O)$_2R^5$.

In one embodiment, -J is independently:

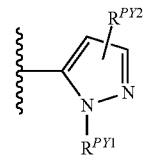

wherein:

—$R^{PY1}$ is independently phenyl or $C_{5-6}$heteroaryl, and is optionally substituted, for example, with one or more substituents selected from —F, —Cl, —Br, —I, —$R^5$, —OH, —$OR^5$, —$CF_3$, —$OCF_3$, wherein each —$R^5$ is independently saturated aliphatic $C_{1-4}$alkyl;

—$R^{PY2}$ is independently —F, —Cl, —Br, —I, —$R^4$, —OH, —$OR^1$, —$CF_3$, —$OCF_3$, and -Ph, wherein each —$R^4$ is independently saturated aliphatic $C_{1-4}$alkyl.

In one embodiment, —$R^{PY1}$ is independently phenyl or pyridyl, and is optionally substituted, for example, with one or more substituents selected from —F, —Cl, —Br, —I, —$R^5$, —OH, —$OR^5$, —$CF_3$, —$OCF_3$.

In one embodiment, —$R^{PY1}$ is independently phenyl, and is optionally substituted, for example, with one or more substituents selected from —F, —Cl, —Br, —I, —$R^5$, —OH, —$OR^5$, —$CF_3$, —$OCF_3$.

In one embodiment, —$R^{PY1}$ is independently phenyl, and is optionally substituted, for example, with one or more substituents selected from —F, —Cl, —Br, —I, —$R^5$, —OH, —$OR^5$.

In one embodiment, —$R^{PY1}$ is independently phenyl, and is optionally substituted, for example, with one or more substituents selected from —$R^5$.

In one embodiment, —$R^{PY1}$ is independently pyridyl, and is optionally substituted, for example, with one or more substituents selected from —F, —Cl, —Br, —I, —$R^5$, —OH, —$OR^5$, —$CF_3$, —$OCF_3$.

In one embodiment, —$R^{PY1}$ is independently pyridyl, and is optionally substituted, for example, with one or more substituents selected from —OH and —$OR^5$.

In one embodiment, each —$R^5$, if present, is -Me.

In one embodiment, —$R^{PY2}$ is independently —$R^4$.

In one embodiment, —$R^{PY2}$ is independently -tBu.

In one embodiment, -J is independently:

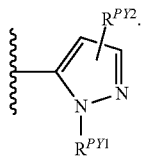

In one embodiment, -J is independently selected from:

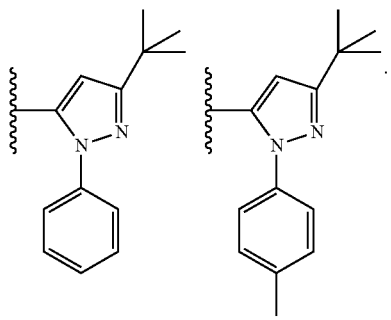 [SMILES: *c1cc(C(C)(C)C)nn1-c1ccccc1 ; *c1cc(C(C)(C)C)nn1-c1ccc(C)cc1]

In one embodiment, -J is independently selected from:

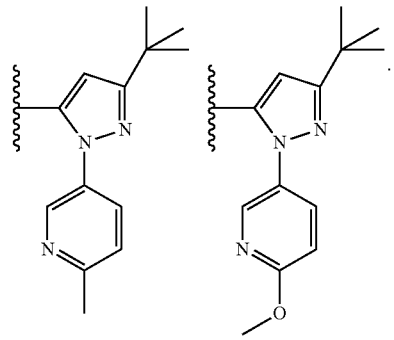 [SMILES: *c1cc(C(C)(C)C)nn1-c1ccc(C)nc1 ; *c1cc(C(C)(C)C)nn1-c1ccc(OC)nc1]

The Group -J: Phenyl and Substituted Phenyl

In one embodiment, -J is independently phenyl, and is optionally substituted.

In one embodiment, -J is independently:

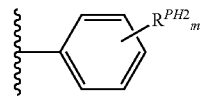

wherein:

m is independently 0, 1, 2, or 3;

each —$R^{PH2}$ is independently selected from:
- —F, —Cl, —Br, —I, —$CF_3$, —$OCF_3$,
- —$R^4$, —$R^{4S}$, —$R^{4A}$, —$R^{4B}$, —$R^{4C}$, -$L^4$-$R^{4C}$, —Ar, -$L^4$-Ar,
- —OH, —$OR^1$, -$L^4$-OH, -$L^4$-$OR^4$, —O-$L^4$-OH, —O-$L^4$-$OR^4$,
- —$OR^{4C}$, —O-$L^4$-$R^{4C}$, —OAr, —O-$L^4$-Ar,
- —SH, —$SR^4$, —CN, —$NO_2$,
- —$NH_2$, —$NHR^{4SS}$, —$R^N$,
- -$L^4$-$NH_2$, -$L^4$-$NHR^{4SS}$, -$L^4$-$R^N$,
- —O-$L^4$-$NH_2$, —O-$L^4$-$NHR^{4SS}$, —O-$L^4$-$R^N$,
- —NH-$L^4$-$NH_2$, —NH-$L^4$-$NHR^{4SS}$, —NH-$L^4$-$R^N$,
- —$NR^4$-$L^4$-$NH_2$, —$NR^4$-$L^4$-$NHR^{4SS}$, and —$NR^4$-$L^4$-$R^N$.

In one embodiment, each —$R^{PH2}$, if present, is independently selected from:
- —F, —Cl, —Br, —I, —$CF_3$, —$OCF_3$,
- —$R^4$, —$R^{4S}$, —$R^{4A}$, —$R^{4B}$, —$R^{4C}$, -$L^4$-$R^{4C}$, —Ar, -$L^4$-Ar,
- —OH, —$OR^1$, -$L^4$-OH, -$L^4$-$OR^4$, —O-$L^4$-OH, —O-$L^4$-$OR^4$,
- —$OR^{4C}$, —O-$L^4$-$R^{4C}$, —OAr, —O-$L^4$-Ar,
- —$NH_2$, —$NHR^{4SS}$, —$R^N$,
- -$L^4$-$NH_2$, -$L^4$-$NHR^{4SS}$, -$L^4$-$R^N$,
- —O-$L^4$-$NH_2$, —O-$L^4$-$NHR^{4SS}$, —O-$L^4$-$R^N$,
- —NH-$L^4$-$NH_2$, —NH-$L^4$-$NHR^{4SS}$, —NH-$L^4$-$R^N$,
- —$NR^4$-$L^4$-$NH_2$, —$NR^4$-$L^4$-$NHR^{4SS}$, and —$NR^4$-$L^4$-$R^N$.

In one embodiment, each —$R^{PH2}$, if present, is independently selected from:
- —F, —Cl, —Br, —I, —$CF_3$, —$OCF_3$,
- —$R^4$, —$R^{4S}$, —Ar, -$L^4$-Ar,
- —OH, —$OR^1$, —OAr, —O-$L^4$-Ar, -$L^4$-OH, -$L^4$-$OR^4$, —O-$L^4$-OH, —O-$L^4$-$OR^4$,
- —$NH_2$, —$NHR^{4SS}$, —$R^N$,
- -$L^4$-$NH_2$, -$L^4$-$NHR^{4SS}$, -$L^4$-$R^N$,
- —O-$L^4$-$NH_2$, —O-$L^4$-$NHR^{4SS}$, —O-$L^4$-$R^N$,
- —NH-$L^4$-$NH_2$, —NH-$L^4$-$NHR^{4SS}$, —NH-$L^4$-$R^N$,
- —$NR^4$-$L^4$-$NH_2$, —$NR^4$-$L^4$-$NHR^{4SS}$, and —$NR^4$-$L^4$-$R^N$.

In one embodiment, each —R$^{PH2}$, if present, is independently selected from:
- —F, —Cl, —Br, —I, —CF$_3$, —OCF$_3$,
- —R$^4$, —R$^{4S}$, —Ar, -L$^4$-Ar,
- —OH, —OR$^4$, —OAr, —O-L$^4$-Ar,
- —NH$_2$, —NHR$^{4SS}$, and —R$^N$.

In one embodiment, each —R$^{PH2}$, if present, is independently selected from:
- —F, —Cl, —Br, —I, —CF$_3$, —OCF$_3$,
- —R$^4$, —R$^{4S}$,
- —OH, —OR$^4$,
- —NH$_2$, —NHR$^{4SS}$, and —R$^N$.

In one embodiment, -J is independently:

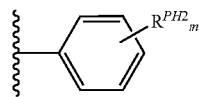

wherein:

m is independently 0, 1, 2, or 3;

each —R$^{PH2}$ is independently —F, —Cl, —Br, —I, —R$^4$, —OH, —OR$^4$, —CF$_3$, or —OCF$_3$, wherein each —R$^4$ is independently saturated aliphatic C$_{1-4}$alkyl.

In one embodiment, m is independently 0, 1, or 2.
In one embodiment, m is independently 1 or 2.
In one embodiment, m is independently 1.
In one embodiment, m is independently 2.
In one embodiment, each —R$^{PH2}$, if present, is independently —F, —Cl, -tBu, —CF$_3$, or —OCF$_3$.

Combinations

Each and every compatible combination of the embodiments described above is explicitly disclosed herein, as if each and every combination was individually and explicitly recited.

Examples of Specific Embodiments

In one embodiment, the compounds are selected from compounds of the following formulae and pharmaceutically acceptable salts, hydrates, and solvates thereof:

| Cmpd. | Structure |
|---|---|
| AA-008 | 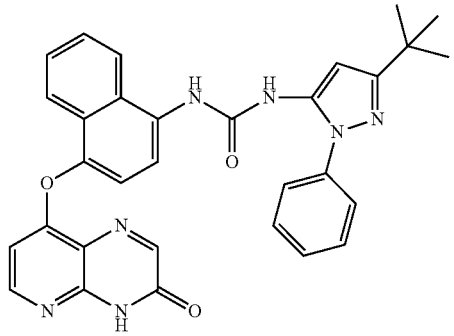 [SMILES: CC(C)(C)c1cc(NC(=O)Nc2ccc(Oc3ccnc4[nH]c(=O)cnc34)c3ccccc23)n(-c2ccccc2)n1] |
| AA-009 | 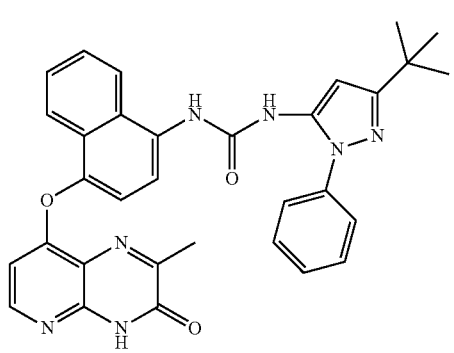 [SMILES: Cc1nc2c(Oc3ccc(NC(=O)Nc4cc(C(C)(C)C)nn4-c4ccccc4)c4ccccc34)ccnc2[nH]c1=O] |
| AA-010 | 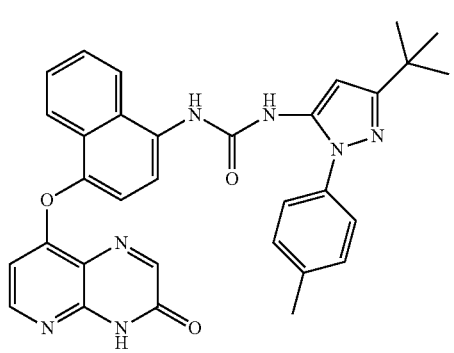 [SMILES: Cc1ccc(-n2nc(C(C)(C)C)cc2NC(=O)Nc2ccc(Oc3ccnc4[nH]c(=O)cnc34)c3ccccc23)cc1] |
| AA-011 | 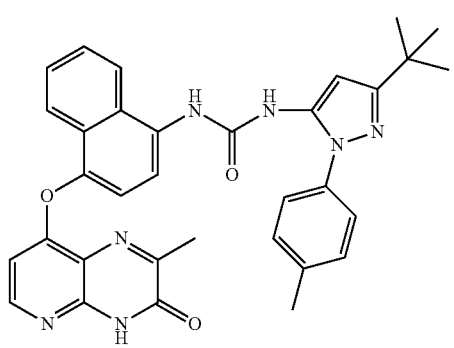 [SMILES: Cc1ccc(-n2nc(C(C)(C)C)cc2NC(=O)Nc2ccc(Oc3ccnc4[nH]c(=O)c(C)nc34)c3ccccc23)cc1] |
| AA-012 | 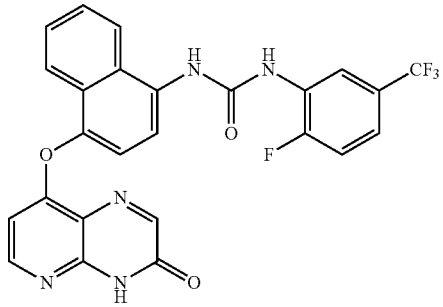 [SMILES: O=C(Nc1cc(C(F)(F)F)ccc1F)Nc1ccc(Oc2ccnc3[nH]c(=O)cnc23)c2ccccc12] |
| AA-013 | 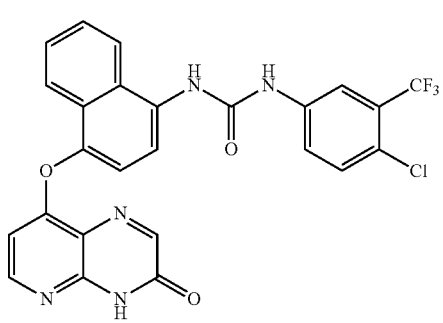 [SMILES: O=C(Nc1ccc(Cl)c(C(F)(F)F)c1)Nc1ccc(Oc2ccnc3[nH]c(=O)cnc23)c2ccccc12] |
| AA-014 | 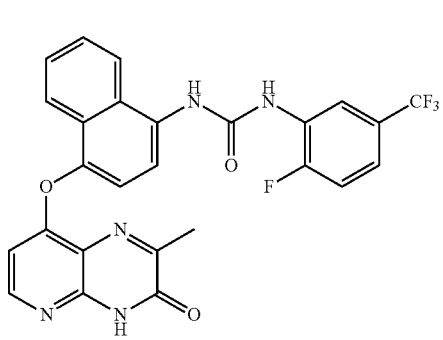 [SMILES: Cc1nc2c(Oc3ccc(NC(=O)Nc4cc(C(F)(F)F)ccc4F)c4ccccc34)ccnc2[nH]c1=O] |
| AA-015 | 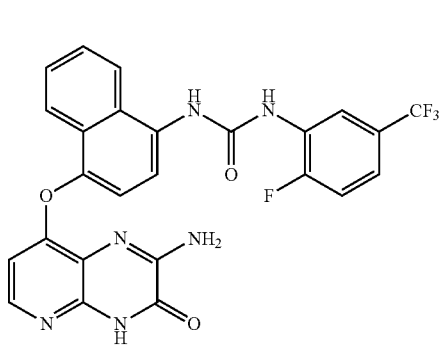 [SMILES: Nc1nc2c(Oc3ccc(NC(=O)Nc4cc(C(F)(F)F)ccc4F)c4ccccc34)ccnc2[nH]c1=O] |

-continued
| Cmpd. | Structure |
|---|---|
| AA-016 | 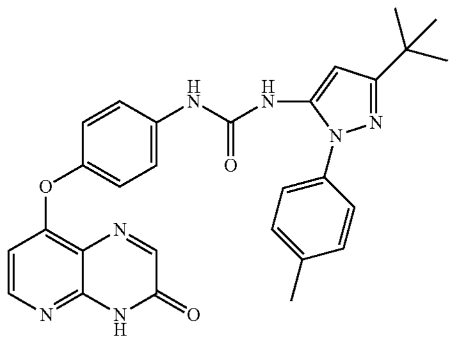 [SMILES: Cc1ccc(-n2nc(C(C)(C)C)cc2NC(=O)Nc2ccc(Oc3ccnc4[nH]c(=O)cnc34)cc2)cc1] |
| AA-017 | 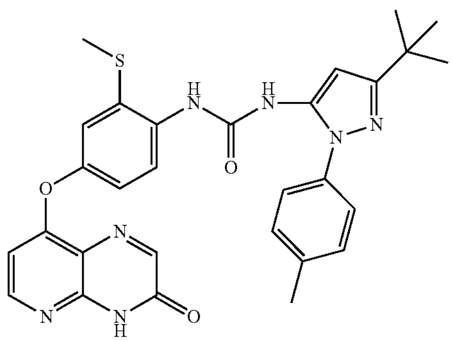 [SMILES: CSc1cc(Oc2ccnc3[nH]c(=O)cnc23)ccc1NC(=O)Nc1cc(C(C)(C)C)nn1-c1ccc(C)cc1] |
| AA-018 | 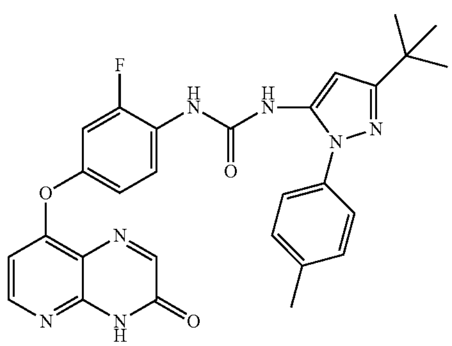 [SMILES: Cc1ccc(-n2nc(C(C)(C)C)cc2NC(=O)Nc2ccc(Oc3ccnc4[nH]c(=O)cnc34)cc2F)cc1] |
| AA-019 | 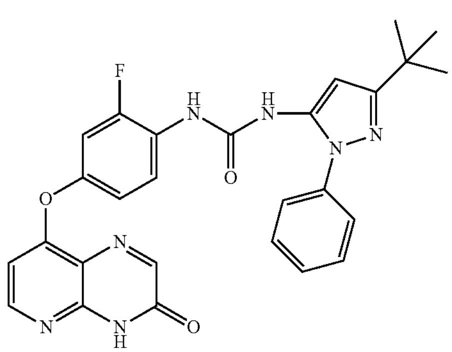 [SMILES: CC(C)(C)c1cc(NC(=O)Nc2ccc(Oc3ccnc4[nH]c(=O)cnc34)cc2F)n(-c2ccccc2)n1] |
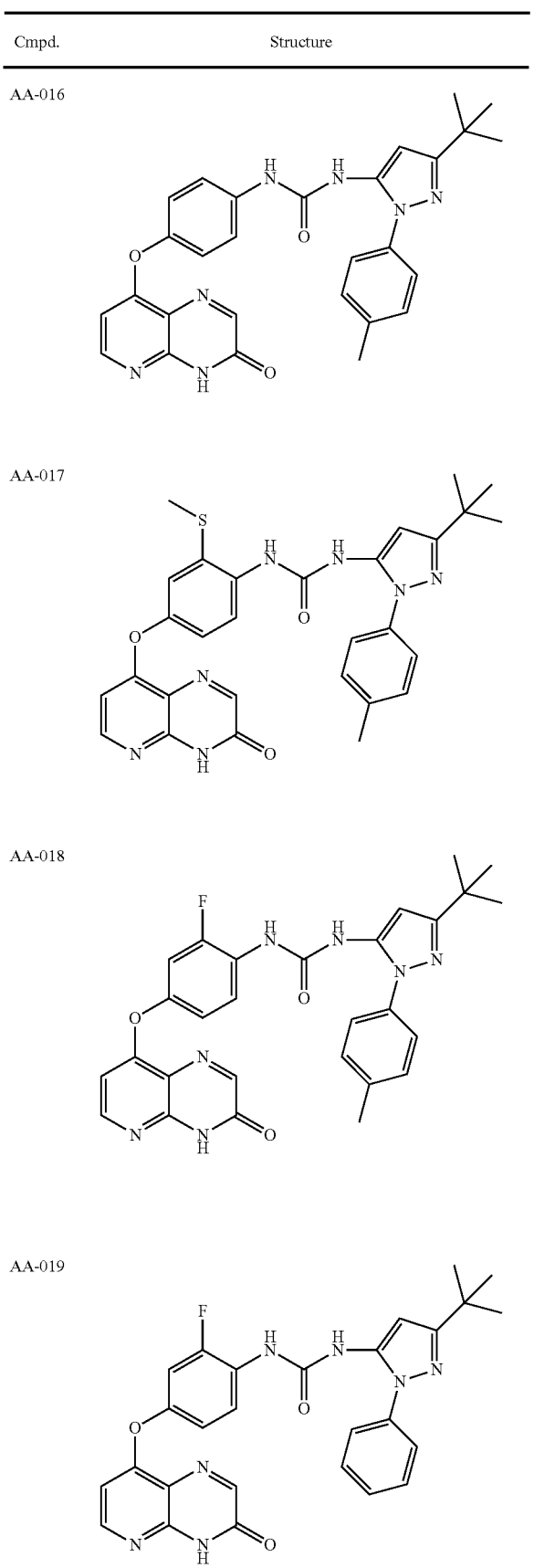
-continued
| Cmpd. | Structure |
|---|---|
| AA-020 | 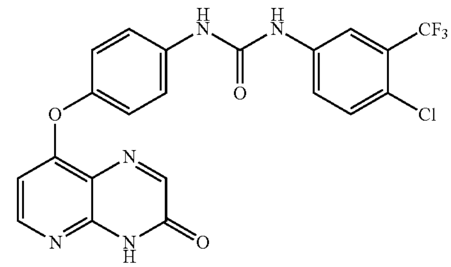 [SMILES: O=C(Nc1ccc(Oc2ccnc3[nH]c(=O)cnc23)cc1)Nc1ccc(Cl)c(C(F)(F)F)c1] |
| AA-021 | 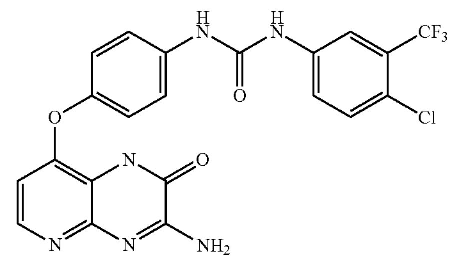 [SMILES: Nc1nc2nccc(Oc3ccc(NC(=O)Nc4ccc(Cl)c(C(F)(F)F)c4)cc3)c2[nH]c1=O] |
| AA-022 | 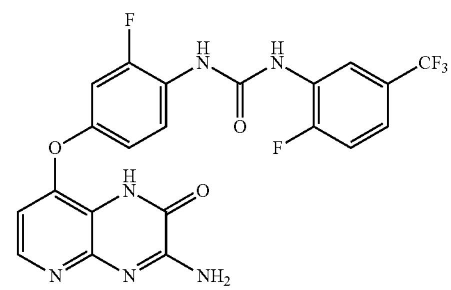 [SMILES: Nc1nc2nccc(Oc3ccc(NC(=O)Nc4cc(C(F)(F)F)ccc4F)c(F)c3)c2[nH]c1=O] |
| AA-023 | 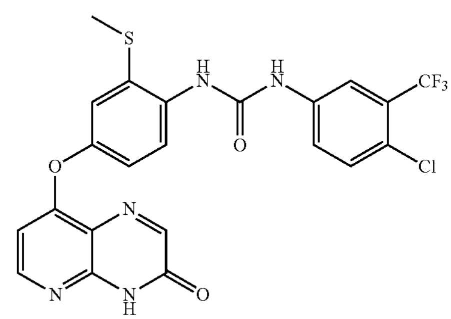 [SMILES: CSc1cc(Oc2ccnc3[nH]c(=O)cnc23)ccc1NC(=O)Nc1ccc(Cl)c(C(F)(F)F)c1] |
| AA-024 | 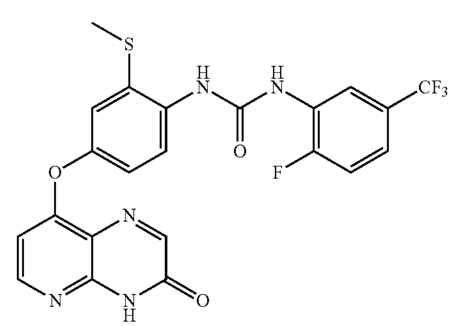 [SMILES: CSc1cc(Oc2ccnc3[nH]c(=O)cnc23)ccc1NC(=O)Nc1cc(C(F)(F)F)ccc1F] |
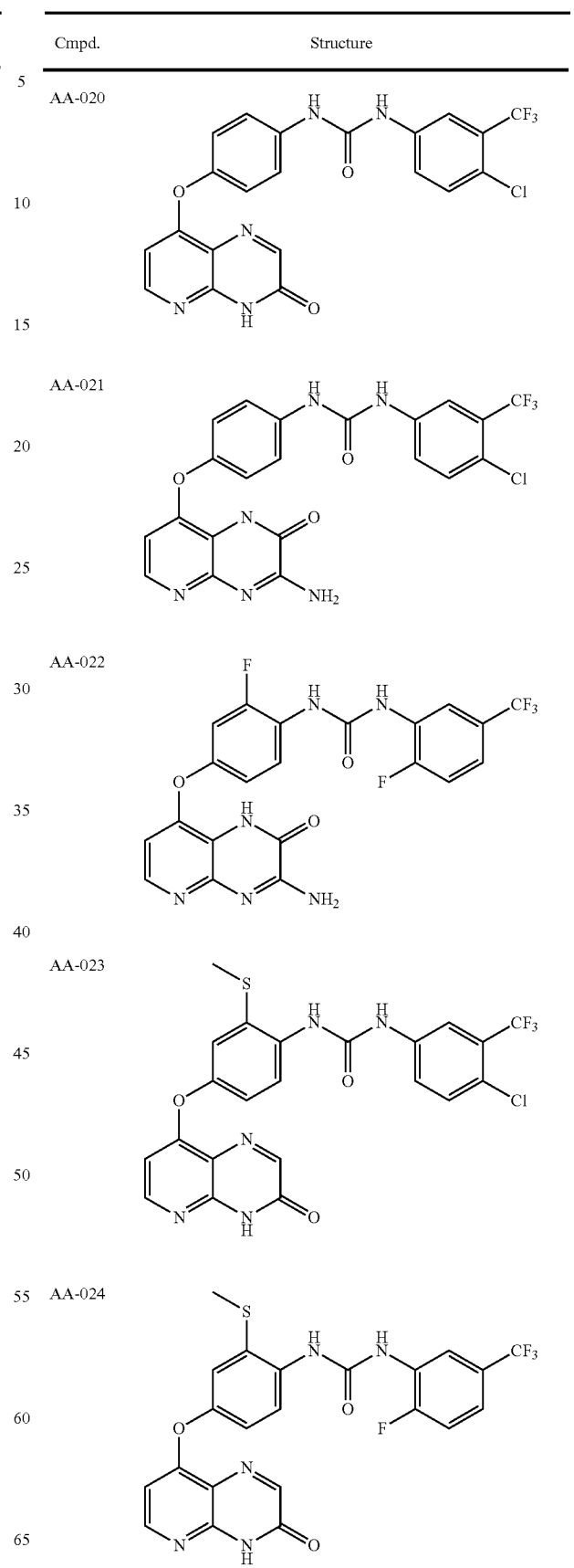

| Cmpd. | Structure |
|---|---|
| AA-025 | 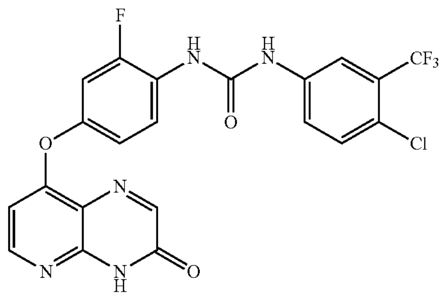 [SMILES: O=C(Nc1ccc(Cl)c(C(F)(F)F)c1)Nc1ccc(Oc2ccnc3[nH]c(=O)cnc23)cc1F] |
| AA-026 | 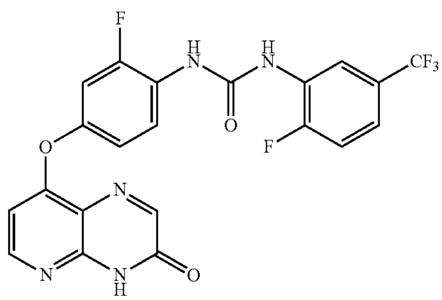 [SMILES: O=C(Nc1ccc(Oc2ccnc3[nH]c(=O)cnc23)cc1F)Nc1cc(C(F)(F)F)ccc1F] |
| AA-027 | 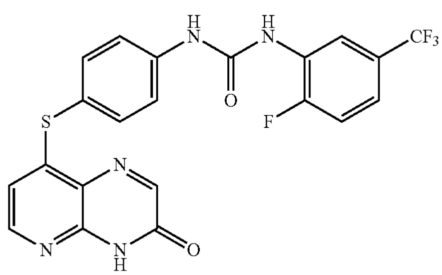 [SMILES: O=C(Nc1ccc(Sc2ccnc3[nH]c(=O)cnc23)cc1)Nc1cc(C(F)(F)F)ccc1F] |
| AA-028 | 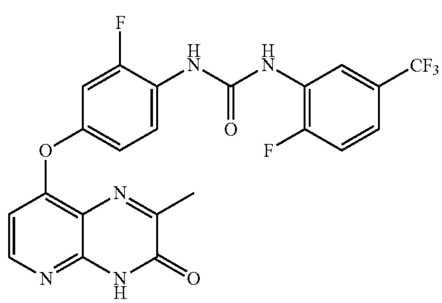 [SMILES: Cc1nc2c(Oc3ccc(NC(=O)Nc4cc(C(F)(F)F)ccc4F)c(F)c3)ccnc2[nH]c1=O] |
| AA-029 | 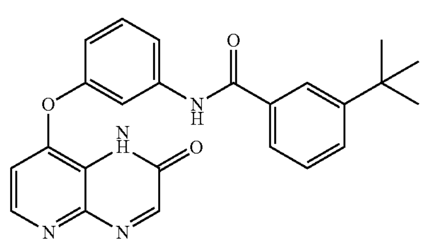 [SMILES: CC(C)(C)c1cccc(C(=O)Nc2cccc(Oc3ccnc4ncc(=O)[nH]c34)c2)c1] |
| AA-030 | |
| AA-031 | |
| AA-032 | |
| AA-033 | |
| AA-034 | |

| Cmpd. | Structure |
|---|---|
| AA-035 | 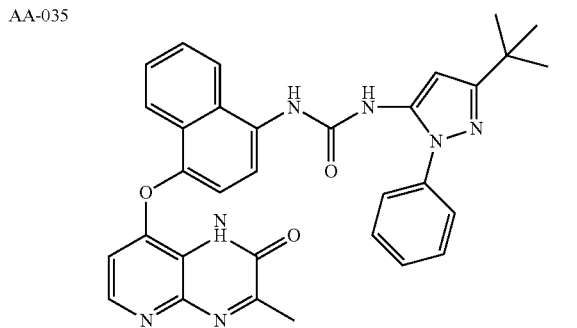 |
| AA-036 | 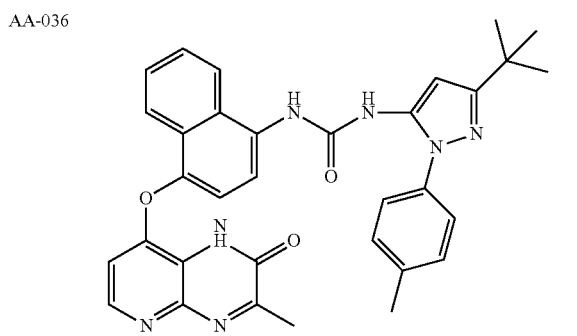 |
| AA-037 | 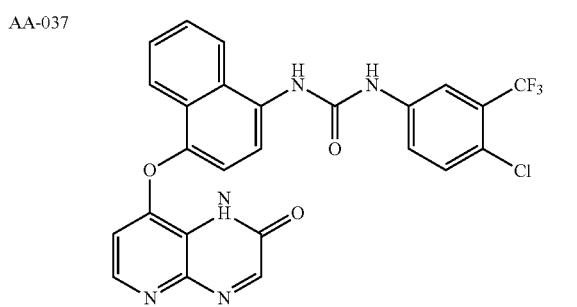 |
| AA-038 | 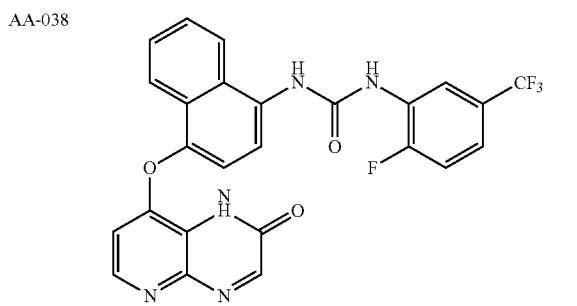 |
| Cmpd. | Structure |
|---|---|
| AA-039 | 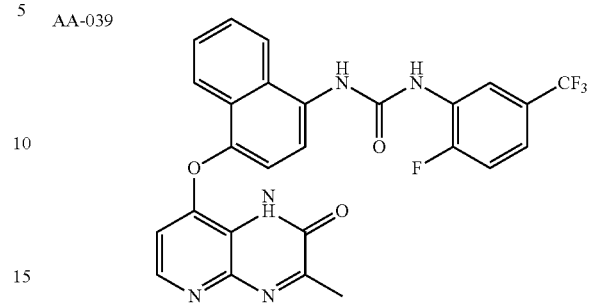 |
| AA-040 | 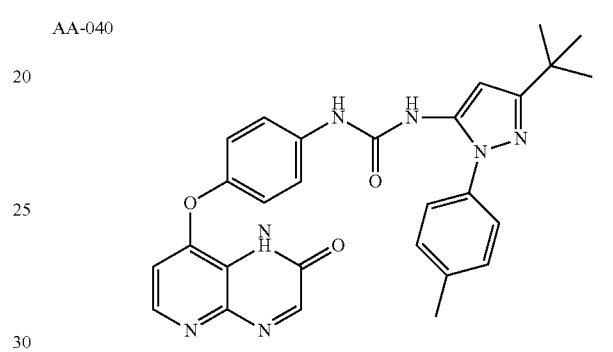 |
| AA-041 | 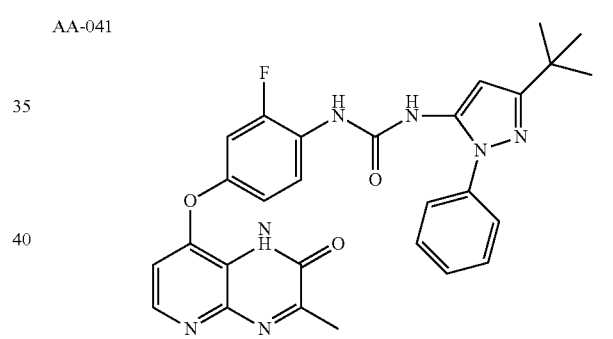 |
| AA-042 | 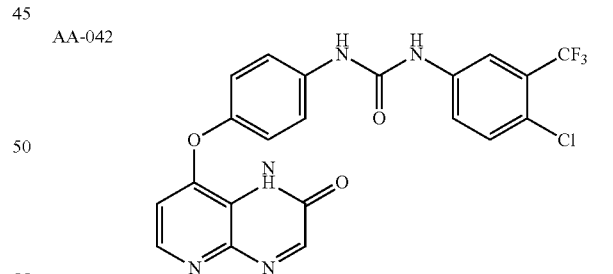 |
| AA-043 | 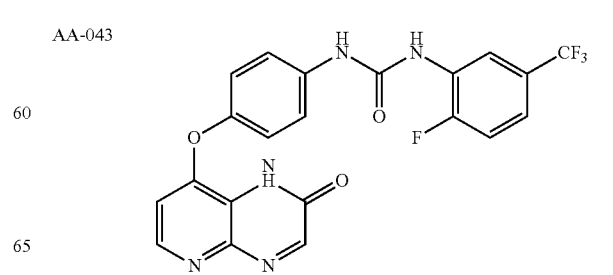 |

| Cmpd. | Structure |
|---|---|
| AA-044 | 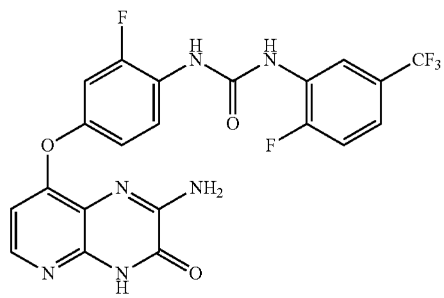 [SMILES: Nc1nc2c(Oc3ccc(NC(=O)Nc4cc(C(F)(F)F)ccc4F)c(F)c3)ccnc2[nH]c1=O] |
| AA-045 | 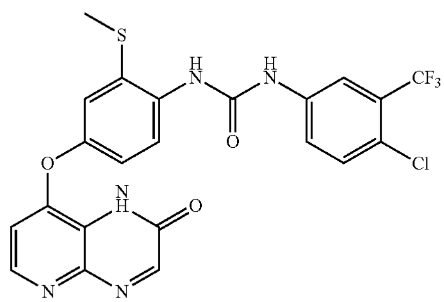 [SMILES: CSc1cc(Oc2ccnc3ncc(=O)[nH]c23)ccc1NC(=O)Nc1ccc(Cl)c(C(F)(F)F)c1] |
| AA-046 | 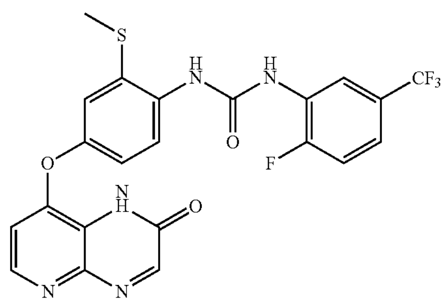 [SMILES: CSc1cc(Oc2ccnc3ncc(=O)[nH]c23)ccc1NC(=O)Nc1cc(C(F)(F)F)ccc1F] |
| AA-047 | 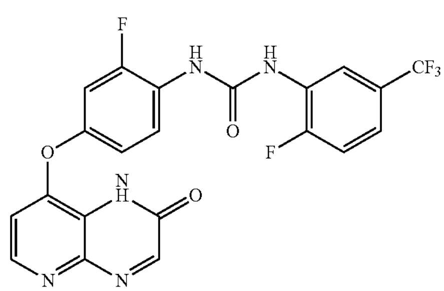 [SMILES: O=C(Nc1ccc(Oc2ccnc3ncc(=O)[nH]c23)cc1F)Nc1cc(C(F)(F)F)ccc1F] |
| AA-048 | 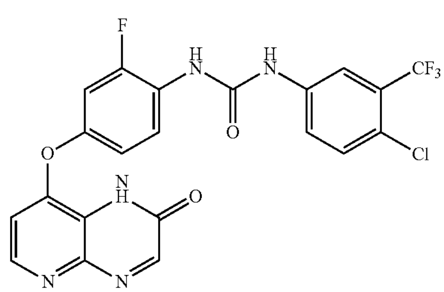 [SMILES: O=C(Nc1ccc(Cl)c(C(F)(F)F)c1)Nc1ccc(Oc2ccnc3ncc(=O)[nH]c23)cc1F] |

| Cmpd. | Structure |
|---|---|
| AA-049 | |
| AA-050 | |
| AA-051 | |
| AA-052 | |
| AA-053 | |

-continued
| Cmpd. | Structure |
|---|---|
| AA-054 | 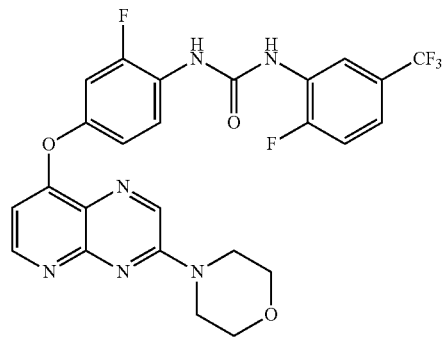 [SMILES: O=C(Nc1ccc(Oc2ccnc3nc(N4CCOCC4)cnc23)cc1F)Nc1cc(C(F)(F)F)ccc1F] |
| AA-055 | 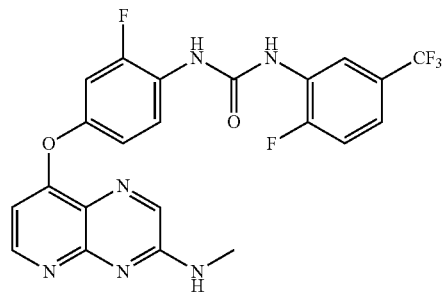 [SMILES: CNc1cnc2c(Oc3ccc(NC(=O)Nc4cc(C(F)(F)F)ccc4F)c(F)c3)ccnc2n1] |
| AA-056 | 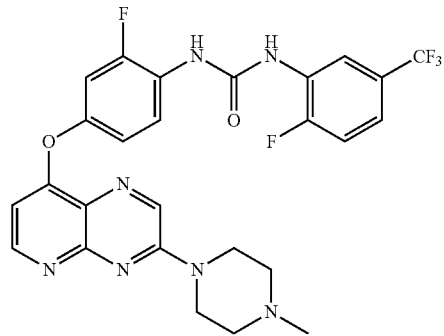 [SMILES: CN1CCN(c2cnc3c(Oc4ccc(NC(=O)Nc5cc(C(F)(F)F)ccc5F)c(F)c4)ccnc3n2)CC1] |
| AA-057 | 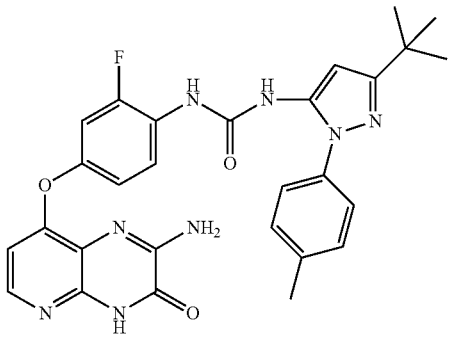 [SMILES: Cc1ccc(-n2nc(C(C)(C)C)cc2NC(=O)Nc2ccc(Oc3ccnc4[nH]c(=O)c(N)nc34)cc2F)cc1] |
| AA-058 | 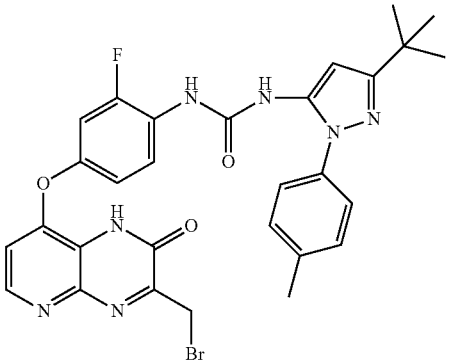 [SMILES: Cc1ccc(-n2nc(C(C)(C)C)cc2NC(=O)Nc2ccc(Oc3ccnc4nc(CBr)c(=O)[nH]c34)cc2F)cc1] |
| AA-059 | 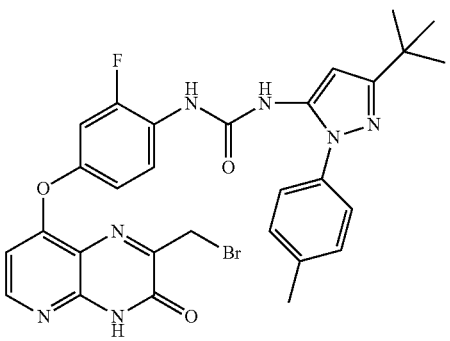 [SMILES: Cc1ccc(-n2nc(C(C)(C)C)cc2NC(=O)Nc2ccc(Oc3ccnc4[nH]c(=O)c(CBr)nc34)cc2F)cc1] |
| AA-060 | 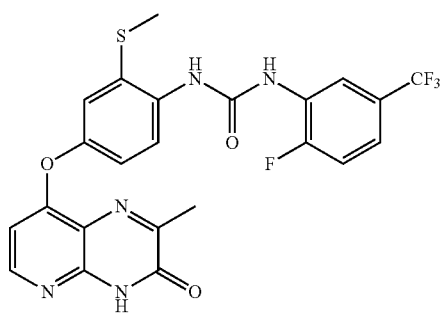 [SMILES: CSc1cc(Oc2ccnc3[nH]c(=O)c(C)nc23)ccc1NC(=O)Nc1cc(C(F)(F)F)ccc1F] |
| AA-061 | 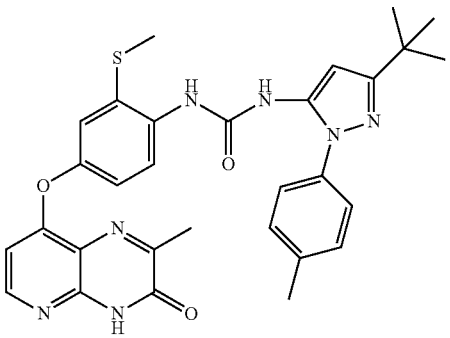 [SMILES: CSc1cc(Oc2ccnc3[nH]c(=O)c(C)nc23)ccc1NC(=O)Nc1cc(C(C)(C)C)nn1-c1ccc(C)cc1] |

| Cmpd. | Structure |
|---|---|
| AA-062 | 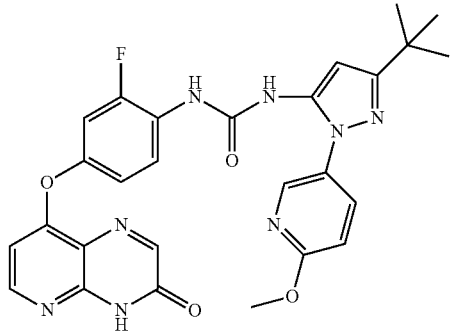 [SMILES: COc1ccc(-n2nc(C(C)(C)C)cc2NC(=O)Nc2ccc(Oc3ccnc4[nH]c(=O)cnc34)cc2F)cn1] |
| AA-063 | 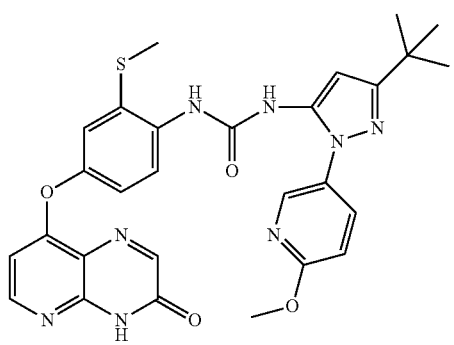 [SMILES: COc1ccc(-n2nc(C(C)(C)C)cc2NC(=O)Nc2ccc(Oc3ccnc4[nH]c(=O)cnc34)cc2SC)cn1] |
| AA-064 | 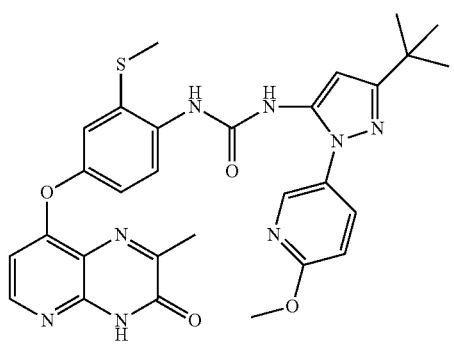 [SMILES: COc1ccc(-n2nc(C(C)(C)C)cc2NC(=O)Nc2ccc(Oc3ccnc4[nH]c(=O)c(C)nc34)cc2SC)cn1] |
| AA-065 | 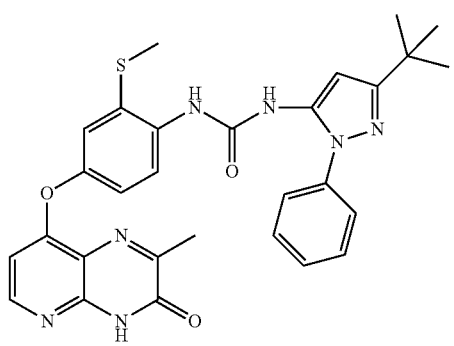 [SMILES: CSc1cc(Oc2ccnc3[nH]c(=O)c(C)nc23)ccc1NC(=O)Nc1cc(C(C)(C)C)nn1-c1ccccc1] |
| AA-066 | 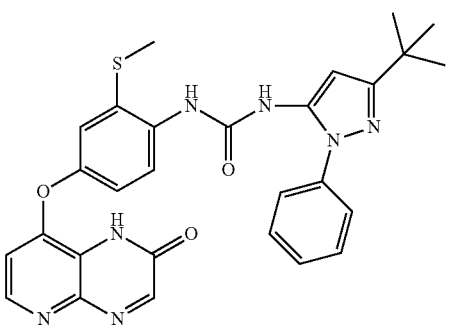 [SMILES: CSc1cc(Oc2ccnc3ncc(=O)[nH]c23)ccc1NC(=O)Nc1cc(C(C)(C)C)nn1-c1ccccc1] |
| AA-067 | 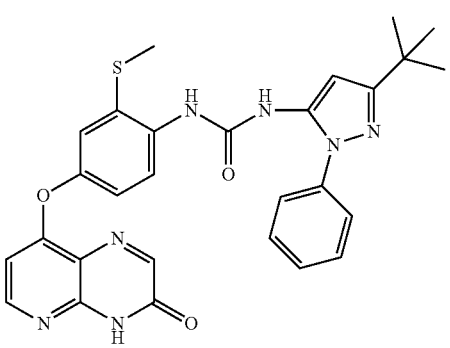 [SMILES: CSc1cc(Oc2ccnc3[nH]c(=O)cnc23)ccc1NC(=O)Nc1cc(C(C)(C)C)nn1-c1ccccc1] |
| AA-068 | 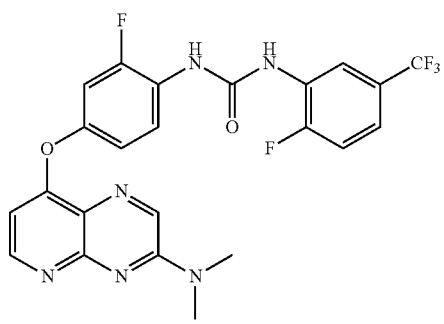 [SMILES: CN(C)c1cnc2c(Oc3ccc(NC(=O)Nc4cc(C(F)(F)F)ccc4F)c(F)c3)ccnc2n1] |
| AA-069 | 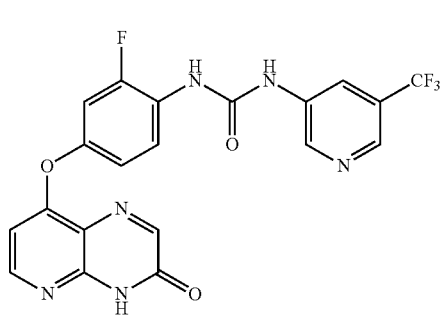 [SMILES: O=C(Nc1cncc(C(F)(F)F)c1)Nc1ccc(Oc2ccnc3[nH]c(=O)cnc23)cc1F] |

| Cmpd. | Structure |
|---|---|
| AA-070 | |
| AA-071 | |
| AA-072 | |
| AA-073 | |
| AA-074 | 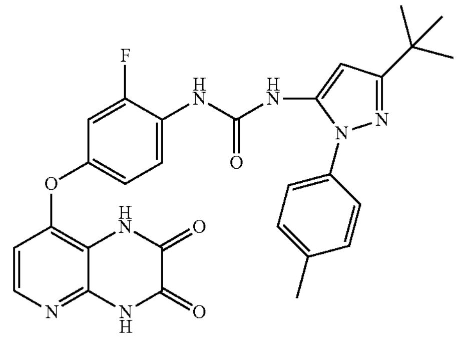 [SMILES: Cc1ccc(-n2nc(C(C)(C)C)cc2NC(=O)Nc2ccc(Oc3ccnc4[nH]c(=O)c(=O)[nH]c34)cc2F)cc1] |
| AA-075 | 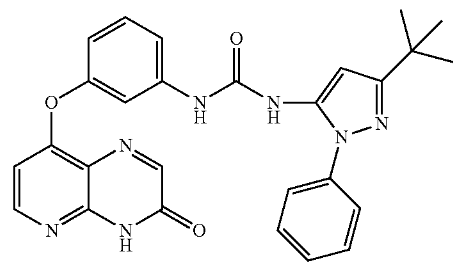 [SMILES: CC(C)(C)c1cc(NC(=O)Nc2cccc(Oc3ccnc4[nH]c(=O)cnc34)c2)n(-c2ccccc2)n1] |
| AA-076 | 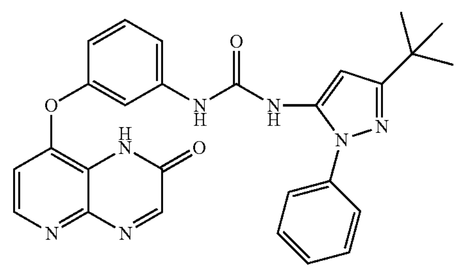 [SMILES: CC(C)(C)c1cc(NC(=O)Nc2cccc(Oc3ccnc4ncc(=O)[nH]c34)c2)n(-c2ccccc2)n1] |
| AA-077 | 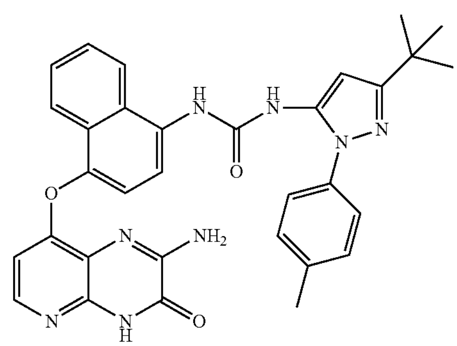 [SMILES: Cc1ccc(-n2nc(C(C)(C)C)cc2NC(=O)Nc2ccc(Oc3ccnc4[nH]c(=O)c(N)nc34)c3ccccc23)cc1] |
| AA-078 | 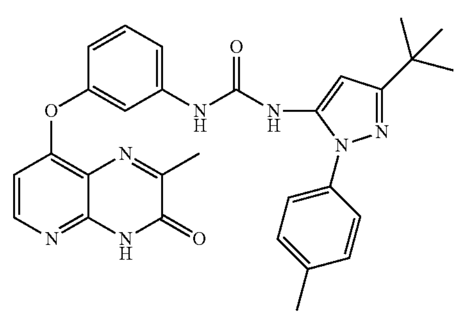 [SMILES: Cc1ccc(-n2nc(C(C)(C)C)cc2NC(=O)Nc2cccc(Oc3ccnc4[nH]c(=O)c(C)nc34)c2)cc1] |

| Cmpd. | Structure |
|---|---|
| AA-079 | 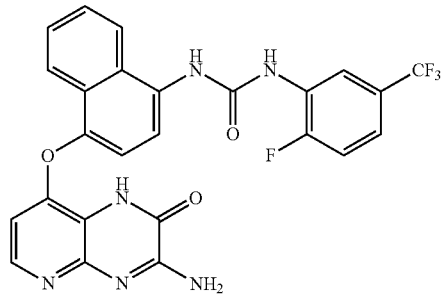 [SMILES: Nc1nc2nccc(Oc3ccc(NC(=O)Nc4cc(C(F)(F)F)ccc4F)c4ccccc34)c2[nH]c1=O] |
| AA-080 | 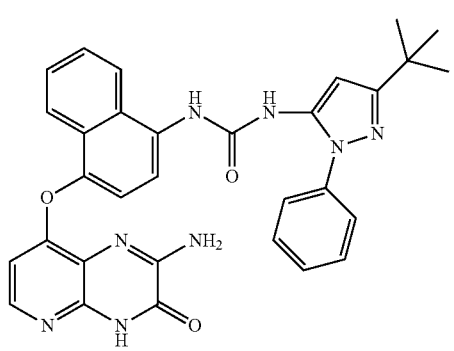 [SMILES: CC(C)(C)c1cc(NC(=O)Nc2ccc(Oc3ccnc4[nH]c(=O)c(N)nc34)c3ccccc23)n(-c2ccccc2)n1] |
| AA-081 | 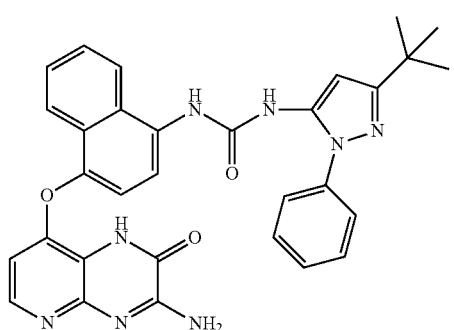 |
| AA-082 | 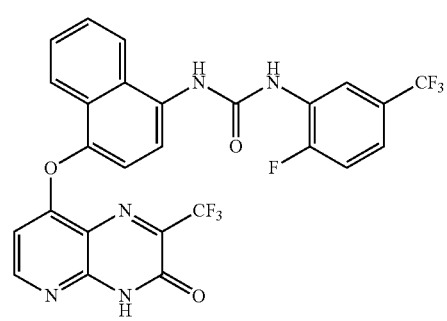 [SMILES: O=C(Nc1cc(C(F)(F)F)ccc1F)Nc1ccc(Oc2ccnc3[nH]c(=O)c(C(F)(F)F)nc23)c2ccccc12] |
| AA-083 | 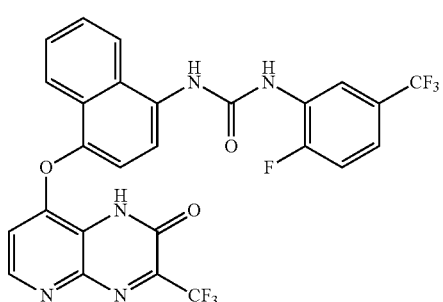 |
| AA-084 | 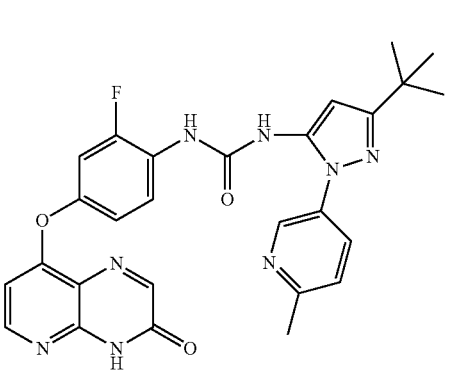 |
| AA-085 | 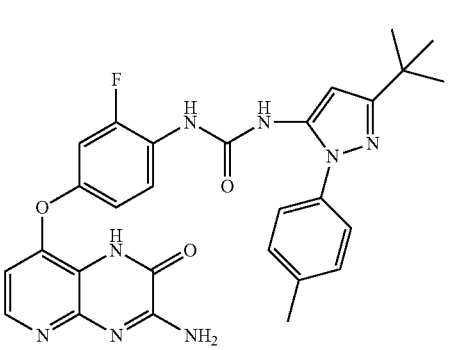 [SMILES: Cc1ccc(-n2nc(C(C)(C)C)cc2NC(=O)Nc2ccc(Oc3ccnc4nc(N)c(=O)[nH]c34)cc2F)cc1] |
| AA-086 | 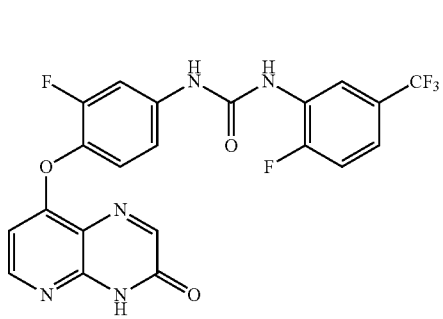 [SMILES: O=C(Nc1ccc(Oc2ccnc3[nH]c(=O)cnc23)c(F)c1)Nc1cc(C(F)(F)F)ccc1F] |

| Cmpd. | Structure |
|---|---|
| AA-087 | 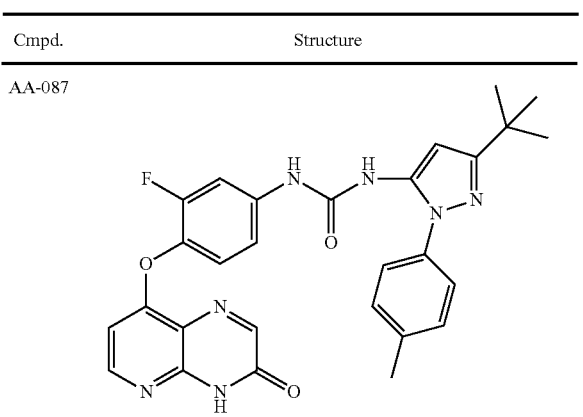 |
| AA-088 | 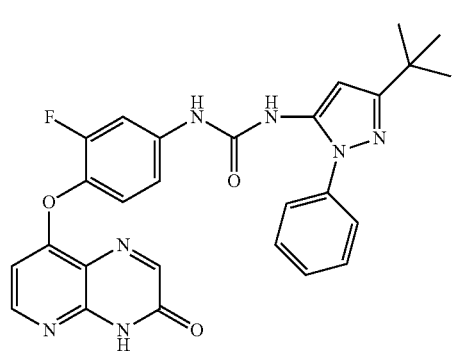 [SMILES: CC(C)(C)c1cc(NC(=O)Nc2ccc(Oc3ccnc4[nH]c(=O)cnc34)c(F)c2)n(-c2ccccc2)n1] |
| AA-089 | 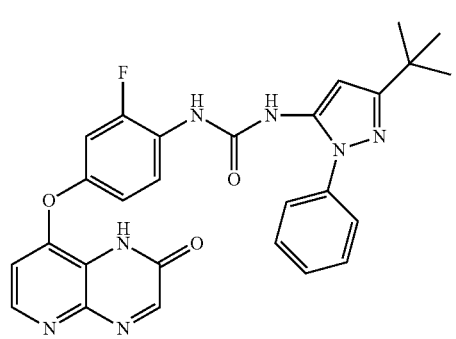 [SMILES: CC(C)(C)c1cc(NC(=O)Nc2ccc(Oc3ccnc4ncc(=O)[nH]c34)cc2F)n(-c2ccccc2)n1] |
| AA-090 | 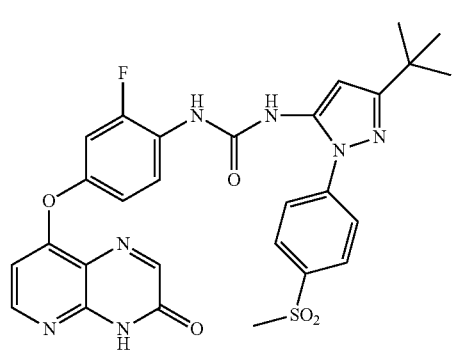 [SMILES: CC(C)(C)c1cc(NC(=O)Nc2ccc(Oc3ccnc4[nH]c(=O)cnc34)cc2F)n(-c2ccc(S(C)(=O)=O)cc2)n1] |
| AA-091 | 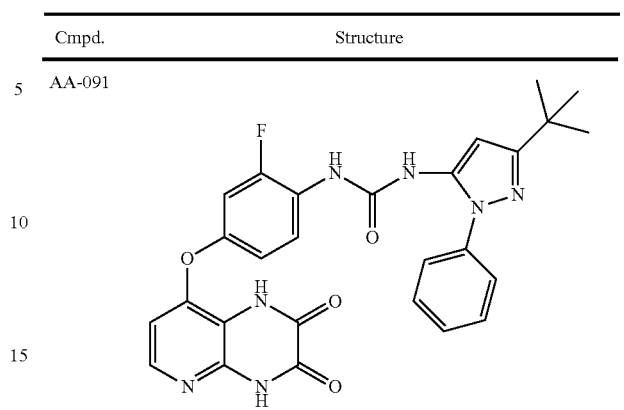 |
| AA-092 | 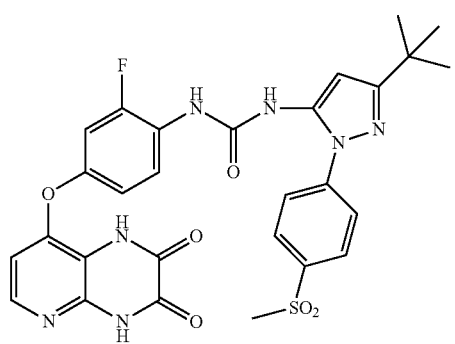 [SMILES: CC(C)(C)c1cc(NC(=O)Nc2ccc(Oc3ccnc4[nH]c(=O)c(=O)[nH]c34)cc2F)n(-c2ccc(S(C)(=O)=O)cc2)n1] |
| AA-093 | 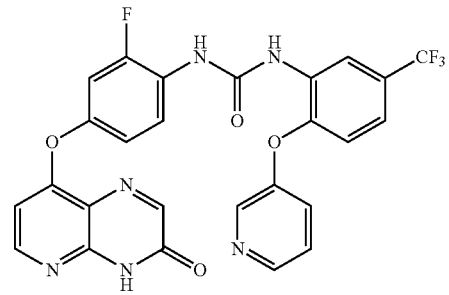 [SMILES: O=C(Nc1ccc(Oc2ccnc3[nH]c(=O)cnc23)cc1F)Nc1cc(C(F)(F)F)ccc1Oc1cccnc1] |
| AA-094 | 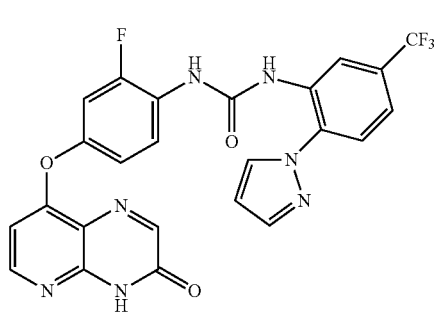 [SMILES: O=C(Nc1ccc(Oc2ccnc3[nH]c(=O)cnc23)cc1F)Nc1cc(C(F)(F)F)ccc1-n1cccn1] |

| Cmpd. | Structure |
|---|---|
| AA-095 | 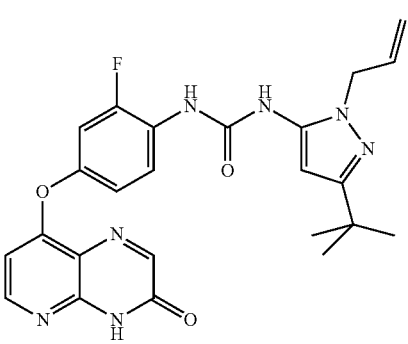 [SMILES: C=CCn1nc(C(C)(C)C)cc1NC(=O)Nc1ccc(Oc2ccnc3[nH]c(=O)cnc23)cc1F] |
| AA-096 | 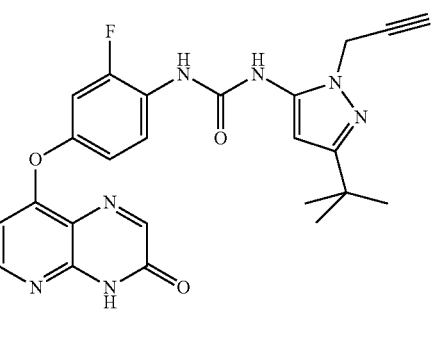 [SMILES: C#CCn1nc(C(C)(C)C)cc1NC(=O)Nc1ccc(Oc2ccnc3[nH]c(=O)cnc23)cc1F] |
| AA-097 | 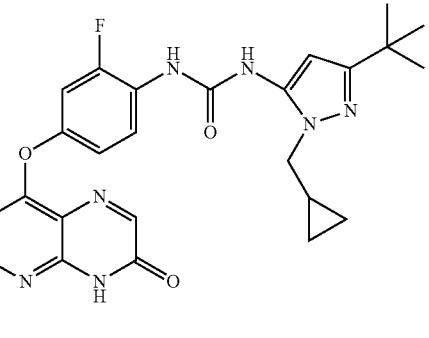 |
| AA-098 | 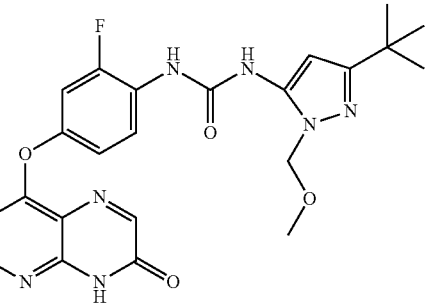 |
| AA-099 | 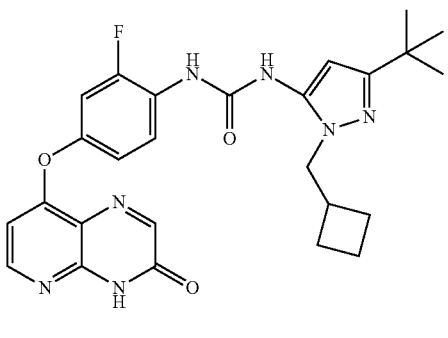 [SMILES: CC(C)(C)c1cc(NC(=O)Nc2ccc(Oc3ccnc4[nH]c(=O)cnc34)cc2F)n(CC2CCC2)n1] |
| AA-100 | 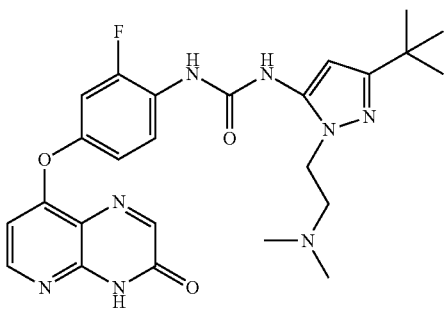 [SMILES: CN(C)CCn1nc(C(C)(C)C)cc1NC(=O)Nc1ccc(Oc2ccnc3[nH]c(=O)cnc23)cc1F] |

Substantially Purified Forms

One aspect of the present invention pertains to PDP8 compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

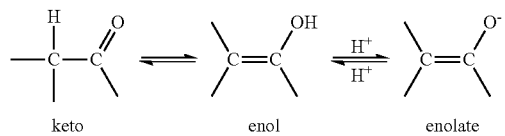

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O•).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of PDP8 compounds of the present invention are described herein. These and/or other well known methods may be modified and/or adapted in known ways in order to facilitate the synthesis of additional compounds within the scope of the present invention.

Compositions

One aspect of the present invention pertains to a composition (e.g., a pharmaceutical composition) comprising a PDP8 compound, as described herein, and a pharmaceutically acceptable carrier, diluent, or excipient.

Another aspect of the present invention pertains to a method of preparing a composition (e.g., a pharmaceutical composition) comprising admixing a PDP8 compound, as described herein, and a pharmaceutically acceptable carrier, diluent, or excipient.

Uses

The compounds described herein are useful, for example, in the treatment of diseases and disorders that are ameliorated by the inhibition of RAF (e.g., B-RAF), such as, for example, proliferative disorders, cancer, etc.

Use in Methods of Inhibiting RAF (e.g., B-RAF)

One aspect of the present invention pertains to a method of inhibiting RAF (e.g., B-RAF) function, in vitro or in vivo, comprising contacting a RAF (e.g., B-RAF) with an effective amount of a PDP8 compound, as described herein.

One aspect of the present invention pertains to a method of inhibiting RAF (e.g., B-RAF) function in a cell, in vitro or in vivo, comprising contacting the cell with an effective amount of a PDP8 compound, as described herein.

In one embodiment, the method is performed in vitro.

In one embodiment, the method is performed in vivo.

One of ordinary skill in the art is readily able to determine whether or not, and/or the degree to which, a candidate compound inhibits RAF (e.g., B-RAF) function. Suitable assays for determining RAF (e.g., B-RAF) function inhibition are described herein and/or are known in the art.

B-RAF Assays:

B-raf kinase activity is measured using a 4-tiered cascade enzyme assay similar to that described by Marais R., et al., 1997, *J. Biol. Chem.*, Vol. 272, pp. 4378-4383. B-Raf containing the V600E mutation (Davies, H., et al., 2002, *Nature*, Vol. 417, pp. 949-954) and an N-terminal MDRGSH6 tag is expressed in SF9 insect cells. Detergent soluble extracts from these cells are diluted 1:100 into an assay mixture containing GST-MEK-H6 (6.5 µg/ml) and GST-ERK-H6 (100 µg/ml) in a buffer containing 800 µM ATP and appropriate concentrations of inhibitor or diluent as control. The mixture is incubated for up to 10 minutes at 30° C. to activate the ERK in a B-Raf dependent manner within the cascade. The reaction is then stopped by addition of 20 mM EDTA. The extent of activation of the GST-ERK is then determined by adding a portion of this quenched reaction mixture to a further reaction mixture containing MBP and 100 μM ATP/gamma [$^{32}$P]ATP. After 12 minutes' incubation at 30° C., the incorporation of [$^{32}$P] into the MBP substrate, as a measure of B-raf activity, is determined by precipitation with phosphoric acid and isolation by filtration on p81 phosphocellulose paper. The % inhibition of the B-raf kinase activity is calculated and plotted in order to determine the concentration of test compound required to inhibit 50% of the B-raf kinase activity (IC$_{50}$).

Alternatively, B-raf kinase activity is measured using a different 4-tiered cascade enzyme assay. B-Raf containing the V600E mutation (Davies, H., et al., 2002, *Nature*, Vol. 417, pp. 949-954) and an N-terminal MDRGSH6 tag is expressed in SF9 insect cells. Detergent soluble extracts from these cells are diluted 1:250 into an assay mixture containing GST-MEK-H6 (25 μg/ml), GST-ERK-H6 (281.25 μg/ml) and MBP in a buffer containing appropriate concentrations of inhibitor or diluent as control. 0.03 μL (100 μM) ATP is added and the mixture is incubated for up to 10 minutes at 30° C. to activate the ERK in a B-Raf dependent manner within the cascade. The extent of activation of the GST-ERK is then determined by adding 0.033 μL (100 μM) HOT $^{32}$Pα. After 10 minutes' incubation at 30° C., the reaction is stopped by isolation of a portion of the reaction mixture on p81 phosphocellulose paper and submersion of this paper in 0.4% orthophosphoric acid. Incorporation of [$^{32}$P] into the MBP substrate, as a measure of B-raf activity, is determined using a Packard Cernekov counter. The % inhibition of the B-raf kinase activity is calculated and plotted in order to determine the concentration of test compound required to inhibit 50% of the B-raf kinase activity (IC$_{50}$).

C-RAF Assay:

C-raf (human) is diluted to a 10× working stock in 50 mM Tris pH 7.5, 0.1 mM EGTA, 0.1 mM sodium vanadate, 0.1% β-mercaptoethanol, 1 mg/ml BSA. One unit equals the incorporation of 1 nmol of phosphate per minute into myelin basic protein per minute. In a final reaction volume of 25 μl, c-raf (5-10 mU) is incubated with 25 mM Tris pH 7.5, 0.02 mM EGTA, 0.66 mg/ml myelin basic protein, 10 mM MgAcetate, [γ-$^{33}$P-ATP] (specific activity approx 500 cpm/pmol, concentration as required) and appropriate concentrations of inhibitor or diluent as control. The reaction is initiated by the addition of Mg$^{2}$+[γ-$^{33}$P-ATP]. After incubation for 40 minutes at room temperature, the reaction is stopped by the addition of 5 μl of a 3% phosphoric acid solution. 10 μl of the reaction is spotted onto a P30 filtermat and washed 3 times for 5 minutes in 75 mM phosphoric acid and once in methanol prior to drying and counting to determine the C-raf activity. The % inhibition of the C-raf kinase activity is calculated and plotted in order to determine the concentration of test compound required to inhibit 50% of the C-raf kinase activity (IC$_{50}$).

Selectivity:

In one embodiment, the PDP8 compound selectively inhibits one RAF (e.g., B-RAF), over at least one other RAF (e.g., A-RAF and/or C-RAF).

For example, in one embodiment, the ratio of the IC$_{50}$ value for B-RAF to the IC$_{50}$ value for the other RAF (e.g., A-RAF and/or C-RAF) is at least 10, more preferably at least 100, most preferably at least 1000.

Use in Methods of Inhibiting Cell Proliferation, Etc.

The PDP8 compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a PDP8 compound, as described herein.

In one embodiment, the method is a method of regulating (e.g., inhibiting) cell proliferation (e.g., proliferation of a cell), in vitro or in vivo, comprising contacting a cell with an effective amount of a PDP8 compound, as described herein.

In one embodiment, the method is performed in vitro.

In one embodiment, the method is performed in vivo.

In one embodiment, the PDP8 compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a PDP8 compound, as described herein, for use in a method of treatment of the human or animal body by therapy.

Use in the Manufacture of Medicaments

Another aspect of the present invention pertains to use of a PDP8 compound, as described herein, in the manufacture of a medicament for use in treatment.

In one embodiment, the medicament comprises the PDP8 compound.

Methods of Treatment

Another aspect of the present invention pertains to a method of treatment comprising administering to a patient in need of treatment a therapeutically effective amount of a PDP8 compound, as described herein, preferably in the form of a pharmaceutical composition.

Conditions Treated—Conditions Ameliorated by the Inhibition of RAF

In one embodiment (e.g., of use in methods of therapy, of use in the manufacture of medicaments, of methods of treatment), the treatment is treatment of a disease or disorder that is characterised by the up-regulation and/or activation of RAF (e.g., B-RAF), and/or is ameliorated by the inhibition of RAF (e.g., B-RAF).

In one embodiment, the treatment is treatment of cancer that is characterised by the up-regulation and/or activation of RAF (e.g., B-RAF), and/or is ameliorated by the inhibition of RAF (e.g., B-RAF).

Conditions Treated—Conditions Ameliorated by the Inhibition of RTKs

In one embodiment (e.g., of use in methods of therapy, of use in the manufacture of medicaments, of methods of treatment), the treatment is treatment of a disease or disorder that is characterised by the up-regulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of cancer that is characterised by the up-regulation and/or activation of a receptor tyrosine kinase (RTK), and/or is ameliorated by the inhibition of a receptor tyrosine kinase (RTK).

Conditions Treated—Conditions characterised by Angiogenesis

In one embodiment (e.g., of use in methods of therapy, of use in the manufacture of medicaments, of methods of treatment), the treatment is treatment of a disease or disorder that is characterised by inappropriate, excessive, and/or undesirable angiogenesis (as "anti-angiogenesis agents"). Examples of such disorders are discussed herein.

Conditions Treated—Proliferative Disorders and Cancer

The PDP8 compounds are useful in the treatment of proliferative disorders (as "anti-proliferative agents"), cancer (as "anti-cancer agents"), etc.

In one embodiment (e.g., of use in methods of therapy, of use in the manufacture of medicaments, of methods of treatment), the treatment is treatment of a proliferative disorder.

The term "proliferative disorder," as used herein, pertains to an unwanted or uncontrolled cellular proliferation of excessive or abnormal cells which is undesired, such as, neoplastic or hyperplastic growth.

In one embodiment, the treatment is treatment of: a proliferative disorder characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of: cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, skin cancer, squamous cancer, Kaposi's sarcoma, melanoma, malignant melanoma, lymphoma, or leukemia.

In one embodiment, the treatment is treatment of:
  a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
  a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
  a hematopoietic tumor of myeloid lineage, for example acute and chronic myelogenous leukemias, myelodysplastic syndrome, or promyelocytic leukemia;
  a tumour of mesenchymal origin, for example fibrosarcoma or habdomyosarcoma;
  a tumor of the central or peripheral nervous system, for example astrocytoma, neuroblastoma, glioma or schwannoma;
  melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of melanoma or malignant melanoma.

In one embodiment, the treatment is treatment of colorectal cancer.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The PDP8 compounds of the present invention may be used in the treatment of the cancers described herein, independent of the mechanisms discussed herein.

Conditions Treated—Proliferative Disorders and Cancer Associated with RAF

Cancers with, for example, activating mutations of ras, raf and EGFR or over expression of ras, raf and EGFR including any of the isoforms thereof, may be particularly sensitive to inhibitors of RAF (e.g., B-RAF) activity. Patients with activating mutants of RAF (e.g., B-RAF) may also find treatment with inhibitors of RAF (e.g., B-RAF) activity particularly beneficial. Cancers with other abnormalities leading to an upregulated raf-MEK-ERK pathway signal may also be particularly sensitive to treatment with inhibitors of RAF (e.g., B-RAF) activity. Examples of such abnormalities include constitutive activation of a growth factor receptor; overexpression of one or more growth factor receptors; and overexpression of one or more growth factors.

In one embodiment (e.g., of use in methods of therapy, of use in the manufacture of medicaments, of methods of treatment), the treatment is treatment of a proliferative disorder as described above, for example, cancer, that is characterised by:
  (a) activating mutants of ras or raf;
  (b) upregulation of ras or raf;
  (c) upregulated raf-MEK-ERK pathway signals;
  (d) upregulation of growth factor receptors, such as ERBB2 and EGFR.

In one embodiment, the proliferative disorder is characterised by cells which overexpress RAF (e.g., B-RAF) or express or overexpress mutant raf (e.g., B-RAF). In one embodiment, the proliferative disorder is characterised by cells which overexpress raf (e.g., B-RAF). In one embodiment, the proliferative disorder is characterised by cells which express or overexpress mutant RAF (e.g., B-RAF). In one embodiment, the proliferative disorder is characterised by cells which overexpress RAF (e.g., B-RAF), or overexpress mutant RAF (e.g., B-RAF), as compared to corresponding normal cells. In one embodiment, the overexpression is by a factor of 1.5, 2, 3, 5, 10, or 20.

In one embodiment (e.g., of use in methods of therapy, of use in the manufacture of medicaments, of methods of treatment), the treatment is treatment of a disease or disorder associated with a mutated form of RAF (e.g., B-RAF), such as, for example, the mutations described in Wan, P., et al., 2004, *Cell*, Vol. 116, pp. 855-867 and Stratton et al., 2003, published international patent application publication number WO 03/056036.

Conditions Treated—Inflammation Etc.

The PDP8 compounds are useful in the treatment of disorders associated with inflammation (as "anti-inflammation agents"), etc.

The function of inflammatory cells is controlled by many factors the effects of which are mediated by different signal transduction pathways. Although some key pro-inflammatory functions are mediated by p38 Map kinase (e.g., TNF release), others are mediated by other pathways. The raf-MEK-ERK pathway, in particular, is an important activating and proliferative signal in many inflammatory cells. B and T lymphocytes, in particular, require activation of the raf-MEK-ERK pathway for clonal expansion and generation of effector populations (see, e.g., Cantrell, D. A., 2003, *Immunol Rev.*, Vol. 192, pp. 122-130; Genot, E. and Cantrell, D. A., 2000, *Curr. Opin. Immunol.*, Vol. 12(3), pp. 289-294).

In one embodiment, the treatment is treatment of: inflammatory diseases, such as rheumatoid arthritis, osteoarthritis, rheumatoid spondylitis, gouty arthritis, traumatic arthritis, rubella arthritis, psoriatic arthritis, and other arthritic conditions; Alzheimer's disease; toxic shock syndrome, the inflammatory reaction induced by endotoxin or inflammatory bowel disease; tuberculosis; atherosclerosis; muscle degeneration; Reiter's syndrome; gout; acute synovitis; sepsis; septic shock; endotoxic shock; gram negative sepsis; adult respiratory distress syndrome; cerebral malaria; chronic pulmonary inflammatory disease; silicosis; pulmonary sarcoisosis; bone resorption diseases; reperfusion injury; graft versus host reaction; allograft rejections; fever and myalgias due to infection, such as influenza, cachexia, in particular cachexia secondary to infection or malignancy, cachexia secondary to acquired immune deficiency syndrome (AIDS); AIDS; ARC (AIDS related complex); keloid formation; scar tissue formation; Crohn's disease; ulcerative colitis; pyresis; chronic obstructive pulmonary disease (COPD); acute respiratory distress syndrome (ARDS); asthma; pulmonary fibrosis; bacterial pneumonia.

In one preferred embodiment, the treatment is treatment of: arthritic conditions, including rheumatoid arthritis and rheumatoid spondylitis; inflammatory bowel disease, including Crohn's disease and ulcerative colitis; and chronic obstructive pulmonary disease (COPD).

In one preferred embodiment, the treatment is treatment of: an inflammatory disorder characterized by T-cell proliferation (T-cell activation and growth), for example, tissue graft rejection, endotoxin shock, and glomerular nephritis.

Screening

Prior to treatment, a patient may be screened to determine whether a disease or disorder from which the patient is or may be suffering is one which would be susceptible to treatment with a compound that inhibits RAF (e.g., B-RAF) activity or has activity against an RTK (e.g., FGFR-1, FGFR-2, FGFR-3, VEGFR-2, Tie2, EphB2).

For example, a biological sample taken from a patient may be analysed to determine whether a disease or disorder, such as cancer, that the patient is or may be suffering from is one which is characterised by elevated expression or activation of RAF (e.g., B-RAF), or an RTK (e.g., FGFR-1, FGFR-2, FGFR-3, VEGFR-2, Tie2, EphB2), or is the result of an activating mutation. Thus, the patient may be subjected to a diagnostic test to detect a marker characteristic of over-expression or activation of RAF (e.g., B-RAF) or an RTK (e.g., FGFR-1, FGFR-2, FGFR-3, VEGFR-2, Tie2, EphB2), or a mutation thereof.

As used herein, the term "marker" includes genetic markers (including, e.g., the measurement of DNA composition to identify mutations of raf, ras, MEK, ERK or a growth factor such as ERBB2 or EGFR) and markers which are characteristic of upregulation of raf, ras, MEK, ERK, growth factors receptors such as ERBB2 or EGFR including enzyme activity, enzyme levels, enzyme state (e.g. phosphorylated or not) and mRNA levels of the aforementioned proteins. Methods for identification and analysis of mutations are well known. See, for example, *Anticancer Research*, 1999, Vol. 19(4A), pp. 2481-2483; *Clin. Chem.*, 2002, Vol. 48, p. 428; *Cancer Research*, 2003, Vol. 63(14), pp. 3955-3957.

The term "marker" further includes genetic markers including, for example, the measurement of DNA composition to identify mutations of RTKs, e.g., FGFR-1, FGFR-2, FGFR-3, VEGFR-2, Tie2, and EphB2. The term "marker" also includes markers that are characteristic of up-regulation of RTKs, including enzyme activity, enzyme levels, enzyme state (e.g., phosphorylated or not) and mRNA levels of the aforementioned proteins.

Upregulation includes elevated expression or over expression, including gene amplification (i.e., multiple gene copies), increased expression by a transcriptional effect, hyper-activity, and activation, including activation by mutations.

Other tumours that have an upregulated raf-MEK-ERK pathway signal may also be particularly sensitive to inhibitors of RAF (e.g., B-RAF) activity. A number of assays exist which can identify tumours that exhibit upregulation in the raf-MEK-ERK pathway, including the commercially available MEK1/2 (MAPK Kinase) assay from Chemicon International. Upregulation can result from over expression or activation of growth factor receptors such as ERBB2 and EGFR, or mutant ras or raf proteins.

Typical methods for screening for over expression, upregulation or mutants include, but are not limited to, standard methods such as reverse-transcriptase polymerase chain reaction (RT-PCR) or in-situ hybridisation.

In screening by RT-PCR, the level of mRNA for the aforementioned proteins in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described, for example, in Ausubel, F. M. et al., eds., *Current Protocols in Molecular Biology*, 2004 (John Wiley & Sons Inc.); Innis, M. A. et-al., eds., *PCR Protocols: A Guide to Methods and Applications*, 1990 (Academic Press). Reactions and manipulations involving nucleic acid techniques are also described in Sambrook et al., *Molecular Cloning: A Laboratory Manual*, 3rd edition, 2001 (Cold Spring Harbor Laboratory Press). Alternatively, a commercially available kit for RT-PCR (e.g., Roche Molecular Biochemicals) may be used, or methodology as set forth in U.S. Pat. Nos. 4,666,828; 4,683,202; 4,801,531; 5,192,659, 5,272,057, 5,882,864, and 6,218,529.

An example of an in-situ hybridisation technique would be fluorescence in situ hybridisation (FISH) (see, e.g., Angerer, 1987, *Meth. Enzymol.*, Vol. 152, p. 649). Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, in order to enable specific hybridization with the target nucleic acid(s) under stringent conditions. Standard methods for carrying out FISH are described, for example, in Ausubel, F. M. et al., eds., *Current Protocols in Molecular Biology,* 2004 (John Wiley & Sons Inc.); Bartlett, John M. S., "Fluorescence In Situ Hybridization: Technical Overview," in: *Molecular Diagnosis of Cancer, Methods and Protocols, 2nd ed.* (*Series: Methods in Molecular Medicine*), March 2004, pp. 77-88 (ISBN: 1-59259-760-2).

Alternatively, the protein products expressed from the mRNAs may be assayed by immunohistochemistry of tumour sections, solid phase immunoassay with microtiter plates, Western blotting, 2-dimensional SDS-polyacrylamide gel electrophoresis, ELISA, and other methods known in the art for detection of specific proteins. Detection methods would include the use of site specific antibodies, such as, phospho raf, phospho ERK, phospho MEK, or phosphotyrosine. In addition to tumour biopsies, other samples which could be utilised include pleural fluid, peritoneal fluid, urine, stool biopsies, sputum, blood (isolation and enrichment of shed tumour cells).

In addition, mutant forms of raf, EGFR or ras can be identified by direct sequencing of, for example, tumour biopsies using PCR and methods to sequence PCR products directly, for example, using methods as described herein. These and other well-known techniques for detection of the over expression, activation, or mutations may be used.

Also, abnormal levels of proteins such as raf, ras and EGFR can be measured using standard enzyme assays, for example for raf those assays described herein.

Alternative methods for the measurement of the over expression or activation of FGFR, Tie, VEGFR or Eph kinases, in particular VEGFR including the isoforms thereof, include the measurement of microvessel density. This can be measured, for example, using methods described by Orre and Rogers, 1999, *Int. J. Cancer*, Vol. 84(2), pp. 101-108. Assay methods also include the use of markers; for example, in the case of VEGFR, markers include CD31, CD34 and CD105 (Mineo et al., 2004, *J. Clin. Pathol.*, Vol. 57(6), pp. 591-597).

Treatment

The term "treatment," as used herein in the context of treating a disease or disorder, pertains generally to treatment and therapy, whether of a human or an animal (e.g., in veterinary applications), in which some desired therapeutic effect is achieved, for example, the inhibition of the progress of the disease or disorder, and includes a reduction in the rate of progress, a halt in the rate of progress, alleviation of symptoms of the disease or disorder, amelioration of the disease or disorder, and cure of the disease or disorder. Treatment as a prophylactic measure (i.e., prophylaxis) is also included. For example, use with patients who have not yet developed the disease or disorder, but who are at risk of developing the disease or disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development.

One aspect of the present invention pertains to a compound as described herein, in combination with one or more additional therapeutic agents, as described below.

Examples of additional therapeutic agents that may be administered together (whether concurrently or at different time intervals) with the compounds described herein include:

(a) topoisomerase I inhibitors;
(b) antimetabolites;
(c) tubulin targeting agents;
(d) DNA binder and topoisomerase II inhibitors;
(e) alkylating agents;
(f) monoclonal antibodies;
(g) anti-hormones;
(h) signal transduction inhibitors;
(i) proteasome inhibitors;
(j) DNA methyl transferases;
(k) cytokines and retinoids.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The PDP8 compounds described herein may also be used as cell culture additives to inhibit RAF (e.g., B-RAF) function, e.g., to inhibit cell proliferation, etc.

The PDP8 compounds described herein may also be used as part of an in vitro assay, for example, in order to determine whether a candidate host is likely to benefit from treatment with the compound in question.

The PDP8 compounds described herein may also be used as a standard, for example, in an assay, in order to identify other compounds, other RAF (e.g., B-RAF) function inhibitors, other anti-proliferative agents, other anti-cancer agents, etc.

Kits

One aspect of the invention pertains to a kit comprising (a) a PDP8 compound as described herein, or a composition comprising a PDP8 compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The PDP8 compound or pharmaceutical composition comprising the PDP8 compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus.

In one preferred embodiment, the subject/patient is a human.

Formulations

While it is possible for the PDP8 compound to be administered alone, it is preferable to present it as a pharmaceutical formulation (e.g., composition, preparation, medicament) comprising at least one PDP8 compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one PDP8 compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringers Solution, or Lactated Ringer's Injection. Typically, the concentration of the compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the PDP8 compounds, and compositions comprising the PDP8 compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular PDP8 compound, the route of administration, the time of administration, the rate of excretion of the PDP8 compound, the duration of the treatment, other drugs, compounds, and/or materials used in combination, the severity of the disease or disorder, and the species, sex, age, weight, condition, general health, and prior medical history of the patient. The amount of PDP8 compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the PDP8 compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Several methods for the chemical synthesis of compounds of the present invention are described herein. These and/or other well known methods may be modified and/or adapted in known ways in order to facilitate the synthesis of additional compounds within the scope of the present invention.

Descriptions of general laboratory methods and procedures, useful for the preparation of the compounds described herein, are provided in *Vogel's Textbook of Practical Organic Chemistry, 5th Edition,* 1989, (Editors: Furniss, B. S., Hannaford, A. J., Smith, P. W. G., Tatchell, A. R.) (published by Longmann, UK).

Methods for the synthesis of pyridine compounds in particular are described in *Heterocyclic Chemistry, 3rd Edition,* 1998, Joule, J. A, Mills, R. and Smith, G. F. (published by Chapman & Hall, UK).

Many of the compounds described herein can be prepared via a key intermediate (2), conveniently substituted on the aromatic ring. This intermediate can be prepared from commercially available starting material, 4-chloro-3-nitro-pyridin-2-amine, (1), and substituted amino-phenols. Compounds 2 are then protected selectively at the amino group, for example as a Boc carbamate or trifluoroacetamide, to afford intermediates, (3). The intermediates, (3), can also be obtained directly from 4-chloro-3-nitro-pyridin-2-amine, (1), and N-Boc-protected amino-phenols. The nitro group of the protected intermediate, (3), may be reduced to an amino group with Pd/C and ammonium formate or hydrogen, to another key diamino intermediate (4). An example of such a method is illustrated in the following Scheme 1.

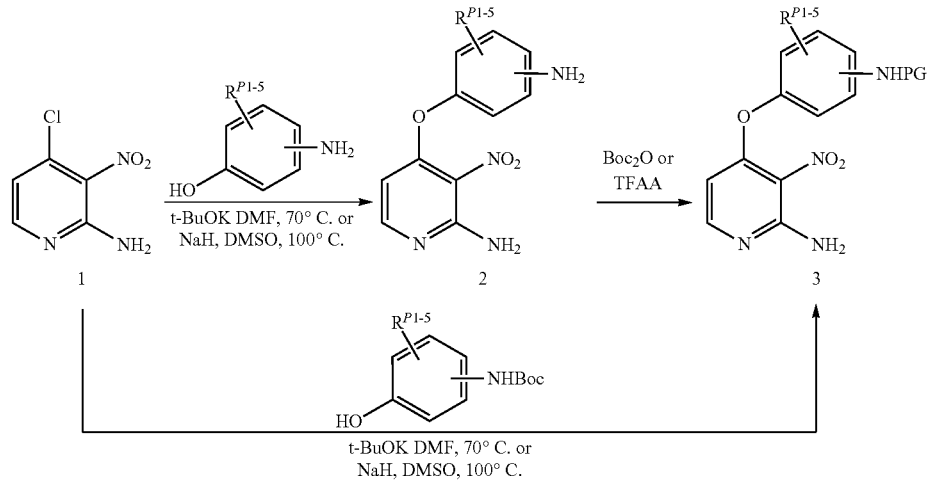

Scheme 1

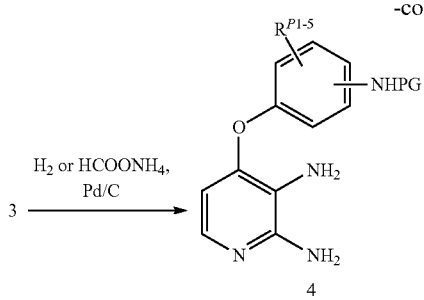

PG = Boc or COCF$_3$

Note that compounds with substituted or unsubstituted phenyl groups have been synthesised and are described herein. The following Schemes are illustrated using unsubstituted phenyl or specifically substituted phenyl, but it should be understood that these methods are also suitable for the preparation of compounds with substituted (or differently substituted) phenyl rings.

Pyridopyrazinones can be obtained from intermediate 4 by reaction with ethyl glyoxylate, ethyl pyruvate or similar a-ketoesters. Both isomers 5 and 6 can be obtained from the reaction of 4 with ethyl glyoxalate. Similarly, two isomers (7 and 8) can be obtained from the reaction of 4 with ethyl pyruvate (R=-Me), ethyltrifluoropyruvate (R=—CF$_3$), ethyl 3-bromo-2-oxopropanoate (R=—CH$_2$Br), or other optionally substituted alkyl 2-oxo esters. Amino-pyridopyrazinones 9 and 10 can be obtained from intermediate 4 by reaction with ethyl 2-ethoxy-2-iminoacetate. The ratio of the two isomers can be influenced by the choice of solvents, so that one is obtained preferentially (Scheme 2).

Scheme 2

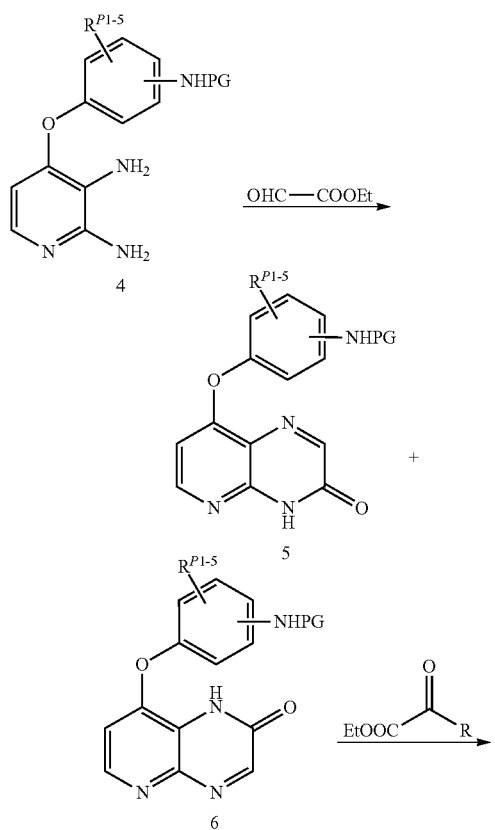

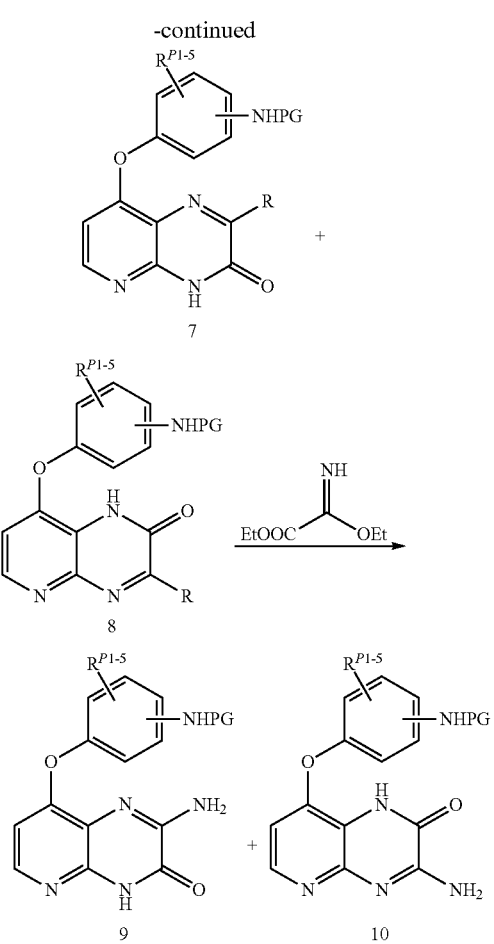

Deprotection of the protecting group (PG) with TFA or tetrabutyl ammonium fluoride (for Boc protecting group) or ammonia (for trifluoroacetamide) produces the common intermediates 11-16 (Scheme 3).

Scheme 3

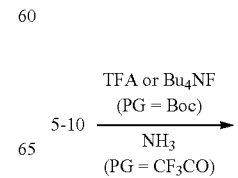

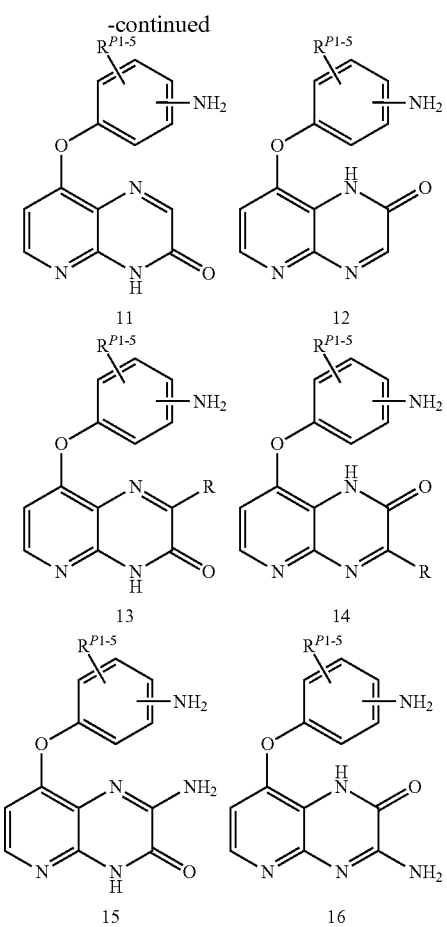

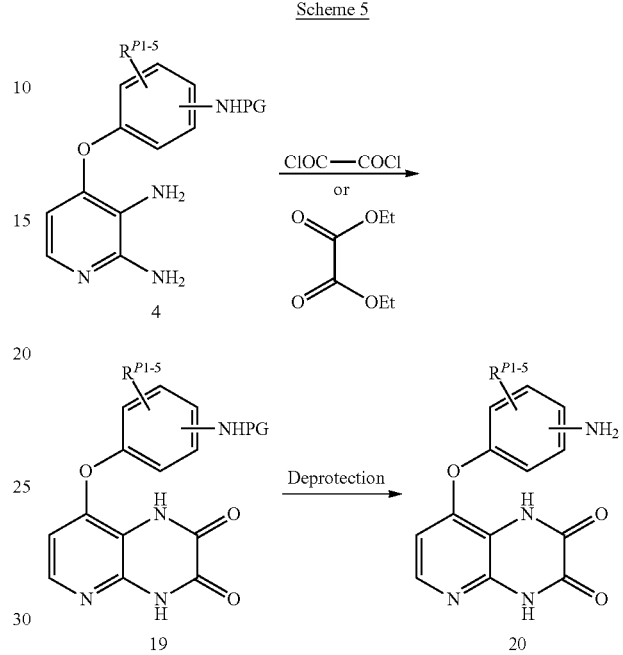

Pyridopyrazin-diones 20 can be obtained from intermediate 4 by reaction with diethyloxalate or oxalyl chloride followed by deprotection (Scheme 5).

Pyridopyrazines 18 can be obtained from intermediate 4 by reaction with glyoxal or 1,4-dioxane-2,3-diol followed by deprotection (Scheme 4).

Amino-pyridopyrazines 25 and 26 can be obtained from intermediates 5 and 6. The carbonyl group of the pyrazinone can be converted to the chloropyrazine intermediates 21 or 22 with $POCl_3$ or $NCS/PPh_3$, then to aminopyrazines 23 or 24 using ammonia or primary or secondary amine. Deprotection affords the common intermediates 25 or 26 (Scheme 6).

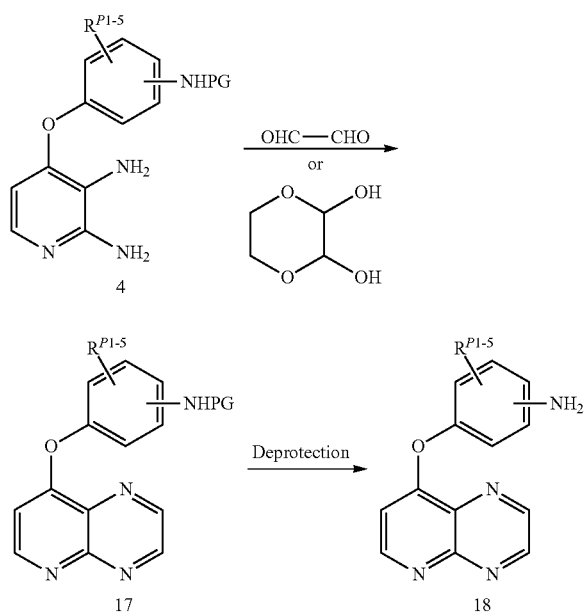

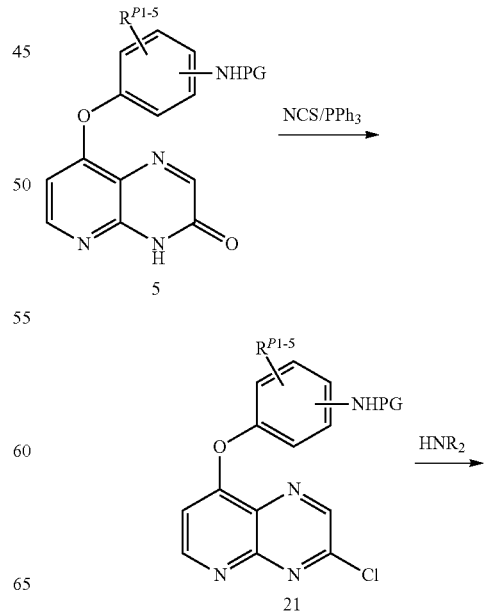

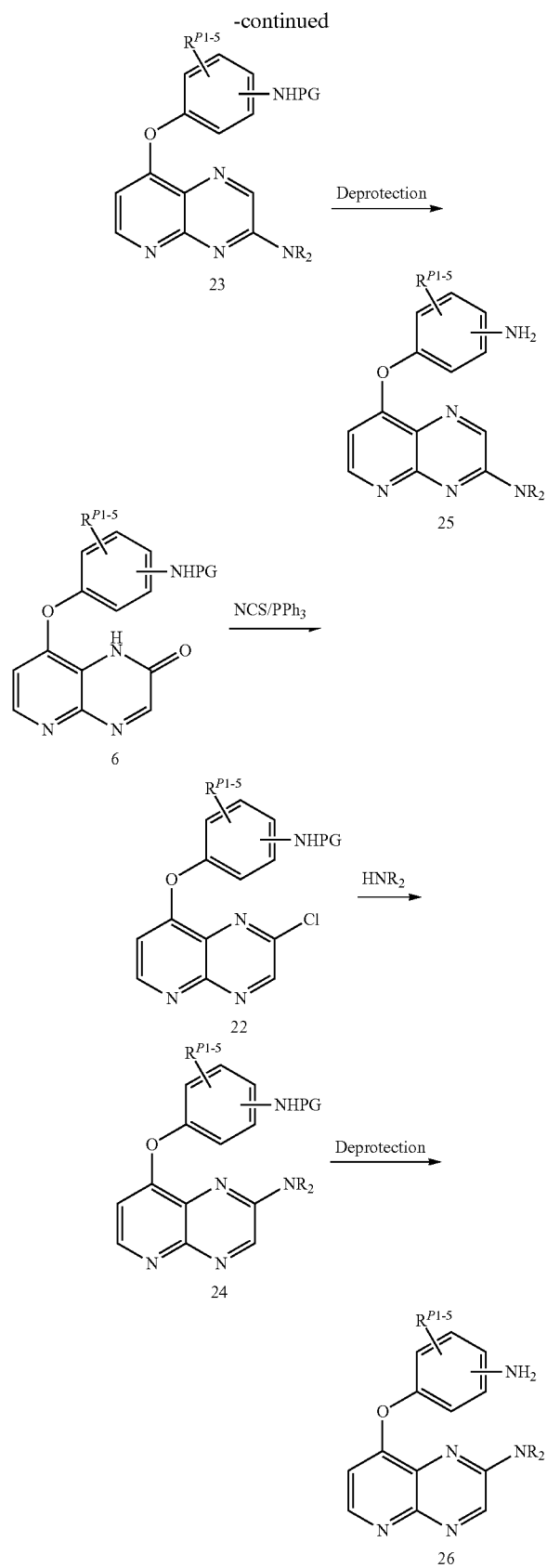

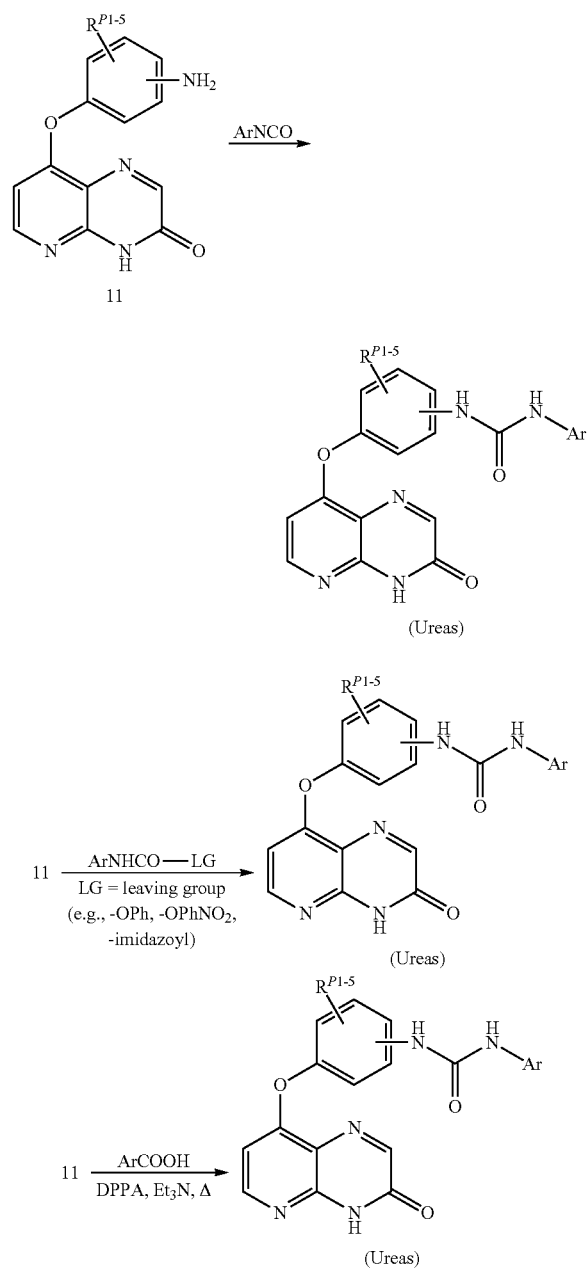

linker groups, L, and different terminal groups, A. For example, the key intermediate 11 can be reacted with activated carboxylic acids or acid chlorides to afford amides (NHCO) or with isocyanates or with activated carbamates to afford ureas (NHCONH). Isocyanates can also be formed in situ by reaction of carboxylic acids with, for example, DPPA (diphenylphosphoryl azide) and Curtius rearrangement of the corresponding azide upon heating. The key intermediate 11 can also react with isothiocyanates to afford thioureas (NHCSNH) and with sulfonyl chlorides to afford sulfonamides (SO$_2$NH). Examples of such methods are illustrated in the following scheme (Scheme 7).

These common intermediates (11-16, 18, 20, 25, 26) may then be used to prepare a range of compounds with different -continued

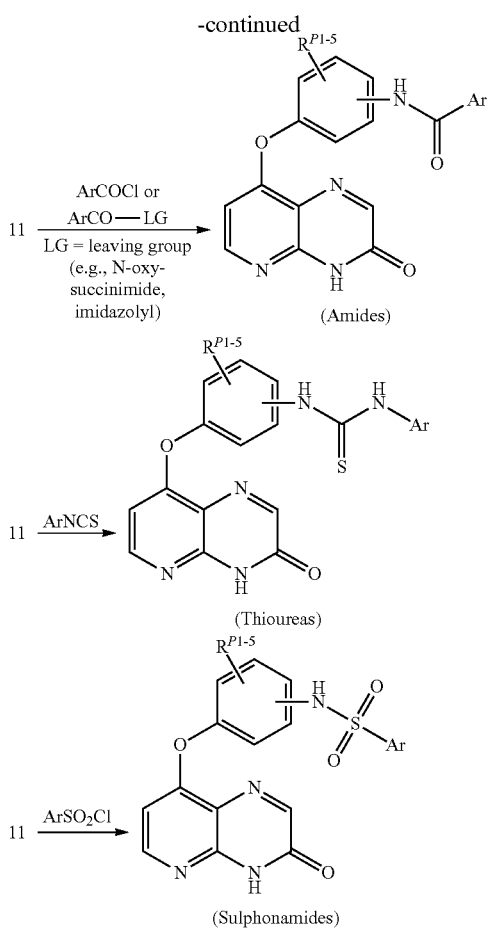

Alternatively, the amino position of the common intermediate 11 can be activated by reaction, for example, with phenyl chloroformate. The activated carbamate so formed can then be reacted with aromatic amines to afford the corresponding ureas, as illustrated in Scheme 8.

Scheme 8

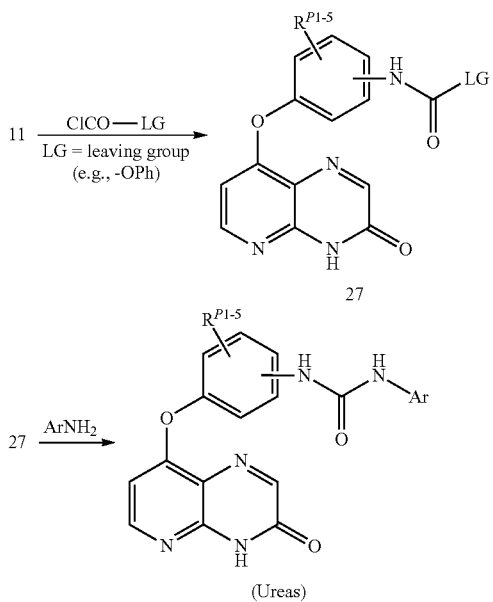

An alternative strategy is to perform the reactions described in Schemes 7 and 8 (formation of urea or amide) on the nitro-amino intermediate 2 prior to cyclisation. Similarly, amino phenols can react with isocyanates to form the intermediate 30, which is then coupled with 1 to afford 28. Such an approach is exemplified for the urea linker in Scheme 9. Similar methods can be used for compounds with other linkers.

Schem 9

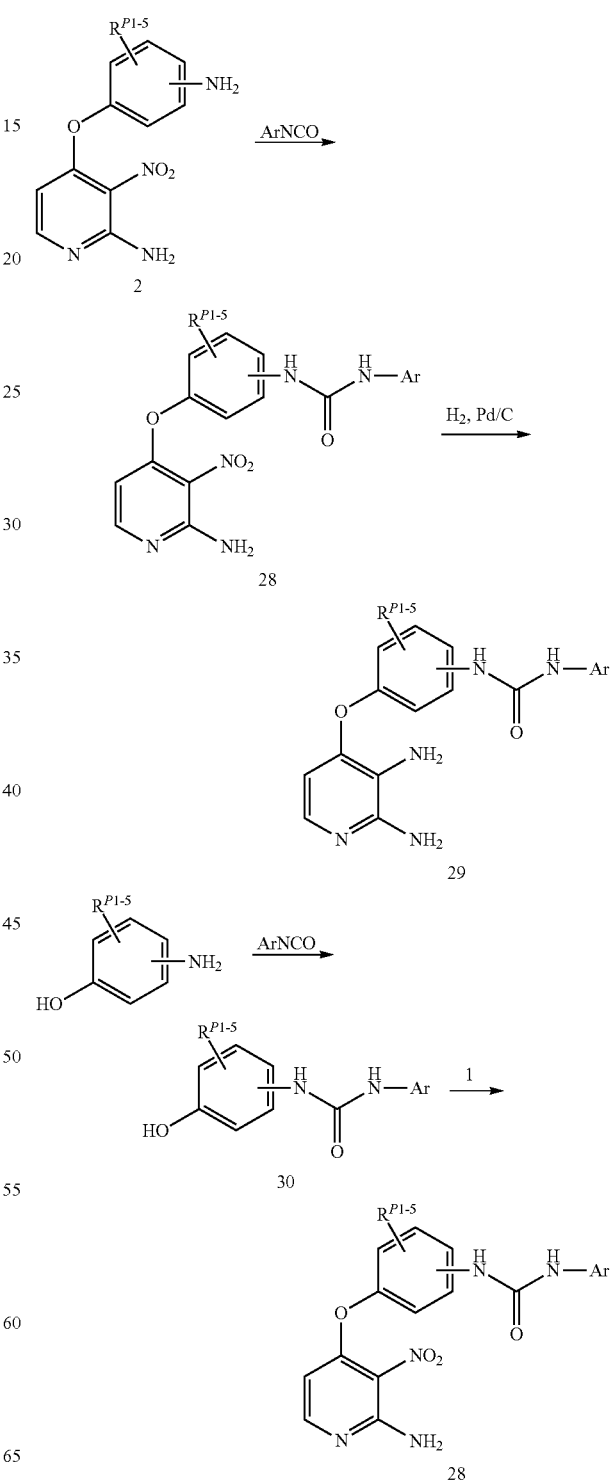

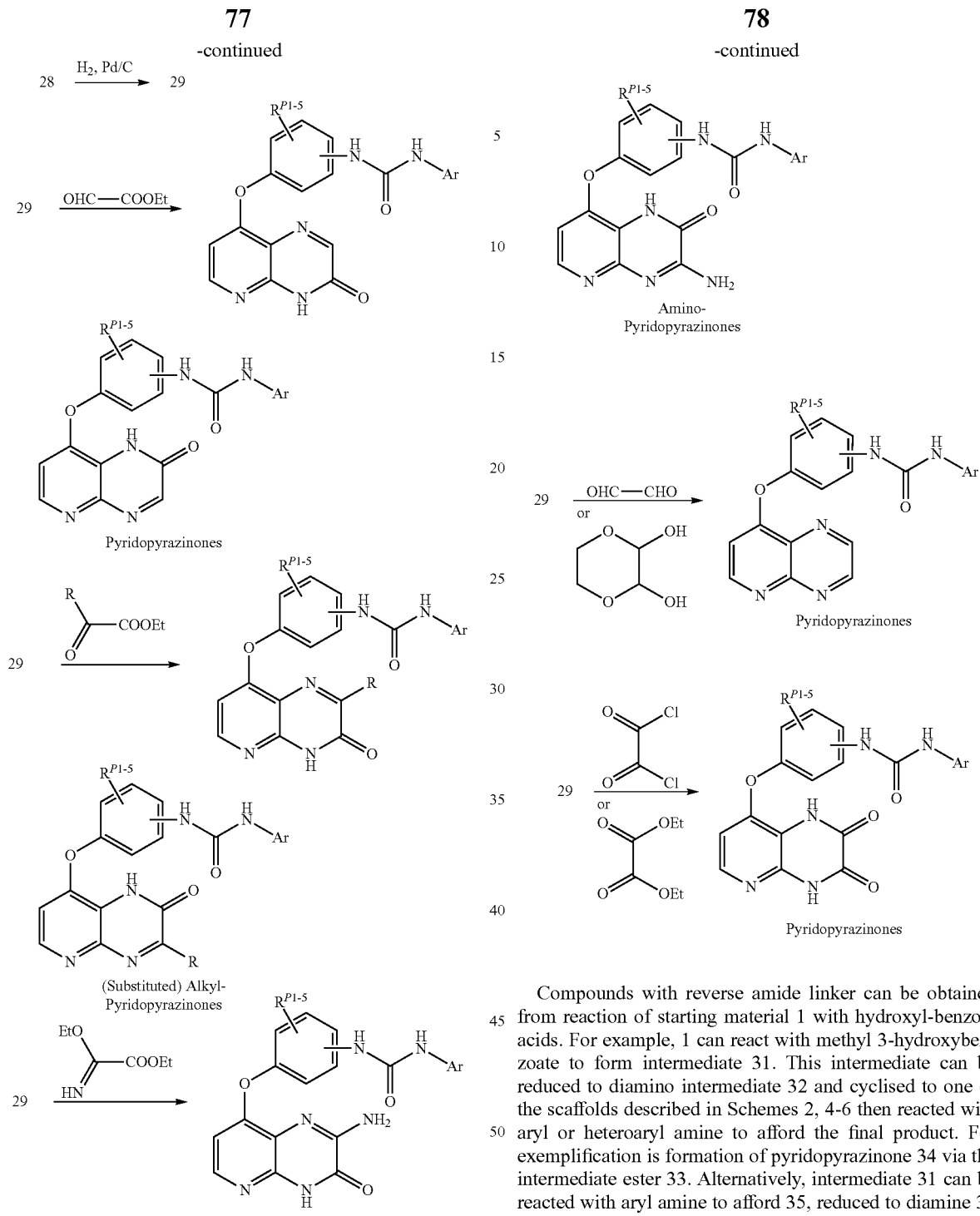

Compounds with reverse amide linker can be obtained from reaction of starting material 1 with hydroxyl-benzoic acids. For example, 1 can react with methyl 3-hydroxybenzoate to form intermediate 31. This intermediate can be reduced to diamino intermediate 32 and cyclised to one of the scaffolds described in Schemes 2, 4-6 then reacted with aryl or heteroaryl amine to afford the final product. For exemplification is formation of pyridopyrazinone 34 via the intermediate ester 33. Alternatively, intermediate 31 can be reacted with aryl amine to afford 35, reduced to diamine 36 and cyclised to the same product 34 (Scheme 10).

Scheme 10

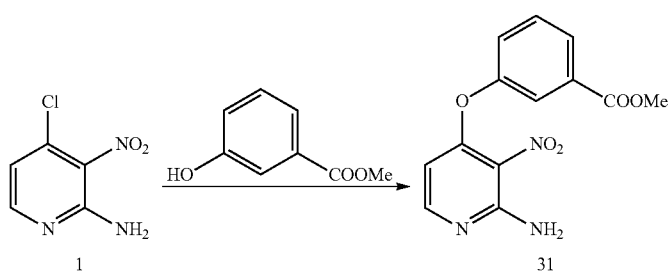

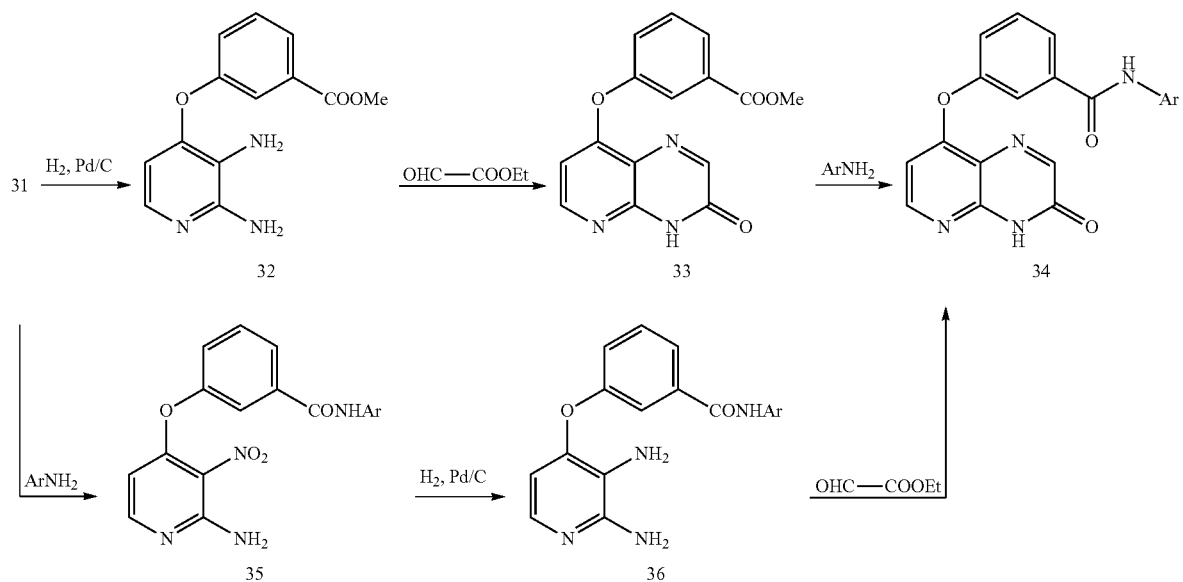

Compounds with other linkers between the hinge-binding bicyclic system and middle ring can be obtained by reacting the starting material 1, with for example mercaptoanilines, aminoanilines or mercaptobenzoic esters, as exemplified in Scheme 11. The intermediates thus obtained can be converted further to inhibitors containing the same scaffolds described for the O-linker compounds using methods similar to those in Schemes 1-10.

Scheme 11

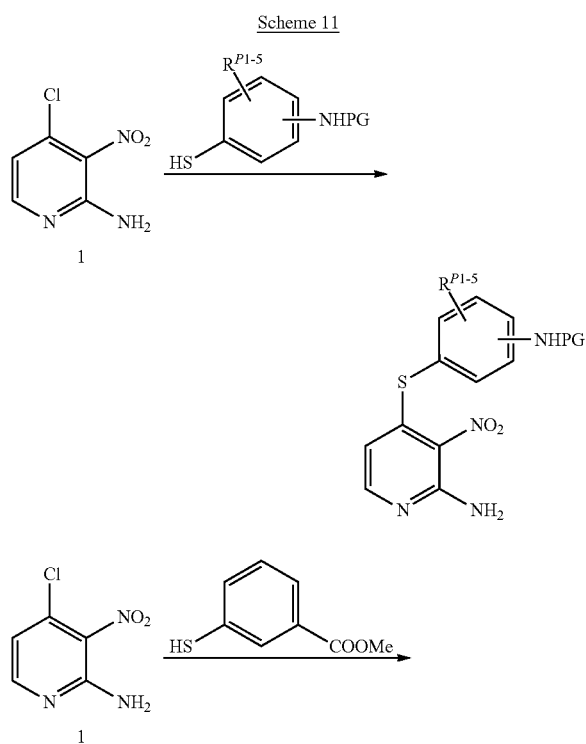

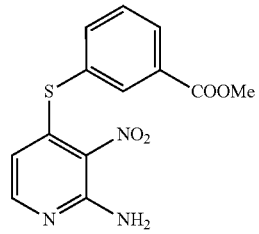

Chemical Synthesis

All starting materials, reagents and solvents for reactions were reagent grade and used as purchased. Chromatography solvents were HPLC grade and were used without further purification. Reactions were monitored by thin layer chromatography (TLC) analysis using Merck silica gel 60 F-254 thin layer plates. Flash column chromatography was carried out on Merck silica gel 60 (0.015-0.040 mm) or in disposable Isolute Flash Si and Si II silica gel columns. Preparative TLC was performed on either Macherey-Nagel [809 023] pre-coated TLC plates SIL G-25 $UV_{254}$ or Analtech [2015] pre-coated preparative TLC plates, 2000 μm with $UV_{254}$. LCMS analyses were performed on a Micromass LCT/ Water's Alliance 2795 HPLC system with a Discovery 5 μm, C18, 50 mm×4.6 mm i.d. column from Supelco at a temperature of 22° C. using the following solvent systems: Solvent A: Methanol; Solvent B: 0.1% formic acid in water at a flow rate of 1 mL/min. Gradient starting with 10% A/90% B from 0-0.5 minutes then 10% A/90% B to 90% A/10% B from 0.5 minutes to 6.5 minutes and continuing at 90% A/10% B up to 10 minutes. From 10-10.5 minutes the gradient reverted back to 10% A/90% where the concentrations remained until 12 minutes. UV detection was at 254 nm and ionisation was positive or negative ion electrospray. Molecular weight scan range is 50-1000. Samples were supplied as 1 mg/mL in DMSO or methanol with 3 μL injected on a partial loop fill. NMR spectra were recorded in DMSO-$d_6$ on a Bruker Advance 500 MHz spectrometer.

(I) Coupling of 2-Amino-3-Nitro-4-Chloropyridine with Phenolates

Synthesis 1

Tert-butyl 4-(2-amino-3-nitropyridin-4-yloxy)phenylcarbamate

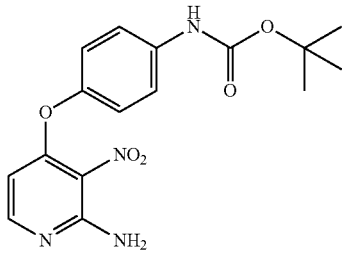

Method A1: Tert-butyl 4-hydroxyphenylcarbamate (3.63 g, 17.4 mmol) was dissolved in dry DMF (150 mL). Potassium tert-butoxide (2.62 g, 23.4 mmol) was added and the stirring was continued for 30 minutes at room temperature. 4-Chloro-3-nitropyridin-2-amine (3.0 g, 17.3 mmol) was added as a solid in one portion and the reaction mixture was subsequently heated at 85° C. for 4 hours. The reaction mixture was cooled, diluted with ethyl acetate (800 ml) and washed with water (1×800 ml) and brine (2×800 ml). The organic layer was dried with magnesium sulphate and evaporated. The crude was chromatographed over silica (eluant ethyl acetate: cyclohexane 1:2) to yield 4.0 g (63 yield) of tert-butyl 4-(2-amino-3-nitropyridin-4-yloxy)phenylcarbamate.

$^1$H-NMR (CDCl$_3$), δ (ppm), J (Hz): $^1$H-NMR, δ (ppm), J (Hz): 1.54 (9H), 6.04 (d, 1H, J=7.4 Hz), 6.15 (bs, 2H), 7.06 (d, 2H, J=8.3 Hz), 7.44 (d, 2H, J=8.3 Hz), 7.96 (d, 1H, J=7.4 Hz). LC-MS (m/z): 347 (M+H, 100).

Synthesis 2

Tert-butyl 4-(2-amino-3-nitropyridin-4-yloxy)naphthalen-1-ylcarbamate

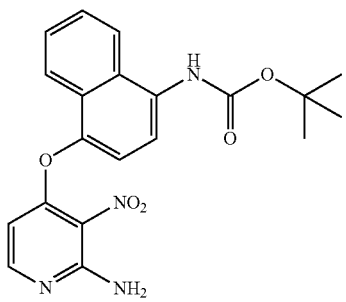 [SMILES: CC(C)(C)OC(=O)Nc1ccc(Oc2ccnc(N)c2[N+](=O)[O-])c2ccccc12]

Method A1 was used with tert-butyl 4-hydroxynaphthalen-1-ylcarbamate (3.9 g, 15 mmol) to yield tert-butyl 4-(2-amino-3-nitropyridin-4-yloxy)naphthalen-1-ylcarbamate (5.4 g, 90% yield) upon recrystallization from dichloromethane.

$^1$H-NMR (CDCl$_3$), δ (ppm), J (Hz): 1.58 (s, 9H), 5.92 (d, 1H, J=5.8 Hz), 6.21 (s, 1H), 7.25 (d, 1H, J=8.3 Hz), 7.56 (t, 1H, J=8.1 Hz), 7.62 (t, 1H, J=8.3 Hz), 7.88 (d, 1H, J=5.8 Hz), 7.93 (s, 1H), 7.95 (d, 1H, J=8.5 Hz), 8.00 (d, 1H, J=8.3 Hz), LC-MS: m/z 397 (M+H, 100).

Synthesis 3

4-(4-amino-3-(methylthio)phenoxy)-3-nitropyridin-2-amine

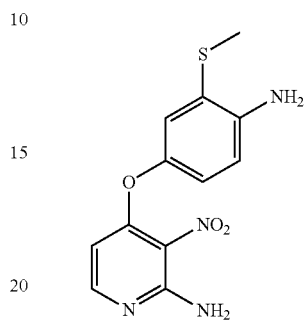

Method A2 Sodium hydride (148 mg) was added to dry DMSO (5.5 mL) and the mixture was stirred at RT for 20 minutes under Ar atmosphere. 4-amino-3-(methylthio)phenol (573 mg, 3.7 mmol) was added thereto, and the mixture stirred for 10 more minutes. Next, 4-Chloro-3-nitropyridin-2-amine (3.7 mmol) was added, and the mixture was heated to 100° C. and stirred for 3 hours. After cooling down, water was added, and the mixture extracted three times with EtOAc. The combined organic layers were washed first with a saturated aqueous sodium hydrogen carbonate solution then water, dried over MgSO$_4$ and evaporated to afford the title compound (657 mg, 61%) was obtained after purification by chromatography on silica gel (EtOAc-DCM, 1:1) as a red brown solid (R$_f$ 0.56, EtOAc-DCM, 1:1).

$^1$H-NMR (DMSO-d$_6$), δ (ppm), J (Hz): 2.36 (s, 3H, CH$_3$); 5.18 (s, 2H, NH$_{2, Ph}$), 5.92 (d, 1H, H$_{Py}$ J=5.8 Hz), 6.75 (dd, 1H, H$_{Ph}$ J=8.6 Hz and J=2.1 Hz), 6.81 (dd, 1H, H$_{Ph}$ J=8.7 and J=2.6 Hz), 6.98 (d, 1H, H$_{Ph}$ J=2.6 Hz), 7.07 (bs, 2H, NH$_{2, Py}$), 7.95 (d, 1H, H$_{Py}$ J=5.7 Hz). $^{13}$C-NMR (DMSO-d$_6$), δ (ppm), J (Hz): 15.6, 99.8, 114.7, 119.7, 120.7, 121.4, 121.5, 143.2, 145.1, 152.8, 153.6, 159.9. LC-MS (m/z): 293 (M+H, 100), rt=5.87 min.

Synthesis 4

4-amino-3-(methylthio)phenol

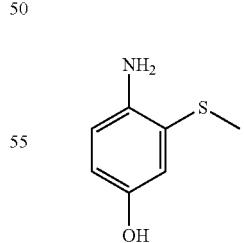

Method C4: A suspension of iron powder (220 mg, 4 mmol), NH$_4$Cl (310 mg, 5.8 mmol) in a mixture EtOH/H$_2$O (4 mL/1.2 mL) was heated to reflux for 10 minutes. 3-(methylthio)-4-nitrophenol (185 mg, 1 mmol) was added and the mixture stirred for 5 hours. After cooling to RT, the dark slurry was filtered over celite and washed with MeOH. After removing the solvent, EtOAc was added and the mixture filtered once again. The filtrate was washed successively with water and brine, and then dried over MgSO$_4$. Removal of the solvent under vacuum provided the title compound as a green-grey powder (80 mg, 53% yield).

$^1$H-NMR (DMSO-d$_6$), δ (ppm), J (Hz): 2.29 (s, 3H, H$_{Me}$), 4.48 (bs, 2H, NH$_2$), 6.44 (d, 1H, H$_{arom}$, J=8.51-14, 6.54 (d, 1H, H$_{arom}$ J=8.5 Hz), 6.61 (s, 1H, H$_{arom}$), 8.58 (bs, 1H, OH). $^{13}$C-NMR (DMSO-d$_6$), δ (ppm), J (Hz): 15.9, 114.7, 115.4, 116.5, 120.1, 139.5, 148.7. GC-MS (m/z): 155.09.

Synthesis 5

3-(methylthio)-4-nitrophenol

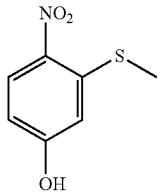

To a solution of 3-fluoro-4-nitrophenol (2 g, 12.7 mmol) in dry DMF (67 mL) were added by aliquots 2 equivalents of sodium thiomethoxide (1.78 g, 25.5 mmol) followed by 3 equivalents of potassium carbonate (5.27 g, 38.2 mmol). The mixture was stirred at RT for 23 hours and then water (100 mL) was added. The mixture was extracted with EtOAc, and the combined organic layers washed successively with water (60 mL) and brine (60 mL) and then dried over MgSO$_4$. The solvent was evaporated under vacuum to provide the title compound (2.12 g, 90%) as a yellow powder.

$^1$H-NMR (DMSO-d$_6$), δ (ppm), J (Hz): 2.44 (s, 3H, H$_{Me}$), 6.72 (d, 1H, H$_{arom}$, J=9.0 Hz), 6.79 (s, 1H, H$_{arom}$), 8.19 (d, 1H, H$_{arom\ 5}$, J=9.1 Hz), 11.20 (bs, 1H, OH). $^{13}$C-NMR (DMSO-d$_6$), δ (ppm), J (Hz): 15.2, 111.3, 112.0, 128.7, 136.7, 142.0, 162.9.

Synthesis 6

4-(4-Amino-3-fluorophenoxy)-3-nitropyridin-2-amine

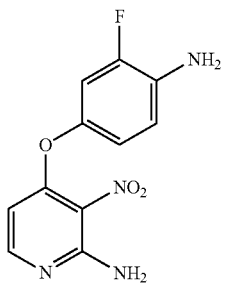 [SMILES: Nc1ccc(Oc2ccnc(N)c2[N+](=O)[O-])cc1F]

Method A2 was used with 4-amino-3-fluorophenol (1.00 g, 7.9 mmol) to give 1.8 g (86% yield) of 4-(4-amino-3-fluorophenoxy)-3-nitropyridin-2-amine as a dark solid.

$^1$H-NMR (DMSO-d6), δ (ppm), J (Hz): 5.17 (bs, 2H), 5.94 (d, 1H, J=5.7 Hz), 6.75-6.84 (m, 2H), 6.97 (d, 1H, J=11.7 Hz) 7.09 (bs, 1H), 7.96 (d, 1H, J=5.7 Hz). LC-MS (m/z): 235 (M+H, 100).

Synthesis 7

4-(4-N-(tert-Butoxycarbonyl)amino-3-fluorophenoxy)-3-nitro-2-amino-pyridine

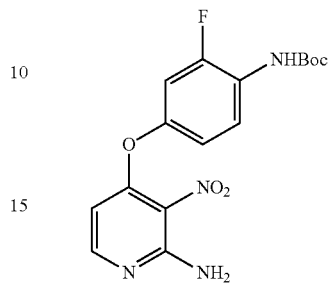

Method A1 was used with 4-N-Boc-amino-3-fluorophenol (1.2 g, 5.4 mmol) to afford the title compound as a glassy yellow solid (1.9 g, 96%).

$^1$H-NMR (DMSO-d$_6$), δ (ppm), J (Hz): 1.46 (s, 9H, tert-Bu), 6.08 (d, 1H, J=5.5, H$_{Py}$), 7.01 (m, 1H, H$_{arom}$), 7.18 (br s, 2H, NH$_2$), 7.22 (m, 1H, H$_{arom}$), 7.67 (m, 1H, H$_{arom}$), 8.04 (d, 1H, J=5.5, Hp), 9.03 (s, 1H, NH$_{Boc}$); $^{13}$C-NMR (DMSO-d$_6$), δ (ppm), J (Hz): 28.0, 79.5, 100.7, 108.8 (d, J$_{FC}$=23.1), 116.2 (d, J$_{FC}$=3.1), 121.7, 124.3 (d, J$_{FC}$=12.2), 125.4, 149.4 (d, J$_{FC}$=10.1), 153.0, 153.3, 153.9, 154.1 (d, J$_{FC}$=249), 158.6; $^{19}$F-NMR (DMSO-d$_6$), δ (ppm): −120.7; LC-MS (m/z): 365.0 (M+H, 100).

Synthesis 8

Tert-butyl 2-fluoro-4-hydroxyphenylcarbamate

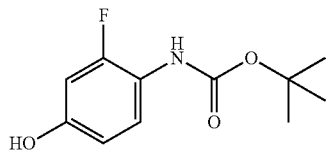 [SMILES: CC(C)(C)OC(=O)Nc1ccc(O)cc1F]

Method B: 4-amino-3-fluorophenol (10.61 g, 83.5 mmol) was added to a molten mixture of Boc$_2$O (18.29 g, 83.8 mmol) and InCl$_3$ (188 mg, 0.85 mmol) at 35° C. The black mixture was stirred at 35° C. for 2 h, during which time it turned into a thick black oil. The mixture was then diluted with EtOAc (200 mL) and H$_2$O (200 mL) and stirring was continued for 10 min. The layers were separated and the organic layer was washed with H$_2$O (3×200 mL), dried (MgSO$_4$), filtered and concentrated to dryness. The resulting black oil was redissolved in CH$_2$Cl$_2$ (50 mL) and loaded onto a silica gel column. Elution with 5→7% EtOAc in CH$_2$Cl$_2$ furnished the title compound as a light yellow, crystalline solid. Yield: 16.7 g (90%).

$^1$H-NMR (DMSO-d$_6$), δ (ppm), J (Hz): 1.46 (s, 9H, tert-Bu), 6.08 (d, 1H, J=5.5, H$_{Py}$), 7.01 (m, 1H, H$_{arom}$), 7.18 (br s, 2H, NH$_2$), 7.22 (m, 1H, H$_{arom}$), 7.67 (m, 1H, H$_{arom}$), 8.04 (d, 1H, J=5.5, $_{Py}$rH), 9.03 (s, 1H, NH$_{Boc}$); $^{13}$C-NMR (DMSO-d$_6$), δ (ppm), J (Hz): 28.0, 78.6, 102.7 d, (J$_{FC}$=22.2), 110.8 (d, J$_{FC}$=2.7), 117.1 (d, J$_{FC}$=12.6), 127.2, 153.7, 155.5 (d, J$_{FC}$=11.3), 156.1 (d, J$_{FC}$=246); $^{19}$F-NMR (DMSO-d$_6$), δ (Ppm): −121.6; LC-MS (m/z): 172.0 (M+H, 100).

Synthesis 9 tert-butyl-4-hydroxy-3-fluorophenylcarbamate

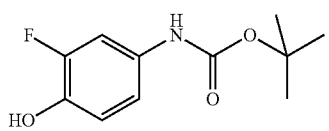 [SMILES: CC(C)(C)OC(=O)Nc1ccc(O)c(F)c1]

Using Method B with 4-amino-2-fluorophenol (1.6 g, 12.7 mmol), the title compound (1.26 g, 44%) was obtained after 1 hour, and purified using Biotage (EtOAc-DCM: 1-1) to give a pale pink powder. (Rf 0.86, EtOAc-DCM, 1-1).
$^1$H-NMR (DMSO-$d_6$), δ (ppm), J (Hz): 1.46 (s, 9H, tert-Bu); 6.82 (t, 1H, $H_{arom}$, J=9.2 Hz), 6.99 (d, 1H, $H_{arom}$, J=8.1 Hz), 7.29 (d, 1H, $H_{arom}$, J=13.5 Hz), 9.18 (s, 1H, OH), 9.36 (s, 1H, $NH_{carbamate}$). $^{13}$C-NMR (DMSO-$d_6$), δ (ppm), J (Hz): 28.9, 79.9, 107.9, 115.4, 118.5, 132.6, 140.3, 150.4, 152.3. $^{19}$F-NMR (δ, ppm, DMSO-d6): −134.62.

Synthesis 10 tert-butyl 4-(2-amino-3-nitropyridin-4-yloxy)-3-fluorophenylcarbamate

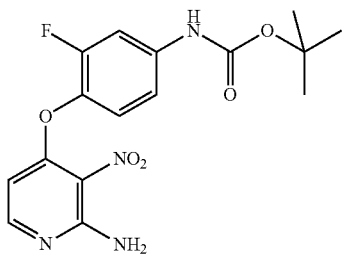

Using Method A1 with tert-butyl-4-hydroxy-3-fluorophenylcarbamate (1.26 g, 5.5 mmol), the title compound (1.99 g, 99%) was obtained after 1 hour stirring as a yellow powder.
$^1$H-NMR (DMSO-$d_6$), δ (ppm), J (Hz): 1.52 (s, 9H, tert-Bu); 5.98 (d, 1H, $H_{Py}$, J=5.7 Hz), 7.21 (s, 2H, $NH_2$), 7.32 (m, 2H, $H_{arom}$), 7.63 (m, 1H, $H_{arom}$), 8.02 (d, 1H, $H_{Py}$, J=5.4 Hz), 9.74 (s, 1H, $NH_{carbamate}$). $^{13}$C-NMR (DMSO-$d_6$), δ (ppm), J (Hz): 28.0, 79.7, 99.0, 106.3, 114.6, 121.0, 123.5, 133.7, 139.0, 152.6, 153.2, 153.7, 154.0, 158.7. $^{19}$F-NMR (δ, ppm, DMSO-$d_6$): −128.76. LC-MS (m/z): 365 (M+H, 100), rt=2.58 min.

Synthesis 11

4-(3-N-(tert-Butoxycarbonyl)aminophenoxy)-3-nitro-2-amino-pyridine

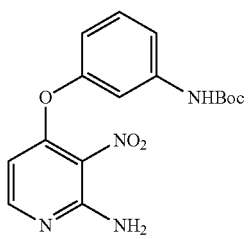

Method A1 was used with 3-N-Boc-amino-phenol (1.2 g, 5.4 mmol) to afford the title compound as a glassy yellow solid (1.7 g, 90%).
$^1$H-NMR (DMSO), δ (ppm), J (Hz): 1.46 (s, 9H, ($CH_3$)$_3$C), 5.36 (s, 2H, $NH_2$), 6.00 (d, 1H, $H_{Pyr}$, J=5.7), 6.77 (d, 1H, $H_{arom}$, J=6.9), 7.32-7.36 (m, 2H, $H_{arom}$), 8.01 (d, 1H, $H_{Pyr}$), 9.56 (s, 1H, NH); LC-MS (m/z): 346.1 (M+H, 100), rt=7.10 min.

Synthesis 12

Methyl 3-(2-amino-3-nitropyridin-4-yloxy)benzoate

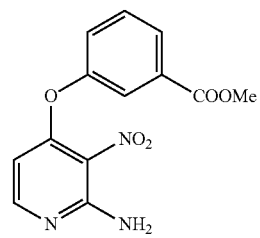

Method A1 was used with methyl 3-hydroxybenzoate (800 mg, 4.7 mmol) to afford the title compound (760 mg, 53% yield).
$^1$H-NMR (DMSO), δ (ppm), J (Hz): 3.86 (s, 3H, Me), 6.04 (d, 1H, $H_{Pyr}$, J=6.0 Hz), 7.23 (s, 2H, $NH_2$), 7.52 (d, 1H, $H_{arom}$, J=8.0 Hz), 7.63-7.66 (m, 1H, $H_{arom}$), 7.88 (d, 1H, $H_{arom}$, J=8.0 Hz), 8.04 (d, 1H, $H_{Pyr}$); LC-MS (m/z): 290 (M+H, 100).

Synthesis 13

Tert-butyl 4-(2-amino-3-nitropyridin-4-ylthio)phenylcarbamate

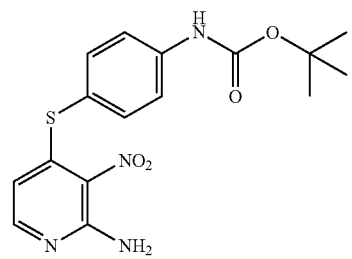

Method A3: Dry DMSO (15 mL) was added to NaH (1.24 g of a 60% dispersion in mineral oil, 25.7 mmol) in a round bottom flask under Ar. After 5 min, solid tert-butyl 4-mercaptophenylcarbamate (6.98 g, 31.0 mmol) was added in three portions, which led to the formation of a yellow solution while effervescence occurred. After 15 min of stirring at RT, 4-chloro-3-nitropyridin-2-amine (5.38 g, 31.0 mmol) at once. The yellow/brown solution was stirred for 30 min and EtOAc (150 mL) and $H_2O$ (400 mL) were subsequently added. The aqueous layer was extracted with EtOAc (3×100 mL) and the combined organic layers were washed once with saturated $NaHCO_3$ (150 mL), dried ($MgSO_4$), filtered, and concentrated to dryness to give the title compound as a bright yellow solid. Yield: 11.2 g (quantitative).
$^1$H-NMR (DMSO-$d_6$), δ (ppm), J (Hz): 1.49 (s, 9H, tert-Bu), 5.83 (d, J=5.4, 1H, $H_{Py}$), 7.47 (d, J=8.7, 2H, $H_{arom}$), 7.64 (d, J=8.7, 2H, $H_{arom}$), 7.87-7.89 (m, 3H), 9.69 (s, 1H, Synthesis 14

Tert-butyl 4-mercaptophenylcarbamate

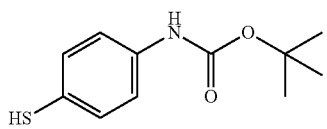

Method B was used with 4-aminobenzenethiol (8.08 g, 64.5 mmol) to afford the title compound Yield: 14.5 g (100%).

$^1$H-NMR (DMSO-d$_6$), δ (ppm), J (Hz): 1.46 (s, 9H, tert-Bu), 5.08 (s, 1H, SH), 7.17 (d, J=8.7, 2H, H$_{arom}$), 7.34 (d, J=8.7, 2H, H$_{arom}$), 9.27 (s, 1H, NH$_{Boc}$); $^{13}$C-NMR (DMSO-d$_6$), δ (ppm), J (Hz): 28.1, 79.0, 118.9, 123.4, 129.6, 130.7, 137.2, 140.0, 152.7.

(II) Boc Protection of Amine

Synthesis 15

4-(4-N-(tert-Butoxycarbonyl)amino-3-thiomethyl-phenoxy)-3-nitro-2-amino-pyridine

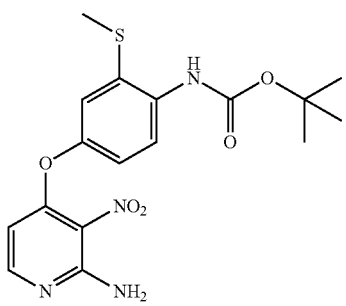

Method B, was used with 4-(4-amino-3-(methylthio)phenoxy)-3-nitropyridin-2-amine (2 g, 6.8 mmol). The title compound (2.42 g, 90%) was obtained after purification by chromatography on silica gel (EtOAc-DCM: 1-1, then EtOAc-MeOH: 95-5) as a powder (R$_f$ 0.33, EtOAc-MeOH, 95:5).

$^1$H-NMR (DMSO-d$_6$), δ (ppm), J (Hz): 1.46 (s, 9H, tert-Bu); 2.81 (s, 3H, CH$_3$); 6.07 (d, 1H, H$_{Py}$ J=5.6 Hz), 7.19 (m, 1H, H$_{arom}$), 7.35 (m, 1H, H$_{arom}$), 7.53 (d, 1H, H$_{arom}$, J=2.8 Hz), 7.55 (d, 1H, H$_{arom}$, J=8.7 Hz), 8.01 (m, 1H, H$_{arom}$), 8.05 (d, 1H, H$_{Py}$, J=5.6 Hz), 9.32 (s, 1H, NH$_{carbamate}$). $^{13}$C-NMR (DMSO-d$_6$), δ (ppm), J (Hz): 14.8, 27.9, 78.8, 103.6, 115.9, 117.3, 121.7, 124.6, 127.5, 132.1, 137.1, 146.0, 148.5, 151.7, 153.4. LC-MS (m/z): 393 (M+H, 100), rt=7.64 min.

NHBoc); $^{13}$C-NMR (DMSO-d$_6$), δ (ppm), J (Hz): 28.0, 79.6, 110.3, 119.4, 121.5, 124.8, 136.4, 141.4, 152.3, 152.5, 153.6, 156.2; LC-MS: 364.0 (M+H, 100); HRMS: m/z calcd. for C$_{16}$H$_{19}$N$_4$O$_4$S [M+H$^+$]: 363.11215; found: 363.11261.

(III) Reduction of Nitro Group En-Route to Common Intermediates (According to Scheme 1)

Synthesis 16

Tert-butyl 4-(2,3-diaminopyridin-4-yloxy)phenylcarbamate

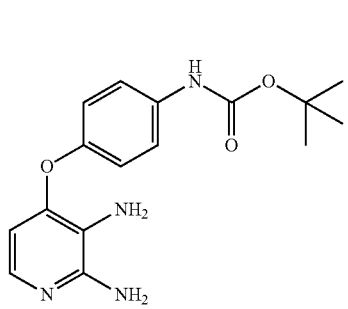 [SMILES: CC(C)(C)OC(=O)Nc1ccc(Oc2ccnc(N)c2N)cc1]

Method C1: 1.56 g (4.5 mmol) of tert-butyl 4-(2-amino-3-nitropyridin-4-yloxy)phenylcarbamate are dissolved in 300 ml of a 1:1 ethanol:ethyl acetate mixture. The solution was mixed with H$_2$ was passed through a cartridge containing Pd/C in a H-cube apparatus, then was evaporated to provide 1.26 g (88% yield) of tert-butyl 4-(2,3-diaminopyridin-4-yloxy)phenylcarbamate as a white foamy solid.

$^1$H-NMR (CDCl$_3$), δ (ppm), J (Hz): 1.54 (9H, s), 2.90 (4H, bs), 6.60 (1H, bs), 6.17 (d, 1H, J=5.7 Hz), 7.01 (2H, d, J=8.9 Hz), 7.38 (d, 2H, J=8.9 Hz), 7.52 (d, 1H, J=5.8 Hz). LC-MS (m/z): 317 (M+H, 100).

Synthesis 17 tert-butyl 4-(2,3-diaminopyridin-4-yloxy)naphthalen-1-ylcarbamate

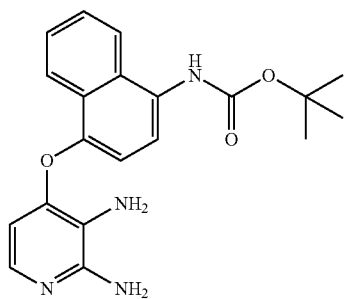

Method C1 was used with tert-butyl 4-(2-amino-3-nitropyridin-4-yloxy)naphthalen-1-ylcarbamate (3.0 g, 7.6 mmol) with solvent mixture MeOH:THF 1:1 to afford the title compound in quantitative yield (2.4 g).

$^1$H-NMR (CDCl$_3$), δ (ppm), J (Hz): 1.56 (s, 9H), 6.03 (d, 1H, J=6.0 Hz), 7.04 (s, 1H), 7.07 (d, 1H, J=8.2 Hz), 7.33 (d, 1H, J=6.0 Hz), 7.50 (t, 1H, J=7.4 Hz), 7.57 (t, 1H, J=8.2 Hz), 7.77 (bs, 1H), 7.95 (d, 1H, J=8.2 Hz), 7.98 (d, 1H, J=8.2 Hz). LC-MS (m/z): 367 (M+H, 100).

Synthesis 18

4-(4-N-(tert-Butoxycarbonyl)amino-3-fluorophenoxy)-2,3-diamino-pyridine

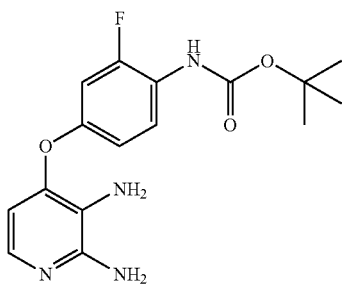 [SMILES: CC(C)(C)OC(=O)Nc1ccc(Oc2ccnc(N)c2N)cc1F]

Method C2: Pd/C (1.09 g) was added to a yellow solution of 4-(4-N-(tert-Butoxycarbonyhamino-3-fluorophenoxy)-3-nitro-2-amino-pyridine (6.20 g, 17.0 mmol) in EtOAc/EtOH (90/150 mL) and the black mixture was stirred under a hydrogen atmosphere for 5 h and filtered over Celite. The dark brown filtrate was concentrated to dryness, redissolved in $CH_2Cl_2$ (20 mL) and loaded onto a silica gel column. The products were eluted with EtOAc and the fractions containing the title compound were compound and evaporated to dryness. The orange oil was dissolved in $CH_2Cl_2$ and an equal amount of hexane was added. The solution was concentrated to dryness to give an orange foam. Yield: 4.30 g (76%).

$^1$H-NMR (DMSO-$d_6$), δ (ppm), J (Hz): δ=8.82 (br s, 1H, $NH_{Boc}$), 7.47 (t, J=8.5 Hz, 1H, $H_{arom}$), 7.28 (d, 1H, J=5.5 Hz, $H_{Py}$), 6.87 (m, 1H, $H_{arom}$), 6.76 (m, 1H, $H_{arom}$), 6.09 (d, 1H, J=5.5 Hz, $H_{Py}$), 5.61 (s, 2H, $NH_2$), 4.47 (s, 2H, $NH_2$), 1.45 ppm (s, 9H, tert-Bu); $^{19}$F NMR (470 MHz, DMSO-$d_6$): δ=−120.7 ppm; LC-MS (m/z): 335.3 (M+H, 100), rt=2.69 min.

Synthesis 19

Tert-butyl 4-(2,3-diaminopyridin-4-yloxy)-2-(methylthio)phenylcarbamate

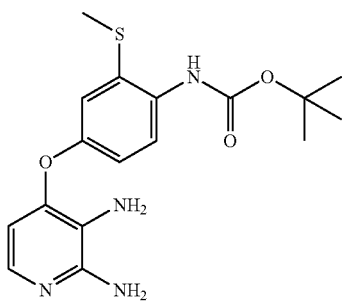 [SMILES: CSc1cc(Oc2ccnc(N)c2N)ccc1NC(=O)OC(C)(C)C]

Using Method C4 with 4-(4-N-(tert-Butoxycarbonyl)amino-3-thiomethyl-phenoxy)-3-nitro-2-amino-pyridine (12.5 g, 31.8 mmol), the title compound (2.07 g, 18%) was obtained after purification by chromatography on silica gel (EtOAc, then EtOAc-MeOH: 95-5) as a powder ($R_f$ 0.33, EtOAc-MeOH, 95:5).

$^1$H-NMR (DMSO-$d_6$), δ (ppm), J (Hz): 1.44 (s, 9H, tert-Bu); 2.39 (s, 3H, $CH_3$); 5.56 (bs, 2H, $NH_2$); 6.29 (d, 1H, $H_{Py}$ J=6.9 Hz), 6.87 (dd, 1H, $H_{arom}$ J=8.6 Hz, J=2.7 Hz), 7.06 (d, 1H, $H_{arom}$ J=2.7 Hz), 7.31 (m, 2H, $H_{Py}$ J=6.8 Hz+$H_{arom}$), 7.56 (bs, 2H, $NH_{2,\ Py}$), 8.44 (s, 1H, $NH_{carbamate}$). $^{13}$C-NMR (DMSO-$d_6$), δ (ppm), J (Hz): 14.8, 27.9, 78.8, 103.6, 115.9, 117.3, 121.7, 124.6, 127.5, 132.1, 137.1, 146.0, 148.5, 151.7, 153.4.

LC-MS (m/z): 362 (M+H, 100), rt=3.04 min.

Synthesis 20

4-(3-N-(tert-Butoxycarbonyl)aminophenoxy)-2,3-diamino-pyridine

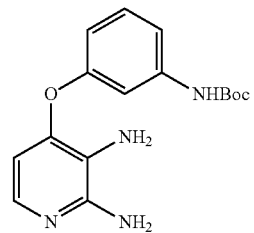 [SMILES: CC(C)(C)OC(=O)Nc1cccc(Oc2ccnc(N)c2N)c1]

Method C2 was used with 4-(3-N-(tert-butoxycarbonyl)aminophenyloxy)-2-amino-3-nitro-pyridine (2.5 g, 7.2 mmol) to afford the title compound as a brown glassy solid (2.17 g, 95%).

$^1$H-NMR (DMSO), δ (ppm), J (Hz): 1.45 (s, 9H, $(CH_3)_3$C), 4.39 (s, 2H, 5-$NH_2$), 5.36 (s, 2H, 6-$NH_2$), 6.02 (d, 1H, $H_{Py}$ J=5.6), 6.58 (d, 1H, $H_{arom}$ J=7.9), 7.19-7.21 (m, 2H, $H_{arom}$), 7.25 (d, 1H, $H_{Py}$), 9.41 (s, 1H, NH); LC-MS (m/z): 316.1 (M+H, 100), rt=4.03 min.

Synthesis 21

Methyl 3-(2,3-diaminopyridin-4-yloxy)benzoate

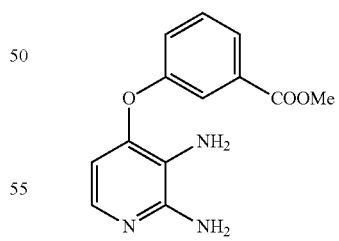

Method C2 was used with methyl 3-(2-amino-3-nitropyridin-4-yloxy) (760 mg, 2.6 mmol), enzoate to afford the title compound (680 mg, 100%).

$^1$H-NMR (DMSO), δ (ppm), J (Hz): 3.83 (s, 3H, Me), 4.54 (s, 2H, $NH_2$), 5.68 (s, 2H, $NH_2$), 6.12 (d, 1H, $H_{Pyr}$, J=6.0 Hz), 7.27-7.32 (m, 1H, $H_{arom}$), 7.43 (d, 1H, $H_{arom}$, J=1.5 Hz), 7.52 (t, 1H, $H_{arom}$, J=8.0 Hz), 7.69 (d, 1H, $H_{Pyr}$); LC-MS (m/z): 260 (M+H, 100).

Synthesis 22 tert-butyl 4-(2,3-diaminopyridin-4-yloxy)-3-fluoro-phenylcarbamate

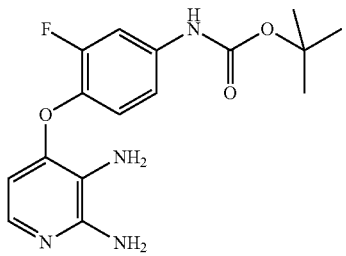 [SMILES: CC(C)(C)OC(=O)Nc1ccc(Oc2ccnc(N)c2N)c(F)c1]

Using Method C2 with tert-butyl 4-(2-amino-3-nitropyridin-4-yloxy)-3-fluorophenylcarbamate (2.15 g, 5.9 mmol), the title compound (1.75 g, 89%) was obtained as a brown solid.

$^1$H-NMR (DMSO-$d_6$), δ (ppm), J (Hz): 1.52 (s, 9H, tert-Bu); 4.51 (bs, 2H, NH$_2$), 5.59 (s, 2H, NH$_2$), 5.88 (d, 1H, H$_{Py}$, 5, J=4.8 Hz), 7.11 (t, 1H, J=8.8 Hz), 7.22-7.27 (m, 2H, H$_{arom}$), 7.56 (dd, 1H, H$_{arom}$, J=12.2 Hz J=1.6 Hz), 9.61 (s, 1H, NH$_{carbamate}$). $^{13}$C-NMR (DMSO-$d_6$), δ (ppm), J (Hz): 29.1, 80.6, 102.2, 107.6, 115.4, 119.2, 123.6, 136.6, 137.3, 138.2, 149.2, 150.9, 153.7, 155.1. $^{19}$F-NMR (δ, ppm, DMSO-d6): −129.68. LC-MS (m/z): 335 (M+H, 100), rt=2.00 min.

Synthesis 23

Tert-butyl 4-(2,3-diaminopyridin-4-ylthio)phenylcarbamate

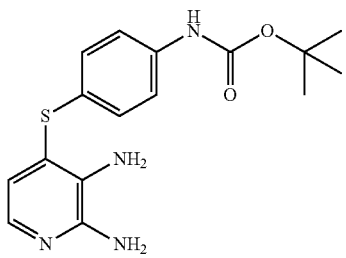 [SMILES: CC(C)(C)OC(=O)Nc1ccc(Sc2ccnc(N)c2N)cc1]

Method C3: Tert-butyl 4-(2-amino-3-nitropyridin-4-ylthio)phenylcarbamate (470 mg, 1.30 mmol) was dissolved in a mixture of EtOAc and EtOH (80 mL/40 mL) and Raney nickel (a spoonful) was added. The suspension was stirred under an H$_2$ atmosphere for 90 min and filtered through a pad of Celite. The colorless filtrate was concentrated to dryness to give the title compound as a colorless oil. Yield: 430 mg (quantitative).

$^1$H-NMR (DMSO-$d_6$), δ (ppm), J (Hz): 1.46 (s, 9H, tert-Bu), 4.78 (br s, 2H, NH$_2$), 5.61 (br s, 2H, NH$_2$), 6.22 (d, J=5.3, 1H, H$_{Py}$), 7.19-7.22 (m, 3H), 7.44 (d, J=8.7, 2H, H$_{arom}$), 9.43 (s, 1H, NHBoc); $^{13}$C-NMR (DMSO-$d_6$), δ (ppm), J (Hz): 28.1, 79.2, 115.3, 119.0, 122.8, 125.1, 128.8, 131.7, 134.9, 139.1, 148.4, 152.5; LC-MS (m/z): 333.2 (M+H, 100), rt=3.06; HRMS (3.98 min): m/z calcd. for C$_{16}$H$_{21}$N$_4$O$_2$S [M+H$^+$]: 333.13797; found: 333.13812.

(IV). Cyclisation En-Route to Common Intermediates

1. Cyclisation to pyridopyrazin-3-one and pyridopyrazine-2-one

Synthesis 24

Tert-butyl 4-(2-oxo-1,2-dihydropyrido[2,3-b]pyrazin-8-yloxy)phenylcarbamate

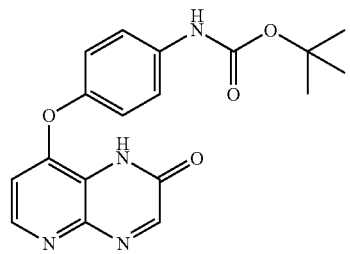 [SMILES: CC(C)(C)OC(=O)Nc1ccc(Oc2ccnc3ncc(=O)[nH]c23)cc1]

Tert-butyl 4-(3-oxo-3,4-dihydropyrido[2,3-b]pyrazin-8-yloxy)phenylcarbamate

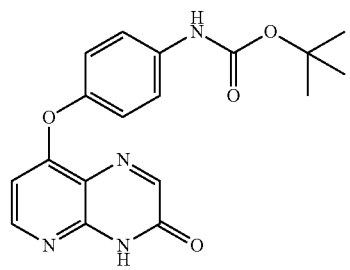 [SMILES: CC(C)(C)OC(=O)Nc1ccc(Oc2ccnc3[nH]c(=O)cnc23)cc1]

Method D1: tert-butyl 4-(2,3-diaminopyridin-4-yloxy)phenylcarbamate (0.86 g, 2.71 mmol) was dissolved in 15 ml of dry ethanol; 0.8 ml (4 mmol) of a 50% ethyl glyoxalate solution in toluene were added and the solution was stirred overnight at room temperature under Argon atmosphere. The solvent was partially evaporated, and tert-butyl 4-(2-oxo-1,2-dihydropyrido[2,3-b]pyrazin-8-yloxy)phenylcarbamate (0.430 g, 45% yield) is precipitated by addition of acetone (10 ml) and filtered off.

tert-butyl 4-(3-oxo-3,4-dihydropyrido[2,3-b]pyrazin-8-yloxy)phenylcarbamate (0.200 g, 21% yield) is isolated by column chromatography over silica gel, eluant dichloromethane: ethyl acetate 1:1 Rf=0.3.

tert-butyl 4-(2-oxo-1,2-dihydropyrido[2,3-b]pyrazin-8-yloxy)phenylcarbamate:

$^1$H-NMR (DMSO-$d_6$), δ (ppm), J (Hz): 1.49 (s, 9H), 6.76 (d, 1H, J=5.4 Hz), 7.15 (d, 2H, J=9.0 Hz), 7.57 (d, 2H, J=9.0 Hz), 8.32 (d, 1H, J=5.0 Hz), 8.40 (s, 1H), 9.44 (bs, 1H), 12.54 (bs, 1H). LC-MS (m/z): 367 (M+H, 100).

tert-butyl 4-(3-oxo-3,4-dihydropyrido[2,3-b]pyrazin-8-yloxy)phenylcarbamate:

$^1$H-NMR (CDCl$_3$), δ (ppm), J (Hz): 1.54 (s, 9H), 6.55 (d, 1H, J=5.5 Hz), 6.67 (bs, 1H), 7.14 (d, 2H, J=8.5 Hz), 7.49 (d, 2H, J=8.5 Hz), 8.36 (s, 1H), 8.46 (d, 1H, J=5.5 Hz), 12.88 (bs, 1H). LC-MS (m/z): 367 (M+H, 100).

Synthesis 25

Tert-butyl 4-(2-oxo-1,2-dihydropyrido[2,3-b]pyrazin-8-yloxy)naphthalen-1-ylcarbamate

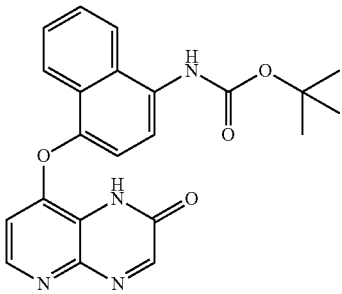 [SMILES: CC(C)(C)OC(=O)Nc1ccc(Oc2ccnc3ncc(=O)[nH]c23)c2ccccc12]

Tert-butyl 4-(2-oxo-1,2-dihydropyrido[2,3-b]pyrazin-8-yloxy)naphthalen-1-ylcarbamate

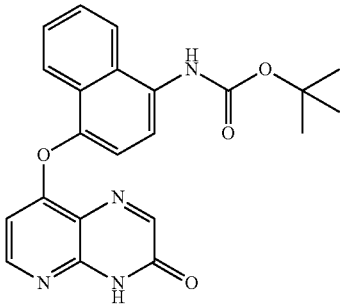 [SMILES: CC(C)(C)OC(=O)Nc1ccc(Oc2ccnc3[nH]c(=O)cnc23)c2ccccc12]

Method D1 was used with tert-butyl 4-(2,3-diaminopyridin-4-yloxy)naphthalen-1-ylcarbamate (3.1 g) to afford the title compounds Tert-butyl 4-(2-oxo-1,2-dihydropyrido[2,3-b]pyrazin-8-yloxy)naphthalen-1-ylcarbamate (1.45 g, 42% yield) and Tert-butyl 4-(2-oxo-1,2-dihydropyrido[2,3-b]pyrazin-8-yloxy)naphthalen-1-ylcarbamate (0.24 g, 9% yield).

Tert-butyl 4-(2-oxo-3,4-dihydropyrido[2,3-b]pyrazin-8-yloxy)naphthalen-1-yl carbamate:

$^1$H-NMR (DMSO-d6), δ (ppm), J (Hz): 1.51 (s, 9H), 6.63 (d, 1H, 5.6 Hz), 7.41 (d, 1H, J=8.3 Hz), 7.56 (m, 1H), 7.62 (m, 1H), 7.64 (d, 1H, J=8.3 Hz), 7.90 (d, 1H, 7.7 Hz), 8.14 (d, 1H, 7.7 Hz), 8.25 (d, 1H, J=5.6 Hz), 8.45 (s, 1H), 9.39 (bs, 1H), 12.86 (bs, 1H). LC-MS (m/z): 405 (M+H, 100).

Tert-butyl 4-(3-oxo-3,4-dihydropyrido[2,3-b]pyrazin-8-yloxy)naphthalen-1-yl carbamate:

$^1$H-NMR (DMSO-d6), δ (ppm), J (Hz): 1.52 (s, 9H), 6.38 (d, 1H, 5.7 Hz), 6.64 (d, 1H, J=8.2 Hz), 7.37 (d, 1H, J=6.6 Hz), 7.51-7.64 (m, 2H), 7.83 (d, 1H, J=8.2 Hz), 8.14 (d, 1H, 6.6 Hz), 8.25 (s, 1H), 8.27 (d, 1H, J=5.7 Hz), 9.38 (bs, 1H), 13.00 (bs, 1H). LC-MS: m/z: LC-MS (m/z): 405 (M+H, 60), 349 (100).

Synthesis 26

Tert-butyl -2-(methylthio)-4-(2-oxo-1,2-dihydropyrido[2,3-b]pyrazin-8-yloxy)phenylcarbamate

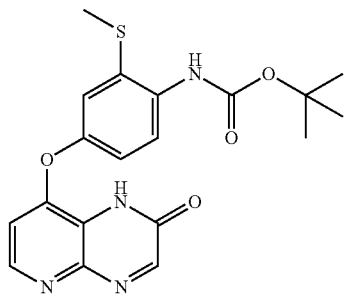 [SMILES: CSc1cc(Oc2ccnc3ncc(=O)[nH]c23)ccc1NC(=O)OC(C)(C)C]

Tert-butyl 2-(methylthio)-4-(3-oxo-3,4-dihydropyrido[3,2-b]pyrazin-8-yloxy)phenylcarbamate

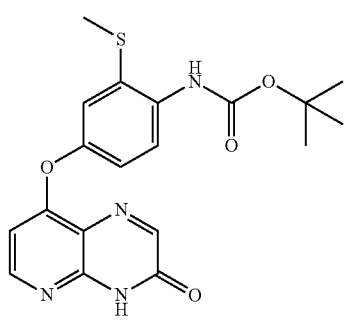 [SMILES: CSc1cc(Oc2ccnc3[nH]c(=O)cnc23)ccc1NC(=O)OC(C)(C)C]

Using Method D1 with tert-butyl 4-(2,3-diaminopyridin-4-yloxy)-2-(methylthio)phenyl carbamate (780 mg, 2.15 mmol), tert-butyl -2-(methylthio)-4-(3-oxo-1,2-dihydropyrido[2,3-b]pyrazin-8-yloxy)phenyl carbamate (134 mg, 15% yield) and tert-butyl -2-(methylthio)-4-(2-oxo-1,2-dihydropyrido[2,3-b]pyrazin-8-yloxy)phenyl carbamate (427 mg, 50% yield) were obtained.

Tert-butyl-2-(methylthio)-4-(2-oxo-1,2-dihydropyrido[2,3-b]pyrazin-8-yloxy)phenyl carbamate: $^1$H-NMR (DMSO-d$_6$), δ (ppm), J (Hz): 1.46 (s, 9H, tert-Bu); 2.40 (s, 3H, CH$_3$); 6.87 (d, 1H, H$_{Py}$, J=5.3 Hz), 7.01 (dd, 1H, H$_{arom}$, J=8.6 Hz, J=2.6 Hz), 7.18 (d, 1H, H$_{arom}$, J=2.6 Hz), 7.37 (d, 1H, H$_{arom}$, J=8.6 Hz), 8.36 (d, 1H, H$_{Py}$, J=5.3 Hz), 8.42 (s, 1H, NH or CH), 8.46 (s, 1H, NH or CH), 12.57 (s, 1H, NH). $^{13}$C-NMR (DMSO-d$_6$), δ (ppm), J (Hz): 14.9, 27.9, 78.9, 110.1, 116.8, 118.0, 127.4, 132.6, 137.0, 151.3, 153.4. LC-MS (m/z): 433 (M+H+MeOH, 100), rt=4.42 min.

Tert-butyl -2-(methylthio)-4-(3-oxo-1,2-dihydropyrido[2,3-b]pyrazin-8-yloxy)phenyl carbamate: $^1$H-NMR (DMSO-d$_6$), δ (ppm), J (Hz): 1.45 (s, 9H, tert-Bu); 2.40 (s, 3H, CH$_3$); 6.59 (d, 1H, H$_{Py}$, J=5.6 Hz), 6.98 (dd, 1H, H$_{arom}$, J=8.6 Hz, J=2.6 Hz), 7.16 (d, 1H, H$_{arom}$, J=2.6 Hz), 7.36 (d, 1H, H$_{arom}$, J=8.6 Hz), 8.17 (s, 1H, NH or CH), 8.36 (d, 1H, H$_{Py}$, J=5.6 Hz), 8.44 (s, 1H, NH or CH), 12.89 (s, 1H, NH). $^{13}$C-NMR (DMSO-d$_6$), δ (ppm), J (Hz): 14.8, 27.9, 78.9, 106.2, 116.7, 117.8, 118.2, 127.5, 132.5, 137.2, 145.4, 150.9, 151.5, 152.0, 153.4, 156.3, 160.5. LC-MS (m/z): 401 (M+H, 100), rt=4.65 min.

Synthesis 27

Tert-butyl 2-fluoro-4-(2-oxo-1,2-dihydropyrido[2,3-b]pyrazin-8-yloxy)phenyl carbamate

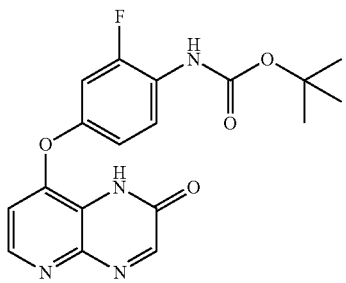 [SMILES: CC(C)(C)OC(=O)Nc1ccc(Oc2ccnc3ncc(=O)[nH]c23)cc1F]

Tert-butyl 2-fluoro-4-(3-oxo-3,4-dihydropyrido[3,2-b]pyrazin-8-yloxy)phenyl carbamate

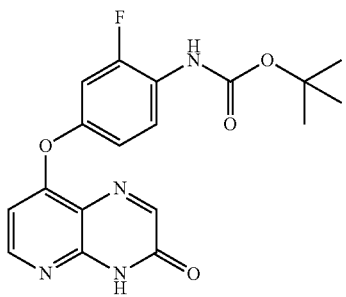 [SMILES: CC(C)(C)OC(=O)Nc1ccc(Oc2ccnc3[nH]c(=O)cnc23)cc1F]

Using Method D1 with tert-butyl 4-(2,3-diaminopyridin-4-yloxy)-2-fluorophenyl carbamate (3.50 g, 10.5 mmol), tert-butyl 2-fluoro-4-(2-oxo-1,2-dihydropyrido[2,3-b]pyrazin-8-yloxy)phenyl carbamate (2.71 g, 69%) and tert-butyl 2-fluoro-4-(3-oxo-1,2-dihydropyrido[2,3-b]pyrazin-8-yloxy)phenyl carbamate (0.96 g, 25%) were obtained.

Tert-butyl 2-fluoro-4-(2-oxo-1,2-dihydropyrido[2,3-b]pyrazin-8-yloxy)phenylcarbamate:
$^1$H-NMR (DMSO-$d_6$), δ (ppm), J (Hz): δ=12.58 (br s, 1H, NHAr), 9.03 (br s, 1H, NH$_{Boc}$), 8.41 (s, 1H, H$_{arom}$), 8.37 (d, J=5.5 Hz, 1H, H$_{Py}$), 7.66 (vt, J=8.5 Hz, 1H, H$_{arom}$), 7.24 (d, 1H, H$_{arom}$), 7.06 (d, 1H, H$_{arom}$), 6.94 (d, J=5.5 Hz, 1H, H$_{Py}$), 1.47 ppm (s, 9H, tert-Bu); $^{13}$C NMR (126 MHz, DMSO-$d_6$): δ=155.8 (br), 154.6, 154.5 (d, $J_{FC}$=248 Hz), 153.1, 151.8 (br), 150.2 (d, $J_{FC}$=10 Hz), 145.4, 144.3 (br), 125.7, 124.0 (d, $J_{FC}$=12 Hz), 119.9 (br), 116.1 (d, $J_{FC}$=3 Hz), 110.7, 108.7 (d, $J_{FC}$=23 Hz), 79.4, 28.0 ppm; $^{19}$F NMR (470 MHz, DMSO-$d_6$): δ=−119.9 ppm; LC-MS (m/z): 373.4 (M+H, 100), rt=4.20 min; HRMS (5.15 min): m/z calcd. for $C_{18}H_{18}FN_4O_4$ [M+H$^+$]: 373.13066; found: 373.13099.

Tert-butyl 2-fluoro-4-(3-oxo-1,2-dihydropyrido[2,3-b]pyrazin-8-yloxy)phenyl carbamate:
$^1$H-NMR (DMSO-$d_6$), δ (ppm), J (Hz): δ=12.90 (br s, 1H, NHAr), 9.01 (br s, 1H, NHBoc), 8.38 (d, J=5.5 Hz, 1H, H$_{Py}$), 8.17 (s, 1H, H$_{arom}$), 7.66 (Vt, J=8.5 Hz, 1H, H$_{arom}$), 7.22 (d, 1H, H$_{arom}$), 7.01 (d, 1H, H$_{arom}$), 6.67 (d, J=5.5 Hz, 1H, H$_{Py}$), 1.47 ppm (s, 9H, tert-Bu); $^{13}$C NMR (126 MHz, DMSO-$d_6$): δ=160.2, 156.4, 154.6 (d, $J_{FC}$=249 Hz), 153.1, 152.2, 151.2, 150.5 (d, $J_{FC}$=10 Hz), 145.6, 125.8, 123.9 (d, $J_{FC}$=12 Hz), 118.5, 116.0 (d, $J_{FC}$=3 Hz), 108.5 (d, $J_{FC}$=23 Hz), 106.8, 79.4, 28.0 ppm; $^{19}$F NMR (470 MHz, DMSO-$d_6$): δ=−119.8 ppm; LC-MS (m/z): 373.1 (M+H, 100), rt=4.40 min; HRMS (5.34 min): m/z calcd. for $C_{18}H_{17}FN_4O_4$ [M+H$^+$]: 373.13066; found: 373.13071.

Synthesis 28 tert-butyl-3-fluoro-4-(3-oxo-3,4-dihydropyrido[2,3-b]pyrazin-8-yloxy)phenylcarbamate

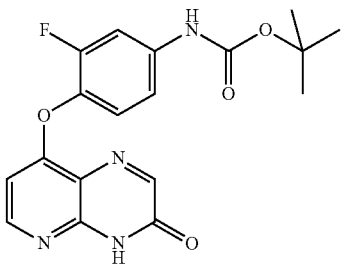 [SMILES: CC(C)(C)OC(=O)Nc1ccc(Oc2ccnc3[nH]c(=O)cnc23)c(F)c1]

tert-butyl-3-fluoro-4-(2-oxo-1,2-dihydropyrido[2,3-b]pyrazin-8-yloxy)phenylcarbamate

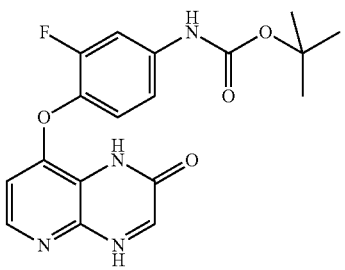 [SMILES: CC(C)(C)OC(=O)Nc1ccc(Oc2ccnc3ncc(=O)[nH]c23)c(F)c1]

Using Method D1 with tert-butyl 4-(2,3-diaminopyridin-4-yloxy)-3-fluorophenylcarbamate (1 g, 2.99 mmol), a mixture of two isomers (1.01 g, 90%) was obtained in a ratio 53/47. The crude powder was purified by Biotage to afford tert-butyl-3-fluoro-4-(3-oxo-3,4-dihydropyrido[2,3-b]pyrazin-8-yloxy)phenylcarbamate (185 mg, 17% yield) and tert-butyl-3-fluoro-4-(2-oxo-1,2-dihydropyrido[2,3-b]pyrazin-8-yloxy)phenylcarbamate (370 mg, 34% yield) as white off powders.

tert-butyl-3-fluoro-4-(3-oxo-3,4-dihydropyrido[2,3-b]pyrazin-8-yloxy)phenylcarbamate:
$^1$H-NMR (DMSO-$d_6$), δ (ppm), J (Hz): 1.55 (s, 9H, tert-Bu); 6.56 (d, 1H, H$_{Py}$ J=5.7 Hz), 7.37 (m, 2H, H$_{arom}$), 7.67 (m, 1H, H$_{arom}$), 8.22 (s, 1H, CH), 8.37 (d, 1H, H$_{Py}$ J=5.7 Hz), 9.75 (s, 1H, NH), 12.95 (s, 1H, NH). $^{13}$C-NMR (DMSO-$d_6$), δ (ppm), J (Hz): 28.9, 80.6, 106.0, 107.4, 115.6, 118.7, 124.6, 135.4, 139.8, 146.4, 152.3, 153.2, 153.7, 155.1, 157.5, 161.5. $^{19}$F-NMR (δ, ppm, DMSO-$d_6$): −128.42. LC-MS (m/z): 373 (M+H, 100), rt=2.43 min.

tert-butyl-3-fluoro-4-(2-oxo-1,2-dihydropyrido[2,3-b]pyrazin-8-yloxy)phenylcarbamate
$^1$H-NMR (DMSO-d6), δ (ppm), J (Hz): 1.53 (s, 9H, tert-Bu); 6.83 (d, 1H, H$_{Py}$ J=5.4 Hz), 7.32-7.41 (m, 2H, H$_{arom}$), 7.67 (m, 1H, H$_{arom}$), 8.37 (d, 1H, H$_{Py}$ J=5.4 Hz), 8.45 (s, 1H, CH), 9.75 (s, 1H, NH), 12.65 (s, 1H, NH). $^{13}$C-NMR (DMSO-$d_6$), δ (ppm), J (Hz): 28.9, 80.6, 107.4, 110.0, 115.6, 124.6, 135.4, 139.8, 146.4, 152.3, 153.0, 153.9, 155.4, 157.5, 161.5. $^{19}$F-NMR (δ, ppm, DMSO-d$_6$): −128.12. LC-MS (m/z): 373 (M+H, 100), rt=2.33 min.

Synthesis 29

Tert-butyl 3-(3-oxo-3,4-dihydropyrido[2,3-b]pyrazin-8-yloxy)phenylcarbamate

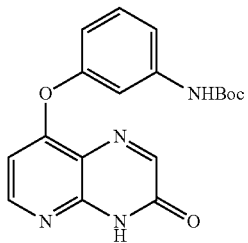 [SMILES: CC(C)(C)OC(=O)Nc1cccc(Oc2ccnc3[nH]c(=O)cnc23)c1]

Tert-butyl 3-(2-oxo-1,2-dihydropyrido[2,3-b]pyrazin-8-yloxy)phenylcarbamate

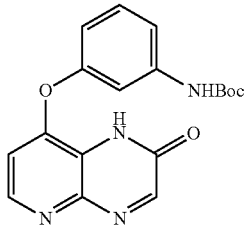 [SMILES: CC(C)(C)OC(=O)Nc1cccc(Oc2ccnc3ncc(=O)[nH]c23)c1]

Using Method D1 with 4-(3-N-(tert-butoxycarbonyl)aminophenoxy)-2,3-diamino-pyridine (1.00 g, 3.16 mmol) tert-butyl 3-(3-oxo-3,4-dihydropyrido[2,3-b]pyrazin-8-yloxy)phenylcarbamate (274 mg, 24%) and tert-butyl 3-(2-oxo-3,4-dihydropyrido[2,3-b]pyrazin-8-yloxy)phenylcarbamate (445 mg, 1.26 mmol, 40%) were obtained.

tert-butyl 3-(3-oxo-3,4-dihydropyrido[2,3-b]pyrazin-8-yloxy)phenylcarbamate:

$^{1}$H-NMR (DMSO-d6), δ (ppm), J (Hz): 1.46 (s, 9H, tert-Bu), 6.59 (d, 1H, H$_{Py}$, J=5.6 Hz), 6.81-6.83 (m, 1H, H$_{arom}$), 7.36-7.39 (m, 3H, H$_{arom}$), 8.17 (s 1H, H$_{arom}$), 8.35 (d, 1H, H$_{Py}$, 6, J=5.6 Hz), 9.56 (s, 1H, NHBoc), 12.89 (s, 1H, NH$_{lactame}$). LC-MS (m/z): 299 (M+H, 100).

tert-butyl 3-(2-oxo-3,4-dihydropyrido[2,3-b]pyrazin-8-yloxy)phenylcarbamate:

$^{1}$H-NMR (DMSO-d$_6$), δ (ppm), J (Hz): 1.46 (s, 9H, tert-Bu), 6.84 (ddd, 1H, H$_{arom}$, J=7.5 Hz, J=2.4 Hz, J=1.5 Hz), 6.86 (d, 1H, H$_{Py}$, J=5.4 Hz), 7.33-7.39 (m, 2H, H$_{arom}$), 7.42 (s, 1H, H$_{arom}$) 8.36 (d, 1H, H$_{Py}$, J=5.4 Hz), 8.41 (s 1H, H$_{arom}$), 9.57 (s, 1H, NH$_{Boc}$), 12.54 (s, 1H, NH$_{lactame}$). LC-MS (m/z): 299 (M+H, 100).

Synthesis 30

Methyl 3-(3-oxo-3,4-dihydropyrido[2,3-b]pyrazin-8-yloxy)benzoate

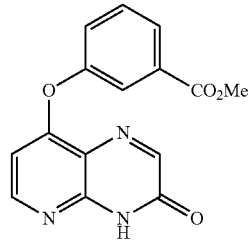 [SMILES: COC(=O)c1cccc(Oc2ccnc3[nH]c(=O)cnc23)c1]

Methyl 3-(2-oxo-1,2-dihydropyrido[2,3-b]pyrazin-8-yloxy)benzoate

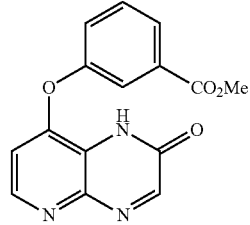 [SMILES: COC(=O)c1cccc(Oc2ccnc3ncc(=O)[nH]c23)c1]

Method D1 was used with methyl 3-(2,3-diaminopyridin-4-yloxy)benzoate (1.00 g, 3.86 mmol) to afford methyl 3-(3-oxo-3,4-dihydropyrido[2,3-b]pyrazin-8-yloxy)benzoate (402 mg, 35%) and methyl 3-(2-oxo-3,4-dihydropyrido[2,3-b]pyrazin-8-yloxy)benzoate (750 mg, 2.52 mmol, 65%).

Methyl 3-(3-oxo-3,4-dihydropyrido[2,3-b]pyrazin-8-yloxy)benzoate: $^{1}$H-NMR (DMSO-d$_6$), δ (ppm), J (Hz): 3.85 (s, 3H, OMe), 6.68 (d, 1H, H$_{Py}$, J=5.6 Hz), 7.53 (ddd, 1H, H$_{arom}$, J=8.2 Hz, J=2.5 Hz, J=1.0 Hz), 7.65 (t, 1H, H$_{arom}$, J=8.0 Hz), 7.68 (dd, 1H, H$_{arom}$, J=2.3 Hz, J=1.6 Hz) 7.88 (ddd, 1H, H$_{arom}$, J=7.7 Hz, J=2.5 Hz, J=1.2 Hz), 8.17 (s 1H, H$_{arom}$), 8.39 (d, 1H, H$_{Py}$, J=5.6 Hz), 12.93 (s, 1H, NH). LC-MS (m/z): 298 (M+H, 100).

Methyl 3-(2-oxo-3,4-dihydropyrido[2,3-b]pyrazin-8-yloxy)benzoate: $^{1}$H-NMR (DMSO-d$_6$), δ (ppm), J (Hz): 3.86 (s, 3H, OMe), 6.97 (d, 1H, H$_{Py}$, 5, J=5.3 Hz), 7.56 (ddd, 1H, H$_{arom}$, J=8.1 Hz, J=2.5 Hz, J=0.8 Hz), 7.66 (t, 1H, H$_{arom}$, J=8.0 Hz), 7.74 (dd, 1H, H$_{arom}$, J=2.1 Hz, J=1.8 Hz) 7.89 (d, 1H, H$_{arom}$, J=7.8 Hz), 8.39 (d, 1H, H$_{Py}$, 6, J=5.3 Hz), 8.43 (s 1H, H$_{arom}$), 12.58 (s, 1H, NH). LC-MS (m/z): 298 (M+H, 100).

Synthesis 31

Tert-butyl 4-(3-oxo-3,4-dihydropyrido[2,3-b]pyrazin-8-ylthio)phenylcarbamate

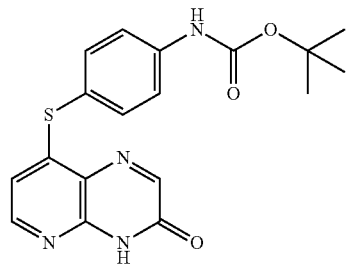 [SMILES: CC(C)(C)OC(=O)Nc1ccc(Sc2ccnc3[nH]c(=O)cnc23)cc1]

Method D1 was used with Tert-butyl 4-(2,3-diaminopyridin-4-ylthio)phenylcarbamate (1.058 g, 3.18 mmol) to afford the title compound as a yellow solid. Yield: 640 mg (54%).

$^1$H-NMR (DMSO-d$_6$), δ (ppm), J (Hz): 1.50 (s, 9H, tert-Bu), 6.35 (d, J=5.4, 1H, H$_{Py}$), 7.52 (d, J=8.7, 2H, H$_{arom}$), 7.67 (d, J=8.7, 2H, H$_{arom}$), 8.19 (d, J=5.4, 1H, H$_{Py}$), 8.20 (s, 1H, H$_{arom}$), 9.70 (s, 1H, NH$_{Boc}$), 12.84 (br s, 1H, NH); $^{13}$C-NMR (DMSO-d$_6$), δ (ppm), J (Hz): 28.1, 79.6, 114.6, 119.2, 119.5, 123.0, 136.7, 141.7, 143.3, 150.0, 150.9, 152.5, 152.6, 156.7; LC-MS (m/z): 371.1 (m+H, 100), rt=4.97 min).

2. Cyclisation to pyridopyrazin-2-methyl-3-one and pyridopyrazine-3-methyl-2-one Synthesis 32

Tert-butyl 2-fluoro-4-(3-methyl-2-oxo-1,2-dihydropyrido[2,3-b]pyrazin-8-yloxy)phenyl carbamate

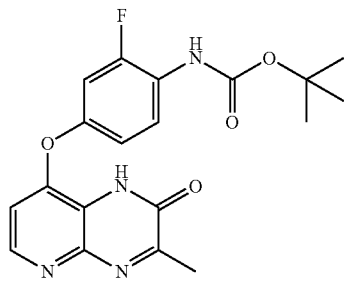 [SMILES: Cc1nc2nccc(Oc3ccc(NC(=O)OC(C)(C)C)c(F)c3)c2[nH]c1=O]

Tert-butyl 2-fluoro-4-(2-methyl-3-oxo-3,4-dihydropyrido[3,2-b]pyrazin-8-yloxy)phenyl carbamate

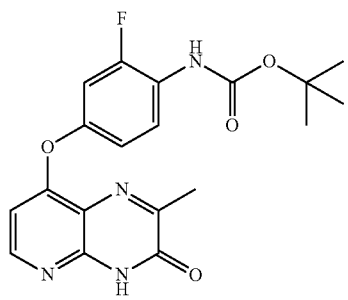 [SMILES: Cc1nc2c(Oc3ccc(NC(=O)OC(C)(C)C)c(F)c3)ccnc2[nH]c1=O]

Method D2. Tert-butyl 4-(2,3-diaminopyridin-4-yloxy)-2-fluorophenylcarbamate (300 mg, 0.9 mmol) was dissolved in dry EtOH (5 mL) and ethyl pyruvate (1 mL, 9 mmol) was added at once. After stirring for 16 h at RT, the precipitate was filtered and the two isomers were separated by column chromatography (silica gel, EtOAc as eluent).

Tert-butyl 2-fluoro-4-(3-methyl-2-oxo-1,2-dihydropyrido[2,3-b]pyrazin-8-yloxy)phenyl carbamate: 200 mg (58%). $^1$H-NMR (DMSO-d$_6$), δ (ppm), J (Hz): 1.47 ppm (s, 9H, tert-Bu); 2.48 (s, 3H, CH$_3$), 6.88 (d, 1H, J=5.5 Hz, H$_{Py}$), 7.03 (d, 1H, H$_{arom}$), 7.22 (d, 1H, H$_{arom}$), 7.66 (vt, J=8.5 Hz, 1H, H$_{arom}$), 8.32 (d, J=5.3 Hz, H$_{Py}$), 9.00 (br s, 1H, NHBoc), 12.41 (br s, 1H, NHAr); $^{13}$C-NMR (DMSO-d$_6$), δ (ppm), J (Hz): 28.0, 79.4, 106.8, 109.0, 116.0, 118.5, 123.9, 125.8, 145.6, 150.5, 151.2, 152.2, 153.1, 156.4, 160.3, ppm;

$^{19}$F NMR (470 MHz, DMSO-d$_6$): δ=−119.9 ppm; LC-MS (m/z): 331.1. (M+H-tert-Bu, 100), rt=4.36 min.

Tert-butyl 2-fluoro-4-(2-methyl-3-oxo-3,4-dihydropyrido[2,3-b]pyrazin-8-yloxy)phenyl carbamate: 130 mg (38%). $^1$H-NMR (DMSO-d$_6$), δ (ppm), J (Hz): 1.47 ppm (s, 9H, tert-Bu), 2.42 (s, 3H, CH$_3$), 6.60 (d, 1H, J=5.5 Hz, H$_{Py}$), 7.03 (d, 1H, H$_{arom}$), 7.22 (d, 1H, H$_{arom}$), 7.66 (vt, $^3$J$_{FH}$=8.5 Hz, 1H, H$_{arom}$), 8.30 (d, J=5.3 Hz, H$_{Py}$), 9.00 (br s, 1H, NH$_{Boc}$), 12.77 (br s, 1H, NH$_{arom}$). $^{13}$C-NMR (DMSO-d$_6$), δ (ppm), J (Hz): 28.0, 79.4, 106.8, 109.0, 116.0, 118.5, 123.9, 125.8, 145.6, 150.5, 151.2, 152.2, 153.1, 156.4, 160.3. $^{19}$F NMR (470 MHz, DMSO-d$_6$): δ=−119.9 ppm; LC-MS (m/z): m/z 331.1 (M+H-tert-Bu, 100), rt=4.55 min Synthesis 33 tert-butyl 4-(2-methyl-3-oxo-3,4-dihydropyrido[2,3-b]pyrazin-8-yloxy)-2-(methylthio)phenylcarbamate

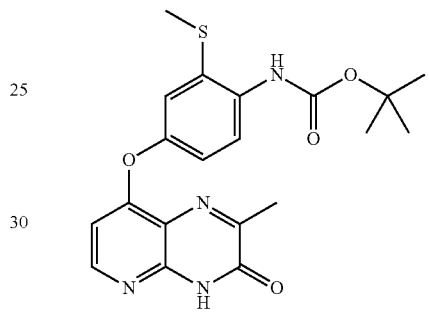

Using Method D2 with tert-butyl 4-(2,3-diaminopyridin-4-yloxy)-2-(methylthio)phenylcarbamate (570 mg, 1.57 mmol), a mixture of two isomers was obtained. After cooling down, the crude was filtered, washed with ethanol and dried. The title compound (131 mg) was obtained as a white powder.

$^1$H-NMR (DMSO-d$_6$), δ (ppm), J (Hz): 1.45 (s, 9H, tert-Bu); 2.39 (s, 3H, CH$_3$); 2.43 (s, 3H, CH$_3$); 6.52 (d, 1H, H$_{Py}$, J=5.6 Hz), 6.97 (dd, 1H, H$_{arom}$, J=8.6 Hz, J=2.6 Hz), 7.15 (d, 1H, H$_{arom}$, J=2.6 Hz), 7.36 (d, 1H, H$_{arom}$, J=8.6 Hz), 8.27 (d, 1H, H$_{Py}$,J=5.6 Hz), 8.44 (s, 1H, NHBoc), 12.75 (s, 1H, NH). LC-MS (m/z): 415 (M+H, 100), rt=4.78 min.

Synthesis 34 tert-butyl 4-(3-methyl-2-oxo-1,2-dihydropyrido[2,3-b]pyrazin-8-yloxy)-2-(methylthio)phenylcarbamate

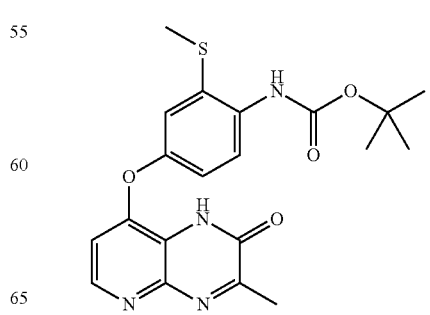

Using Method D2 with tert-butyl 4-(2,3-diaminopyridin-4-yloxy)-2-(methylthio)phenylcarbamate (570 mg, 1.57 mmol), a mixture of the two isomers was obtained. The crude was purified on silica gel (eluent: pure EtOAc), to afford the title compound (206 mg) as a pale yellow powder.

$^1$H-NMR (DMSO-d$_6$), δ (ppm), J (Hz): 1.45 (s, 9H, tert-Bu); 2.43 (s, 3H, CH$_3$); 2.48 (s, 3H, CH$_3$); 6.83 (d, 1H, H$_{Py}$, J=5.2 Hz), 6.98 (dd, 1H, H$_{arom}$, J=8.6 Hz, J=2.6 Hz), 7.15 (d, 1H, H$_{arom}$, J=2.6 Hz), 7.35 (d, 1H, H$_{arom}$, J=8.6 Hz), 8.31 (d, 1H, H$_{Py}$, J=5.2 Hz), 8.45 (s, 1H, NH), 12.51 (bs, 1H, NH). LC-MS (m/z): 531 (M+H+C$_5$H$_8$O$_3$, 100), rt=4.78 min.

Synthesis 35 tert-butyl 3-(2-methyl-3-oxo-3,4-dihydropyrido[2,3-b]pyrazin-8-yloxy)phenyl carbamate

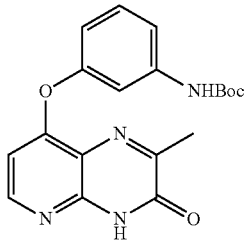 [SMILES: Cc1nc2c(Oc3cccc(NC(=O)OC(C)(C)C)c3)ccnc2[nH]c1=O]

tert-butyl 3-(3-methyl-2-oxo-1,2-dihydropyrido[2,3-b]pyrazin-8-yloxy)phenyl carbamate

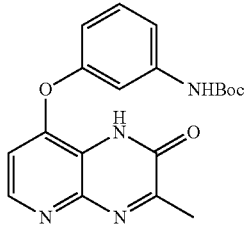 [SMILES: Cc1nc2nccc(Oc3cccc(NC(=O)OC(C)(C)C)c3)c2[nH]c1=O]

Method D2 was used with 4-(3-N-(tert-butoxycarbonyl)aminophenoxy)-2,3-diamino-pyridine to afford a mixture of the 2 isomers. The mixture was chromatographed (eluent: CH$_2$Cl$_2$/EtOAc: 1/0 towards 0/1) to afford at first the tert-butyl 3-(2-methyl-3-oxo-3,4-dihydropyrido[2,3-b]pyrazin-8-yloxy)phenyl carbamate as a yellow solid (194 mg, 0.527 mmol, 11%) and then tert-butyl 3-(3-methyl-2-oxo-1,2-dihydropyrido[2,3-b]pyrazin-8-yloxy)phenyl carbamate as a yellow solid (841 mg, 2.28 mmol, 48%).

tert-butyl 3-(2-methyl-3-oxo-3,4-dihydropyrido[2,3-b]pyrazin-8-yloxy)phenyl carbamate:

$^1$H-NMR (DMSO-d$_6$), δ (ppm), J (Hz): 1.46 (s, 9H, tert-Bu), 2.43 (s, 3H, Me), 6.53 (d, 1H, H$_{Py}$, 5, J=5.6 Hz), 6.81-6.83 (m, 1H, H$_{arom}$), 7.36-7.37 (m, 3H, H$_{arom}$), 8.27 (d, 1H, H$_{Py}$, 6, J=5.6 Hz), 9.56 (s, 1H, NH$_{Boc}$), 12.75 (s, 1H, NH$_{lactame}$). LC-MS (m/z): 369 (M+H, 100).

tert-butyl 3-(3-methyl-2-oxo-1,2-dihydropyrido[2,3-b]pyrazin-8-yloxy)phenyl carbamate:

$^1$H-NMR (DMSO-d$_6$), δ (ppm), J (Hz): 1.46 (s, 9H, tert-Bu), 2.48 (s, 3H, Me), 6.80-6.83 (m, 2H, H$_{arom}$), 7.32-7.37 (m, 2H, H$_{arom}$), 7.40 (s, 1H, H$_{arom}$), 8.31 (d, 1H, H$_{Py}$, J=5.4 Hz), 9.55 (s, 1H, NH$_{Boc}$), 12.38 (s, 1H, NH$_{lactame}$). LC-MS (m/z): 369 (M+H, 100).

Synthesis 36 tert-butyl 4-(2-methyl-3-oxo-3,4-dihydropyrido[2,3-b]pyrazin-8-yloxy) naphthalen-1-ylcarbamate

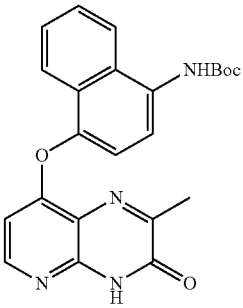 [SMILES: Cc1nc2c(Oc3ccc(NC(=O)OC(C)(C)C)c4ccccc34)ccnc2[nH]c1=O]

tert-butyl 4-(3-methyl-2-oxo-1,2-dihydropyrido[2,3-b]pyrazin-8-yloxy) naphthalen-1-ylcarbamate

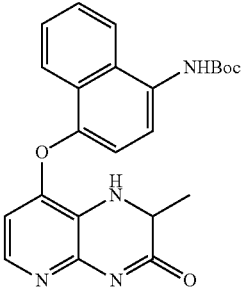

Method D2 was used with tert-butyl 4-(2,3-diaminopyridin-4-yloxy)naphthalen-1-ylcarbamate to afford a mixture of isomers. The residue was chromatographed (eluent: CH$_2$Cl$_2$/EtOAc: 6/1 towards 0/1 then EtOAc/MeOH: 95/5) to afford at first tert-butyl 4-(2-methyl-3-oxo-3,4-dihydropyrido[2,3-b]pyrazin-8-yloxy) naphthalen-1-ylcarbamate as a slightly yellow solid (401 mg, 0.958 mmol, 35%) and then tert-butyl 4-(3-methyl-2-oxo-1,2-dihydropyrido[2,3-b] pyrazin-8-yloxy) naphthalen-1-ylcarbamate as a yellow solid (607 mg, 1.45 mmol, 53%).

tert-butyl 4-(2-methyl-3-oxo-3,4-dihydropyrido[2,3-b] pyrazin-8-yloxy) naphthalen-1-ylcarbamate: $^1$H-NMR (DMSO-d$_6$), δ (ppm), J (Hz): 1.53 (s, 9H, tert-Bu), 2.01 (s, 3H, Me), 6.32 (d, 1H, H$_{Py}$, J=5.7 Hz), 7.38 (d, 1H, H$_{arom}$, J=8.2 Hz), 7.55-7.58 (m, 1H, H$_{arom}$), 7.62-7.67 (m, 2H, H$_{arom}$), 7.85 (d, 1H, H$_{arom}$, J=8.4 Hz), 8.17 (d, 1H, H$_{arom}$, J=8.6 Hz), 8.20 (d, 1H, H$_{Py}$, J=5.6 Hz), 9.35 (s, 1H, NH$_{Boc}$), 12.82 (s, 1H, NH$_{lactame}$). $^{13}$C-NMR (δ, ppm, DMSO-d$_6$): 20.50 (CH$_3$), 28.05 (tert-Bu), 79.03 (tert-Bu), 105.56, 116.89, 117.37, 121.10, 121.13, 123.56, 126.26, 126.52, 126.79, 129.23, 132.08, 145.63, 146.03, 150.51, 153.98, 156.28, 159.14, 160.49. LC-MS (m/z): 419 (M+H, 100).

tert-butyl 4-(3-methyl-2-oxo-1,2-dihydropyrido[2,3-b] pyrazin-8-yloxy) naphthalen-1-ylcarbamate: $^1$H-NMR (DMSO-d$_6$), δ (ppm), J (Hz): 1.51 (s, 9H, tert-Bu), 2.52 (s, 3H, Me), 6.58 (d, 1H, H$_{Py}$, 5, J=5.4 Hz), 7.37 (d, 1H, H$_{arom}$, J=8.2 Hz), 7.53-7.64 (m, 2H, H$_{arom}$), 7.91 (d, 1H, H$_{arom}$, J=8.1 Hz), 8.14 (d, 1H, H$_{arom}$, J=8.5 Hz), 8.22 (d, 1H, H$_{Py}$, 6, J=5.4 Hz), 9.32 (s, 1H, NH$_{Boc}$), 12.66 (s, 1H, NH$_{lactame}$). $^{13}$C-NMR (δ, ppm, DMSO-d$_6$): 20.93 (CH$_3$), 28.05 (tert-Bu), 79.01 (tert-Bu), 108.55, 116.54, 118.89, 121.02, 121.48, 123.38, 126.23, 126.53, 126.59, 129.24, 132.03, 143.82, 144.89, 145.87, 152.08, 153.97, 154.52, 164.03. LC-MS (m/z): 419 (M+H, 100).

3. Cyclisation to pyridopyrazin-2,3-dione

Synthesis 37

8-(4-aminophenoxy)pyrido[2,3-b]pyrazine-2,3(1H,4H)-dione

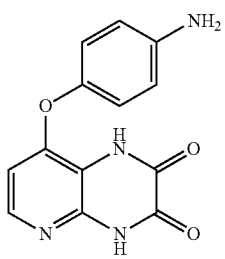 [SMILES: Nc1ccc(Oc2ccnc3[nH]c(=O)c(=O)[nH]c23)cc1]

Method D3. A solution of tert-butyl 4-(2,3-diamino pyridin-4-yloxy)phenylcarbamate (0.320 g, 1.0 mmol) in diethyl oxalate (2 ml) is reacted twice for 10 minutes in a microwave reactor (180 C, 150 W). The solution is cooled and the solid filtered and washed with cold ethanol. Obtained 8-(4-aminophenoxy)pyrido[2,3-b]pyrazine-2,3(1H,4H)-dione (70 mg, 25% yield) as a grey solid.

$^1$H-NMR (DMSO-d6), δ (ppm), J (Hz): 6.36 (d, 1H, J=5.7 Hz), 6.67 (d, 2H, J=8.6 Hz), 6.88 (d, 2H, J=8.6 Hz), 7.82 (d, 2H, J=5.7 Hz), 11.76 (bs, 1H), 12.28 (bs, 1H). LC-MS (m/z): 271 (M+H, 100).

Synthesis 38

8-(4-Amino-3-fluorophenoxy)pyrido[3,2-b]pyrazine-2,3(1H,4H)-dione

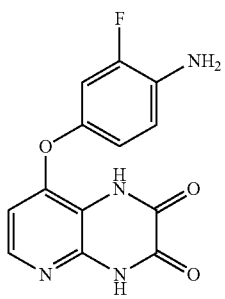 [SMILES: Nc1ccc(Oc2ccnc3[nH]c(=O)c(=O)[nH]c23)cc1F]

A solution of tert-butyl 4-(2,3-diaminopyridin-4-yloxy)-2-fluorophenylcarbamate (1.03 g, 3.08 mmol) was dissolved in dry EtOH (10 mL), diethyl oxalate (10 mL) was added and the solution was heated to reflux for 96 h, cooled to RT and filtered. The title compound was isolated as a white solid. Yield: 820 mg (92%).

$^1$H-NMR (DMSO-d$_6$), δ (ppm), J (Hz): 5.20 (br s, 2H, NH$_2$), 6.44 (d, J=5.7, 1H, H$_{Py}$), 6.79 (m, 1H, H$_{arom}$), 6.85 (m, 1H, H$_{arom}$), 6.98 (m, 1H, H$_{arom}$), 7.91 (d, J=5.7, 1H, rH$_{Py}$), 11.81 (s, 1H, NH), 12.34 (s, 1H, NH); $^{13}$C-NMR (DMSO-d$_6$), δ (ppm), J (Hz): 107.4, 108.4 (d, J$_{FC}$=21.9), 113.0, 116.2 (d, J$_{FC}$=3.0), 121.9 (br), 123.0 (br), 140.7, 143.2, 149.6 (d, J$_{FC}$=10.1), 151.2, 153.8 (d, J$_{FC}$=240), 154.8, 155.9; $^{19}$F-NMR (DMSO-d$_6$), δ (ppm), J (Hz): −123.5 ppm; LC-MS (m/z): 289.1 (M+H, 100).

4. Cyclisation to 2-aminopyridopyrazin-3-one

Synthesis 39 tert-butyl 4-(2-amino-3-oxo-3,4-dihydropyrido[2,3-b]pyrazin-8-yloxy)naphthalen-1-ylcarbamate

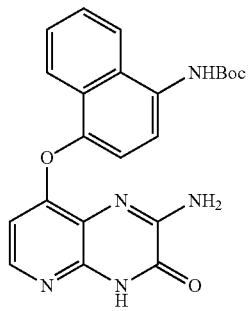 [SMILES: CC(C)(C)OC(=O)Nc1ccc(Oc2ccnc3[nH]c(=O)c(N)nc23)c2ccccc12]

tert-butyl 4-(3-amino-2-oxo-1,2-dihydropyrido[2,3-b]pyrazin-8-yloxy)naphthalen-1-ylcarbamate

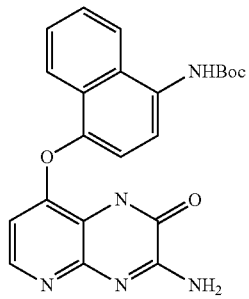 [SMILES: CC(C)(C)OC(=O)Nc1ccc(Oc2ccnc3nc(N)c(=O)[nH]c23)c2ccccc12]

Method D4. To tert-butyl 4-(2,3-diaminopyridin-4-yloxy)naphthalen-1-ylcarbamate (1.16 g, 3.17 mmol) dissolved in 15 mL of anhydrous ethanol under argon was added the ethyl carboethoxyformimidate hydrochloride (1.72 g, 9.51 mmol). The reaction mixture was stirred at reflux for 48 hours. After cooling at RT, a precipitate was formed. It was collected and rinsed with ether. The first isomer was obtained as a slightly pink solid (275 mg, 21%). Solvent was evaporated under vacuum and the residue was retaken in EtOAc. The organic phases were washed with a saturated solution of NaHCO$_3$, then brine, dried over MgSO$_4$ and concentrated under vacuum. The residue was chromatographed (eluent: EtOAc/MeOH: 1/0 towards 9/1) to afford the second isomer as a slightly yellow solid (463 mg, 35%).

tert-butyl 4-(2-amino-3-oxo-3,4-dihydropyrido[2,3-b]pyrazin-8-yloxy)naphthalen-1-ylcarbamate: $^1$H-NMR (DMSO-d$_6$), δ (ppm), J (Hz): 1.51 (s, 9H, tert-Bu), 6.31 (d, 1H, H$_{Py}$, 5, J=5.6 Hz), 7.20 (d, 1H, H$_{arom}$, J=8.2 Hz), 7.52-7.62 (m, 3H, H$_{arom}$), 7.89-7.91 (m, 2H, H$_{arom}$), 8.10 (d, 1H, H$_{arom}$, J=8.4 Hz), 9.26 (s, 1H, NHBoc), 12.61 (s, 1H, NH$_{lactame}$). $^{13}$C-NMR (DMSO-d$_6$), δ (ppm), J (Hz): 28.06 (C(CH$_3$)), 78.91 (C(CH$_3$)), 106.62, 115.63, 119.47, 121.28, 121.58, 123.43, 126.26, 126.42, 126.48, 129.44, 131.17, 142.99, 143.57, 147.15, 151.74, 152.72, 154.07, 156.97. LC-MS (m/z): 420 (M+H, 100).

Second isomer tert-butyl 4-(3-amino-2-oxo-1,2-dihydropyrido[2,3-b]pyrazin-8-yloxy)naphthalen-1-ylcarbamate:
$^1$H-NMR (DMSO-d$_6$), δ (ppm), J (Hz): 1.51 (s, 9H, tert-Bu), 6.28 (d, 1H, H$_{Py}$, J=5.5 Hz), 7.30 (d, 1H, H$_{arom}$, J=8.2 Hz), 7.62-7.53 (m, 2H, H$_{arom}$), 7.95 (d, 1H, H$_{arom}$, J=8.4 Hz), 8.00 (d, 1H, H$_{arom}$, J=5.5 Hz), 8.04 (t, 1H, H$_{arom}$, J=8.3 Hz), 8.12 (d, 1H, H$_{arom}$, J=8.7 Hz), 9.29 (s, 1H, NHBoc), 12.41 (s, 1H, NH$_{lactame}$). $^{13}$C-NMR (DMSO-d$_6$), δ (ppm), J (Hz): 28.17 (tert-Bu), 79.06 (tert-Bu), 104.81, 114.12, 116.17, 119.24, 121.27, 121.77, 123.40, 126.52, 126.57, 129.39, 131.69, 144.40, 146.51, 146.90, 151.12, 151.13, 154.13, 154.89.

5. Conversion of pyridopyrazin-2-one and pyridopyrazin-3-one to 2-amino-pyridopyrazine and 3-amino-pyridopyrazine Synthesis 40

Tert-butyl 4-(3-chloropyrido[2,3-b]pyrazin-8-yloxy)-2-fluorophenylcarbamate

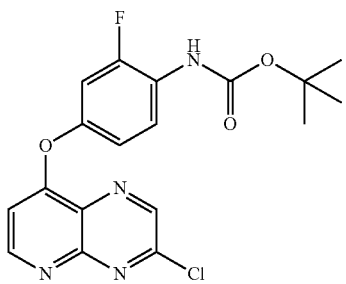 [SMILES: CC(C)(C)OC(=O)Nc1ccc(Oc2ccnc3nc(Cl)cnc23)cc1F]

Method D5: N-chloro succinimide (91 mg, 681 μmol) was added to a solution of triphenyl phosphine (178 mg, 678 μmol) in dry 1,4-dioxane (4 mL) under Ar, yielding a white suspension. After 30 min, tert-butyl 2-fluoro-4-(3-oxo-3,4-dihydropyrido[2,3-b]pyrazin-8-yloxy)phenylcarbamate (48 mg, 129 μmol) was added at once and the mixture was heated to reflux for 1 h. The black mixture was cooled to RT, Et$_3$N (1 mL) was added, and all volatiles were evaporated. The black residue was dissolved in CH$_2$Cl$_2$ (3 mL) and loaded onto a silica gel column (packed with Et$_2$O). Elution with ether furnished the title compound as the first, fast-running band (R$_1$=0.83 in Et$_2$O), which was concentrated to dryness to a white solid. Yield: 34 mg (68%).

$^1$H-NMR (DMSO-d$_6$), δ (ppm), J (Hz): 1.48 (s, 9H, tert-Bu), 7.09-7.13 (m, 2H), 7.32 (m, 1H, H$_{arom}$), 7.71 (m, 1H, H$_{arom}$), 8.98 (d, 1H, J=5.3, H$_{Py}$), 9.06 (s, 1H, NH$_{Boc}$), 9.12 (s, 1H, H$_{arom}$); $^{13}$C-NMR (DMSO-d$_6$), δ (ppm), J (Hz): 28.0, 79.5, 108.8 (d, J$_{FC}$=23.1), 109.9, 116.2 (d, J$_{FC}$=3.1), 124.3 (d, J$_{FC}$=11.6), 125.8, 129.3, 145.3, 149.8, 150.2 (d, J$_{FC}$=10.3), 150.8, 153.1, 154.6 (d, J$_{FC}$=248), 156.1, 161.0; $^{19}$F-NMR (DMSO-d$_6$), δ (ppm): −119.6; LC-MS (m/z): 391.1 (M+H, 100), rt=4.40 min.

Synthesis 41

Tert-butyl 4-(2-chloropyrido[2,3-b]pyrazin-8-yloxy)-2-fluorophenylcarbamate

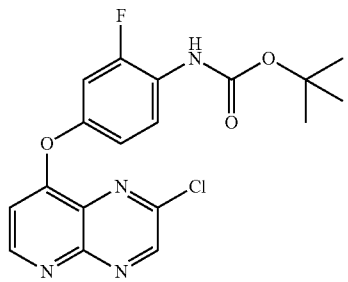 [SMILES: CC(C)(C)OC(=O)Nc1ccc(Oc2ccnc3ncc(Cl)nc23)cc1F]

Method D5 was used with tert-butyl 2-fluoro-4-(2-oxo-3,4-dihydropyrido[2,3-b]pyrazin-8-yloxy)phenylcarbamate to give the title product as off-white crystals. Yield: 250 mg (50%).

$^1$H-NMR (DMSO-d$_6$), δ (ppm), J (Hz): 1.48 (s, 9H, tert-Bu), 7.09-7.14 (m, 2H, H$_{arom}$), 7.34 (m, 1H, H$_{arom}$), 7.73 (m, 1H, H$_{arom}$), 8.97 (d, 1H, J=5.3, $_{Py}$rH), 9.07 (s, 1H, NHBoc), 9.23 (s, 1H, H$_{arom}$); $^{13}$C-NMR (DMSO-d$_6$), δ (ppm), J (Hz): 28.0, 79.5, 109.0 (d, J$_{FC}$=23.1), 110.0, 116.4 (d, J$_{FC}$=3.1), 124.5 (d, J$_{FC}$=11.6), 125.7, 129.8, 146.6, 149.0, 149.8 (d, J$_{FC}$=10.3), 150.7, 153.1, 154.6 (d, J$_{FC}$=248), 155.0, 160.1; $^{19}$F-NMR (DMSO-d$_6$), δ (ppm): −119.6; LC-MS (m/z): 391.1 (M+H, 100), rt=4.80 min.

Synthesis 42

Tert-butyl 2-fluoro-4-(2-morpholinopyrido[2,3-b]pyrazin-8-yloxy)phenyl-carbamate

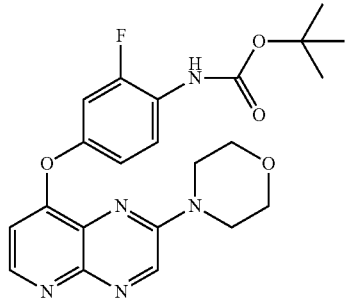 [SMILES: CC(C)(C)OC(=O)Nc1ccc(Oc2ccnc3ncc(N4CCOCC4)nc23)cc1F]

Method D6: Morpholine (500 μL, excess) was added to tert-butyl 4-(2-chloropyrido[2,3-b]pyrazin-8-yloxy)-2-fluorophenylcarbamate (68 mg, 174 μmol) under argon and the yellow solution was stirred at RT for 45 min. Next, H$_2$O (10 mL) was added and the precipitated yellow solid was filtered to give the title compound as a yellow solid. Yield: 69 mg (90%).

$^1$H-NMR (DMSO-d$_6$), δ (ppm), J (Hz): 1.47 (s, 9H, tert-Bu), 3.69 (br s, 8H, N(CH$_2$CH$_2$)$_2$O) 6.96 (m, 2H, H$_{arom}$), 7.04 (d, 1H, J=5.3, H$_{Py}$), 7.15 (m, 1H, H$_{arom}$), 7.59 (m, 1H, H$_{arom}$), 8.57 (d, 1H, J=5.3, H$_{Py}$), 8.96 (s, 1H, NH$_{Boc}$), 8.98 (s, 1H, H$_{arom}$); $^{13}$C-NMR (DMSO-d$_6$), δ (ppm), J (Hz): 28.0, 44.5, 65.8, 79.3, 107.8 (d, J$_{FC}$=23.1), 111.5, 115.3 (d, J$_{FC}$=3.1), 122.9 (d, J$_{FC}$=11.6), 125.8, 128.8, 139.5, 147.8, 147.9, 151.1, 152.3 (d, $J_{FC}$=10.3), 153.2, 154.8 (d, $J_{FC}$=248), 157.6; $^{19}$F-NMR (DMSO-$d_6$), δ (ppm): −120.3; LC-MS (m/z): 442.2 (M+H, 100) rt=4.70 min.

Synthesis 43

Tert-butyl 2-fluoro-4-(3-morpholinopyrido[2,3-b]pyrazin-8-yloxy)phenyl-carbamate

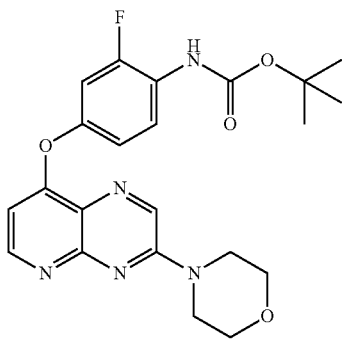 [SMILES: CC(C)(C)OC(=O)Nc1ccc(Oc2ccnc3nc(N4CCOCC4)cnc23)cc1F]

Method D6 was used with morpholine and tert-butyl 4-(3-chloropyrido[2,3-b]pyrazin-8-yloxy)-2-fluorophenyl-carbamate to give the title compound as a white solid. Yield: 117 mg (89%).

$^1$H-NMR (DMSO-$d_6$), δ (ppm), J (Hz): 1.48 (s, 9H, tert-Bu), 3.77 (m, 4H, N(CH$_2$CH$_2$)$_2$O), 3.84 (m, 4H, N(CH$_2$CH$_2$)$_2$O), 6.72 (d, 1H, J=5.3, H$_{Py}$), 7.00 (m, 2H, H$_{arom}$), 7.21 (m, 1H, H$_{arom}$), 7.63 (m, 1H, H$_{arom}$), 8.65 (d, 1H, J=5.3, H$_{Py}$), 8.85 (s, 1H, H$_{arom}$), 9.00 (s, 1H, NH$_{Boc}$); $^{13}$C-NMR (DMSO-$d_6$), δ (ppm), J (Hz): 28.0, 44.4, 65.9, 79.4, 106.4, 108.2 (d, $J_{FC}$=23.1), 115.7 (d, $J_{FC}$=3.1), 122.6, 123.3 (d, $J_{FC}$=11.6), 125.9, 136.4, 146.7, 151.4 (d, $J_{FC}$=10.3), 152.2, 153.2, 153.8, 153.9, 154.7 (d, $J_{FC}$=248), 160.0; $^{19}$F-NMR (DMSO-$d_6$), δ (ppm): −120.0; LC-MS (m/z): 442.2 (M+H, 100), rt=3.48 min.

Synthesis 44

Tert-butyl 2-fluoro-4-(3-(methylamino)pyrido[2,3-b]pyrazin-8-yloxy)phenylcarbamate

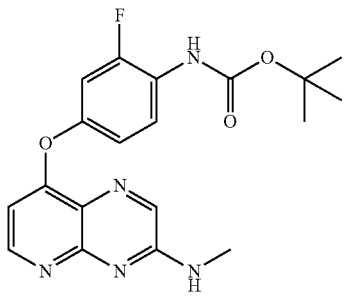 [SMILES: CNc1cnc2c(Oc3ccc(NC(=O)OC(C)(C)C)c(F)c3)ccnc2n1]

Method D6 was used with methylamine and Tert-butyl 4-(3-chloropyrido[2,3-b]pyrazin-8-yloxy)-2-fluorophenyl-carbamate to give the title compound as a white solid. Yield: 80 mg (90%).

$^1$H-NMR (DMSO-$d_6$), δ (ppm), J (Hz): 1.47 (s, 9H, tert-Bu), 2.95 (d, J=4.7, 3H, NHCH$_3$), 6.62 (d, J=5.4, 1H, H$_{Py}$), 6.97 (m, 1H, H$_{arom}$), 7.18 (m, 1H, H$_{arom}$), 7.61 (m, 1H, H$_{arom}$), 8.03 (br q, J=4.7, 1H, NHCH$_3$), 8.30 (s, 1H, H$_{arom}$), 8.55 (d, J=5.4, 1H, H$_{Py}$), 8.97 (s, 1H, NH); $^{13}$C-NMR (DMSO-$d_6$), δ (ppm), J (Hz): 27.1, 28.0, 79.4, 105.6, 108.3 (d, $J_{FC}$=23.0), 115.8 (d, $J_{FC}$=2.9), 122.3, 123.4 (d, $J_{FC}$=11.9), 125.8 (br), 139.7 (br), 151.3 (d, $J_{FC}$=10.0), 152.8, 153.2, 153.4, 154.7 (d, $J_{FC}$=248), 155.3, 160.1; $^{19}$F-NMR (DMSO-$d_6$), δ (ppm): −120.0; LC-MS (m/z): 386.1 (M+H, 100), rt=3.13 min.

Synthesis 45

Tert-butyl 2-fluoro-4-(3-(4-methylpiperazin-1-yl)pyrido[3,2-b]pyrazin-8-yloxy)phenylcarbamate

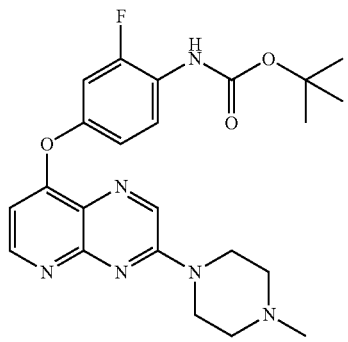 [SMILES: CN1CCN(c2cnc3c(Oc4ccc(NC(=O)OC(C)(C)C)c(F)c4)ccnc3n2)CC1]

Method D6 was used with N-methylpiperazine and tert-butyl 4-(3-chloropyrido[2,3-b]pyrazin-8-yloxy)-2-fluorophenylcarbamate to give the title compound as a yellow solid. Yield: 142 mg (92%).

$^1$H-NMR (DMSO-$d_6$), δ (ppm), J (Hz): 1.47 (s, 9H, tert-Bu), 2.24 (s, 3H, CH$_3$), 2.46 (m, 4H, N(CH$_2$CH$_2$)$_2$NMe), 3.84 (m, 4H, N(CH$_2$CH$_2$)$_2$NMe), 6.68 (d, J=5.3, 1H, H$_{Py}$), 6.98 (m, 1H, H$_{arom}$), 7.19 (m, 1H, H$_{arom}$), 7.61 (m, 1H, H$_{arom}$), 8.62 (d, J=5.3, 1H, H$_{Py}$), 8.84 (s, 1H, H$_{arom}$), 8.97 (s, 1H, NH); $^{13}$C-NMR (DMSO-$d_6$), δ (ppm), J (Hz): 28.0, 43.9, 45.6, 54.2, 79.4, 106.2, 108.2 (d, $J_{FC}$=22.8), 115.7 (d, $J_{FC}$=3.1), 122.4, 123.4 (d, $J_{FC}$=11.9), 125.9, 136.4, 151.4 (d, $J_{FC}$=10.0), 152.3, 153.2, 153.7, 154.7 (d, $J_{FC}$=248), 160.1; $^{19}$F-NMR (DMSO-$d_6$), δ (ppm): −120.0; LC-MS (m/z): 455.2 (M+H, 100), rt=2.43 min.

Synthesis 46

Tert-butyl 4-(3-(dimethylamino)pyrido[3,2-b]pyrazin-8-yloxy)-2-fluorophenylcarbamate

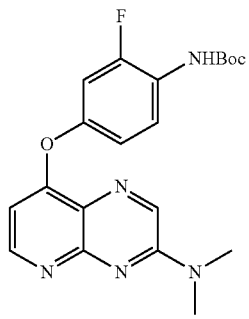 [SMILES: CN(C)c1cnc2c(Oc3ccc(NC(=O)OC(C)(C)C)c(F)c3)ccnc2n1]

Method D6 was used with tert-butyl 4-(3-chloropyrido[2,3-b]pyrazin-8-yloxy)-2-fluorophenylcarbamate (270 mg, 0.67 mmol) and dimethylamine to give the product as a yellow solid. Yield: 233 mg (91%).

$^1$H-NMR (DMSO-d$_6$), δ (ppm), J (Hz): 1.47 (s, 9H, tert-Bu), 2.95 (d, J=4.7, 3H, NHCH$_3$), 6.62 (d, J=5.4, 1H, H$_{Py}$), 6.97 (m, 1H, H$_{arom}$), 7.18 (m, 1H, H$_{arom}$), 7.61 (m, 1H, H$_{arom}$), 8.03 (br q, J=4.7, 1H, NHCH$_3$), 8.30 (s, 1H, H$_{arom}$), 8.55 (d, J=5.4, 1H, H$_{Py}$), 8.97 (s, 1H, NH); $^{13}$C-NMR (DMSO-d$_6$), δ (ppm), J (Hz): 28.0, 37.4, 79.4, 105.8, 108.2 (d, J$_{FC}$=23.0), 115.7 (d, J$_{FC}$=2.9), 122.0, 123.4 (d, J$_{FC}$=11.9), 125.9 (br), 136.1, 151.5 (d, J$_{FC}$=10.0), 152.5, 153.2, 153.5, 154.7 (d, J$_{FC}$=248), 160.1; $^{19}$F-NMR (DMSO-d$_6$), δ (ppm): −120.0; LC-MS (m/z): 400.1 (M+H, 100), rt=1.97 min.

6. Cyclisation to other substituted pyridopyrazinones

Synthesis 47 tert-butyl 4-(3-oxo-2-(trifluoromethyl)-3,4-dihydropyrido[2,3-b]pyrazin-8-yloxy)naphthalen-1-ylcarbamate

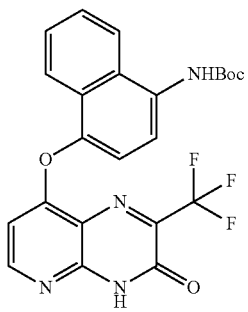 [SMILES: CC(C)(C)OC(=O)Nc1ccc(Oc2ccnc3[nH]c(=O)c(C(F)(F)F)nc23)c2ccccc12]

tert-butyl 4-(2-oxo-3-(trifluoromethyl)-1,2-dihydropyrido[2,3-b]pyrazin-8-yloxy)naphthalen-1-ylcarbamate

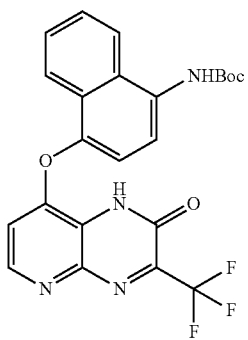 [SMILES: CC(C)(C)OC(=O)Nc1ccc(Oc2ccnc3nc(C(F)(F)F)c(=O)[nH]c23)c2ccccc12]

Method D7. To tert-butyl 4-(2,3-diaminopyridin-4-yloxy)naphthalen-1-ylcarbamate (1.00 g, 2.73 mmol) dissolved in 20 mL of anhydrous ethanol under argon and at reflux was added the ethyl trifluoropyruvate (697 mg, 0.50 mL, 4.10 mmol). The reaction mixture was stirred at reflux for 3 hours. After cooling at RT, a precipitate was formed, filtered off and rinsed with Et$_2$O. tert-butyl 4-(3-oxo-2-(trifluoromethyl)-3,4-dihydropyrido[2,3-b]pyrazin-8-yloxy)naphthalen-1-ylcarbamate was obtained as a white solid (116 mg, 0.246 mmol, 9%). The filtrate was evaporated under vacuum. The residue was chromatographed (eluent: CH$_2$Cl$_2$/EtOAc: 4/1 towards 0/1) to afford the second isomer as a slightly yellow solid (540 mg, 1.14 mmol, 42%).

First isomer tert-butyl 4-(3-oxo-2-(trifluoromethyl)-3,4-dihydropyrido[2,3-b]pyrazin-8-yloxy)naphthalen-1-ylcarbamate: $^1$H-NMR (DMSO-d$_6$), δ (ppm), J (Hz): 1.52 (s, 9H, tert-Bu), 6.37 (d, 1H, H$_{Py}$, J=5.7 Hz), 7.45 (d, 1H, H$_{arom}$, J=8.2 Hz), 7.54-7.57 (m, 1H, H$_{arom}$), 7.62-7.65 (m, 1H, H$_{arom}$), 7.69 (d, 1H, H$_{arom}$, J=8.2 Hz), 7.80 (d, 1H, H$_{arom}$, J=8.4 Hz), 8.18 (d, 1H, H$_{arom}$, J=8.6 Hz), 8.37 (d, 1H, H$_{Py}$, J=5.7 Hz), 9.38 (s, 1H, NHBoc), 13.55 (s, 1H, NH$_{lactame}$). $^{13}$C-NMR (DMSO-d$_6$), δ (ppm), J (Hz): 28.04 (tert-Bu), 79.09 (tert-Bu), 105.71, 116.54, 117.35, 118.78, 120.84, 120.97, 123.62, 126.06, 126.58, 126.97, 129.09, 132.63, 143.17, 145.24, 146.71, 153.20, 153.90, 154.84, 162.26. LC-MS (m/z): 473 (M+H, 100).

Second isomer tert-butyl 4-(2-oxo-3-(trifluoromethyl)-1,2-dihydropyrido[2,3-b]pyrazin-8-yloxy)naphthalen-1-ylcarbamate: $^1$H-NMR (DMSO-d$_6$), δ (ppm), J (Hz): 1.53 (s, 9H, tert-Bu), 6.76 (d, 1H, H$_{Py}$, J=5.3 Hz), 7.43 (d, 1H, H$_{arom}$, J=8.2 Hz), 7.55-7.58 (m, 1H, H$_{arom}$), 7.63-7.69 (m, 2H, H$_{arom}$), 7.92 (d, 1H, H$_{arom}$, J=8.4 Hz), 8.17 (d, 1H, H$_{arom}$, J=8.6 Hz), 8.39 (d, 1H, H$_{Py}$, J=5.3 Hz), 9.38 (s, 1H, NH$_{Boc}$), 13.51 (s, 1H, NH$_{lactame}$). $^{13}$C-NMR (DMSO-d$_6$), δ (ppm), J (Hz): 28.06 (tert-Bu), 79.08 (tert-Bu), 90.66 (CF$_3$), 110.72, 116.81, 118.62, 120.88, 120.97, 121.42, 123.17, 123.46, 125.47, 126.07, 126.68, 129.25, 132.38, 145.51, 146.71, 151.66, 153.97, 166.39. LC-MS (m/z): 473 (M+H, 100).

(V) Deprotection of Boc

Synthesis 48

8-(4-amino-3-fluorophenoxy)pyrido[2,3-b]pyrazin-2(1H)-one

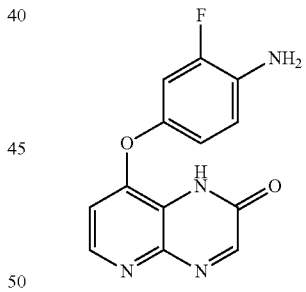

Method E1: Tert-butyl 2-fluoro-4-(2-oxo-1,2-dihydropyrido[2,3-b]pyrazin-8-yloxy)phenyl carbamate (250 mg, 671 μmol) was added to a round bottom flask under Ar. TBAF (7 mL of a 1M solution in THF, 7 mmol) was added and the solution was heated to reflux for 5 h. The volatiles were evaporated and the oily residue was diluted with H$_2$O (80 mL). The pH was adjusted to 7 (NaHCO$_3$) and after 1 h of stirring at RT, the precipitate was filtered off and stripped twice with toluene (30 mL) to give the title compound as a yellow solid. Yield: 180 mg (98%).

$^1$H-NMR (DMSO-d$_6$), δ (ppm), J (Hz): 5.19 ppm (br s, 2H, NH$_2$), 6.79 (d, J=5.4 Hz, 1H, H$_{Py}$), 6.88-6.82 (m, 2H, H$_{arom}$), 7.06 (m, 1H, H$_{arom}$), 8.32 (d, J=5.4 Hz, 1H, H$_{Py}$), 8.40 (s, 1H, H$_{arom}$), 12.49 (br s, 1H, NHAr). $^{13}$C-NMR (DMSO-d$_6$), δ (ppm), J (Hz): 108. (d, J$_{FC}$=21 Hz), 109.3, 116.3 (d, J$_{FC}$=6 Hz), 117.1 (d, J$_{FC}$=3 Hz), 119.2 (br), 134.7

(d, $J_{FC}$=13 Hz), 142.6 (d, $J_{FC}$=9 Hz), 144.0 (br), 145.4, 150.1 (d, $J_{FC}$=240 Hz), 153.2, 154.5, 155.6 (br); LC-MS (m/z): 273.1 (M+H, 100), rt=2.37 min

Synthesis 49

8-(4-amino-3-fluorophenoxy)pyrido[2,3-b]pyrazin-3(4H)-one

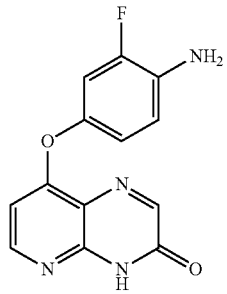 [SMILES: Nc1ccc(Oc2ccnc3[nH]c(=O)cnc23)cc1F]

Method E1 was used with tert-butyl 2-fluoro-4-(3-oxo-3,4-dihydropyrido[3,2-b]pyrazin-8-yloxy)phenyl carbamate to afford the title compound. Yield: 191 mg (93%).

$^1$H-NMR (DMSO-d$_6$), δ (ppm), J (Hz): 5.21 ppm (br s, 2H, NH$_2$); 6.52 (d, J=4.8 Hz, 1H, H$_{Py}$), 6.89-6.82 (m, 2H, H$_{arom}$), 7.05 (d, $^3J_{FC}$=11.5 Hz, 1H, H$_{arom}$), 8.17 (s, 1H, H$_{arom}$), 8.32 (d, J=4.8 Hz, 1H, H$_{Py}$), 12.86 (br s, 1H, NHAr); $^{13}$C-NMR (DMSO-d$_6$), δ (ppm), J (Hz): 105.5, 108.8 (d, $J_{FC}$=21 Hz), 116.4 (d, $J_{FC}$=6 Hz), 117.0 (d, $J_{FC}$=3 Hz), 118.0, 134.6 (d, $J_{FC}$=13 Hz), 142.6 (d, $J_{FC}$=9 Hz), 145.3, 150.8, 150.1 (d, $J_{FC}$=241 Hz), 152.1, 156.5, 161.7; $^{19}$F NMR (470 MHz, DMSO-d$_6$): δ=−131.2 ppm; LC-MS (m/z): 273.1 (M+H, 100), rt=2.86 min.

Synthesis 50

8-(4-amino-3-(methylthio)phenoxy)pyrido[2,3-b]pyrazin-2(1H)-one

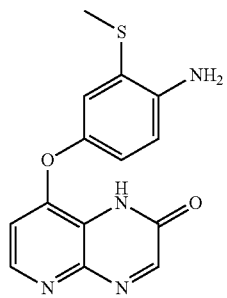 [SMILES: CSc1cc(Oc2ccnc3ncc(=O)[nH]c23)ccc1N]

Using Method E1 with tert-butyl -2-(methylthio)-4-(2-oxo-1,2-dihydropyrido[2,3-b]pyrazin-8-yloxy)phenylcarbamate (170 mg, 0.4 mmol), the title compound (81 mg, 63%) was obtained as a pale brown powder.

$^1$H-NMR (DMSO-d$_6$), δ (ppm), J (Hz): 2.36 (s, 3H, CH$_3$); 5.19 (s, 2H, NH$_2$), 6.75 (d, 1H, H$_{Py}$ J=5.3 Hz), 6.79 (d, 1H, H$_{arom}$, J=8.6 Hz), 6.90 (dd, 1H, H$_{arom}$, J=8.6 Hz, J=2.5 Hz), 7.07 (d, 1H, H$_{arom}$, J=2.5 Hz), 8.31 (d, 1H, H$_{Py}$ J=5.3 Hz), 8.39 (s, 1H, NH or CH), 12.48 (s, 1H, NH). $^{13}$C-NMR (DMSO-d$_6$), δ (ppm), J (Hz): 15.7, 108.9, 114.8, 119.8, 120.7, 121.8, 143.6, 145.0, 145.3, 154.4. LC-MS (m/z): 301 (M+H, 100), rt=2.90 min.

Synthesis 51

8-(4-amino-3-(methylthio)phenoxy)pyrido[3,2-b]pyrazin-3(4H)-one

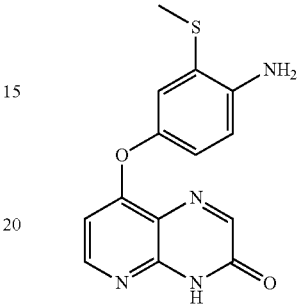

Using Method E1 with tert-butyl 2-(methylthio)-4-(3-oxo-3,4-dihydropyrido[3,2-b]pyrazin-8-yloxy)phenylcarbamate (110 mg, 0.3 mmol), the title compound (63 mg, 76%) was obtained as a pale yellow powder.

$^1$H-NMR (DMSO-d$_6$), δ (ppm), J (Hz): 2.37 (s, 3H, CH$_3$); 5.18 (s, 2H, NH$_2$), 6.48 (d, 1H, H$_{Py}$ J=5.6 Hz), 6.79 (d, 1H, H$_{arom}$, J=8.6 Hz), 6.87 (dd, 1H, H$_{arom}$, J=8.6 Hz, J=2.6 Hz), 7.04 (d, 1H, H$_{arom}$, J=2.6 Hz), 8.16 (s, 1H, NH or CH), 8.29 (d, 1H, H$_{Py}$, J=5.6 Hz), 12.82 (s, 1H, NH). $^{13}$C-NMR (DMSO-d$_6$), δ (ppm), J (Hz): 15.6, 105.2, 114.8, 117.8, 119.7, 120.8, 121.5, 143.7, 144.9, 145.1, 150.5, 151.9, 156.4, 161.8. LC-MS (m/z): 301 (M+H, 100), rt=3.35 min.

Synthesis 52

8-(4-amino-3-fluorophenoxy)-3-methylpyrido[3,2-b]pyrazin-2(1H)-one

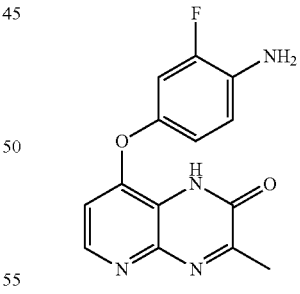

Method E1 was used with tert-butyl 2-fluoro-4-(3-methyl-2-oxo-1,2-dihydropyrido[2,3-b]pyrazin-8-yloxy)phenyl carbamate; yield: 96%.

$^1$H-NMR (DMSO-d$_6$), δ (ppm), J (Hz): 2.48 ppm (s, 3H, CH$_3$), 6.72 (d, 1H, J=5.3 Hz, H$_{Py}$), 6.84 (m, 2H, H$_{arom}$), 7.03 (m, 1H, H$_{arom}$), 8.27 (d, 1H, H$_{Py}$, J=5.3 Hz), 12.32 (br s, 1H, NHAr); $^{13}$C-NMR (DMSO-d$_6$), δ (ppm), J (Hz): 28.0, 79.4, 106.8, 109.0, 116.0, 118.5, 123.9, 125.8, 145.6, 150.5, 151.2, 152.2, 153.1, 156.4, 160.3; $^{19}$F NMR (470 MHz, DMSO-d$_6$): δ=−131.3 ppm; LC-MS (2.79 min): 287.1 (M+H, 100)

Synthesis 53

8-(4-amino-3-fluorophenoxy)-2-methylpyrido[2,3-b]pyrazin-3(4H)-one

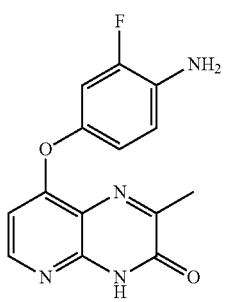 [SMILES: Cc1nc2c(Oc3ccc(N)c(F)c3)ccnc2[nH]c1=O]

Method E1 was used with tert-butyl 2-fluoro-4-(2-methyl-3-oxo-3,4-dihydropyrido[2,3-b]pyrazin-8-yloxy)phenyl carbamate to afford the title compound in 97% yield.

$^1$H-NMR (DMSO-$d_6$), δ (ppm), J (Hz): 2.43 ppm (s, 3H, CH$_3$), 5.18 (br s, 2H, NH$_2$), 6.46 (d, J=4.8 Hz, 1H, H$_{Py}$), 6.81 (m, 1H, H$_{arom}$), 7.02 (s, 1H, H$_{arom}$), 8.23 (d, J=4.8 Hz, 1H, H$_{Py}$), 12.70 (br s, 1H, NHAr); $^{19}$F NMR (470 MHz, DMSO-$d_6$): δ=−131.2 ppm; LC-MS (m/z): 287.1 (M+H, 100), rt=3.20 min.

Synthesis 54

8-(4-amino-2-fluorophenoxy)pyrido[2,3-b]pyrazin-3(4H)-one

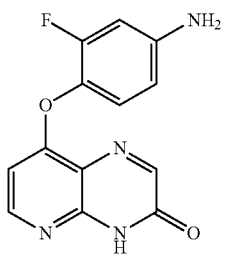 [SMILES: Nc1ccc(Oc2ccnc3[nH]c(=O)cnc23)c(F)c1]

Using Method E1 with tert-butyl-3-fluoro-4-(3-oxo-3,4-dihydropyrido[2,3-b]pyrazin-8-yloxy)phenylcarbamate (335 mg, 0.9 mmol), the title compound (164 mg, 67%) was obtained as a brown powder.

$^1$H-NMR (DMSO-$d_6$), δ (ppm), J (Hz): 5.66 (bs, 2H, NH2); 6.57 (d, 1H, H$_{Py}$, J=5.4 Hz), 6.72 (dd, 1H, H$_{arom}$, J=8.7 Hz and J=2.0 Hz), 6.84 (dd, 1H, H$_{arom}$, J=12.6 Hz and J=2.5 Hz), 7.20 (t, 1H, H$_{arom}$, J=8.8 Hz), 8.21 (s, 1H, CH), 8.38 (d, 1H, H$_{Py}$, J=5.7 Hz). $^{13}$C-NMR (DMSO-$d_6$), δ (ppm), J (Hz): 105.1, 106.0, 114.0, 118.7, 124.8, 133.0, 145.0, 146.4, 152.1, 153.2, 155.8, 157.5, 161.9. $^{19}$F-NMR (δ, ppm, DMSO-d6): −129.18. LC-MS (m/z): 273 (M+H, 100), rt=1.45 min.

Synthesis 55

8-(3-aminophenoxy)pyrido[2,3-b]pyrazin-3(4H)-one

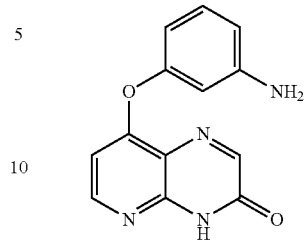

Method E1 was used with tert-butyl 3-(3-oxo-3,4-dihydropyrido[2,3-b]pyrazin-8-yloxy)phenylcarbamate (226 mg, 0.638 mmol) to afford the title compound as a slightly yellow solid (132 mg, 0.519 mmol, 81%).

$^1$H-NMR (DMSO-$d_6$), δ (ppm), J (Hz): 5.37 (bs, 2H, NH$_2$), 6.30 (ddd, 1H, H$_{arom}$, J=7.9 Hz, J=2.3 Hz, J=0.7 Hz), 6.35 (t, 1H, H$_{arom}$, J=2.2 Hz), 6.50 (ddd, 1H, H$_{arom}$, J=8.1 Hz, J=2.0 Hz, J=0.8 Hz), 6.58 (d, 1H, H$_{Py}$, J=5.6 Hz), 7.11 (t, 1H, H$_{arom}$, J=8.0 Hz), 8.16 (s, 1H, H$_{arom}$), 8.33 (d, 1H, H$_{Py}$, J=5.6 Hz), 12.84 (s, 1H, NH). $^{13}$C-NMR (DMSO-$d_6$), δ (ppm), J (Hz): 105.03, 106.21, 106.83, 111.13, 118.24, 130.33, 145.30, 150.75, 150.78, 151.89, 154.70, 156.36, 160.82. LC-MS (m/z): 255 (M+H, 100).

Synthesis 56

8-(3-aminophenoxy)pyrido[2,3-b]pyrazin-2(1H)-one

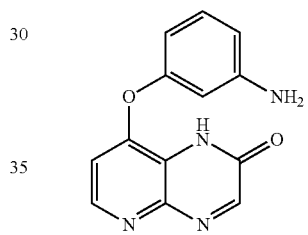

Method E1 was used with tert-butyl 3-(2-oxo-1,2-dihydropyrido[2,3-b]pyrazin-8-yloxy)phenylcarbamate (635 mg, 1.8 mmol) to afford the title compound as a slightly yellow solid (123 mg, 0.484 mmol, 27%).

$^1$H-NMR (DMSO-$d_6$), δ (ppm), J (Hz): 5.38 (bs, 2H, NH$_2$), 6.37 (ddd, 1H, H$_{arom}$, J=7.9 Hz, J=2.3 Hz, J=0.7 Hz), 6.35 (t, 1H, H$_{arom}$, J=2.2 Hz), 6.50 (ddd, 1H, H$_{arom}$, J=8.1 Hz, J=2.0 Hz, J=0.8 Hz), 6.85 (d, 1H, H$_{Py}$, J=5.6 Hz), 7.11 (t, 1H, H$_{arom}$, J=8.0 Hz), 8.16 (s, 1H, H$_{arom}$), 8.35 (d, 1H, H$_{Py}$, J=5.3 Hz), 8.40 (s, 1H, H$_{arom}$), 12.49 (s, 1H, NH). LC-MS (m/z): 255 (M+H, 100).

Synthesis 57

8-(3-aminophenoxy)-2-methylpyrido[2,3-b]pyrazin-3(4H)-one

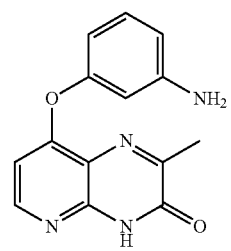 [SMILES: Cc1nc2c(Oc3cccc(N)c3)ccnc2[nH]c1=O]

Method E1 was used with tert-butyl 3-(2-methyl-3-oxo-3,4-dihydropyrido[2,3-b]pyrazin-8-yloxy)phenylcarbamate (190 mg, 0.5 mmol) to afford the title compound as a slightly yellow solid (120 mg, 0.447 mmol, 90%).

$^1$H-NMR (DMSO-d$_6$), δ (ppm), J (Hz): 2.42 (s, 3H, Me), 5.37 (bs, 2H, NH$_2$), 6.31 (d, 1H, H$_{arom}$, J=7.9 Hz), 6.36 (s, 1H, H$_{arom}$), 6.50 (d, 1H, H$_{arom}$, J=8.0 Hz), 6.53 (d, 1H, H$_{Py}$, J=5.7 Hz), 7.12 (t, 1H, H$_{arom}$, J=8.0 Hz), 8.26 (d, 1H, H$_{Py}$, J=5.7 Hz), 12.77 (s, 1H, NH). $^{13}$C-NMR (DMSO-d$_6$), δ (ppm), J (Hz): 20.49 (Me), 105.26, 105.96, 107.06, 111.14, 117.72, 130.40, 145.96, 150.36, 150.84, 154.87, 156.61, 158.70, 160.10. LC-MS (m/z): 269 (M+H, 100).

Synthesis 58

8-(4-aminophenylthio)pyrido[2,3-b]pyrazin-3(4H)-one

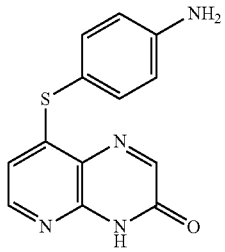 [SMILES: Nc1ccc(Sc2ccnc3[nH]c(=O)cnc23)cc1]

Method E1 was used with Tert-butyl 4-(3-oxo-3,4-dihydropyrido[2,3-b]pyrazin-8-ylthio)phenylcarbamate (438 mg, 1.18 mmol) to give the title compound as a yellow solid. Yield: 160 mg (50%).

$^1$H-NMR (DMSO-d$_6$), δ (ppm), J (Hz): 5.68 (br s, 2H, NH$_2$), 6.39 (d, J=5.3, 1H, H$_{Py}$), 6.71 (d, J=8.3, 2H, H$_{arom}$), 7.22 (d, J=8.3, 2H, H$_{arom}$), 8.17 (m, 2H, H$_{Py}$), 12.78 (br s, 1H, NH); $^{13}$C-NMR (DMSO-d$_6$), δ (ppm), J (Hz): 110.0, 114.5, 115.2, 123.0, 137.1, 143.2, 149.9, 150.7, 151.0, 154.1, 156.7; LC-MS (m/z): 271.0 (M+H, 100), rt=3.46 min.

Synthesis 59

2-fluoro-4-(3-morpholinopyrido[2,3-b]pyrazin-8-yloxy)aniline

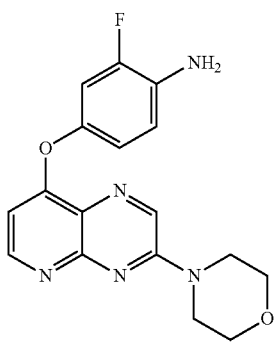 [SMILES: Nc1ccc(Oc2ccnc3nc(N4CCOCC4)cnc23)cc1F]

Method E1 was used with Tert-butyl 2-fluoro-4-(3-morpholinopyrido[2,3-b]pyrazin-8-yloxy)phenyl-carbamate (100 mg, 0.23 mmol) to give the title compound as a yellow solid. Yield: 69 mg (87%).

$^1$H-NMR (DMSO-d$_6$), δ (ppm), J (Hz): 3.76 (m, 4H, N(CH$_2$CH$_2$)$_2$O), 3.82 (m, 4H, N(CH$_2$CH$_2$)$_2$O), 5.16 (s, 2H, NH$_2$), 6.52 (d, 1H, J=5.3, H$_{Py}$), 6.80-6.88 (m, 2H, H$_{arom}$), 7.03 (m, 1H, H$_{arom}$), 8.55 (d, 1H, J=5.3, H$_{Py}$), 8.82 (s, 1H, H$_{arom}$); $^{13}$C-NMR (DMSO-d$_6$), δ (ppm), J (Hz): 44.4, 65.9, 104.5, 108.7 (d, J$_{FC}$=21.2), 116.4 (d, J$_{FC}$=5.8), 117.0 (d, J$_{FC}$=2.9), 122.3, 134.4 (d, J$_{FC}$=12.9), 135.9, 143.2 (d, J$_{FC}$=9.5), 150.2 (d, J$_{FC}$=240), 151.9, 153.2, 153.9, 161.6; $^{19}$F-NMR (DMSO-d$_6$), δ (ppm): −131.3; LC-MS (m/z): 342.1 (M+H, 100), rt=2.03 min.

Synthesis 60

8-(4-amino-3-fluorophenoxy)-N-methylpyrido[3,2-b]pyrazin-3-amine

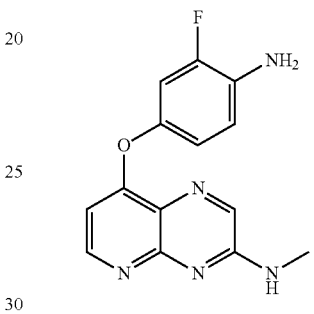

Method E1 was used with tert-butyl 2-fluoro-4-(3-(methylamino)pyrido[2,3-b]pyrazin-8-yloxy)phenylcarbamate (65 mg, 0.17 mmol) to give 41 mg of the title compound (85%). $^1$H-NMR (DMSO-d$_6$), δ (ppm), J (Hz): 2.95 (d, J=4.6, 3H, NHCH$_3$), 5.17 (s, 2H, NH$_2$), 6.45 (d, J=5.4, 1H, H$_{Py}$), 6.80-6.88 (m, 2H, H$_{arom}$), 7.02 (m, 1H, H$_{arom}$), 8.03 (br q, J=4.6, 1H, NHCH$_3$), 8.31 (s, 1H, H$_{arom}$), 8.48 (d, J=5.4, 1H, H$_{Py}$);

$^{13}$C-NMR (DMSO-d$_6$), δ (ppm), J (Hz): 27.1, 104.0, 108.7 (d, J$_{FC}$=21.2), 116.4 (d, J$_{FC}$=5.6), 117.0 (d, J$_{FC}$=21.2), 121.9, 134.3 (d, J$_{FC}$=12.9), 139.2 (br), 143.2 (d, J$_{FC}$=9.3), 150.2 (d, J$_{FC}$=240), 152.7, 153.1, 155.3, 160.1; $^{19}$F-NMR (DMSO-d$_6$), δ (ppm): −131.3; LC-MS (m/z): 286.1 (M+H, 100), rt=1.87 min.

Synthesis 61

2-fluoro-4-(3-(4-methylpiperazin-1-yl)pyrido[3,2-b]pyrazin-8-yloxy)aniline

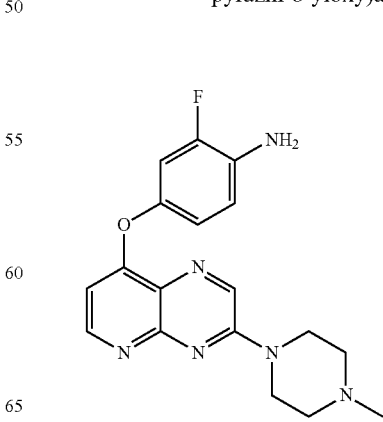

Method E1 was used with Tert-butyl 2-fluoro-4-(3-(4-methylpiperazin-1-yl)pyrido[3,2-b]pyrazin-8-yloxy)phenylcarbamate (125 mg, 0.28 mmol) to give the title compound as a yellow solid. Yield: 76 mg (75%).

$^1$H-NMR (DMSO-$d_6$), δ (ppm), J (Hz): 2.24 (s, 3H, CH$_3$), 2.46 (m, 4H, N(CH$_2$CH$_2$)$_2$NMe), 3.84 (m, 4H, N(CH$_2$CH$_2$)$_2$NMe), 5.16 (s, 2H, NH$_2$), 6.49 (d, J=5.3, 1H, H$_{Py}$), 6.80 (m, 1H, H$_{arom}$), 6.86 (m, 1H, H$_{arom}$), 7.02 (m, 1H, H$_{arom}$), 8.53 (d, J=5.3, 1H, H$_{Py}$), 8.83 (s, 1H, H$_{arom}$); $^{13}$C-NMR (DMSO-$d_6$), δ (ppm), J (Hz): 43.9, 45.7, 54.2, 104.4, 108.7 (d, J$_{FC}$=21.1), 116.4 (d, J$_{FC}$=5.8), 117.0 (d, J$_{FC}$=2.8), 122.1, 134.4 (d, J$_{FC}$=12.8), 136.0, 143.2 (d, J$_{FC}$=9.4), 150.2 (d, J$_{FC}$=240), 152.0, 153.5, 153.8, 161.6; $^{19}$F-NMR (DMSO-$d_6$), δ (ppm): −131.3; LC-MS (0.67 min): m/z calcd. for C$_{18}$H$_{20}$FN$_6$O [M+H$^+$]: 355.1; found: 355.1.

Synthesis 62

8-(4-amino-3-(methylthio)phenoxy)-2-methylpyrido[2,3-b]pyrazin-3(4H)-one

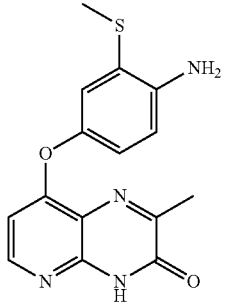 [SMILES: CSc1cc(Oc2ccnc3[nH]c(=O)c(C)nc23)ccc1N]

Using Method E1 with tert-butyl 4-(2-methyl-3-oxo-3,4-dihydropyrido[2,3-b]pyrazin-8-yloxy)-2-(methylthio)phenylcarbamate (131 mg, 0.3 mmol), the title compound (97 mg, 99%) was obtained as a pale yellow powder.

$^1$H-NMR (DMSO-$d_6$), δ (ppm), J (Hz): 2.37 (s, 3H, CH$_3$); 2.42 (s, 3H, CH$_3$); 5.17 (bs, 2H, NH$_2$), 6.43 (d, 1H, H$_{Py}$, J=5.6 Hz), 6.79 (d, 1H, H$_{arom}$, J=8.6 Hz), 6.86 (dd, 1H, H$_{arom}$, J=8.6 Hz, J=2.6 Hz), 7.04 (d, 1H, H$_{arom}$, J=2.6 Hz), 8.21 (d, 1H, H$_{Py}$, J=5.6 Hz), 12.69 (s, 1H, NH). $^{13}$C-NMR (DMSO-$d_6$), δ (ppm), J (Hz): 15.6, 20.3, 105.0, 114.8, 117.1, 119.7, 120.8, 121.6, 143.7, 144.8, 145.3, 150.4, 156.2, 158.4, 161.0. LC-MS (m/z): 315 (M+H, 100), rt=3.68 min.

Synthesis 63

8-(4-amino-3-(methylthio)phenoxy)-3-methylpyrido[2,3-b]pyrazin-2(1H)-one

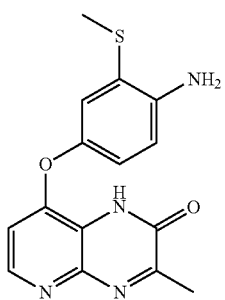 [SMILES: CSc1cc(Oc2ccnc3nc(C)c(=O)[nH]c23)ccc1N]

Using Method E1 with tert-butyl 4-(3-methyl-2-oxo-1,2-dihydropyrido[2,3-b]pyrazin-8-yloxy)-2-(methylthio)phenylcarbamate (200 mg, 0.48 mmol), the title compound (34 mg, 23%) was obtained as a pale yellow powder.

$^1$H-NMR (DMSO-$d_6$), δ (ppm), J (Hz): 2.36 (s, 3H, CH$_3$); 2.37 (s, 3H, CH$_3$); 5.19 (s, 2H, NH2), 5.96 (d, 1H, H$_{Py}$, J=5.5 Hz), 6.75 (d, 1H, H$_{arom}$, J=8.4 Hz), 6.88 (dd, 1H, H$_{arom}$, J=8.5 Hz, J=2.6 Hz), 7.06 (d, 1H, H$_{arom}$, J=2.6 Hz), 8.28 (d, 1H, H$_{Py}$, J=5.5 Hz), 12.33 (s, 1H, NH). LC-MS (m/z): 315 (M+H, 100), rt=1.86 min.

Synthesis 64

8-(4-aminonaphthalen-1-yloxy)-2-methylpyrido[2,3-b]pyrazin-3(4H)-one

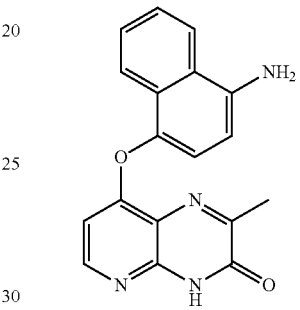

Method E1 was used with tert-butyl 4-(2-methyl-3-oxo-3,4-dihydropyrido[2,3-b]pyrazin-8-yloxy)naphthalen-1-ylcarbamate to afford the title compound as a slightly yellow solid (309 mg, 0.971 mmol, Quantitative).

$^1$H-NMR (DMSO-$d_6$), δ (ppm), J (Hz): 2.49 (s, 3H, Me), 5.86 (bs, 2H, NH2), 6.21 (d, 1H, H$_{arom}$, J=5.7 Hz), 6.72 (d, 1H, H$_{arom}$, J=8.2 Hz), 7.14 (d, 1H, H$_{arom}$, J=8.1 Hz), 7.40-7.46 (m, 2H, H$_{arom}$), 7.59 (d, 1H, H$_{arom}$, J=7.8 Hz), 8.12 (d, 1H, H$_{Py}$, J=5.7 Hz), 8.17 (d, 1H, H$_{arom}$, J=8.2 Hz), 12.73 (s, 1H, NH). $^{13}$C-NMR (DMSO-$d_6$), δ (ppm), J (Hz): 20.47 (Me), 104.90, 106.34, 117.05, 118.71, 120.74, 123.08, 123.33, 124.41, 126.39, 126.56, 138.40, 143.32, 145.42, 150.38, 156.29, 158.53, 161.56. LC-MS (m/z): 319 (M+H, 100).

Synthesis 65

8-(4-aminonaphthalen-1-yloxy)-3-methylpyrido[2,3-b]pyrazin-2(1H)-one

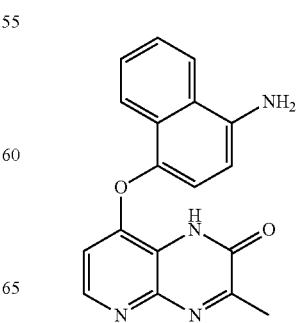

Method E1 was used with tert-butyl 4-(3-methyl-2-oxo-1,2-dihydropyrido[2,3-b]pyrazin-8-yloxy)naphthalen-1-ylcarbamate to afford the title compound as a slightly yellow solid (354 mg, 1.11 mmol, 66%).

$^1$H-NMR (DMSO-$d_6$), δ (ppm), J (Hz): 2.50 (s, 3H, Me), 5.85 (bs, 2H, NH$_2$), 6.46 (d, 1H, H$_{py}$, J=5.4 Hz), 6.72 (d, 1H, H$_{arom}$, J=8.1 Hz), 7.17 (d, 1H, H$_{arom}$, J=8.1 Hz), 7.41-7.46 (m, 2H, H$_{arom}$), 7.66 (d, 1H, H$_{arom}$, J=7.4 Hz), 8.15-8.17 (m, 2H, H$_{arom}$), 12.55 (s, 1H, NH). $^{13}$C-NMR (DMSO-$d_6$), δ (ppm), J (Hz): 20.93 (Me), 106.20, 107.66, 118.38, 118.76, 121.00, 122.97, 123.33, 124.45, 126.32, 126.52, 138.28, 143.37, 143.57, 144.89, 153.31, 154.48, 163.78. LC-MS (m/z): 319 (M+H, 100).

Synthesis 66

2-amino-8-(4-aminonaphthalen-1-yloxy)pyrido[2,3-b]pyrazin-3(4H)-one

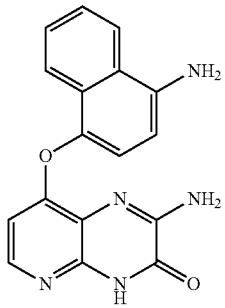 [SMILES: Nc1nc2c(Oc3ccc(N)c4ccccc34)ccnc2[nH]c1=O]

Method E1 was used with tert-butyl 4-(2-amino-3-oxo-3,4-dihydropyrido[2,3-b]pyrazin-8-yloxy)naphthalen-1- to afford the title compound as a slightly pink solid (207 mg, 0.648 mmol, 75%).

$^1$H-NMR (DMSO-$d_6$), δ (ppm), J (Hz): 5.76 (bs, 2H, NH2), 6.14 (d, 1H, H$_{arom}$, J=5.6 Hz), 6.70 (d, 1H, H$_{arom}$, J=8.1 Hz), 7.07 (d, 1H, H$_{arom}$, J=8.1 Hz), 7.39-7.44 (m, 2H, H$_{arom}$), 7.62 (dd, 1H, H$_{arom}$, J=7.5 Hz, J=2.0 Hz), 7.80 (d, 1H, H$_{Py}$, 6, J=5.6 Hz), 8.14 (d, 1H, H$_{arom}$, J=7.5 Hz), 12.50 (s, 1H, NH). $^{13}$C-NMR (DMSO-$d_6$), δ (ppm), J (Hz): 105.15, 106.46, 118.43, 118.59, 120.93, 122.97, 123.42, 124.32, 126.15, 126.78, 139.07, 142.66, 142.84, 143.56, 151.49, 152.72, 158.57. LC-MS (m/z): 320 (M+H, 100).

Synthesis 67

8-(4-amino-3-fluorophenoxy)-N,N-dimethylpyrido[3,2-b]pyrazin-3-amine

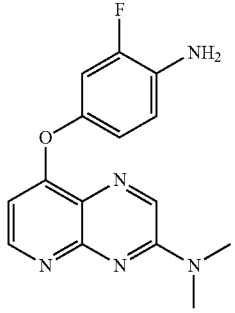 [SMILES: CN(C)c1cnc2c(Oc3ccc(N)c(F)c3)ccnc2n1]

Method E1 was used with tert-butyl 4-(3-(dimethylamino)pyrido[3,2-b]pyrazin-8-yloxy)-2-fluorophenylcarbamate to give the crude product (5% TBAF) as a beige solid, which was used in subsequent steps. Yield: 128 mg (78%).

$^1$H-NMR (DMSO-$d_6$), δ (ppm), J (Hz): 3.27 (s, 6H, N(CH$_3$)$_2$), 5.15 (s, 2H, NH$_2$), 6.47 (d, J=5.2, 1H, H$_{Py}$), 6.80-6.88 (m, 2H, H$_{arom}$), 7.01 (m, 1H, H$_{arom}$), 8.52 (d, J=5.2, 1H, H$_{Py}$), 8.69 (s, 1H, H$_{arom}$); $^{19}$F-NMR (DMSO-$d_6$), δ (ppm): −131.3; LC-MS (m/z): 300.1 (M+H, 100), rt=1.29 min.

Synthesis 68

3-amino-8-(4-aminonaphthalen-1-yloxy)pyrido[2,3-b]pyrazin-2(1H)-one

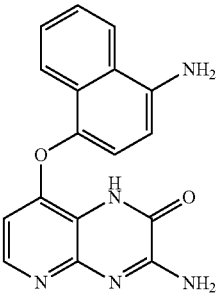 [SMILES: Nc1nc2nccc(Oc3ccc(N)c4ccccc34)c2[nH]c1=O]

Method E1 was used with tert-butyl 4-(3-amino-2-oxo-1,2-dihydropyrido[2,3-b]pyrazin-8-yloxy)naphthalen-1-ylcarbamate to afford the title compound as a slightly pink solid (198 mg, 0.620 mmol, 60%).

$^1$H-NMR (DMSO-$d_6$), δ (ppm), J (Hz): 5.80 (bs, 2H, NH2), 6.14 (d, 1H, H$_{arom}$, J=5.5 Hz), 6.70 (d, 1H, H$_{arom}$, J=8.2 Hz), 7.13 (d, 1H, H$_{arom}$, J=8.1 Hz), 7.42-7.44 (m, 2H, H$_{arom}$), 7.68 (d, 1H, H$_{arom}$, J=8.2 Hz), 7.93 (d, 1H, H$_{Py}$, J=5.5 Hz), 8.15 (d, 1H, H$_{arom}$, J=7.2 Hz), 12.28 (s, 1H, NH). $^{13}$C-NMR (DMSO-$d_6$), δ (ppm), J (Hz): 103.72, 106.23, 113.28, 118.67, 121.16, 122.88, 123.32, 124.38, 126.16, 126.78, 138.63, 143.06, 144.24, 146.42, 150.93, 152.39, 154.68. LC-MS (m/z): 320 (M+H, 100).

Synthesis 69

8-(4-aminonaphthalen-1-yloxy)-2-(trifluoromethyl)pyrido[2,3-b]pyrazin-3(4H)-one

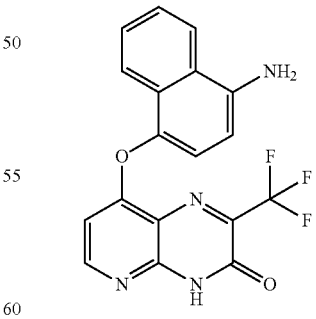

Method E1 was used with tert-butyl 4-(3-oxo-2-(trifluoromethyl)-3,4-dihydropyrido[2,3-b]pyrazin-8-yloxy)naphthalen-1-ylcarbamate to afford the title compound as a slightly yellow solid (56 mg, 0.150 mmol, 66%).

$^1$H-NMR (DMSO-$d_6$), δ (ppm), J (Hz): 5.91 (bs, 2H, NH2), 6.30 (d, 1H, H$_{Py}$, J=5.7 Hz), 6.73 (d, 1H, H$_{arom}$, J=8.2

Hz), 7.19 (d, 1H, H$_{arom}$, J=8.2 Hz), 7.41-7.48 (m, 2H, H$_{arom}$), 7.59 (d, 1H, H$_{arom}$, J=8.5 Hz), 8.19 (d, 1H, H$_{arom}$, J=8.0 Hz), 8.32 (d, 1H, H$_{Py}$, J=5.7 Hz), 13.46 (s, 1H, NH). $^{13}$C-NMR (DMSO-d$_6$), δ (ppm), J (Hz): 105.28, 106.21, 116.39, 118.80, 120.63, 121.09, 123.14, 123.28, 124.50, 126.31, 126.55, 137.91, 142.76 (CF$_3$), 143.69, 146.74, 153.37, 154.68, 163.25. LC-MS (m/z): 373 (M+H, 100).

Synthesis 69A 8-(4-aminonaphthalen-1-yloxy)-3-(trifluoromethyl) pyrido[2,3-b]pyrazin-2(1H)-one

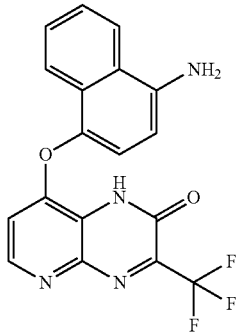 [SMILES: Nc1ccc(Oc2ccnc3nc(C(F)(F)F)c(=O)[nH]c23)c2ccccc12]

Method E1 was used with tert-butyl 4-(2-oxo-3-(trifluoromethyl)-1,2-dihydropyrido[2,3-b]pyrazin-8-yloxy)naphthalen-1-ylcarbamate to afford the title compound as a yellow solid (222 mg, 0.596 mmol, 53%).
$^1$H-NMR (DMSO-d$_6$), δ (ppm), J (Hz): 5.89 (bs, 2H, NH2), 6.57 (d, 1H, H$_{arom}$, J=5.2 Hz), 6.73 (d, 1H, H$_{arom}$, J=8.1 Hz), 7.17 (d, 1H, H$_{arom}$, J=8.1 Hz), 7.41-7.47 (m, 2H, H$_{arom}$), 7.67 (d, 1H, H$_{arom}$, J=7.8 Hz), 8.17 (d, 1H, H$_{arom}$, J=7.7 Hz), 6.26 (d, 1H, H$_{arom}$, J=5.2 Hz), 13.54 (s, 1H, NH). $^{13}$C-NMR (DMSO-d$_6$), δ (ppm), J (Hz): 118.80, 119.18, 121.09, 121.38, 123.12, 123.47, 124.58, 126.43, 126.49, 131.55, 138.40, 141.98, 143.55, 146.04, 153.36, 155.01. LC-MS (m/z): 373 (M+H, 100).
(VI) Ureas from Common Intermediates Synthesis 70

1-(4-chloro-3-(trifluoromethyl)phenyl)-3-(4-(2-oxo-1,2-dihydro pyrido[2,3-b]pyrazin-8-yloxy)phenyl) urea (AA-042)

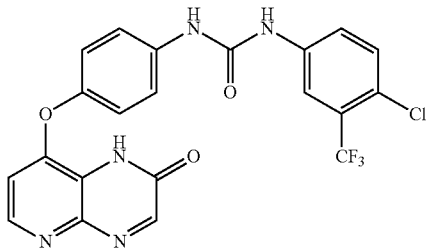 [SMILES: O=C(Nc1ccc(Oc2ccnc3ncc(=O)[nH]c23)cc1)Nc1ccc(Cl)c(C(F)(F)F)c1]

Method F1 (one pot deprotection of Boc and coupling with isocyanate): Tert-butyl 4-(2-oxo-1,2-dihydropyrido[2,3-b]pyrazin-8-yloxy)phenylcarbamate (0.240 g, 0.67 mmol) is dissolved in trifluoroacetic acid (2 ml) and the solution is stirred at room temperature under Argon atmosphere for 2 h. The solvent is evaporated under reduced pressure and the resulting dark oil is dissolved in THF (3 ml) and triethylamine (1 ml). 1-chloro-4-isocyanato-2-(trifluoromethyl) benzene (0.180 g, 0.80 mmol) is added in one portion, and the solution was stirred overnight at 45 C under Ar atmosphere. The solution is then cooled and evaporated and the crude was crystallised from dichloromethane and diethyl ether to afford the title compound (15 mg, 5% yield) as a brown solid.
$^1$H-NMR (DMSO-d6), δ (ppm), J (Hz): 6.82 (d, 1H, J=5.5 Hz), 7.24 (d, 2H, J=8.9 Hz), 7.62 (d, 1H, J=9.0 Hz), 7.66 (dd, 1H, J=9.0, 2.6 Hz), 7.71 (d, 2H, J=8.9 Hz), 8.12 (d, 1H, J=2.6 Hz), 8.34 (d, 1H, J=5.5 Hz), 8.41 (s, 1H), 8.98 (bs, 1H), 9.18 (bs, 1H), 12.54 (bs, 1H); LC-MS (m/z): 476 (M+H, 100).

Synthesis 71

1-(4-chloro-3-(trifluoromethyl)phenyl)-3-(4-(3-oxo-3,4-dihydropyrido[2,3-b]pyrazin-8-yloxy)phenyl) urea (AA-020)

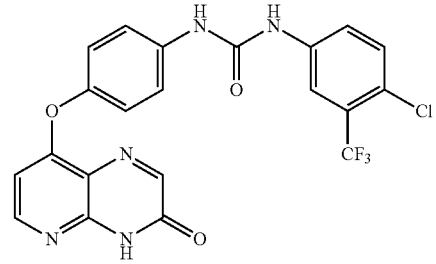 [SMILES: O=C(Nc1ccc(Oc2ccnc3[nH]c(=O)cnc23)cc1)Nc1ccc(Cl)c(C(F)(F)F)c1]

Method F1 was used with tert-butyl 4-(2-oxo-1,2-dihydropyrido[2,3-b]pyrazin-8-yloxy)phenylcarbamate and 4-chloro-3-trifluoromethylphenyl isocyanate to obtain the tithe compound (yield 83%).
$^1$H-NMR (DMSO-d6), δ (ppm), J (Hz): 6.53 (d, 1H, J=5.6 Hz), 7.18 (d, 2H, J=8.8 Hz), 7.58-7.70 (m, 4H), 8.13 (d, 1H, 1.9 Hz), 8.19 (s, 1H), 8.34 (d, 1H, J=5.6 Hz), 9.14 (bs, 1H), 9.36 (bs, 1H), 12.88 (bs, 1H). LC-MS (m/z): 476 (M+H, 100).

Synthesis 72

1-(3-tert-butyl-1-p-tolyl-1H-pyrazol-5-yl)-3-(4-(3-oxo-3,4-dihydropyrido[2,3-b]pyrazin-8-yloxy)phenyl)urea (AA-016)

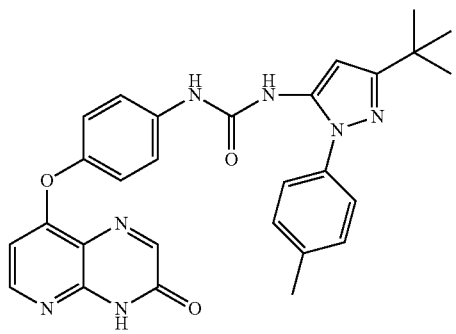 [SMILES: Cc1ccc(-n2nc(C(C)(C)C)cc2NC(=O)Nc2ccc(Oc3ccnc4[nH]c(=O)cnc34)cc2)cc1]

Method F1 was used with Tert-butyl 4-(3-oxo-3,4-dihydropyrido[2,3-b]pyrazin-8-yloxy)phenylcarbamate and 3-tert-butyl-5-isocyanato-1-p-tolyl-1H-pyrazole to obtain the title compound (yield 55%).

$^1$H-NMR (DMSO-d$_6$), δ (ppm), J (Hz): 1.25 (s, 3H), 1.28 (s, 9H), 6.35 (s, 1H), 6.52 (d, 1H, J=5.4 Hz), 7.17 (d, 2H, J=9.0 Hz), 7.32-7.43 (AB system, 4H), 7.51 (d, 2H, J=9.0 Hz), 8.17 (s, 1H), 8.32 (d, 1H, 5.4 Hz), 8.34 (bs, 1H), 9.12 (bs, 1H), 12.87 (bs, 1H); LC-MS (m/z): 510 (M+H, 100).

Synthesis 73

1-(3-tert-butyl-1-p-tolyl-1H-pyrazol-5-yl)-3-(4-(2-oxo-1,2-dihydropyrido[2,3-b]pyrazin-8-yloxy)phenyl)urea (AA-040)

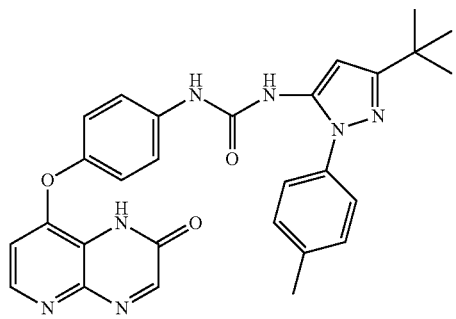 [SMILES: Cc1ccc(-n2nc(C(C)(C)C)cc2NC(=O)Nc2ccc(Oc3ccnc4ncc(=O)[nH]c34)cc2)cc1]

Method F1 was used with tert-butyl 4-(2-oxo-1,2-dihydropyrido[2,3-b]pyrazin-8-yloxy)phenylcarbamate and 3-tert-butyl-5-isocyanato-1-p-tolyl-1H-pyrazole to obtain the title compound (yield 64%).

$^1$H-NMR (DMSO-d6), δ (ppm), J (Hz): 1.27 (s, 3H), 1.29 (s, 9H), 5.41 (s, 1H), 6.07 (d, 1H, 5.8 Hz), 7.26 (d, 2H, 8.8 Hz), 7.32-7.41 (AB system, 4H), 7.45 (d, 2H, J=8.8 Hz), 7.54 (d, 1H, 5.8 Hz), 8.28 (s, 1H), 8.30 (bs, 1H), 9.0 (bs, 1H), 10.12 (bs, 1H). LC-MS (m/z): 510 (M+H, 100).

Synthesis 74

1-(4-chloro-3-(trifluoromethyl)phenyl)-3-(4-(2,3-dioxo-1,2,3,4-tetrahydropyrido[2,3-b]pyrazin-8-yloxy)phenyl)urea (AA-050)

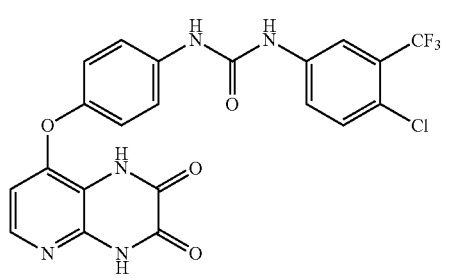 [SMILES: O=C(Nc1ccc(Oc2ccnc3[nH]c(=O)c(=O)[nH]c23)cc1)Nc1ccc(Cl)c(C(F)(F)F)c1]

Method F2 was used with 8-(4-aminophenoxy)pyrido[2,3-b]pyrazine-2,3(1H,4H)-dione and 4-chloro-3-trifluoromethylphenyl isocyanate to obtain the tithe compound (yield 38%).

$^1$H-NMR (DMSO-d6), δ (ppm), J (Hz): 6.62 (d, 1H, J=5.3 Hz), 7.41 (d, 2H, J=8.6 Hz), 7.52 (d, 2H, J=8.6 Hz), 8.26 (d, 1H, J=5.3 Hz), 9.03 (bs, 1H), 9.41 (bs, 1H), 12.39 (bs, 1H), 12.98 (bs, 1H). LC-MS (m/z): 492 (M+H, 100).

Synthesis 75

1-(2-fluoro-5-(trifluoromethyl)phenyl)-3-(4-(3-oxo-3,4-dihydropyrido[2,3-b]pyrazin-8-yloxy)naphthalen-1-yl)urea (AA-012)

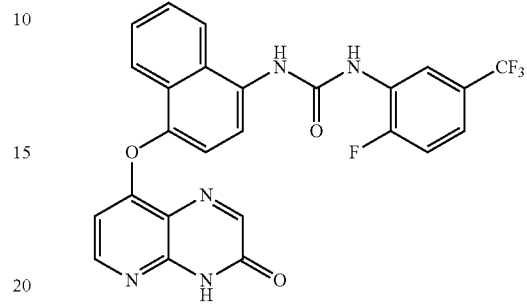

Method F1 was used with tert-butyl 4-(2-oxo-1,2-dihydropyrido[2,3-b]pyrazin-8-yloxy)naphthalen-1-ylcarbamate and 2-fluoro-5-trifluoromethylphenyl isocyanate to obtain the title compound (yield 69%).

$^1$H-NMR (DMSO-d6), δ (ppm), J (Hz): 6.32 (d, 1H, J=4.8 Hz), 7.38-7.62 (m, 6H), 7.88-7.94 (AB system, 2H), 8.06 (s, 1H), 8.18 (d, 1H, J=8.0 Hz), 8.43 (d, 1H, J=4.8 Hz), 8.64 (bs, 1H), 10.52 (bs, 1H), 10.93 (bs, 1H). LC-MS (m/z): 510 (M+H, 100).

Synthesis 76

1-(4-chloro-3-(trifluoromethyl)phenyl)-3-(4-(1-oxo-1,2-dihydropyrido[2,3-b]pyrazin-8-yloxy)naphthalen-1-yl)urea (AA-037)

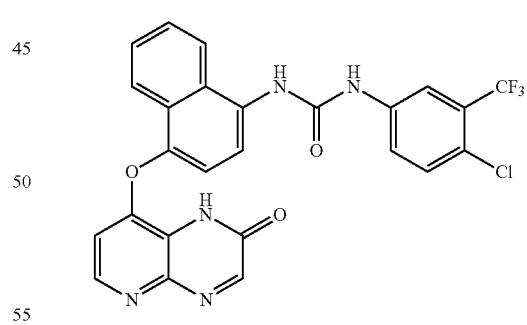

Method F1 was used with tert-butyl 4-(2-oxo-1,2-dihydropyrido[2,3-b]pyrazin-8-yloxy)naphthalen-1-ylcarbamate and 4-chloro-3-trifluoromethylphenyl isocyanate to obtain the title compound (yield 87%).

$^1$H-NMR (DMSO-d6), δ (ppm), J (Hz): 6.23 (d, 1H, J=5.9 Hz), 7.23 (d, 1H, J=8.0 Hz), 7.53-7.59 (m, 3H), 7.79 (d, 1H, 8.0 Hz), 7.84 (d, 2H, 8.5 Hz), 8.08 (s, 1H), 8.21 (d, 1H, 6.8 Hz), 8.33 (d, 1H, 2.9 Hz), 8.38 (d, 1H, 8.5 Hz), 11.46 (s, bs, 1H), 12.39 (bs, 1H). LC-MS (m/z): 526 (M+H, 100).

125

Synthesis 77

1-(3-tert-butyl-1-p-tolyl-1H-pyrazol-5-yl)-3-(4-(3-oxo-3,4-dihydropyrido[2,3-b]pyrazin-8-yloxy)naphthalen-1-yl)urea (AA-033)

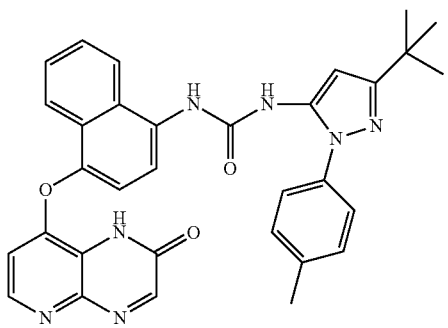 [SMILES: Cc1ccc(-n2nc(C(C)(C)C)cc2NC(=O)Nc2ccc(Oc3ccnc4ncc(=O)[nH]c34)c3ccccc23)cc1]

Method F1 was used with tert-butyl 4-(2-oxo-1,2-dihydropyrido[2,3-b]pyrazin-8-yloxy)naphthalen-1-ylcarbamate and 3-tert-butyl-5-isocyanato-1-p-tolyl-1H-pyrazole to obtain the title compound (yield 40%).

$^1$H-NMR (DMSO-d6), δ (ppm), J (Hz): 6.4 (m, 2H) 7.35-7.66 (m, 4H), 7.87 (d, 1H, 8.5 Hz), 7.97 (d, 1H, 8.5 Hz), 8.12 (d, 1H, 8.7 Hz), 8.23 (s, 1H), 8.27 (d, 1H, 5.7 Hz), 8.80 (bs, 1H), 9.18 (bs, 1H), 12.83 (bs, 1H). LC-MS (m/z): 560 (M+H, 100).

Synthesis 78

1-(4-chloro-3-(trifluoromethyl)phenyl)-3-(4-(2-oxo-1,2-dihydropyrido[2,3-b]pyrazin-8-yloxy)naphthalen-1-yl)urea (AA-013)

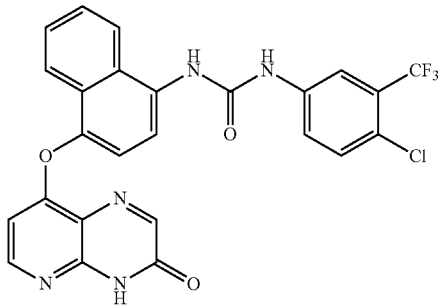 [SMILES: O=C(Nc1ccc(Cl)c(C(F)(F)F)c1)Nc1ccc(Oc2ccnc3[nH]c(=O)cnc23)c2ccccc12]

Method F1 was used with tert-butyl 4-(3-oxo-3,4-dihydropyrido[2,3-b]pyrazin-8-yloxy)naphthalen-1-ylcarbamate and 4-chloro-3-trifluoromethylphenyl isocyanate to obtain the title compound (yield 91%).

$^1$H-NMR (CD3OD), δ (ppm), J (Hz): 6.72 (d, 1H, J=5.7 Hz), 7.46 (d, 1H, J=7.4 Hz), 7.42-7.63 (m, 4H), 7.82 (d, 1H, J=7.4 Hz), 7.91 (s, 1H), 7.99 (d, 1H, J=3.0 Hz), 8.20 (d, 1H, J=8.3 Hz), 8.27 (d, 1H, J=5.7 Hz), 8.51 (bs, 1H). LC-MS (m/z): 526 (M+H, 100).

126

Synthesis 79

1-(4-chloro-3-(trifluoromethyl)phenyl)-3-(2-(methylthio)-4-(3-oxo-3,4-dihydropyrido[3,2-b]pyrazin-8-yloxy)phenyl)urea (AA-023)

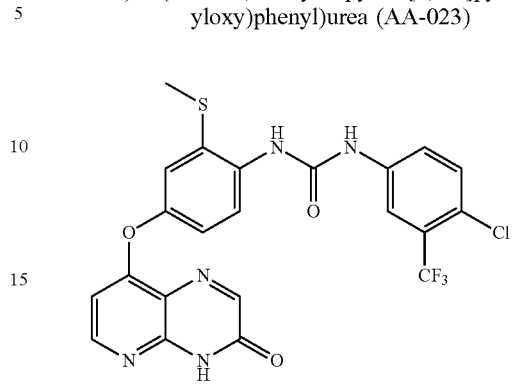

Using Method F2 with 8-(4-amino-3-(methylthio)phenoxy)pyrido[3,2-b]pyrazin-3(4H)-one and 4-chloro-3-trifluoromethylphenyl isocyanate, the title compound (48 mg, 92%) was obtained as a pale white powder.

$^1$H-NMR (DMSO-d$_6$), δ (ppm), J (Hz): 2.47 (s, 3H, CH$_3$); 6.61 (d, 1H, H$_{Py}$, J=5.6 Hz), 7.07 (dd, 1H, H$_{arom}$, J=8.8 Hz, J=2.6 Hz), 7.26 (d, 1H, H$_{arom}$, J=2.6 Hz), 7.62 (m, 2H, H$_{arom}$), 7.86 (d, 1H, H$_{arom}$, J=8.7 Hz), 8.11 (m, 1H, H$_{arom}$), 8.18 (s, 1H, NH or CH), 8.21 (s, 1H, NH or CH), 8.36 (d, 1H, H$_{Py}$, J=5.6 Hz), 9.75 (s, 1H, NH or CH), 12.89 (s, 1H, NH). $^{13}$C-NMR (DMSO-d$_6$), δ (ppm), J (Hz): 15.6, 106.1, 116.4, 117.9, 118.2, 119.7, 121.6, 122.7, 123.4, 123.7, 124.2, 126.6, 131.9, 133.6, 139.2, 145.3, 150.0, 150.9, 152.0, 152.4, 156.4, 160.7. LC-MS (m/z): 522 (M+H, 100), rt=5.24 min.

Synthesis 80

1-(2-fluoro-5-(trifluoromethyl)phenyl)-3-(2-fluoro-4-(2-oxo-1,2-dihydro pyrido[2,3-b]pyrazin-8-yloxy)phenyl)urea (AA-023)

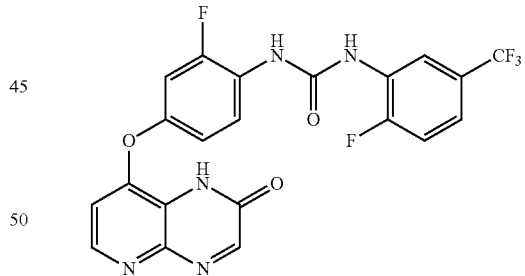

Method F2: A solution of 8-(4-amino-3-fluorophenoxy)pyrido[2,3-b]pyrazin-2(1H)-one (21.4 mg, 78.6 μmol) in dry DMSO (1 mL) under Ar was treated with 2-fluoro-5-trifluoro-phenylisocyanate (11.5 μL, 80 μmol) and the pale yellow solution was stirred at RT. After 3 h, the solution was diluted with H$_2$O (20 mL) and the precipitate was isolated by filtration. Stripping with toluene (3×20 mL) furnished the title compound as a beige powder. Yield: 30 mg (81%).

$^1$H-NMR (DMSO-d$_6$), δ (ppm), J (Hz): 6.94 ppm (d, 1H, J=5.5 Hz, H$_{Py}$), 7.09 (m, 1H, H$_{arom}$)), 7.32 (m, 1H, H$_{arom}$), 7.40 (m, 1H, H$_{arom}$), 7.50 (m, 1H, H$_{arom}$), 8.23 (t, J=8.1 Hz, H$_{arom}$), 8.37 (d, J=5.5 Hz, H$_{Py}$), 8.40 (s, 1H, H$_{arom}$), 8.63 (m, 1H, H$_{arom}$), 9.23 (s, 1H, NH), 9.38 (s, 1H, NH), 12.58 (br s, 1H, NHAr); $^{13}$C-NMR (DMSO-d$_6$), δ (ppm), J (Hz): 108.5, 110.4, (d, J$_{FC}$=22,) Hz116.1 (d, J$_{FC}$=21 Hz), 116.5 (m), 119.5 (br), 121.9, 122.8, 124.6 (d, $J_{FC}$=11 Hz), 125.0, 125.4 (d, $J_{FC}$=30 Hz), 128.5, 144.4 (br), 145.3, 148.7 (d, $J_{FC}$=10 Hz), 151.4, 152.0, 152.3 (br), 152.4 (d, $J_{FC}$=246 Hz), 153.5 (d, $J_{FC}$=248 Hz), 155.0, 155.4 (br); $^{19}$F NMR (470 MHz, DMSO-d$_6$): δ=−60.7, −123.9, −125.2 ppm; LC-MS (m/z): 478.1 (M+H, 100), rt=4.89 min; HRMS (3.38 min): m/z calcd. for $C_{21}H_{13}F_5N_5O_3$ [M+H$^+$]: 478.09331; found: 478.09355.

Synthesis 81

1-(4-chloro-3-(trifluoromethyl)phenyl)-3-(2-(methylthio)-4-(2-oxo-1,2-dihydropyrido[2,3-b]pyrazin-8-yloxy)phenyl)urea (AA-045)

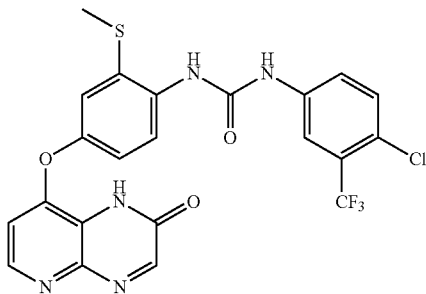 [SMILES: CSc1cc(Oc2ccnc3ncc(=O)[nH]c23)ccc1NC(=O)Nc1ccc(Cl)c(C(F)(F)F)c1]

Using Method F2 with 8-(4-amino-3-(methylthio)phenoxy)pyrido[2,3-b]pyrazin-2(1H)-one and 4-chloro-3-trifluoromethylphenyl isocyanate, the title compound (15 mg, 29%) was obtained as a pale brown powder.

$^1$H-NMR (DMSO-d$_6$), δ (ppm), J (Hz): 2.47 (s, 3H, CH$_3$); 6.90 (d, 1H, H$_{Py}$, J=5.3 Hz), 7.10 (dd, 1H, H$_{arom}$, J=8.8 Hz, J=2.4 Hz), 7.29 (d, 1H, H$_{arom}$, J=2.4 Hz), 7.63 (m, 2H, H$_{arom}$), 7.87 (d, 1H, H$_{arom}$, J=8.8 Hz), 8.11 (m, 1H, H$_{arom}$), 8.22 (s, 1H, NH or CH), 8.36 (m, 1H, H$_{Py}$), 8.42 (s, 1H, NH or CH), 9.76 (s, 1H, NH or CH), 12.57 (s, 1H, NH). $^{13}$C-NMR (DMSO-d$_6$), δ (ppm), J (Hz): 15.7, 110.0, 116.4, 118.0, 119.9, 122.2, 122.7, 123.4, 124.1, 126.7, 131.6, 131.9, 133.7, 138.8, 139.2, 149.8, 152.4. LC-MS (m/z): 522 (M+H, 100), rt=5.10 min.

Synthesis 82

1-(2-fluoro-5-(trifluoromethyl)phenyl)-3-(2-(methylthio)-4-(3-oxo-3,4-dihydropyrido[3,2-b]pyrazin-8-yloxy)phenyl)urea (AA-024)

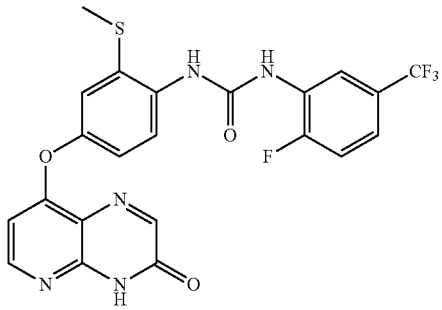 [SMILES: CSc1cc(Oc2ccnc3[nH]c(=O)cnc23)ccc1NC(=O)Nc1cc(C(F)(F)F)ccc1F]

Using Method F2 with 8-(4-amino-3-(methylthio)phenoxy)pyrido[3,2-b]pyrazin-3(4H)-one and 2-fluoro-5-trifluoromethylphenyl isocyanate, the title compound (26 mg, 62%) was obtained as a powder.

$^1$H-NMR (DMSO-d$_6$), δ (ppm), J (Hz): 2.48 (s, 3H, CH$_3$), 6.61 (d, 1H, H$_{Py}$, J=5.6 Hz), 7.06 (dd, 1H, H$_{arom}$, J=8.6 Hz, J=2.3 Hz), 7.24 (d, 1H, H$_{arom}$, J=2.3 Hz), 7.39 (m, 1H, H$_{arom}$), 7.49 (m, 1H, H$_{arom}$), 7.85 (d, 1H, H$_{arom}$, J=8.7 Hz), 8.18 (s, 1H, NH or CH), 8.36 (d, 1H, H$_{Py, 6}$, J=5.6 Hz), 8.64 (m, 1H, H$_{arom}$), 8.68 (s, 1H, NH or CH), 9.53 (s, 1H, NH or CH), 12.90 (s, 1H, NH). $^{13}$C-NMR (DMSO-d$_6$), δ (ppm), J (Hz): 15.3, 106.1, 115.9, 116.1, 116.7, 117.6, 118.2, 119.2, 122.7, 125.1, 125.4, 128.6, 132.2, 133.2, 145.4, 150.1, 150.9, 152.0, 152.4, 154.4, 156.3, 160.7. LC-MS (m/z): 506 (M+H, 100), rt=4.85 min.

Synthesis 83

1-(2-fluoro-5-(trifluoromethyl)phenyl)-3-(2-(methylthio)-4-(2-oxo-1,2-dihydropyrido[2,3-b]pyrazin-8-yloxy)phenyl)urea (AA-046)

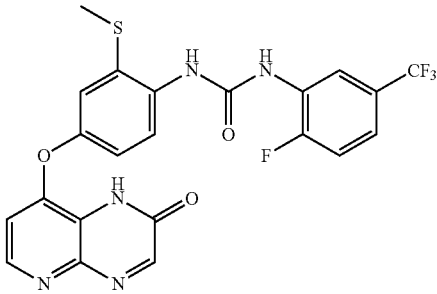 [SMILES: CSc1cc(Oc2ccnc3ncc(=O)[nH]c23)ccc1NC(=O)Nc1cc(C(F)(F)F)ccc1F]

Using Method F2 with 8-(4-amino-3-(methylthio)phenoxy)pyrido[2,3-b]pyrazin-2(1H)-one and 2-fluoro-5-trifluoromethylphenyl isocyanate, the title compound (37 mg, 73%) was obtained as a powder.

$^1$H-NMR (DMSO-d$_6$), δ (ppm), J (Hz): 2.48 (s, 3H, CH$_3$), 6.89 (d, 1H, H$_{Py, 5}$, J=5.3 Hz), 7.09 (dd, 1H, H$_{arom}$, J=8.8 Hz, J=2.5 Hz), 7.26 (d, 1H, H$_{arom}$, J=2.5 Hz), 7.39 (m, 1H, H$_{arom}$), 7.50 (m, 1H, H$_{arom}$), 7.85 (d, 1H, H$_{arom}$, J=8.8 Hz), 8.36 (d, 1H, H$_{Py, 6}$, J=5.2 Hz), 8.42 (s, 1H, NH or CH), 8.64 (m, 1H, H$_{arom}$), 8.69 (s, 1H, NH or CH), 9.54 (s, 1H, NH or CH), 12.60 (s, 1H, NH). $^{13}$C-NMR (DMSO-d$_6$), δ (ppm), J (Hz): 15.4, 110.0, 115.9, 116.1, 116.7, 117.7, 119.1, 119.4, 122.7, 124.8, 125.1, 125.4, 128.5, 132.0, 133.3, 145.3, 149.9, 152.4, 154.5. LC-MS (m/z): 506 (M+H, 100), rt=5.00 min.

Synthesis 84

1-(3-tert-butyl-1-p-tolyl-1H-pyrazol-5-yl)-3-(2-(methylthio)-4-(3-oxo-3,4-dihydropyrido[2,3-b]pyrazin-8-yloxy)phenyl)urea (AA-017)

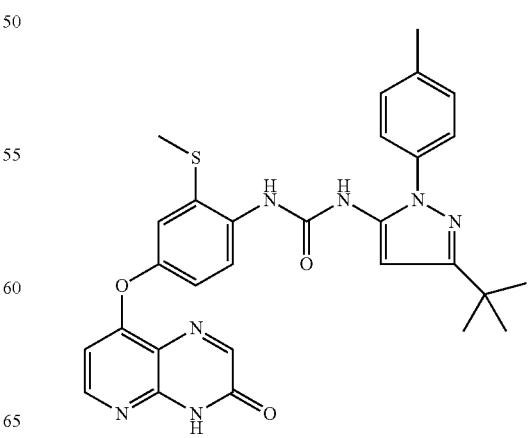

Using Method F2 with 8-(4-amino-3-(methylthio)phenoxy)pyrido[3,2-b]pyrazin-3(4H)-one and -tert-butyl-5-isocyanato-1-tolyl-1H-pyrazole, the title compound (5 mg, 8%) was obtained as a white powder after purification on silica gel (Eluent: DCM/EtOAc: 1/1, Rf=0.57).

$^1$H-NMR (CDCl$_3$), δ (ppm), J (Hz): 1.31 (s, 9H, tert-Bu), 2.23 (s, 3H, CH$_3$), 2.31 (s, 3H, SCH$_3$), 6.30 (s, 1H), 6.36 (s, 1H), 6.49 (d, 1H, H$_{Py}$, J=5.8 Hz), 7.02 (dd, 1H, H$_{arom}$, J=8.9 Hz, J=2.7 Hz), 7.19 (m, 4H, H$_{arom}$), 7.31 (d, 1H, H$_{arom}$, J=8.3 Hz), 7.81 (s, 1H, NH or CH), 8.16 (d, 1H, H$_{arom}$, J=8.9 Hz), 8.26 (s, 1H, NH or CH), 8.30 (d, 1H, H$_{Py}$, J=5.8 Hz), 11.37 (s, 1H, NH). LC-MS (m/z): 556 (M+H, 100).

Synthesis 85

1-(4-Chloro-3-(trifluoromethyl)phenyl)-3-(2-fluoro-4-(3-oxo-3,4-dihydro pyrido[2,3-b]pyrazin-8-yloxy)phenyl)urea (AA-025)

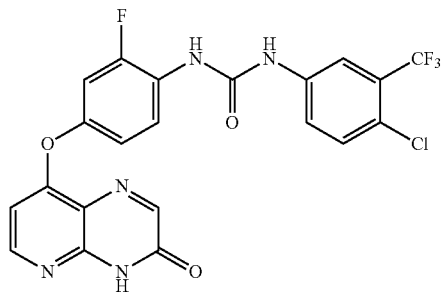 [SMILES: O=C(Nc1ccc(Cl)c(C(F)(F)F)c1)Nc1ccc(Oc2ccnc3[nH]c(=O)cnc23)cc1F]

Method F2 was used with 8-(4-amino-3-fluorophenoxy)pyrido[2,3-b]pyrazin-3(4H)-one and 3-trifluoromethyl-4-chloro-phenylisocyanate to afford the title compound, yield: 88%. $^1$H-NMR (DMSO-d$_6$), δ (ppm), J (Hz): 6.67 ppm (d, 1H, J=5.5 Hz, H$_{Py}$), 7.06 (d, 1H, H$_{arom}$), 7.30 (d, 1H, H$_{arom}$), 7.66 (m, 2H, H$_{arom}$), 8.12 (m, 2H, H$_{arom}$), 8.17 (s, 1H, H$_{arom}$), 8.38 (d, J=5.5 Hz, H$_{Py}$), 8.88 (s, 1H, NH), 9.92 (s, 1H, NH), 12.91 (br s, 1H, NHAr); $^{19}$F NMR (470 MHz, DMSO-d$_6$): δ=−61.5, −124.2 ppm; LC-MS (m/z): 494.1 (M+H, 100), rt=5.24 min; HRMS (6.17 min): m/z calcd. for C$_{21}$H$_{13}$ClF$_4$N$_5$O$_3$ [M+H$^+$]: 494.06376; found: 494.06335.

Synthesis 86

1-(2-Fluoro-5-(trifluoromethyl)phenyl)-3-(2-fluoro-4-(3-oxo-3,4-dihydro pyrido[2,3-b]pyrazin-8-yloxy)phenyl)urea (AA-026)

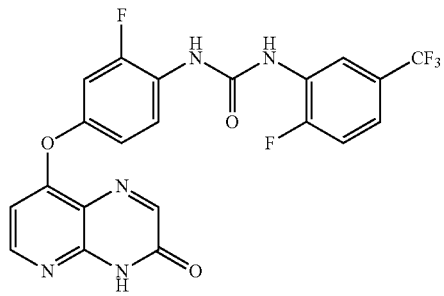 [SMILES: O=C(Nc1ccc(Oc2ccnc3[nH]c(=O)cnc23)cc1F)Nc1cc(C(F)(F)F)ccc1F]

Method F2 was used with 8-(4-amino-3-fluorophenoxy)pyrido[2,3-b]pyrazin-3(4H)-one and 2-fluoro-5-trifluoromethyl-phenylisocyanate to afford the title compound, yield=80%.

$^1$H-NMR (DMSO-d$_6$), δ (ppm), J (Hz): 6.67 ppm (d, 1H, J=5.5 Hz, H$_{Py}$), 7.08 (m, 1H, H$_{arom}$), 7.34 (m, 1H, H$_{arom}$), 7.40 (m, 1H, H$_{arom}$), 7.51 (m, 1H, H$_{arom}$), 8.17 (s, 1H, H$_{arom}$), 8.23 (t, J=8.1 Hz, H$_{arom}$) 8.38 (d, J=5.5 Hz, H$_{Py}$), 8.64 (m, 1H, H$_{arom}$), 9.20 (s, 1H, NH), 9.35 (s, 1H, NH), 12.91 (br s, 1H, NHAr); $^{19}$F NMR (470 MHz, DMSO-d$_6$): δ=−60.8, −124.0, 125.2 ppm; LC-MS (m/z): 478.1 (M+H, 100), rt=5.04 min; HRMS (3.38 min): m/z calcd. for C$_{21}$H$_{13}$F$_5$N$_5$O$_3$ [M+H$^+$]: 478.09331; found: 478.09355.

Synthesis 87

1-(4-Chloro-3-(trifluoromethyl)phenyl)-3-(2-fluoro-4-(2-oxo-1,2-dihydro pyrido[2,3-b]pyrazin-8-yloxy)phenyl)urea (AA-048)

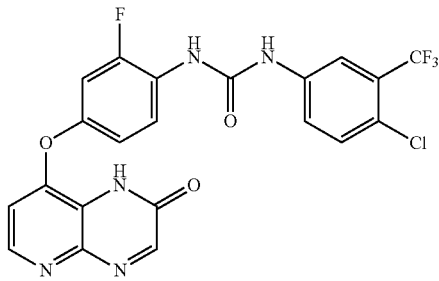 [SMILES: O=C(Nc1ccc(Cl)c(C(F)(F)F)c1)Nc1ccc(Oc2ccnc3ncc(=O)[nH]c23)cc1F]

Method F2 was used with 8-(4-amino-3-fluorophenoxy)pyrido[2,3-b]pyrazin-2(1H)-one and 3-trifluoromethyl-4-chloro-phenylisocyanate to afford the title compound as a beige powder. Yield: 60 mg (79%).

$^1$H-NMR (DMSO-d$_6$), δ (ppm), J (Hz): 6.93 ppm (d, J=5.5 Hz, 1H, H$_{Py}$), 7.08 (m, 1H, H$_{arom}$), 7.30 (m, 1H, H$_{arom}$), 7.64 (m, 2H, H$_{arom}$), 8.12 (m, 2H, H$_{arom}$), 8.37 (d, J=5.5 Hz, 1H, H$_{Py}$), 8.41 (s, 1H, H$_{arom}$), 8.78 (s, 1H, NH), 9.57 (s, 1H, NH), 12.58 (br s, 1H, NHAr); $^{13}$C-NMR (DMSO-d$_6$), δ (ppm), J (Hz): 116.5, 108.6 110.4, ppm (d, J$_{FC}$=23 Hz), 154.9 (br), 116.6 (d, J$_{FC}$=6 Hz), 121.7, 122.6, 123.0, 123.5, 123.8, 124.6 (d, J$_{FC}$=11 Hz), 125.3, 126.0, 126.8 (qu, J$_{FC}$=30 Hz), 128.5, 132.1, 139.1, 144.4 (br), 145.3, 148.9 (d, J$_{FC}$=10 Hz), 152.2, 152.8 (d, J$_{FC}$=248 Hz); $^{19}$F NMR (470 MHz, DMSO-d$_6$): δ=−61.5, −125.0 ppm; LC-MS (m/z): 494.1 (M+H, 100), rt=4.89 min; HRMS (3.38 min): m/z calcd. for C$_{21}$H$_{13}$F$_5$N$_5$O$_3$ [M+H$^+$]: 478.09331; found: 478.09355.

Synthesis 88

1-(3-tert-butyl-1-p-tolyl-1H-pyrazol-5-yl)-3-(2-fluoro-4-(3-oxo-3,4-dihydropyrido[3,2-b]pyrazin-8-yloxy)phenyl)urea (AA-018)

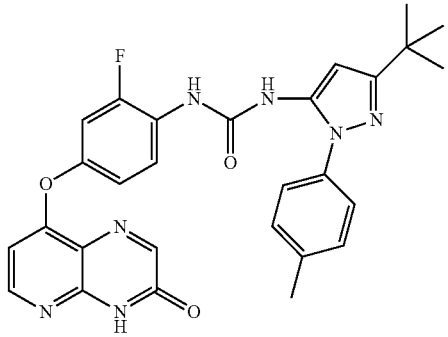

Method F2 was used with 8-(4-amino-3-fluorophenoxy)pyrido[2,3-b]pyrazin-3(4H)-one and 3-tert-butyl-5-isocyanato-1-p-tolyl-1H-pyrazole to afford the title compound as an off-white solid. Yield: 35 mg (42%).

¹H-NMR (DMSO-d₆), δ (ppm), J (Hz): 1.28 ppm (s, 9H, tert-Bu 2.40 (s, 3H, CH₃), 6.39 (s, 1H, H$_{Py}$), 6.66 (d, J=5.6 Hz, 1H, $_{Py}$rH), 7.41-7.29 (m, 5H, H$_{arom}$), 7.06 (m, 1H, H$_{arom}$), 8.21-8.17 (m, 2H, H$_{arom}$), 8.38 (d, J=5.6 Hz, 1H, H$_{Py}$), 8.79 (s, 1H, NH), 9.00 (s, 1H, NH), 12.93 (br s, 1H, NH$_{arom}$); ¹⁹F NMR (470 MHz, DMSO-d₆): δ=−125.2 ppm;
LC-MS (m/z): 528.1 (M+H, 100), rt=5.07 min; HRMS (6.12 min): m/z calcd. for C₂₈H₂₆FN₇NaO₃ [M+Na]⁺: 514.09090; found: 514.09051.

Synthesis 89

1-(3-tert-butyl-1-phenyl-1H-pyrazol-5-yl)-3-(2-fluoro-4-(3-oxo-3,4-dihydropyrido[3,2-b]pyrazin-8-yloxy)phenyl)urea (AA-019)

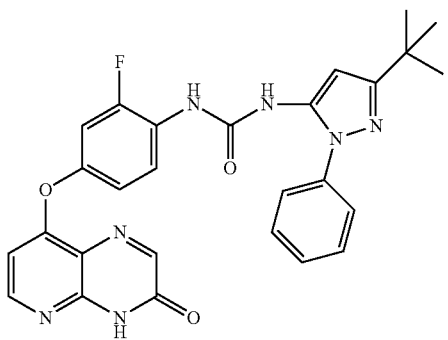 [SMILES: CC(C)(C)c1cc(NC(=O)Nc2ccc(Oc3ccnc4[nH]c(=O)cnc34)cc2F)n(-c2ccccc2)n1]

Method F2 was used with 8-(4-amino-3-fluorophenoxy)pyrido[2,3-b]pyrazin-3(4H)-one and 3-tert-butyl-5-isocyanato-1-phenyl-1H-pyrazole to afford the title compound. Yield: 50 mg (60%) of a cream colored solid.

¹H-NMR (DMSO-d₆), δ (ppm), J (Hz): 1.28 ppm (s, 9H, tert-Bu), 6.40 (s, 1H, H$_{pyr}$), 6.66 (d, J=5.6 Hz, 1H, H$_{Py}$), 7.04 (m, 1H, H$_{arom}$), 7.29 (m, 1H, H$_{arom}$), 7.42 (m, 1H, H$_{arom}$), 7.55-7.53 (m, 4H, H$_{arom}$), 8.17-8.16 (m, 2H, H$_{arom}$), 8.37 (d, J=5.6 Hz, 1H, H$_{Py}$), 8.83 (s, 1H, NH), 8.98 (s, 1H, NH), 12.90 (br s, 1H, NHAr); ¹³C-NMR (DMSO-d₆), δ (ppm), J (Hz): 30.2, 32.0, 95.1, 106.5, 108.5 (d, $J_{FC}$=22 Hz), 116.4 (d, $J_{FC}$=3 Hz), 118.4, 121.8, 124.4, 124.9 (d, $J_{FC}$=12 Hz), 127.4, 129.3, 136.9, 138.4, 145.5, 148.6 (d, $J_{FC}$=10 Hz), 151.2, 151.3, 152.2, 152.3 (d, $J_{FC}$=245 Hz), 153.3, 156.4, 160.5, 160.8, 171.2; ¹⁹F NMR (470 MHz, DMSO-d₆): δ=−125.2 ppm; LC-MS (m/z): 514.2 (M+H, 100), rt=4.93 min; HRMS (5.95 min): m/z calcd. for C₂₇H₂₅FN₇O₃ [M+H]⁺: 514.19974; found: 514.19964.

Synthesis 90

1-(2-fluoro-4-(3-methyl-2-oxo-1,2-dihydropyrido[3,2-b]pyrazin-8-yloxy)phenyl)-3-(2-fluoro-5-(trifluoromethyl)phenyl)urea (AA-049)

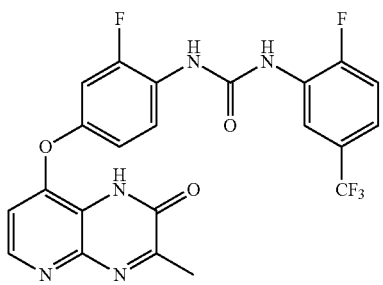 [SMILES: Cc1nc2nccc(Oc3ccc(NC(=O)Nc4cc(C(F)(F)F)ccc4F)c(F)c3)c2[nH]c1=O]

Method F2 was used with 8-(4-amino-3-fluorophenoxy)-3-methylpyrido[3,2-b]pyrazin-2(1H)-one and 2-fluoro-5-trifluoromethylphenyl isocyanate to afford the title compound. yield=85%.

¹H-NMR (DMSO-d₆), δ (ppm), J (Hz): 2.49 ppm (s, 3H, CH₃) 6.89 (d, 1H, J=5.6 Hz, $_{Py}$rH), 7.08 (m, 1H, H$_{arom}$), 7.32 (m, 1H, H$_{arom}$), 7.41 (m, 1H, H$_{arom}$), 7.53 (m, 1H, H$_{arom}$), 8.23 (t, 1H, H$_{arom}$), 8.33 (d, J=5.6 Hz, 1H, H$_{Py}$), 8.64 (m, 1H, H$_{arom}$), 9.19 (s, 1H, NH), 9.35 (s, 1H, NH), 12.42 (br s, 1H, NH$_{arom}$); ¹³C-NMR (DMSO-d₆), δ (ppm), J (Hz): 28.0, 79.4, 106.8, 109.0, 116.0, 118.5, 123.9, 125.8, 145.6, 150.5, 151.2, 152.2, 153.1, 156.4, 160.3; ¹⁹F NMR (470 MHz, DMSO-d₆): δ=−60.7, −124.0, −125.3 ppm; LC-MS (m/z): 492.1 (M+H, 100), rt=4.98 min; HRMS (6.04 min): m/z calcd. for C₂₂H₁₄F₅N₅NaO₃ [M+Na]⁺: 514.09090; found: 514.09051.

Synthesis 91

1-(2-Fluoro-5-(trifluoromethyl)phenyl)-3-(4-(3-oxo-3,4-dihydropyrido[2,3-b]pyrazin-8-ylthio)phenyl)urea (AA-027)

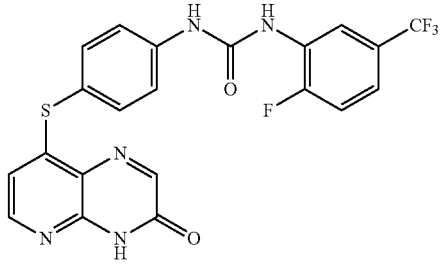 [SMILES: O=C(Nc1ccc(Sc2ccnc3[nH]c(=O)cnc23)cc1)Nc1cc(C(F)(F)F)ccc1F]

Method F2 was used with 8-(4-aminophenylthio)pyrido[2,3-b]pyrazin-3(4H)-one (36.7 mg, 136 μmol) and 2-fluoro-5-trifluoromethyl-phenylisocyanate (22.54, 156 136 μmol) to afford the title compound. Yield: 53 mg (82%).

¹H-NMR (DMSO-d₆), δ (ppm), $_J$ (Hz): 6.40 (d, J=5.3, 1H, H$_{Py}$), 7.43 (m, 1H, H$_{arom}$), 7.52 (m, 1H, H$_{arom}$), 7.60 (d, J=8.3, 2H, H$_{arom}$), 7.70 (d, J=8.3, 2H, H$_{arom}$), 8.20-8.22 (m, 2H, H$_{Py}$), 8.62 (m, 1H, H$_{arom}$), 9.03 (d, ⁴$J_{FH}$=2.6, 1H, NH), 9.53 (s, 1H, NH), 12.87 (br s, 1H, NH); ¹³C-NMR (DMSO-d₆), δ (ppm), J (Hz): 114.6, 116.2 (d, $J_{FC}$=21.1), 116.8 (m), 119.6, 119.7, 122.8, 123.0, 125.1 (d, $J_{FC}$=40), 125.4 (m), 128.4 (d, $J_{FC}$=11.1), 136.9, 141.2, 143.4, 150.0, 151.0, 152.0, 152.4, 153.6 (d, $J_{FC}$=21.1), 156.8; LC-MS (m/z): 476.0 (M+H, 100), rt=5.42 min; HRMS (6.53 min): m/z calcd. for C₂₁H₁₄F₄N₅O₂S [M+H⁺]: 476.07988; found: 476.07980.

Synthesis 92

1-(2-Fluoro-4-(2-methyl-3-oxo-3,4-dihydropyrido[2,3-b]pyrazin-8-yloxy)phenyl)-3-(2-fluoro-5-(trifluoromethyl)phenyl)urea (AA-028)

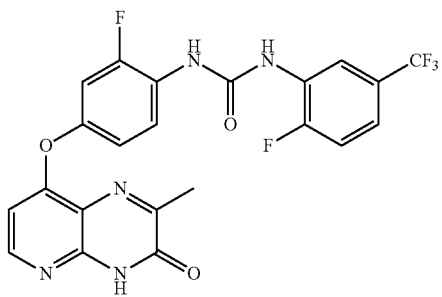 [SMILES: Cc1nc2c(Oc3ccc(NC(=O)Nc4cc(C(F)(F)F)ccc4F)c(F)c3)ccnc2[nH]c1=O]

Method F2 was used with 2-fluoro-5-trifluoromethyl-phenylisocyanate and 8-(4-amino-3-fluorophenoxy)-2-methylpyrido[2,3-b]pyrazin-3(4H)-one to afford the title compound, yield 81%.

$^1$H-NMR (DMSO-d$_6$), δ (ppm), J (Hz): 2.43 (s, 3H, CH$_3$), 6.60 (d, J=5.4, 1H, H$_{Py}$), 7.07 (m, 1H, H$_{arom}$), 7.33 (m, 1H, H$_{arom}$), 7.41 (m, 1H, H$_{arom}$), 7.51 (m, 1H, H$_{arom}$), 8.24 (m, 1H, H$_{arom}$), 8.29 (m, 1H, H$_{arom}$), 8.64 (d, J=5.4, 1H, H$_{Py}$), 9.20 (s, 1H, NH), 9.35 (s, 1H, NH); $^{13}$C NMR (126 MHz, DMSO-d$_6$): δ=160.3, 156.4, 153.1, 152.2, 151.2, 150.5, 145.6, 125.8, 123.9, 118.5, 116.0, 109.0, 106.8, 79.4, 28.0 ppm; $^{19}$F NMR (470 MHz, DMSO-d$_6$): δ=−60.7, −124.0, −125.3 ppm; LC-MS (m/z): 492.1 (M+H, 100), 5.17 min; HRMS (7.15 min): m/z calcd. for C$_{22}$H$_{14}$F$_5$N$_5$O$_3$ [M+H$^+$]: 492.10896; found: 492.10843.

Synthesis 93

1-(3-Tert-butyl-1-phenyl-1H-pyrazol-5-yl)-3-(4-(2,3-dioxo-1,2,3,4-tetrahydropyrido[3,2-b]pyrazin-8-yloxy)-2-fluorophenyl)urea (AA-091)

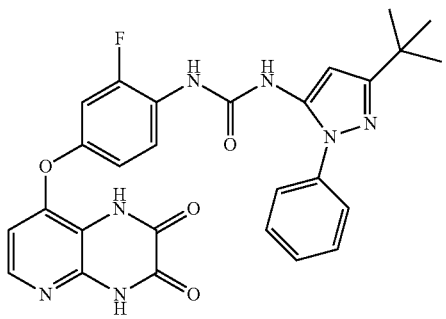 [SMILES: CC(C)(C)c1cc(NC(=O)Nc2ccc(Oc3ccnc4[nH]c(=O)c(=O)[nH]c34)cc2F)n(-c2ccccc2)n1]

Method F2 was used with 8-(4-amino-3-fluorophenoxy)pyrido[3,2-b]pyrazine-2,3(1H,4H)-dione (50 mg, 173 µmol) and a solution of 3-tert-butyl-5-isocyanato-1-phenyl-1H-pyrazole (5.7 mL of a 61 mM solution in CH$_2$Cl$_2$, 347 µmol) to give the title compound as a white solid. Yield: 65 mg (71%).

$^1$H-NMR (DMSO-d$_6$), δ (ppm), J (Hz): 1.28 (s, 9H, tert-Bu), 6.38 (s, 1H, $_{Py}$razole H), 6.57 (d, 1H, J=5.3, H$_{Py}$), 7.00 (m, 1H, H$_{arom}$), 7.22 (m, 1H, H$_{arom}$), 7.42 (m, 1H, J=8.3, H$_{arom}$), 7.54 (m, 4H, H$_{arom}$), 7.96 (d, 1H, J=5.3, H$_{Py}$), 8.11 (m, 1H, H$_{arom}$), 9.05 (s, 1H, NH), 9.10 (s, 1H, H$_{arom}$), 11.91 (br s, 1H, NH), 12.40 (br s, 1H, NH); $^{13}$C-NMR (DMSO-d$_6$), δ (ppm), J (Hz): 30.2, 32.0, 95.7, 108.2 (d, J$_{FC}$=22.4), 112.5, 116.1, 121.8, 124.3, 124.6 (d, J$_{FC}$=10.7), 127.3, 129.2, 136.9, 138.5, 140.6, 143.2, 148.7 (d, J$_{FC}$=9.8), 150.3, 151.6, 152.3 (d, J$_{FC}$=245), 154.8, 156.0, 160.8; $^{19}$F-NMR (DMSO-d$_6$), δ (ppm): −124.4; LC-MS (m/z): 531.1 (M+H, 100), rt=2.54 min; HRMS (3.07 min): m/z calcd. for C$_{27}$H$_{25}$FN$_7$O$_4$ [M+H$^+$]: 530.19466; found: 530.19433.

Synthesis 94

1-(3-fluoro-4-(3-oxo-3,4-dihydropyrido[2,3-b]pyrazin-8-yloxy)phenyl)-3-(2-fluoro-5-(trifluoromethyl)phenyl)urea (AA-086)

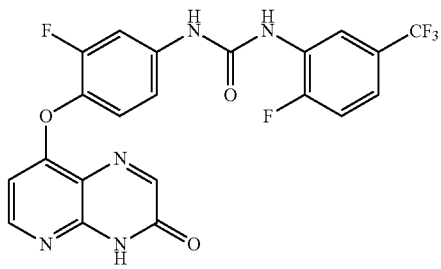 [SMILES: O=C(Nc1ccc(Oc2ccnc3[nH]c(=O)cnc23)c(F)c1)Nc1cc(C(F)(F)F)ccc1F]

Using Method F2 with 8-(4-amino-2-fluorophenoxy)pyrido[2,3-b]pyrazin-3(4H)-one (50 mg, 0.18 mmol), the title compound (42 mg, 49%) was obtained as a brown powder.

$^1$H-NMR (DMSO-d$_6$), δ (ppm), J (Hz): 6.60 (d, 1H, H$_{Py}$, J=5.7 Hz), 7.27-7.30 (m, 1H, H$_{arom}$), 7.44-7.49 (m, 2H, H$_{arom}$), 7.53-7.57 (m, 1H, H$_{arom}$), 7.81 (dd, 1H, H$_{arom}$, J=12.9 Hz, J=2.3 Hz), 8.24 (s, 1H, NH or CH), 8.39 (d, 1H, H$_{Py}$, J=5.7 Hz), 8.63 (dd, 1H, H$_{arom}$, J=7.4 Hz and J=2.0 Hz), 9.04 (s, 1H, NH or CH), 9.54 (s, 1H, NH or CH), 13.00 (s, 1H, NH). $^{19}$F-NMR (δ, ppm, DMSO-d$_6$): −60.06, −123.20, −128.06. LC-MS (m/z): 478 (M+H, 100), rt=2.65 min. HRMS (EI): m/z (M+H, 100) calcd for C$_{21}$H$_{12}$F$_5$N$_5$O$_3$: 478.0933; found: 478.0929.

Synthesis 95

1-(3-tert-butyl-1-phenyl-1H-pyrazol-5-yl)-3-(3-fluoro-4-(3-oxo-3,4-dihydropyrido[2,3-b]pyrazin-8-yloxy)phenyl)urea (AA-087)

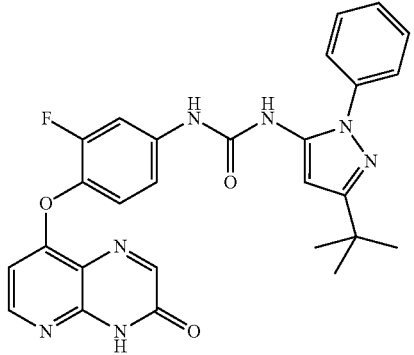 [SMILES: CC(C)(C)c1cc(NC(=O)Nc2ccc(Oc3ccnc4[nH]c(=O)cnc34)c(F)c2)n(-c2ccccc2)n1]

Using Method F2 with 8-(4-amino-2-fluorophenoxy)pyrido[2,3-b]pyrazin-3(4H)-one (50 mg, 0.18 mmol), the title compound (26 mg, 28%) was obtained as a brown powder.

$^1$H-NMR (DMSO-d$_6$), δ (ppm), J (Hz): 1.32 (s, 9H, tert-Bu), 6.43 (s, 1H, CH), 6.58 (d, 1H, H$_{Py}$, J=5.5 Hz), 7.21-7.25 (m, 1H, H$_{arom}$), 7.37 (t, 1H, H$_{arom}$, J=9.0 Hz), 7.43-7.48 (m, 1H, H$_{arom}$), 7.56-7.59 (m, 4H, H$_{arom}$), 7.74 (dd, 1H, H$_{arom}$, J=13.2 Hz, J=2.0 Hz), 8.23 (s, 1H, NH or CH), 8.38 (d, 1H, H$_{Py}$, J=5.3 Hz), 8.57 (s, 1H, NH or CH), 9.41 (s, 1H, NH or CH), 12.99 (s, 1H, NH). $^{19}$F-NMR (δ, ppm, DMSO-d6): −128.21. LC-MS (m/z): 514 (M+H, 100), rt=2.61 min. HRMS (EI): m/z (M+H, 100) calcd for C27H24FN7O3: 514.1997; found: 514.2001.

Synthesis 96

1-(3-tert-butyl-1-p-tolyl-1H-pyrazol-5-yl)-3-(3-fluoro-4-(3-oxo-3,4-dihydropyrido[2,3-b]pyrazin-8-yloxy)phenyl)urea (AA-088)

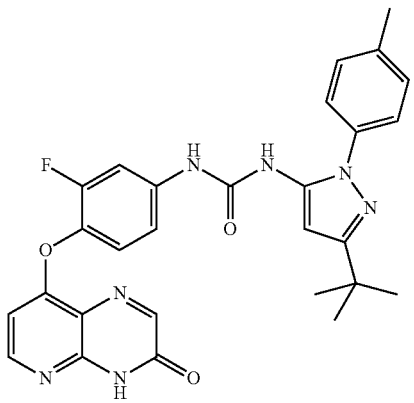 [SMILES: Cc1ccc(-n2nc(C(C)(C)C)cc2NC(=O)Nc2ccc(Oc3ccnc4[nH]c(=O)cnc34)c(F)c2)cc1]

Using Method F2 with 8-(4-amino-2-fluorophenoxy)pyrido[2,3-b]pyrazin-3(4H)-one (50 mg, 0.18 mmol), the title compound (26 mg, 27%) was obtained as a brown powder.

$^1$H-NMR (DMSO-d$_6$), δ (ppm), J (Hz): 1.32 (s, 9H, tert-Bu), 2.41 (s, 3H, CH$_3$), 6.41 (s, 1H, CH), 6.58 (d, 1H, H$_{Py}$, J=5.7 Hz), 7.21-7.24 (m, 1H, H$_{arom}$), 7.35-7.40 (m, 3H, H$_{arom}$), 7.42-7.45 (m, 2H, H$_{arom}$), 7.74 (dd, 1H, H$_{arom}$, J=13.2 Hz, J=2.2 Hz), 8.23 (s, 1H, NH or CH), 8.38 (d, 1H, H$_{Py}$, J=5.7 Hz), 8.51 (s, 1H, NH or CH), 9.41 (s, 1H, NH or CH), 12.99 (s, 1H, NH). $^{19}$F-NMR (δ, ppm, DMSO-d6): −128.21. LC-MS (m/z): 528 (M+H, 100), rt=2.67 min. HRMS (EI): m/z (M+H, 100) calcd for C28H26FN7O3: 528.2153; found: 528.2156.

Synthesis 97

1-(2-Fluoro-4-(3-morpholinopyrido[2,3-b]pyrazin-8-yloxy)phenyl)-3-(2-fluoro-5-(trifluoromethyl)phenyl)urea (AA-054)

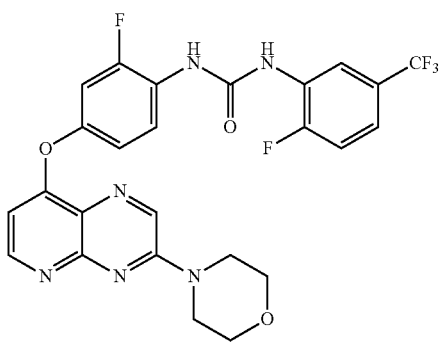 [SMILES: O=C(Nc1ccc(Oc2ccnc3nc(N4CCOCC4)cnc23)cc1F)Nc1cc(C(F)(F)F)ccc1F]

Method F3: 2-Fluoro-4-(3-morpholinopyrido[2,3-b]pyrazin-8-yloxy)aniline (29 mg, 85 μmol) was dissolved in dry THF (5 mL) to give a light yellow solution. 2-Fluoro-5-trifluoromethyl-phenylisocyanate (254, 170 μmol) was added to this solution and after 3 h, all volatiles were evaporated. The resulting yellow oil was dissolved in CH$_2$Cl$_2$ and purified by column chromatography on silica. Elution with EtOAc gave the product as a yellow band. Yield: 44 mg (96%).

$^1$H-NMR (DMSO-d$_6$), δ (ppm), J (Hz): 3.76 (m, 4H, N(CH$_2$CH$_2$)$_2$O), 3.84 (m, 4H, N(CH$_2$CH$_2$)$_2$O), 6.70 (d, 1H, J=5.3, H$_{Py}$), 7.04 (m, 1H, H$_{arom}$), 7.30 (m, 1H, H$_{arom}$), 7.41 (m, 1H, H$_{arom}$), 7.51 (m, 1H, H$_{arom}$), 8.21 (m, 1H, H$_{arom}$), 8.62-8.65 (m, 2H, H$_{arom}$+H$_{Py}$), 8.84 (s, 1H, H$_{arom}$), 9.18 (s, 1H, NH), 9.35 (s, 1H, NH); $^{13}$C-NMR (DMSO-d$_6$), δ (ppm), J (Hz): 44.4, 65.9, 105.9, 108.3 (d, J$_{FC}$=22.3), 116.1 (d, J$_{FC}$=20.7), 116.3, 116.6, 119.5, 122.6, 122.8, 124.2 (d, J$_{FC}$=10.7), 125.0, 125.4 (m), 128.5 (d, J$_{FC}$=11.4), 136.3, 149.6 (d, J$_{FC}$=10.4), 152.1 (d, J$_{FC}$=16.4), 152.4 (d, J$_{FC}$=245), 153.4 (d, J$_{FC}$=248), 153.7, 153.9, 160.3; $^{19}$F-NMR (DMSO-d$_6$), δ (ppm): −60.7, −124.0, −125.3; LC-MS (m/z): 547.0 (M+H, 100), rt=4.35 min; HRMS (6.65 min): m/z calcd. for C$_{25}$H$_{19}$F$_5$N$_6$O$_3$ [M+H$^+$]: 547.15116; found: 547.15163.

Synthesis 98

1-(2-fluoro-4-(3-(methylamino)pyrido[3,2-b]pyrazin-8-yloxy)phenyl)-3-(2-fluoro-5-(trifluoromethyl)phenyl)urea (AA-055)

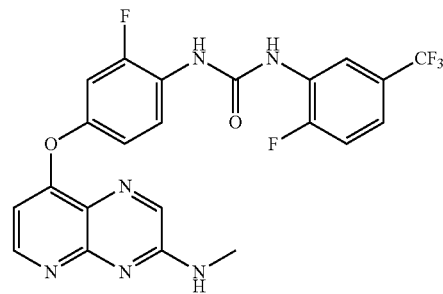 [SMILES: CNc1cnc2c(Oc3ccc(NC(=O)Nc4cc(C(F)(F)F)ccc4F)c(F)c3)ccnc2n1]

Method F2 was used with 2-fluoro-5-(trifluoromethyl)phenyl isocyanate and 8-(4-amino-3-fluorophenoxy)-N-methylpyrido[3,2-b]pyrazin-3-amine to give the title compound as a white solid. Yield: 56 mg (80%).

$^1$H-NMR (DMSO-d$_6$), δ (ppm), J (Hz): 2.95 (d, J=4.6, 3H, NHCH$_3$), 6.61 (d, J=5.4, 1H, H$_{Py}$), 7.03 (m, 2H, H$_{arom}$), 7.28 (m, 1H, H$_{arom}$), 7.40 (m, 1H, H$_{arom}$), 7.50 (m, 1H, H$_{arom}$), 8.03 (br q, J=4.6, 1H, NH$_{Me}$), 8.20 (m, 1H, H$_{arom}$), 8.31 (s, 1H, H$_{arom}$), 8.54 (d, J=5.4, 1H, H$_{Py}$), 8.64 (m, 1H, H$_{arom}$), 9.17 (s, 1H, NH), 9.34 (s, 1H, NH);

$^{13}$C-NMR (DMSO-d$_6$), δ (ppm), J (Hz): 27.1, 105.3, 108.3 (d, J$_{FC}$=22.3), 116.1 (d, J$_{FC}$=20.5), 116.3 (d, J$_{FC}$=2.6), 116.6 (m), 119.4 (m), 122.0 (d, J$_{FC}$=2.3), 122.8, 125.0, 125.4 (m), 128.5 (d, J$_{FC}$=11.4), 139.6 (br), 149.6 (d, J$_{FC}$=10.3), 152.0, 152.4 (d, J$_{FC}$=245), 152.8, 153.4, 153.4 (d, J$_{FC}$=248), 155.3, 160.4; $^{19}$F-NMR (DMSO-d$_6$), δ (ppm): −60.8, −124.0, −125.3; LC-MS (m/z): LC-MS: m/z 491.0 (M+H, 100), rt=1.87 min; HRMS (6.65 min): m/z calcd. for C$_{26}$H$_{19}$F$_5$N$_6$O$_3$ [M+H$^+$]: 547.15116; found: 547.15163.

Synthesis 99

1-(3-Tert-butyl-1-phenyl-1H-pyrazol-5-yl)-3-(2-fluoro-4-(3-methyl-2-oxo-1,2-dihydropyrido[2,3-b]pyrazin-8-yloxy)phenyl)urea (AA-041)

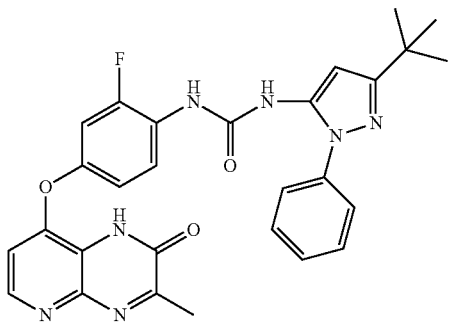 [SMILES: Cc1nc2nccc(Oc3ccc(NC(=O)Nc4cc(C(C)(C)C)nn4-c4ccccc4)c(F)c3)c2[nH]c1=O]

Method F3 was used with 3-tert-butyl-5-isocyanato-1-phenyl-1H-pyrazole and 8-(4-Amino-3-fluorophenoxy)-3-methylpyrido[2,3-b]pyrazin-2(1H)-one.

$^1$H-NMR (DMSO-d$_6$), δ (ppm), J (Hz): 1.28 (s, 9H, tert-Bu), 2.49 (s, 3H, CH$_3$), 6.85 (s, 1H, H$_{Py}$), 6.85 (d, 1H, J=5.6 Hz, H$_{Py}$), 7.04 (m, 1H, H$_{arom}$), 7.27 (m, 1H, H$_{arom}$), 7.43 (m, 1H, H$_{arom}$), 7.54 (m, 4H, H$_{arom}$), 8.15 (m, 1H, H$_{arom}$), 8.31 (d, J=5.6 Hz, 1H, H$_{Py}$), 8.83 (s, 1H, NH), 8.99 (s, 1H, NH), 12.40 (br s, 1H, NHAr); $^{13}$C-NMR (DMSO-d$_6$), δ (ppm), J (Hz): 21.0, 108.5 (d, J$_{FC}$=21), 109.7, 116.1 (d, J$_{FC}$=6), 116.6 (m), 119.5 (br), 121.8 (m), 122.8, 124.5 (d, J$_{FC}$=10.8), 125.0, 125.4 (m), 128.1, 128.5 (d, J$_{FC}$=11.4), 143.9, 145.0, 148.8 (d, J$_{FC}$=10.4), 151.3, 152.0, 152.3 (d, J$_{FC}$=246), 153.4 (d, J$_{FC}$=249), 154.5; $^{19}$F NMR (470 MHz, DMSO-d$_6$): δ=−125.3 ppm LC-MS (m/z): 528.1 (M+H, 100), rt=4.97 min; HRMS (6.04 min): m/z calcd. for C$_{22}$H$_{14}$F$_5$N$_5$NaO$_3$ [M+Na$^+$]: 514.09090; found: 514.09051.

Synthesis 100

1-(2-Fluoro-4-(3-(4-methylpiperazin-1-yl)pyrido[3,2-b]pyrazin-8-yloxy)phenyl)-3-(2-fluoro-5-(trifluoromethyl)phenyl)urea (AA-056)

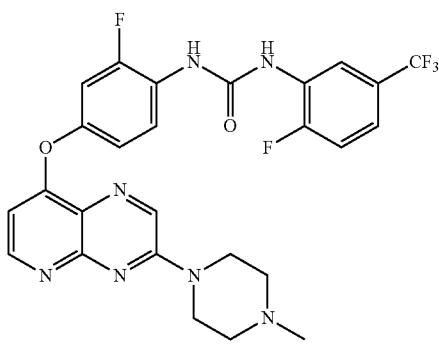 [SMILES: CN1CCN(c2cnc3c(Oc4ccc(NC(=O)Nc5cc(C(F)(F)F)ccc5F)c(F)c4)ccnc3n2)CC1]

Method F3 was used with 2-Fluoro-5-(trifluoromethyl)phenyl isocyanate and 2-fluoro-4-(3-(4-methylpiperazin-1-yl)pyrido[3,2-b]pyrazin-8-yloxy)aniline to give the title compound as a yellow solid. Yield: 30 mg (64%).

$^1$H-NMR (DMSO-d$_6$), δ (ppm), J (Hz): 2.26 (s, 3H, CH$_3$), 2.48 (m, 4H, N(CH$_2$CH$_2$)$_2$NMe), 3.86 (m, 4H, N(CH$_2$CH$_2$)$_2$NMe), 6.68 (d, J=5.4, 1H, H$_{Py}$), 7.06 (m, 2H, H$_{arom}$), 7.32 (m, 1H, H$_{arom}$), 7.43 (m, 1H, H$_{arom}$), 7.52 (m, 1H, H$_{arom}$), 8.22 (m, 1H, H$_{arom}$), 8.63 (d, J=5.4, 1H, H$_{Py}$), 8.66 (m, 1H, H$_{arom}$), 8.86 (s, 1H, H$_{arom}$), 9.19 (s, 1H, NH), 9.36 (s, 1H, NH);

$^{13}$C-NMR (DMSO-d$_6$), δ (ppm), J (Hz): 43.9, 45.7, 54.2, 105.8, 108.3 (d, J$_{FC}$=22.3), 116.1 (d, J$_{FC}$=21.4), 116.3 (d, J$_{FC}$=2.6), 116.6 (m), 119.5 (m), 122.0 (d, J$_{FC}$=2.3), 122.3, 125.0, 125.4 (m), 128.5 (d, J$_{FC}$=11.4), 136.4, 149.6, 149.7, 151.5, 152.4 (d, J$_{FC}$=245), 153.4, 153.4 (d, J$_{FC}$=248), 153.6, 153.8, 160.3; $^{19}$F-NMR (DMSO-d$_6$), δ (ppm): −60.8, −124.0, −125.3 ppm; LC-MS (m/z): 560.1 (M+H, 100), rt=3.18 min; HRMS (6.65 min): m/z calcd. for C$_{25}$H$_{19}$F$_5$N$_6$O$_3$ [M+H$^+$]: 547.15116; found: 547.15163.

Synthesis 1013

1-(3-Tert-butyl-1-phenyl-1H-pyrazol-5-yl)-3-(2-fluoro-4-(3-(4-methylpiperazin-1-yl)pyrido[2,3-b]pyrazin-8-yloxy)phenyl)urea (AA-053)

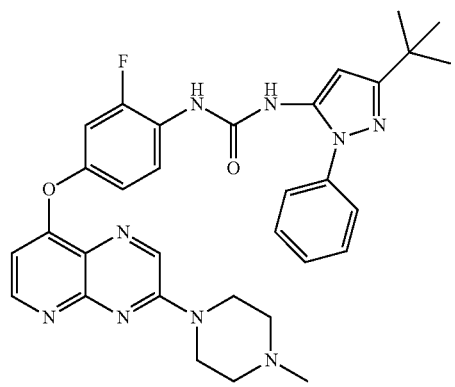 [SMILES: CN1CCN(c2cnc3c(Oc4ccc(NC(=O)Nc5cc(C(C)(C)C)nn5-c5ccccc5)c(F)c4)ccnc3n2)CC1]

Method F3 was used with 3-tert-butyl-5-isocyanato-1-phenyl-1H-pyrazole and 2-fluoro-4-(3-(4-methylpiperazin-1-yl)pyrido[3,2-b]pyrazin-8-yloxy)aniline to give the title compound as a cream-colored solid. Yield: 44 mg (77%).

$^1$H-NMR (DMSO-d$_6$), δ (ppm), J (Hz): 1.28 (s, 9H, tert-Bu), 2.31 (br, 3H, CH$_3$), 2.56 (br, 4H, N(CH$_2$CH$_2$)$_2$NMe), 3.88 (m, 4H, N(CH$_2$CH$_2$)$_2$NMe), 6.41 (s, 1H, H$_{Pyz}$), 6.66 (d, J=5.3, 1H, H$_{Py}$), 7.03 (m, 1H, H$_{arom}$), 7.27 (m, 1H, H$_{arom}$), 7.45 (m, 1H, H$_{arom}$), 7.56 (m, 4H, H$_{arom}$), 8.15 (m, 1H, H$_{arom}$), 8.61 (d, J=5.3, 1H, H$_{Py}$), 8.86 (m, 2H, NH+H$_{arom}$), 9.00 (s, 1H, NH); $^{13}$C-NMR (DMSO-d$_6$), δ (ppm), J (Hz): 30.2, 32.0, 43.7, 45.3, 54.0, 95.2, 105.8, 108.3 (d, J$_{FC}$=22.3), 116.2 (d, J$_{FC}$=2.6), 121.8 (d, J$_{FC}$=2.3), 122.4, 124.4, 124.5 (d, J$_{FC}$=11.8), 127.3, 129.3, 136.4, 137.0, 138.5, 149.3 (d, J$_{FC}$=10.6), 151.4, 152.2, 152.4 (d, J$_{FC}$=245), 153.6, 153.8, 160.3, 160.8; $^{19}$F-NMR (DMSO-d$_6$), δ (ppm): −60.8, −124.0, −125.3 ppm; LC-MS (m/z): 596.1 (M+H, 100), rt=3.10 min; HRMS (6.65 min): m/z calcd. for C$_{26}$H$_{19}$F$_5$N$_6$O$_3$ [M+H$^+$]: 547.15116; found: 547.15163.

Synthesis 102

1-(3-tert-butyl-1-p-tolyl-1H-pyrazol-5-yl)-3-(3-(3-oxo-3,4-dihydropyrido[2,3-b]pyrazin-8-yloxy)phenyl)urea (AA-006)

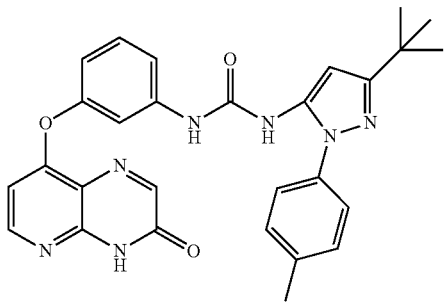 [SMILES: Cc1ccc(-n2nc(C(C)(C)C)cc2NC(=O)Nc2cccc(Oc3ccnc4[nH]c(=O)cnc34)c2)cc1]

Method F2 was used with 8-(3-aminophenoxy)pyrido[2,3-b]pyrazin-3(4H)-one and 3-tert-butyl-5-isocyanato-1-p-tolyl-1H-pyrazole to afford the title compound as a white solid (46 mg, 65%).

$^1$H-NMR (DMSO-d6), δ (ppm), J (Hz): 1.26 (s, 9H, tert-Bu), 2.36 (s, 3H, Me), 6.32 (s, 1H, H$_{arom}$,), 6.58 (d, 1H, H$_{Py}$, J=6.6 Hz), 6.82 (d, 1H, H$_{arom}$, J=6.8 Hz), 7.21 (d, 1H, H$_{arom}$, J=7.2 Hz), 7.30-7.43 (m, 6H, H$_{arom}$), 8.14 (s, 1H, H$_{arom}$,), 8.35 (d, 1H, H$_{Py}$, J=6.8 Hz), 8.74 (s, 1H, NH$_{urea}$), 9.30 (s, 1H, NH$_{urea}$), 12.88 (s, 1H, NH$_{lactame}$). $^{13}$C-NMR (δ, ppm, DMSO-d$_6$): 20.55 (CH$_3$), 30.17 (tert-Bu), 31.96 (tert-Bu), 95.84, 99.49, 106.47, 109.65, 113.47, 115.03, 118.50, 124.15 (2*C), 129.30, 129.57 (2*C), 130.48, 136.12, 136.59, 136.84, 141.56, 151.00, 151.72, 152.06, 154.39, 160.41, 160.50. HRMS (EI): m/z [M+H] calcd for C$_{28}$H$_{27}$N$_7$O$_3$: 510.2248; found: 510.2253.

Synthesis 103

1-(3-tert-butyl-1-phenyl-1H-pyrazol-5-yl)-3-(4-(2-oxo-1,2-dihydropyrido[2,3-b]pyrazin-8-yloxy)naphthalen-1-yl)urea (AA-034)

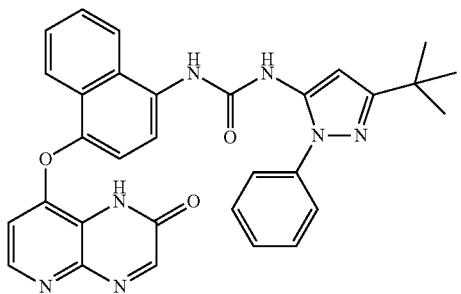 [SMILES: CC(C)(C)c1cc(NC(=O)Nc2ccc(Oc3ccnc4ncc(=O)[nH]c34)c3ccccc23)n(-c2ccccc2)n1]

Method F2 was used with 8-(4-aminonaphthalen-1-yloxy)pyrido[2,3-b]pyrazin-2(1H)-one and 3-tert-butyl-5-isocyanato-1-phenyl-1H-pyrazole to afford the title compound as a white solid (11 mg, 17%).

$^1$H-NMR (DMSO-d6), δ (ppm), J (Hz): 1.31 (s, 9H, tert-Bu), 6.44 (s, 1H, H$_{arom}$), 6.65 (d, 1H, H$_{arom}$, J=5.4 Hz), 7.41-7.47 (m, 2H, H$_{arom}$), 7.57-7.62 (m, 5H, H$_{arom}$), 7.66-7.69 (m, 1H, H$_{arom}$), 7.93 (d, 1H, H$_{arom}$, J=8.4 Hz), 7.96 (d, 1H, H$_{arom}$, J=8.3 Hz), 8.11 (d, 1H, H$_{arom}$, J=8.5 Hz), 8.27 (d, 1H, H$_{arom}$, J=4.5 Hz), 8.47 (s, 1H, H$_{arom}$), 8.82 (s, 1H, NH$_{urea}$), 9.15 (s, 1H, NH$_{urea}$), 12.82 (s, 1H, NH$_{lactame}$). $^{13}$C-NMR (DMSO-d6), δ (ppm), J (Hz): 30.17 (tert-Bu), 32.02 (tert-Bu), 95.74, 109.39, 111.11, 118.36, 121.83, 122.27, 124.24 (2*C), 126.33, 126.76, 127.24, 129.28 (2*C), 132.25, 137.19, 138.65, 144.91, 145.29, 152.31, 154.65, 160.81. HRMS (EI): m/z [M+H] calcd for C$_{31}$H$_{27}$N$_7$O$_3$: 546.2248; found: 546.2248.

Synthesis 104

1-(2-fluoro-5-(trifluoromethyl)phenyl)-3-(4-(2-oxo-1,2-dihydropyrido[2,3-b]pyrazin-8-yloxy)naphthalen-1-yl)urea (AA-038)

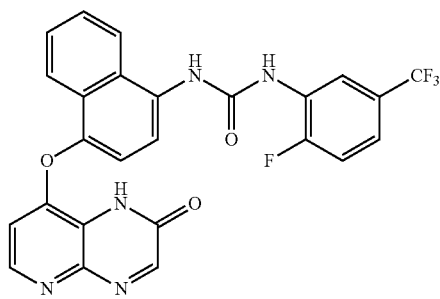 [SMILES: O=C(Nc1cc(C(F)(F)F)ccc1F)Nc1ccc(Oc2ccnc3ncc(=O)[nH]c23)c2ccccc12]

Method F2 was used with 8-(4-aminonaphthalen-1-yloxy)pyrido[2,3-b]pyrazin-2(1H)-one and 1-fluoro-2-isocyanato-4-(trifluoromethyl)benzene to afford the title compound as a white solid (65 mg, 98%).

$^1$H-NMR (DMSO-d6), δ (ppm), J (Hz): 6.64 (d, 1H, H$_{arom}$, J=5.3 Hz), 7.38-7.42 (m, 2H, H$_{arom}$), 7.53 (t, 1H, H$_{arom}$, J=8.9 Hz), 7.59 (t, 1H, H$_{arom}$, J=7.6 Hz), 7.70 (t, 1H, H$_{arom}$, J=7.7 Hz), 7.94 (d, 1H, H$_{arom}$, J=8.5 Hz), 8.07 (d, 1H, H$_{arom}$, J=8.4 Hz), 8.26 (d, 1H, H$_{arom}$, J=5.3 Hz), 8.28 (d, 1H, H$_{arom}$, J=8.6 Hz), 8.44 (s, 1H, H$_{arom}$), 8.68 (d, 1H, H$_{arom}$, J=7.2 Hz), 9.47 (s, 1H, NH$_{urea}$), 9.51 (s, 1H, NH$_{urea}$), 12.77 (s, 1H, NH$_{lactame}$). $^{13}$C-NMR (DMSO-d6), δ (ppm), J (Hz): 109.22, 115.97, 116.14, 116.66, 116.89, 118.09, 119.27, 121.82, 122.07, 122.75, 123.01, 124.92, 125.18, 125.46, 126.29, 126.76, 126.81, 127.54, 128.70, 128.79, 131.73. HRMS (EI): m/z [M+H] calcd for C$_{25}$H$_{15}$F$_4$N$_5$O$_3$: 510.1184; found: 510.1180.

Synthesis 105

1-(2-fluoro-5-(trifluoromethyl)phenyl)-3-(4-(2-methyl-3-oxo-3,4-dihydropyrido[2,3-b]pyrazin-8-yloxy)naphthalen-1-yl)urea (AA-014)

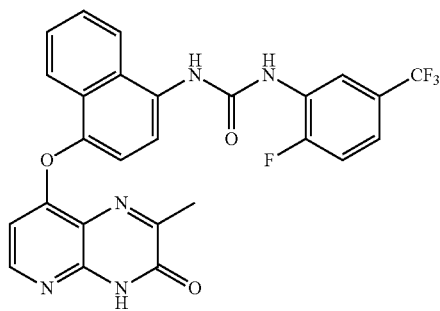 [SMILES: Cc1nc2c(Oc3ccc(NC(=O)Nc4cc(C(F)(F)F)ccc4F)c4ccccc34)ccnc2[nH]c1=O]

Method F2 was used with 8-(4-aminonaphthalen-1-yloxy)-2-methylpyrido[2,3-b]pyrazin-3(4H)-one and 1-fluoro-2-isocyanato-4-(trifluoromethyl)benzene to afford the title compound as a slightly pink solid (50 mg, 61%).

¹H-NMR (DMSO-d6), δ (ppm), J (Hz): 2.54 (s, 3H, Me), 6.33 (d, 1H, H$_{arom}$, J=5.7 Hz), 7.40-7.43 (m, 2H, H$_{arom}$), 7.54 (t, 1H, H$_{arom}$, J=8.8 Hz), 7.60 (t, 1H, H$_{arom}$, J=7.5 Hz), 7.72 (t, 1H, H$_{arom}$, J=8.2 Hz), 7.88 (d, 1H, H$_{arom}$, J=8.4 Hz), 8.10 (d, 1H, H$_{arom}$, J=8.3 Hz), 8.19 (d, 1H, H$_{arom}$, J=5.3 Hz), 8.27 (d, 1H, H$_{arom}$, J=8.7 Hz), 8.70 (dd, 1H, H$_{arom}$, J=7.3 Hz, J=2.0 Hz), 9.34 (s, 1H, NH$_{urea}$), 9.40 (s, 1H, NH$_{urea}$), 12.79 (s, 1H, NH$_{lactame}$). ¹³C-NMR (DMSO-d6), δ (ppm), J (Hz): 20.51 (Me), 105.50, 115.97, 116.50, 117.29, 117.98, 119.22, 121.50, 122.07, 122.72, 124.89, 125.29, 126.35, 126.87, 127.38, 128.69, 131.71, 145.11, 145.67, 150.51, 152.39, 152.55, 154.36, 156.33, 159.10, 160.59. HRMS (EI): m/z [M+H] calcd for $C_{26}H_{17}F_4N_5O_3$: 524.1340; found: 524.1324.

Synthesis 106

1-(2-fluoro-5-(trifluoromethyl)phenyl)-3-(4-(3-methyl-2-oxo-1,2-dihydropyrido[2,3-b]pyrazin-8-yloxy)naphthalen-1-yl)urea (AA-039)

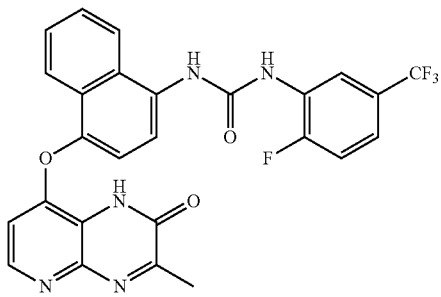 [SMILES: Cc1nc2nccc(Oc3ccc(NC(=O)Nc4cc(C(F)(F)F)ccc4F)c4ccccc34)c2[nH]c1=O]

Method F2 was used with 8-(4-aminonaphthalen-1-yloxy)-3-methylpyrido[2,3-b]pyrazin-2(1H)-one and 1-fluoro-2-isocyanato-4-(trifluoromethyl)benzene to afford the title compound as a slightly yellow solid (28 mg, 42%).

¹H-NMR (DMSO-d6), δ (ppm), J (Hz): 2.52 (s, 3H, Me), 6.60 (d, 1H, H$_{arom}$, J=5.3 Hz), 7.39-7.41 (m, 2H, H$_{arom}$), 7.51-7.54 (m, 1H, H$_{arom}$), 7.60 (t, 1H, H$_{arom}$, J=7.7 Hz), 7.71 (t, 1H, H$_{arom}$, J=7.6 Hz), 7.95 (d, 1H, H$_{arom}$, J=8.4 Hz), 8.07 (d, 1H, H$_{arom}$, J=8.3 Hz), 8.22 (d, 1H, H$_{arom}$, J=5.3 Hz), 8.26 (d, 1H, H$_{arom}$, J=8.5 Hz), 8.68 (d, 1H, H$_{arom}$, J=6.6 Hz), 9.39 (s, 1H, NH$_{urea}$), 9.44 (s, 1H, NH$_{urea}$), 12.66 (s, 1H, NH$_{lactame}$). ¹³C-NMR (DMSO-d6), δ (ppm), J (Hz): 20.97 (Me), 108.47, 115.95, 116.11, 116.58, 116.86, 117.98, 119.20, 121.86, 121.97, 122.73, 124.90, 125.32, 126.30, 126.72, 126.80, 127.06, 127.47, 128.68, 131.67, 143.93, 144.82, 145.02, 152.44, 152.61, 154.41. HRMS (EI): m/z [M+H] calcd for $C_{26}H_{17}F_4N_5O_3$: 524.1340; found: 524.1341.

Synthesis 107

1-(3-tert-butyl-1-phenyl-1H-pyrazol-5-yl)-3-(4-(3-oxo-3,4-dihydropyrido[2,3-b]pyrazin-8-yloxy)naphthalen-1-yl)urea (AA-008)

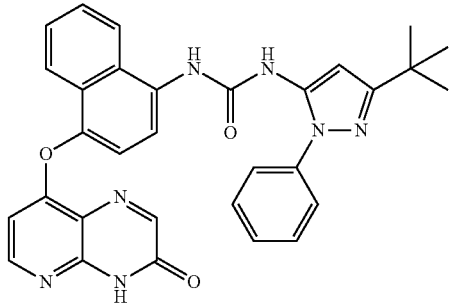 [SMILES: CC(C)(C)c1cc(NC(=O)Nc2ccc(Oc3ccnc4[nH]c(=O)cnc34)c3ccccc23)n(-c2ccccc2)n1]

Method F2 was used with 8-(4-aminonaphthalen-1-yloxy)pyrido[2,3-b]pyrazin-3(4H)-one and 3-tert-butyl-5-isocyanato-1-phenyl-1H-pyrazole to afford the title compound as a slightly yellow solid (65 mg, 80%).

¹H-NMR (DMSO-d6), δ (ppm), J (Hz): 1.29 (s, 9H, tert-Bu), 6.39 (d, 1H, H$_{arom}$, J=5.7 Hz), 6.43 (s, 1H, H$_{arom}$), 7.38 (d, 1H, H$_{arom}$, J=8.3 Hz), 7.44 (t, 1H, H$_{arom}$, J=7.0 Hz), 7.55-7.61 (m, 5H, H$_{arom}$), 7.66 (t, 1H, H$_{arom}$, J=7.6 Hz), 7.85 (d, 1H, H$_{arom}$, J=8.4 Hz), 7.94 (d, 1H, H$_{arom}$, J=8.3 Hz), 8.10 (d, 1H, H$_{arom}$, J=8.6 Hz), 8.25 (s, 1H, H$_{arom}$), 8.27 (d, 1H, H$_{arom}$, J=5.7 Hz), 8.80 (s, 1H, NH$_{urea}$), 9.13 (s, 1H, NH$_{urea}$), 12.94 (s, 1H, NH$_{lactame}$). ¹³C-NMR (DMSO-d6), δ (ppm), J (Hz): 30.10 (tert-Bu), 31.95 (tert-Bu), 95.68, 105.78, 117.03, 118.05, 118.40, 121.32, 122.35, 124.16 (2*C), 126.22, 126.68, 126.92, 127.17, 127.71, 129.21 (2*C), 132.12, 137.12, 138.58, 145.13, 145.44, 151.12, 152.10, 152.24, 156.46, 160.74, 161.31. HRMS (EI): m/z [M+H] calcd for $C_{31}H_{27}N_7O_3$: 546.2248; found: 546.2250.

Synthesis 108

1-(3-tert-butyl-1-phenyl-1H-pyrazol-5-yl)-3-(4-(2-methyl-3-oxo-3,4-dihydropyrido[2,3-b]pyrazin-8-yloxy)naphthalen-1-yl)urea (AA-009)

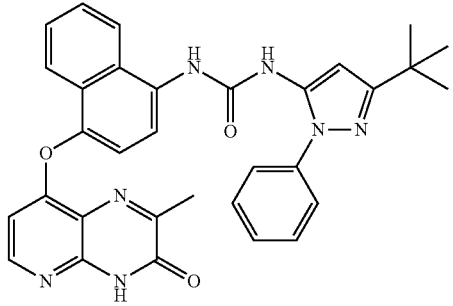 [SMILES: Cc1nc2c(Oc3ccc(NC(=O)Nc4cc(C(C)(C)C)nn4-c4ccccc4)c4ccccc34)ccnc2[nH]c1=O]

Method F2 was used with 8-(4-aminonaphthalen-1-yloxy)-2-methylpyrido[2,3-b]pyrazin-3(4H)-one and 3-tert-butyl-5-isocyanato-1-phenyl-1H-pyrazole to afford the title compound as a slightly pink solid (56 mg, 71%).

¹H-NMR (DMSO-d6), δ (ppm), J (Hz): 1.30 (s, 9H, tert-Bu), 2.48 (s, 3H, Me), 6.31 (d, 1H, H$_{arom}$ J=5.6 Hz), 6.43 (s, 1H, H$_{arom}$), 7.37 (d, 1H, H$_{arom}$, J=8.3 Hz), 7.43-7.46 (m, 1H, H$_{arom}$), 7.55-7.67 (m, 6H, H$_{arom}$), 7.84 (d, 1H, H$_{arom}$, J=8.3 Hz), 7.95 (d, 1H, H$_{arom}$, J=8.3 Hz), 8.10 (d, 1H, H$_{arom}$, J=8.6 Hz), 8.18 (d, 1H, H$_{arom}$, J=5.6 Hz), 8.80 (s, 1H, NHurea), 9.12 (s, 1H, NHurea), 12.78 (s, 1H, NH$_{lactame}$). $^{13}$C-NMR (DMSO-d6), δ (ppm), J (Hz): 20.58 (CH$_3$), 30.13 (tert-Bu), 31.98 (tert-Bu), 95.63, 105.52, 117.30, 117.33, 118.37, 121.44, 122.36, 124.21 (2*C), 126.34, 126.68, 126.92, 127.21, 127.69, 129.26 (2*C), 132.14, 137.15, 138.58, 145.08, 145.64, 150.55, 152.23, 156.34, 159.15, 160.64, 160.75. HRMS (EI): m/z [M+H] calcd for C$_{32}$H$_{29}$N$_7$O$_3$: 560.2405; found: 560.2407.

Synthesis 109

1-(3-tert-butyl-1-phenyl-1H-pyrazol-5-yl)-3-(4-(3-methyl-2-oxo-1,2-dihydropyrido[2,3-b]pyrazin-8-yloxy)naphthalen-1-yl)urea (AA-035)

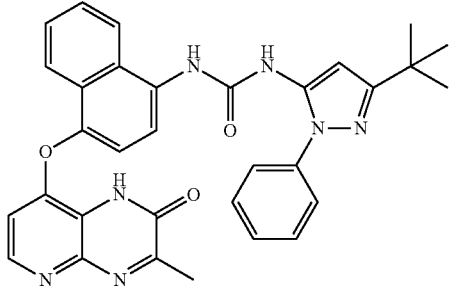 [SMILES: Cc1nc2nccc(Oc3ccc(NC(=O)Nc4cc(C(C)(C)C)nn4-c4ccccc4)c4ccccc34)c2[nH]c1=O]

Method F2 was used with 8-(4-aminonaphthalen-1-yloxy)-3-methylpyrido[2,3-b]pyrazin-2(1H)-one and 3-tert-butyl-5-isocyanato-1-phenyl-1H-pyrazole to afford the title compound as a white solid (50 mg, 41%).

$^1$H-NMR (DMSO-d6), δ (ppm), J (Hz): 1.29 (s, 9H, tert-Bu), 2.51 (3H, s, Me), 6.43 (d, 1H, H$_{arom}$, J=5.3 Hz), 6.59 (s, 1H, H$_{arom}$), 7.38 (d, 1H, H$_{arom}$, J=8.3 Hz), 7.44 (t, 1H, H$_{arom}$, J=7.3 Hz), 7.55-7.61 (m, 5H, H$_{arom}$), 7.66 (t, 1H, H$_{arom}$, J=7.6 Hz), 7.91-7.95 (m, 2H, H$_{arom}$), 8.09 (d, 1H, H$_{arom}$, J=8.6 Hz), 8.21 (d, 1H, H$_{arom}$, J=5.4 Hz), 8.80 (s, 1H, NH$_{urea}$), 9.13 (s, 1H, NH$_{urea}$), 12.65 (s, 1H, NH$_{lactame}$). $^{13}$C-NMR (DMSO-d6), δ (ppm), J (Hz): 20.95 (CH$_3$), 30.09 (tert-Bu), 31.95 (tert-Bu), 95.66, 108.51, 116.89, 118.33, 118.81, 121.79, 122.17, 124.16 (2*C), 126.28, 126.66, 126.69, 127.17, 127.74, 129.21 (2*C), 132.04, 137.12, 138.58, 143.77, 144.88, 144.99, 152.15, 152.24, 154.54, 160.74, 164.12. HRMS (EI): m/z [M+H] calcd for C$_{32}$H$_{29}$N$_7$O$_3$: 560.2405; found: 560.2402.

Synthesis 110

1-(3-tert-butyl-1-p-tolyl-1H-pyrazol-5-yl)-3-(4-(3-oxo-3,4-dihydropyrido[2,3-b]pyrazin-8-yloxy)naphthalen-1-yl)urea (AA-010)

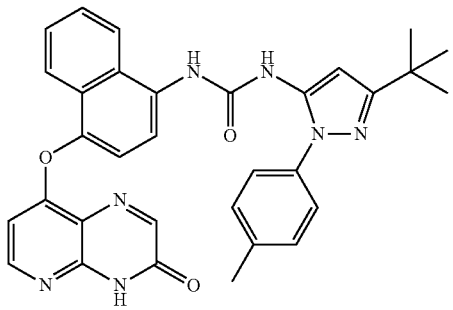 [SMILES: Cc1ccc(-n2nc(C(C)(C)C)cc2NC(=O)Nc2ccc(Oc3ccnc4[nH]c(=O)cnc34)c3ccccc23)cc1]

Method F2 was used with 8-(4-aminonaphthalen-1-yloxy)pyrido[2,3-b]pyrazin-3(4H)-one and 3-tert-butyl-5-isocyanato-1-tolyl-1H-pyrazole to afford the title compound as a slightly yellow solid (80 mg, 70%).

$^1$H-NMR (DMSO-d6), δ (ppm), J (Hz): 1.29 (s, 9H, tert-Bu), 2.40 (s, 3H, Me), 6.40 (d, 1H, H$_{arom}$, J=5.6 Hz), 6.41 (s, 1H, H$_{arom}$), 7.37-7.39 (m, 3H, H$_{arom}$), 7.47 (d, 2H, H$_{arom}$, J=8.1 Hz), 7.57 (t, 1H, H$_{arom}$, J=7.6 Hz), 7.66 (t, 1H, H$_{arom}$, J=7.6 Hz), 7.86 (d, 1H, H$_{arom}$, J=8.4 Hz), 7.97 (d, 1H, H$_{arom}$, J=8.3 Hz), 8.11 (d, 1H, H$_{arom}$, J=8.6 Hz), 8.25 (s, 1H, H$_{arom}$), 8.26 (d, 1H, H$_{arom}$, J=5.7 Hz), 8.77 (s, 1H, NH$_{urea}$), 9.13 (s, 1H, NH$_{urea}$), 12.94 (s, 1H, NH$_{lactame}$). $^{13}$C-NMR (DMSO-d6), δ (ppm), J (Hz): 20.51 (CH$_3$), 30.11 (tert-Bu), 31.90 (tert-Bu), 95.01, 105.75, 117.02, 118.03, 118.17, 121.30, 122.30, 124.26 (2*C), 126.21, 126.62, 126.89, 127.61, 129.61 (2*C), 132.14, 136.05, 136.71, 137.09, 145.02, 145.44, 151.09, 152.08, 156.44, 160.46, 161.30. HRMS (EI): m/z [M+H] calcd for C$_{32}$H$_{29}$N$_7$O$_3$: 560.2405; found: 560.2403.

Synthesis 111

1-(3-tert-butyl-1-p-tolyl-1H-pyrazol-5-yl)-3-(4-(2-methyl-3-oxo-3,4-dihydropyrido[2,3-b]pyrazin-8-yloxy)naphthalen-1-yl)urea (AA-011)

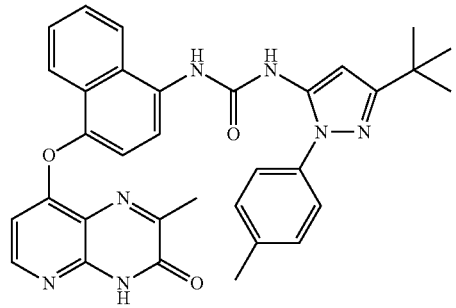 [SMILES: Cc1ccc(-n2nc(C(C)(C)C)cc2NC(=O)Nc2ccc(Oc3ccnc4[nH]c(=O)c(C)nc34)c3ccccc23)cc1]

Method F2 was used with 8-(4-aminonaphthalen-1-yloxy)-2-methylpyrido[2,3-b]pyrazin-3(4H)-one and 3-tert-butyl-5-isocyanato-1-tolyl-1H-pyrazole to afford the title compound as a slightly pink solid (67 mg, 69%).

$^1$H-NMR (DMSO-d6), δ (ppm), J (Hz): 1.29 (s, 9H, tert-Bu), 2.40 (s, 3H, Me), 2.48 (s, 3H, Me), 6.31 (d, 1H, H$_{arom}$, J=5.6 Hz), 6.41 (s, 1H, H$_{arom}$), 7.37-7.38 (m, 3H, H$_{arom}$), 7.47 (d, 2H, H$_{arom}$, J=8.3 Hz), 7.56 (t, 1H, H$_{arom}$, J=7.5 Hz), 7.66 (t, 1H, H$_{arom}$, J=7.4 Hz), 7.84 (d, 1H, H$_{arom}$, J=8.4 Hz), 7.97 (d, 1H, H$_{arom}$, J=8.3 Hz), 8.11 (d, 1H, H$_{arom}$, J=8.6 Hz), 8.18 (d, 1H, H$_{arom}$, J=5.6 Hz), 8.77 (s, 1H, NH$_{urea}$), 9.13 (s, 1H, NH$_{urea}$), 12.80 (s, 1H, NH$_{lactame}$). $^{13}$C-NMR (DMSO-d6), δ (ppm), J (Hz): 20.51 (2*CH$_3$), 30.11 (tert-Bu), 31.91 (tert-Bu), 95.03, 105.51, 117.21, 117.33, 118.21, 121.40, 122.30, 124.26 (2*C), 126.31, 126.60, 126.85, 127.60, 129.61 (2*C), 132.11, 136.05, 136.71, 137.09, 145.04, 145.61, 150.48, 152.09, 156.28, 159.09, 160.47, 160.60. HRMS (EI): m/z [M+H] calcd for C$_{33}$H$_{31}$N$_7$O$_3$: 574.2561; found: 574.2558.

Synthesis 112

1-(3-tert-butyl-1-p-tolyl-1H-pyrazol-5-yl)-3-(4-(3-methyl-2-oxo-1,2-dihydropyrido[2,3-b]pyrazin-8-yloxy)naphthalen-1-yl)urea (AA-036)

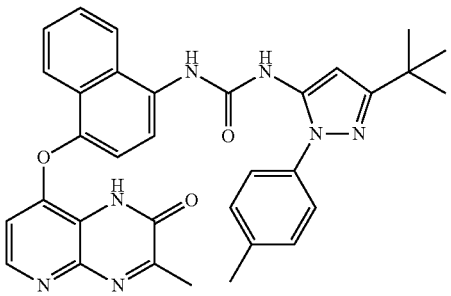 [SMILES: Cc1ccc(-n2nc(C(C)(C)C)cc2NC(=O)Nc2ccc(Oc3ccnc4nc(C)c(=O)[nH]c34)c3ccccc23)cc1]

Method F2 was used with 8-(4-aminonaphthalen-1-yloxy)-3-methylpyrido[2,3-b]pyrazin-2(1H)-one and 3-tert-butyl-5-isocyanato-1-tolyl-1H-pyrazole to afford the title compound as a white solid (71 mg, 49%).

$^1$H-NMR (DMSO-d6), δ (ppm), J (Hz): 1.29 (s, 9H, tert-Bu), 2.40 (3H, s, Me), 2.52 (3H, s, Me), 6.41 (s, 1H, H$_{arom}$), 6.59 (d, 1H, H$_{arom}$, J=5.4 Hz), 7.37-7.39 (m, 3H, H$_{arom}$), 7.47 (d, 2H, H$_{arom}$, J=8.2 Hz), 7.57 (t, 1H, H$_{arom}$, J=7.6 Hz), 7.66 (t, 1H, H$_{arom}$, J=7.6 Hz), 7.92 (d, 1H, H$_{arom}$, J=8.4 Hz), 7.96 (d, 1H, H$_{arom}$, J=8.3 Hz), 8.09 (d, 1H, H$_{arom}$, J=8.6 Hz), 8.21 (d, 1H, H$_{arom}$, J=5.4 Hz), 8.76 (s, 1H, NH$_{urea}$), 9.12 (s, 1H, NH$_{urea}$), 12.65 (s, 1H, NH$_{lactame}$). $^{13}$C-NMR (DMSO-d6), δ (ppm), J (Hz): 20.51 (CH$_3$), 20.93 (CH$_3$), 30.11 (tert-Bu), 31.90 (tert-Bu), 95.00, 108.48, 116.88, 118.10, 118.75, 121.77, 122.13, 124.26 (2*C), 126.26, 126.61, 126.67, 127.61, 129.61 (2*C), 132.05, 136.04, 136.71, 137.09, 143.72, 144.88, 152.08, 154.51, 160.46, 164.11. HRMS (EI): m/z [M+H] calcd for C$_{33}$H$_{31}$N$_7$O$_3$: 574.2561; found: 574.2560.

Synthesis 113

1-(3-tert-butyl-1-p-tolyl-1H-pyrazol-5-yl)-3-(3-(2-oxo-1,2-dihydropyrido[2,3-b]pyrazin-8-yloxy)phenyl)urea (AA-031)

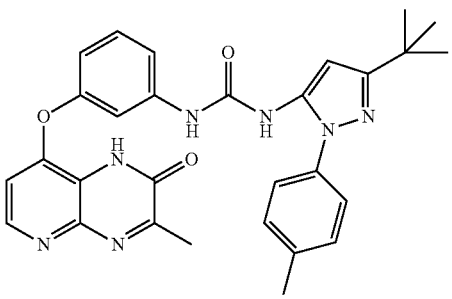 [SMILES: Cc1ccc(-n2nc(C(C)(C)C)cc2NC(=O)Nc2cccc(Oc3ccnc4nc(C)c(=O)[nH]c34)c2)cc1]

Method F2 was used with 8-(3-aminophenoxy)pyrido[2,3-b]pyrazin-2(1H)-one and 3-tert-butyl-5-isocyanato-1-p-tolyl-1H-pyrazole to afford the title compound as a slightly yellow solid (9 mg, 13%).

$^1$H-NMR (DMSO-d6), δ (ppm), J (Hz): 1.26 (s, 9H, tert-Bu), 2.37 (s, 3H, Me), 6.32 (s, 1H, H$_{arom}$), 6.85 (dd, 1H, H$_{arom}$, J=8.1 Hz, J=1.7 Hz), 6.89 (d, 1H, H$_{Py}$, 5, J=5.3 Hz), 7.19 (d, 1H, H$_{arom}$, J=8.2 Hz), 7.31-7.33 (m, 2H, H$_{arom}$), 7.37-7.40 (m, 3H, H$_{arom}$), 7.47 (s, 1H, H$_{arom}$), 8.37-8.41 (m, 3H, H$_{arom}$), 9.23 (s, 1H, NH$_{urea}$), 12.54 (s, 1H, NH$_{lactame}$). $^{13}$C-NMR (δ, ppm, DMSO-d$_6$): 20.55 (CH$_3$), 30.16 (tert-Bu), 31.95 (tert-Bu), 95.15, 109.72, 110.44, 113.64, 115.03, 124.32 (2*C), 129.63 (2*C), 130.46, 135.97, 136.78, 136.82, 141.30, 145.25, 151.41, 154.18, 154.65, 160.48. HRMS (EI): m/z [M+H] calcd for C$_{28}$H$_{27}$N$_7$O$_3$: 510.2248; found: 510.2250.

Synthesis 114

1-(4-(2-amino-3-oxo-3,4-dihydropyrido[2,3-b]pyrazin-8-yloxy)naphthalen-1-yl)-3-(2-fluoro-5-(trifluoromethyl)phenyl)urea (AA-015)

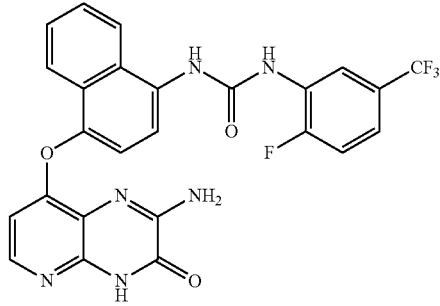 [SMILES: Nc1nc2c(Oc3ccc(NC(=O)Nc4cc(C(F)(F)F)ccc4F)c4ccccc34)ccnc2[nH]c1=O]

Method F2 was used with 2-amino-8-(4-aminonaphthalen-1-yloxy)pyrido[2,3-b]pyrazin-3(4H)-one and 1-fluoro-2-isocyanato-4-(trifluoromethyl)benzene to afford the title compound as a slightly pink solid (73 mg, 89%).

$^1$H-NMR (DMSO-d6), δ (ppm), J (Hz): 6.32 (d, 1H, H$_{arom}$, J=5.5 Hz), 7.27 (d, 1H, H$_{arom}$, J=8.3 Hz), 7.40-7.42 (m, 1H, H$_{arom}$), 7.54 (t, 1H, H$_{arom}$, J=9.8 Hz), 7.59 (t, 1H, H$_{arom}$, J=7.6 Hz), 7.70 (t, 1H, H$_{arom}$, J=8.1 Hz), 7.90 (d, 1H, H$_{arom}$, J=5.5 Hz), 7.93 (d, 1H, H$_{arom}$, J=8.3 Hz), 8.01 (d, 1H, H$_{arom}$, J=8.3 Hz), 8.22 (d, 1H, H$_{arom}$, J=8.6 Hz), 8.69 (dd, 1H, H$_{arom}$, J=7.3 Hz, J=1.9 Hz), 9.27 (s, 1H, NH$_{urea}$), 9.36 (s, 1H, NH$_{urea}$), 12.59 (s, 1H, NH$_{lactame}$). $^{13}$C-NMR (DMSO-d6), δ (ppm), J (Hz): 106.41, 115.99, 116.14, 116.44, 118.47, 119.10, 119.36, 121.67, 121.90, 122.72, 124.89, 125.32, 126.38, 126.67, 127.61, 128.74, 130.87, 142.97, 143.57, 146.16, 151.73, 152.35, 152.68, 154.32, 157.17. HRMS (EI): m/z [M+H] calcd for C$_{25}$H$_{16}$F$_4$N$_6$O$_3$: 525.1293; found: 525.1292.

Synthesis 115

1-(2-fluoro-5-(trifluoromethyl)phenyl)-3-(3-(3-oxo-3,4-dihydropyrido[2,3-b]pyrazin-8-yloxy)phenyl)urea (AA-007)

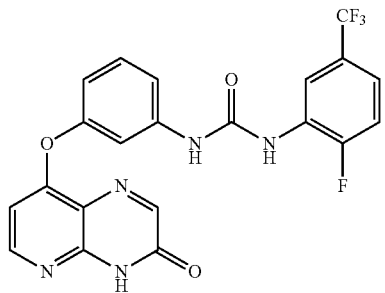 [SMILES: O=C(Nc1cccc(Oc2ccnc3[nH]c(=O)cnc23)c1)Nc1cc(C(F)(F)F)ccc1F]

Method F2 was used with 8-(3-aminophenoxy)pyrido[2,3-b]pyrazin-3(4H)-one and 1-fluoro-2-isocyanato-4-(trifluoromethyl)benzene to afford the title compound as a white solid (30 mg, 42%).

¹H-NMR (DMSO-d6), δ (ppm), J (Hz): 6.61 (d, 1H, H$_{Py}$, J=5.6 Hz), 6.89 (dd, 1H, H$_{arom}$, J=8.0 Hz, J=1.9 Hz), 7.26 (d, 1H, H$_{arom}$, J=8.1 Hz), 7.39-7.53 (m, 4H, H$_{arom}$), 8.18 (s, 1H, H$_{arom}$), 8.37 (d, 1H, H$_{Py}$, J=5.6 Hz), 8.55 (d, 1H, H$_{arom}$, J=7.2 Hz), 8.99 (s, 1H, NH$_{urea}$), 9.44 (s, 1H, NH$_{urea}$), 12.94 (s, 1H, NH$_{lactame}$). ¹³C-NMR (DMSO-d6), δ (ppm), J (Hz): 106.41, 109.96, 113.96, 115.31, 116.00, 116.96, 118.50, 119.56, 122.74, 125.30, 128.43, 130.63, 141.05, 145.76, 151.01, 152.06, 152.68, 154.43, 154.66, 156.71, 160.53. HRMS (EI): m/z [M+H] calcd for C$_{21}$H$_{13}$F$_4$N$_5$O$_3$: 460.1027; found: 460.1023.

Synthesis 116

1-(2-fluoro-5-(trifluoromethyl)phenyl)-3-(3-(2-oxo-1,2-dihydropyrido[2,3-b]pyrazin-8-yloxy)phenyl)urea (AA-032)

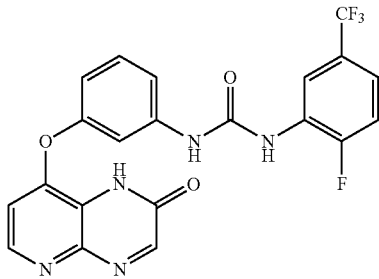 [SMILES: O=C(Nc1cccc(Oc2ccnc3ncc(=O)[nH]c23)c1)Nc1cc(C(F)(F)F)ccc1F]

Method F2 was used with 8-(3-aminophenoxy)pyrido[2,3-b]pyrazin-2(1H)-one and 1-fluoro-2-isocyanato-4-(trifluoromethyl)benzene to afford the title compound as a white solid (49 mg, 73%).

¹H-NMR (DMSO-d6), δ (ppm), J (Hz): 6.87-6.88 (m, 2H, H$_{arom}$), 7.26 (d, 1H, H$_{arom}$, J=7.9 Hz), 7.40-7.54 (m, 4H, H$_{arom}$), 8.35 (d, 1H, H$_{Py}$, 6, J=5.3 Hz), 8.40 (s, 1H, H$_{arom}$), 8.54 (d, 1H, H$_{arom}$, J=7.2 Hz), 9.05 (s, 1H, NH$_{urea}$), 9.52 (s, 1H, NH$_{urea}$), 12.62 (s, 1H, NH$_{lactame}$). ¹³C-NMR (DMSO-d6), δ (ppm), J (Hz): 109.88, 110.21, 113.78, 115.14, 115.92, 116.09, 116.85, 119.46, 122.66, 125.11, 128.36, 130.41, 140.91, 144.46, 145.05, 151.96, 152.32, 152.60, 154.22, 154.57, 155.06. HRMS (EI): m/z [M+H] calcd for C$_{21}$H$_{13}$F$_4$N$_5$O$_3$: 460.1027; found: 460.1025.

Synthesis 117

1-(2-fluoro-5-(trifluoromethyl)phenyl)-3-(4-(2-methyl-3-oxo-3,4-dihydropyrido[2,3-b]pyrazin-8-yloxy)-2-(methylthio)phenyl)urea (AA-060)

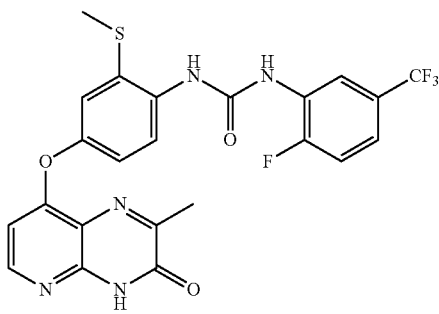 [SMILES: CSc1cc(Oc2ccnc3[nH]c(=O)c(C)nc23)ccc1NC(=O)Nc1cc(C(F)(F)F)ccc1F]

Method F2 was used with 8-(4-amino-3-(methylthio)phenoxy)-2-methylpyrido[2,3-b]pyrazin-3(4H)-one and 1-fluoro-2-isocyanato-4-(trifluoromethyl)benzene, to afford the title compound was obtained as a white solid (5 mg, 12%).

¹H-NMR (DMSO-d6), δ (ppm), J (Hz): 2.50 (s, 3H, CH$_3$), 2.52 (s, 3H, CH$_3$), 6.66 (d, 1H, H$_{Py}$, J=5.6 Hz), 7.17 (m, 1H, H$_{arom}$), 7.35 (d, 1H, H$_{arom}$, J=2.7 Hz), 7.42 (m, 2H, H$_{arom}$), 8.17 (d, 1H, H$_{arom}$, J=8.8 Hz), 8.31 (m, 2H, H$_{Py}$, +H$_{arom}$), 8.83 (m, 1H, H$_{arom}$), 9.01 (m, 1H, H$_{arom}$), 11.59 (bs, 1H, NH). LC-MS (m/z): 520 (M+H, 100), rt=2.73 min.

Synthesis 118

1-(3-tert-butyl-1-p-tolyl-1H-pyrazol-5-yl)-3-(4-(2-methyl-3-oxo-3,4-dihydropyrido[2,3-b]pyrazin-8-yloxy)-2-(methylthio)phenyl)urea (AA-061)

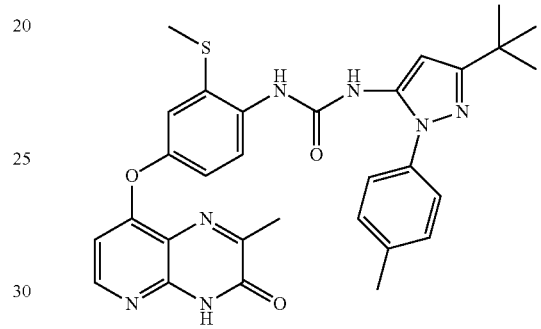

Method F2 was used with 8-(4-amino-3-(methylthio)phenoxy)-2-methylpyrido[2,3-b]pyrazin-3(4H)-one and 3-tert-butyl-5-isocyanato-1-tolyl-1H-pyrazole, to afford the title compound (9 mg, 20%) as a white solid.

¹H-NMR (DMSO-d6), δ (ppm), J (Hz): 1.29 (s, 9H, tert-Bu), 2.35 (s, 3H, CH$_3$), 2.37 (s, 3H, CH$_3$), 2.43 (s, 3H, CH$_3$), 6.44 (s, 1H, CH), 6.56 (d, 1H, H$_{Py}$, J=5.6 Hz), 7.06 (dd, 1H, H$_{arom}$, J=8.8 Hz and J=2.7 Hz), 7.23-7.27 (m, 3H, H$_{arom}$, J=2.7 Hz), 7.42 (m, 2H, H$_{arom}$), 7.97 (s, 1H, H$_{arom}$), 8.12 (d, 1H, H$_{arom}$, J=8.8 Hz), 8.22 (d, 1H, H$_{Py}$, J=5.6 Hz), 8.32 (m, 1H, H$_{arom}$), 11.28 (bs, 1H, NH). LC-MS (m/z): 570 (M+H, 100), rt=2.70 min. HRMS (EI): m/z (M+H, 100) calcd for C30H31N7O3S: 570.2281; found: 570.2282.

Synthesis 119

1-(3-tert-butyl-1-(6-methoxypyridin-3-yl)-1H-pyrazol-5-yl)-3-(2-fluoro-4-(3-oxo-3,4-dihydropyrido[2,3-b]pyrazin-8-yloxy)phenyl)urea (AA-062)

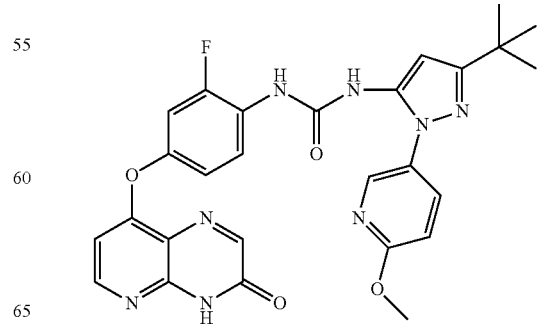

Method F2 was used with 8-(4-amino-3-fluorophenoxy) pyrido[2,3-b]pyrazin-3(4H)-one and 5-(3-tert-butyl-5-isocyanato-1H-pyrazol-1-yl)-2-methoxypyridine to afford the title compound (6 mg, 7%) as a white solid.

$^1$H-NMR (DMSO-d6), δ (ppm), J (Hz): 1.77 (s, 9H, tert-Bu), 4.40 (s, 3H, CH$_3$), 6.93 (s, 1H, CH), 7.15 (d, 1H, H$_{Py}$, J=5.6 Hz), 7.36 (d, 1H, H$_{arom}$, J=8.8 Hz), 7.51 (d, 1H, H$_{arom}$, J=8.4 Hz), 7.59 (dd, 1H, H$_{arom}$, J=11.7 Hz and J=2.6 Hz), 8.31 (dd, 1H, H$_{arom}$, J=8.7 Hz and J=2.6 Hz), 8.58 (s, 1H, H$_{arom}$), 8.68 (bs, 1H, H$_{arom}$), 8.75-8.82 (m, 4H, H$_{Py}$+H$_{arom}$), 11.95 (bs, 1H, NH). $^{13}$C-NMR (DMSO-d6), δ (ppm), J (Hz): 40.3, 42.6, 63.6, 106.0, 117.3, 118.5, 118.7, 121.4, 126.9, 129.4, 132.5, 132.6, 135.7, 140.5, 146.6, 147.8, 153.3, 156.2, 161.5, 161.7, 162.6, 166.5, 171.8, 172.2, 173.6. $^{19}$F-NMR (δ, ppm, DMSO-d$_6$): −126.99. LC-MS (m/z): 545 (M+H, 100), rt=2.58 min.

Synthesis 120

1-(3-tert-butyl-1-(6-methoxypyridin-3-yl)-1H-pyrazol-5-yl)-3-(2-(methylthio)-4-(3-oxo-3,4-dihydropyrido[2,3-b]pyrazin-8-yloxy)phenyl)urea (AA-063)

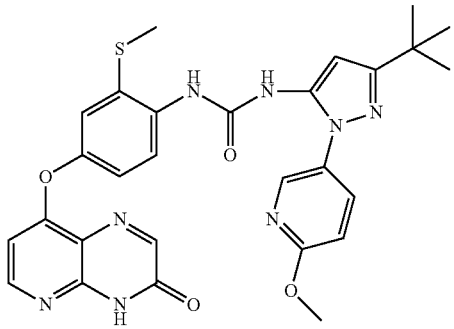 [SMILES: COc1ccc(-n2nc(C(C)(C)C)cc2NC(=O)Nc2ccc(Oc3ccnc4[nH]c(=O)cnc34)cc2SC)cn1]

Method F2 was used with 8-(4-amino-3-(methylthio)phenoxy)pyrido[3,2-b]pyrazin-3(4H)-one and 5-(3-tert-butyl-5-isocyanato-1H-pyrazol-1-yl)-2-methoxypyridine to afford the title compound (97 mg, 53%) as a white powder.

$^1$H-NMR (DMSO-d6), δ (ppm), J (Hz): 1.27 (s, 9H, tert-Bu), 2.43 (s, 3H, CH$_3$), 3.92 (s, 3H, SCH$_3$), 6.37 (s, 1H, CH), 6.59 (d, 1H, H$_{Py}$, J=5.6 Hz), 6.99 (d, 1H, H$_{arom}$, J=8.8 Hz), 7.03 (dd, 1H, H$_{arom}$, J=8.8 Hz, J=2.6 Hz), 7.21 (d, 1H, H$_{arom}$, J=2.6 Hz), 7.74 (d, 1H, H$_{arom}$, J=8.8 Hz), 7.85 (dd, 1H, H$_{arom}$, J=8.8 Hz, J=2.6 Hz), 8.18 (s, 1H, NH), 8.33 (d, 1H, H$_{arom}$, J=2.6 Hz), 8.35 (d, 1H, H$_{Py}$, J=5.6 Hz), 8.37 (s, 1H, CH), 8.98 (s, 1H, NH), 12.94 (s, 1H, NH). $^{13}$C-NMR (DMSO-d6), δ (ppm), J (Hz): 15.3, 30.0, 31.9, 53.5, 95.3, 106.1, 110.8, 117.7, 118.2, 119.3, 124.4, 129.6, 132.0, 133.6, 136.3, 136.6, 142.6, 145.3, 149.9, 150.9, 151.9, 152.0, 156.3, 160.7, 161.0, 162.4. LC-MS (m/z): 573 (M+H, 100), rt=2.56 min.

Synthesis 121

1-(3-tert-butyl-1-(6-methoxypyridin-3-yl)-1H-pyrazol-5-yl)-3-(4-(2-methyl-3-oxo-3,4-dihydropyrido[2,3-b]pyrazin-8-yloxy)-2-(methylthio)phenyl)urea (AA-064)

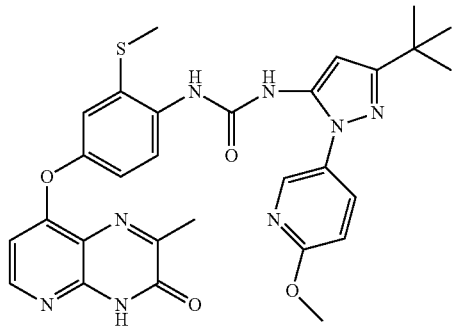 [SMILES: COc1ccc(-n2nc(C(C)(C)C)cc2NC(=O)Nc2ccc(Oc3ccnc4[nH]c(=O)c(C)nc34)cc2SC)cn1]

Method F2 was used with 8-(4-amino-3-(methylthio)phenoxy)-2-methylpyrido[2,3-b]pyrazin-3(4H)-one and 5-(3-tert-butyl-5-isocyanato-1H-pyrazol-1-yl)-2-methoxypyridine to afford the title compound (33 mg, 35%) as a white powder.

$^1$H-NMR (DMSO-d6), δ (ppm), J (Hz): 1.27 (s, 9H, tert-Bu), 2.43 (s, 3H, CH$_3$), 2.44 (s, 3H, CH$_3$), 3.92 (s, 3H, SCH$_3$), 6.37 (s, 1H, CH), 6.53 (d, 1H, H$_{Py}$, J=5.6 Hz), 7.99 (d, 1H, H$_{arom}$, J=8.8 Hz), 7.03 (dd, 1H, H$_{arom}$, J=8.8 Hz, J=2.6 Hz), 7.21 (d, 1H, H$_{arom}$, J=2.6 Hz), 7.76 (d, 1H, H$_{arom}$, J=8.8 Hz), 7.85 (dd, 1H, H$_{arom}$, J=8.8 Hz, J=2.6 Hz), 8.26 (d, 1H, H$_{Py}$, J=5.6 Hz), 8.33 (d, 1H, H$_{arom}$, J=2.6 Hz), 8.35 (s, 1H, NH), 8.96 (s, 1H, NH), 12.76 (s, 1H, NH). $^{13}$C-NMR (DMSO-d6), δ (ppm), J (Hz): 15.3, 20.3, 30.0, 31.9, 53.5, 95.3, 105.8, 110.7, 117.5, 117.8, 119.4, 124.3, 129.5, 131.9, 133.5, 136.3, 137.6, 142.6, 145.5, 149.9, 150.4, 151.8, 156.2, 158.8, 159.9, 161.0, 162.3. LC-MS (m/z): 587 (M+H, 100), rt=2.63 min. HRMS (EI): m/z (M+H, 100) calcd for C29H30N8O4S: 587.2183; found: 587.2186.

Synthesis 122

1-(3-tert-butyl-1-phenyl-1H-pyrazol-5-yl)-3-(4-(2-methyl-3-oxo-3,4-dihydropyrido[2,3-b]pyrazin-8-yloxy)-2-(methylthio)phenyl)urea (AA-065)

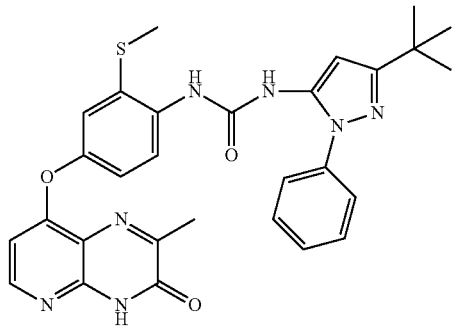 [SMILES: CSc1cc(Oc2ccnc3[nH]c(=O)c(C)nc23)ccc1NC(=O)Nc1cc(C(C)(C)C)nn1-c1ccccc1]

Method F2 was used with 8-(4-amino-3-(methylthio)phenoxy)-2-methylpyrido[2,3-b]pyrazin-3(4H)-one and 3-tertbutyl-5-isocyanato-1-phenyl-1H-pyrazole to afford the title compound (45 mg, 51%) as a white solid.

¹H-NMR (acetone-d6), δ (ppm), J (Hz): 1.28 (s, 9H, tert-Bu), 2.43 (s, 3H, CH₃), 2.44 (s, 3H, CH₃), 6.37 (s, 1H, CH), 6.54 (d, 1H, H$_{Py}$, J=5.6 Hz), 7.02 (dd, 1H, H$_{arom}$, J=8.8 Hz and J=2.6 Hz), 7.21 (d, 1H, H$_{arom}$, J=2.6 Hz), 7.39-7.42 (m, 1H, H$_{arom}$), 7.53-7.55 (m, 4H, H$_{arom}$), 7.77 (d, 1H, H$_{arom}$, J=8.8 Hz), 8.27 (d, 1H, H$_{Py}$, J=5.6 Hz), 8.37 (s, 1H, NH), 8.98 (s, 1H, NH), 12.75 (bs, 1H, NH). ¹³C-NMR (DMSO-d6), δ (ppm), J (Hz): 15.3, 20.3, 30.0, 31.9, 96.2, 105.8, 117.5, 117.8, 119.5, 123.9 (2), 124.2, 127.0, 129.1 (2), 131.8, 133.6, 136.8, 138.6, 145.5, 149.8, 150.4, 152.0, 156.2, 158.8, 159.9, 160.7. LC-MS (m/z): 556 (M+H, 100), rt=2.66 min. HRMS (EI): m/z (M+H, 100) calcd for C29H29N7O3S: 556.2125; found: 556.2125.

Synthesis 123

1-(3-tert-butyl-1-phenyl-1H-pyrazol-5-yl)-3-(2-(methylthio)-4-(2-oxo-1,2-dihydropyrido[2,3-b]pyrazin-8-yloxy)phenyl)urea (AA-066)

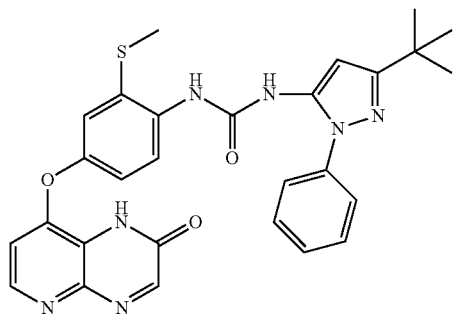 [SMILES: CSc1cc(Oc2ccnc3ncc(=O)[nH]c23)ccc1NC(=O)Nc1cc(C(C)(C)C)nn1-c1ccccc1]

Method F2 was used with 8-(4-amino-3-(methylthio)phenoxy)pyrido[2,3-b]pyrazin-2(1H)-one and 3-tert-butyl-5-isocyanato-1-phenyl-1H-pyrazole to afford the title compound (54 mg, 59%) was obtained as a pale brown powder.

¹H-NMR (CDCl₃), δ (ppm), J (Hz): 1.28 (s, 9H, tert-Bu), 2.43 (s, 3H, CH₃), 6.36 (s, 1H), 6.88 (d, 1H, H$_{Py}$, J=5.3 Hz), 7.06 (dd, 1H, H$_{arom}$, J=8.8 Hz, J=2.7 Hz), 7.24 (d, 1H, H$_{arom}$, J=2.7 Hz), 7.39-7.43 (m, 1H, H$_{arom}$), 7.52-7.55 (m, 4H, H$_{arom}$), 7.78 (d, 1H, H$_{arom}$, J=8.8 Hz), 8.36 (m, 1H, H$_{arom}$), 8.38 (s, 1H, NH or CH), 8.41 (s, 1H, NH or CH), 8.98 (s, 1H, NH), 12.55 (bs, 1H, NH). ¹³C-NMR (DMSO-d6), δ (ppm), J (Hz): 15.5, 30.0, 31.9, 96.2, 110.0, 117.8, 119.6, 123.9 (3), 124.1, 127.0, 129.1 (3), 131.6, 133.8, 136.8, 138.5, 144.0, 145.2, 149.7, 152.0, 154.4, 156.1, 160.7. LC-MS (m/z): 542 (M+H, 100), rt=2.52 min. HRMS (EI): m/z (M+H, 100) calcd for C28H27N7O3S: 542.1968; found: 542.1969.

Synthesis 124

1-(3-tert-butyl-1-phenyl-1H-pyrazol-5-yl)-3-(2-(methylthio)-4-(3-oxo-3,4-dihydropyrido[2,3-b]pyrazin-8-yloxy)phenyl)urea (AA-067)

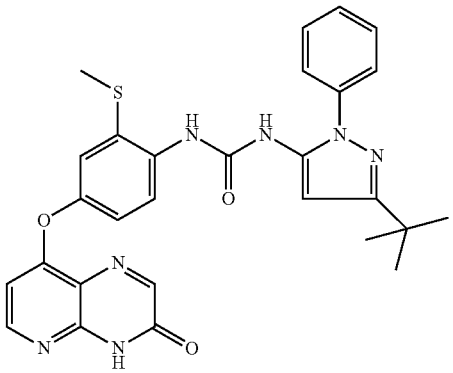 [SMILES: CSc1cc(Oc2ccnc3[nH]c(=O)cnc23)ccc1NC(=O)Nc1cc(C(C)(C)C)nn1-c1ccccc1]

Method F2 was used with 8-(4-amino-3-(methylthio)phenoxy)pyrido[3,2-b]pyrazin-3(4H)-one and 3-tert-butyl-5-isocyanato-1-phenyl-1H-pyrazole to afford the title compound (175 mg, 97%) as a white powder.

¹H-NMR (CDCl₃-d6), δ (ppm), J (Hz): 1.28 (s, 9H, tert-Bu), 2.43 (s, 3H, CH₃), 6.36 (s, 1H), 6.60 (d, 1H, H$_{Py,5}$, J=5.6 Hz), 7.03 (dd, 1H, H$_{arom}$, J=8.8 Hz, J=2.7 Hz), 7.21 (d, 1H, H$_{arom}$, J=2.7 Hz), 7.39-7.43 (m, 1H, H$_{arom}$), 7.53-7.54 (m, 4H, H$_{arom}$), 7.77 (d, 1H, H$_{arom}$, J=8.8 Hz), 8.18 (s, 1H, NH or CH), 8.35 (d, 1H, H$_{Py}$, J=5.6 Hz), 8.37 (s, 1H, NH or CH), 8.98 (s, 1H, NH or CH), 12.89 (s, 1H, NH). ¹³C-NMR (DMSO-d6), δ (ppm), J (Hz): 15.3, 30.0 (3), 31.9, 96.2, 106.1, 117.7, 118.2, 119.3, 123.9 (2), 124.3, 127.0, 129.1 (2), 131.8, 133.7, 136.8, 138.5, 145.3, 149.9, 150.8, 152.0 (2), 156.3, 160.6, 160.7.

LC-MS (m/z): 542 (M+H, 100), rt=2.60 min. HRMS (EI): m/z (M+H, 100) calcd for C28H27N7O3S: 542.1968; found: 542.1968.

Synthesis 125

1-(4-(3-(dimethylamino)pyrido[3,2-b]pyrazin-8-yloxy)-2-fluorophenyl)-3-(2-fluoro-5-(trifluoromethyl)phenyl)urea (AA-068)

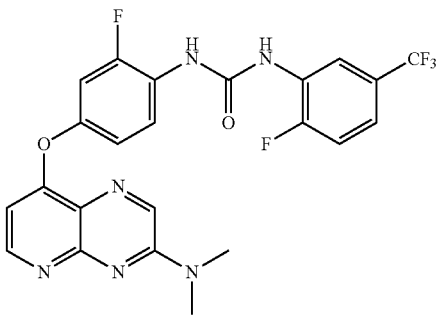 [SMILES: CN(C)c1cnc2c(Oc3ccc(NC(=O)Nc4cc(C(F)(F)F)ccc4F)c(F)c3)ccnc2n1]

Method F2 was used with 8-(4-amino-3-fluorophenoxy)-N,N-dimethylpyrido[3,2-b]pyrazin-3-amine and 1-fluoro-2- isocyanato-4-(trifluoromethyl)benzene to afford the title compound as a white solid. Yield: 40 mg (66%).

$^1$H-NMR (DMSO-d$_6$), δ (ppm), J (Hz): 3.28 (s, 6H, N(CH$_3$)$_2$), 6.65 (d, J=5.3, 1H, H$_{Py}$), 7.05 (m, 2H, H$_{arom}$), 7.30 (m, 1H, H$_{arom}$), 7.41 (m, 1H, H$_{arom}$), 7.51 (m, 1H, H$_{arom}$), 8.22 (m, 1H, H$_{arom}$), 8.60 (d, J=5.3, 1H, H$_{Py}$), 8.65 (m, 1H, H$_{arom}$), 8.71 (s, 1H, H$_{arom}$), 9.19 (s, 1H, NH), 9.36 (s, 1H, NH); $^{13}$C-NMR (DMSO-d$_6$), δ (ppm), J (Hz): 27.1, 105.3, 108.3 (d, J$_{FC}$=22.3), 116.1 (d, J$_{FC}$=20.5), 116.3 (d, J$_{FC}$=2.6), 116.6 (m), 119.4 (m), 122.0 (d, J$_{FC}$=2.3), 122.8, 125.0, 125.4 (m), 128.5 (d, J$_{FC}$=11.4), 139.6 (br), 149.6 (d, J$_{FC}$=10.3), 152.0, 152.4 (d, J$_{FC}$=245), 152.8, 153.4, 153.4 (d, J$_{FC}$=248), 155.3, 160.4; $^{19}$F-NMR (DMSO-d$_6$), δ (ppm): −60.8, −124.0, −125.3; LC-MS (2.28 min): m/z 505.2 (M+H, 100); HRMS (2.80 min): m/z calcd. for C$_{23}$H$_{17}$F$_5$N$_6$O$_2$ [M+H$^+$]: 505.14059; found: 505.13996.

Synthesis 126

1-(3-Tert-butyl-1-phenyl-1H-pyrazol-5-yl)-3-(4-(3-(dimethylamino)pyrido[3,2-b]pyrazin-8-yloxy)-2-fluorophenyl)urea (AA-070)

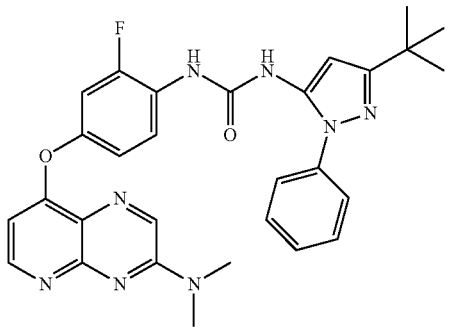 [SMILES: CN(C)c1cnc2c(Oc3ccc(NC(=O)Nc4cc(C(C)(C)C)nn4-c4ccccc4)c(F)c3)ccnc2n1]

Method F2 was used with 8-(4-amino-3-fluorophenoxy)-N,N-dimethylpyrido[3,2-b]pyrazin-3-amine and 3-tert-butyl-5-isocyanato-1-phenyl-1H-pyrazole to give the product as a light yellow solid. Yield: 65 mg (90%).

$^1$H-NMR (DMSO-d$_6$), δ (ppm), J (Hz): 1.29 (s, 9H, tert-Bu), 3.28 (s, 6H, N(CH$_3$)$_2$), 6.41 (s, 1H, H$_{arom}$), 6.62 (d, 1H, J=5.2, H$_{Py}$), 7.02 (m, 1H, H$_{arom}$), 7.26 (m, 1H, H$_{arom}$), 7.44 (m, 1H, H$_{arom}$), 7.55 (m, 4H, H$_{arom}$), 8.14 (m, 1H, H$_{arom}$), 8.59 (d, 1H, J=5.2, H$_{Py}$), 8.71 (s, 1H, H$_{arom}$), 8.87 (s, 1H, NH), 8.99 (s, 1H, NH); $^{13}$C-NMR (DMSO-d$_6$), δ (ppm), J (Hz): 30.2, 32.0, 37.4, 95.2, 105.3, 108.3 (d, J$_{FC}$=22.3), 116.2, 121.8, 121.9, 124.4 (d, J$_{FC}$=10.7), 124.5, 127.4, 129.3, 136.0, 137.0, 138.5, 149.4 (d, J$_{FC}$=10.2), 151.4, 152.4, 152.4 (d, J$_{FC}$=245), 153.5, 154.2, 160.4, 160.8; $^{19}$F-NMR (DMSO-d$_6$), δ (ppm): −125.3; LC-MS (2.25 min): m/z 541.1 (M+H, 100); HRMS (2.85 min): m/z calcd. for C$_{29}$H$_{29}$FN$_8$NaO$_2$ [M+Na$^+$]: 563.22897; found: 563.22865.

Synthesis 127

3-tert-butyl-1-(4-(methylsulfonyl)phenyl)-1H-pyrazol-5-amine

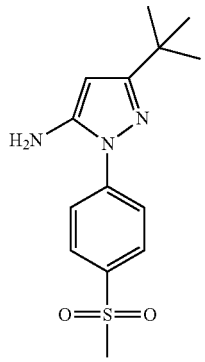 [SMILES: CC(C)(C)c1cc(N)n(-c2ccc(S(C)(=O)=O)cc2)n1]

4-(methylsulfonyl)phenylhydrazine hydrochloride (1.133 g, 5.09 mmol) and 4,4-dimethyl-3-oxopentanenitrile (0.697 g, 5.57 mmol) were weighed into a 100 mL RBF. 0.2 M HCl in EtOH (42 mL) was added and the suspension was heated to reflux for 27 h, during which time all solids gradually dissolved to give a yellow solution. The solution was diluted with 1 M NaOH$_{(aq)}$ (~16 mL) to pH 12-13, EtOAc (70 mL) was added and the biphasic system was vigorously stirred for 5 min. The organic layer was isolated, dried (MgSO$_4$), filtered and concentrated to give a yellow crystalline solid. Yield: 1.42 g (95%).

$^1$H-NMR (DMSO-d$_6$), δ (ppm), J (Hz): 1.23 (s, 9H, tert-Bu), 3.22 (s, 3H, Me), 5.45 (br s, 2H, NH$_2$), 5.46 (s, 1H, H$_{Pyz}$), 7.90 (d, 2H, J=8.7, H$_{arom}$), 7.98 (d, 2H, J=8.7, H$_{arom}$); $^{13}$C-NMR (DMSO-d$_6$), δ (ppm), J (Hz): 30.0, 31.9, 43.7, 88.3, 121.6, 128.1, 136.7, 143.8, 148.0, 162.2; LC-MS (1.98 min): m/z 294.1 (M+H, 100).

Synthesis 128

Solution of 3-tert-butyl-5-isocyanato-1-(4-(methylsulfonyl)phenyl)-1H-pyrazole in CH$_2$Cl$_2$

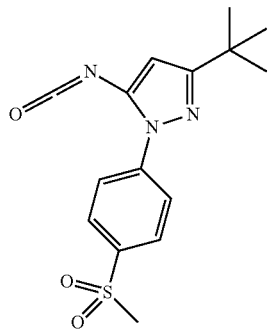 [SMILES: CC(C)(C)c1cc(N=CC=O)n(-c2ccc(S(C)(=O)=O)cc2)n1]

3-tert-butyl-1-(4-(methylsulfonyl)phenyl)-1H-pyrazol-5-amine (295 mg, 1.01 mmol) was weighed into a 100 mL RBF and CH$_2$Cl$_2$ (20 mL) and saturated aqueous NaHCO$_3$ (20 mL) were added. The resulting biphasic system was stirred and cooled to 0° C., and subsequently treated dropwise with 1.9 M phosgene in toluene (1.06 mL, 2.02 mmol) over 30 s. The mixture was stirred vigorously for 10 min, the organic phase was isolated, washed with H$_2$O (20 mL), dried (MgSO$_4$), filtered and concentrated to 10 mL to give a 100 mM solution of the title compound. IR (ν, cm$^{-1}$): 2260 (N═C═O).

Synthesis 129

1-(3-tert-butyl-1-(4-(methylsulfonyl)phenyl)-1H-pyrazol-5-yl)-3-(2-fluoro-4-(3-oxo-3,4-dihydropyrido[3,2-b]pyrazin-8-yloxy)phenyl)urea (AA-090)

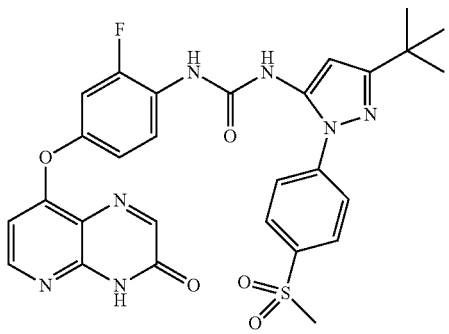 [SMILES: CC(C)(C)c1cc(NC(=O)Nc2ccc(Oc3ccnc4[nH]c(=O)cnc34)cc2F)n(-c2ccc(S(C)(=O)=O)cc2)n1]

Method F2 was used with 8-(4-amino-3-fluorophenoxy)pyrido[2,3-b]pyrazin-3(4H)-one (56 mg, 0.206 mmol) and a 0.1 M solution of 3-tert-butyl-5-isocyanato-1-(4-(methylsulfonyl)phenyl)-1H-pyrazole in CH$_2$Cl$_2$ (5.8 mL, 0.58 mmol). The title compound was obtained as a yellow solid in 41% yield (50 mg) after chromatography on a Biotage 25+M column.

$^1$H-NMR (DMSO-d$_6$), δ (ppm), J (Hz): 1.30 (s, 9H, tert-Bu), 3.27 (s, 3H, SO$_2$CH$_3$), 6.46 (s, 1H, H$_{Py}$), 6.65 (d, J=5.6, 1H, H$_{Pyz}$), 7.05 (m, 1H, H$_{arom}$), 7.30 (m, 1H, H$_{arom}$), 7.85 (d, J=8.7, 2H, H$_{arom}$), 8.08 (d, J=8.7, 2H, H$_{arom}$), 8.12 (m, 1H, H$_{arom}$), 8.17 (s, 1H, H$_{arom}$), 8.37 (d, J=5.6, 1H, H$_{Py}$), 8.97 (s, 1H, NH), 8.99 (s, 1H, NH), 12.90 (s, 1H, NH);
$^{13}$C-NMR (DMSO-d$_6$), δ (ppm), J (Hz): 30.0, 32.1, 43.5, 97.0, 106.5, 108.5 (d, J$_{FC}$=22.4), 116.4, 118.4, 122.0, 123.9, 124.7 (d, J$_{FC}$=10.8), 128.3, 137.4, 138.7, 142.5, 145.6, 148.8 (d, J$_{FC}$=10.5), 151.1, 151.5, 152.2, 152.5 (d, J$_{FC}$=245), 156.6, 160.5, 162.1; $^{19}$F-NMR (DMSO-d$_6$), δ (ppm): −124.3; LC-MS (m/z): LC-MS 592.1 (M+H, 100), rt=2.44 min; HRMS (7.17 min): m/z calcd. for C$_{28}$H$_{27}$FN$_7$O$_5$S (M+H, 100)$^+$: 461.09798; found: 461.09771.

Synthesis 130

1-(3-tert-butyl-1-(4-(methylsulfonyl)phenyl)-1H-pyrazol-5-yl)-3-(4-(2,3-dioxo-1,2,3,4-tetrahydropyrido[3,2-b]pyrazin-8-yloxy)-2-fluorophenyl)urea (AA-092)

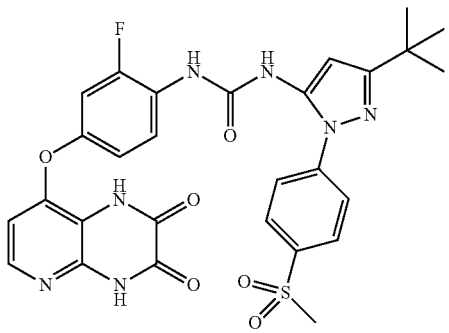 [SMILES: CC(C)(C)c1cc(NC(=O)Nc2ccc(Oc3ccnc4[nH]c(=O)c(=O)[nH]c34)cc2F)n(-c2ccc(S(C)(=O)=O)cc2)n1]

Method F2 was used with 8-(4-amino-3-fluorophenoxy)pyrido[3,2-b]pyrazine-2,3(1H,4H)-dione (58 mg, 101 μmol) and a 0.06 M solution of 3-tert-butyl-5-isocyanato-1-(4-(methylsulfonyl)phenyl)-1H-pyrazole in CH$_2$Cl$_2$ (6.8 mL, 0.41 mmol). The title compound was obtained as a white solid. Yield: 30 mg (49%).

$^1$H-NMR (DMSO-d$_6$), δ (ppm), J (Hz): 1.30 (s, 9H, tert-Bu), 3.27 (s, 3H, SO$_2$CH$_3$), 6.45 (s, 1H, H$_{Py}$), 6.57 (d, 1H, J=5.7, H$_{Py}$), 7.00 (m, 1H, H$_{arom}$), 7.22 (m, 1H, H$_{arom}$), 7.85 (d, 2H, J=8.7, H$_{arom}$), 7.95 (d, 1H, J=5.7, H$_{Py}$), 8.07 (d, 2H, J=8.7, H$_{arom}$), 8.09 (m, 1H, H$_{arom}$), 8.94 (s, 1H, NH), 8.97 (s, 1H, H$_{arom}$), 11.89 (s, 1H, NH), 12.38 (s, 1H, NH); $^{19}$F-NMR (DMSO-d$_6$), δ (ppm): −124.6; LC-MS (m/z): 608.1 (M+H, 100), rt=2.39 min; HRMS (3.07 min): m/z calcd. for C$_{28}$H$_{27}$FN$_7$O$_6$S [M+H$^+$]: 608.17221; found: 608.17142.

Synthesis 131

1-(4-(2,3-Dioxo-1,2,3,4-tetrahydropyrido[3,2-b]pyrazin-8-yloxy)-2-fluorophenyl)-3-(2-fluoro-5-(trifluoromethyl)phenyl)urea (AA-072)

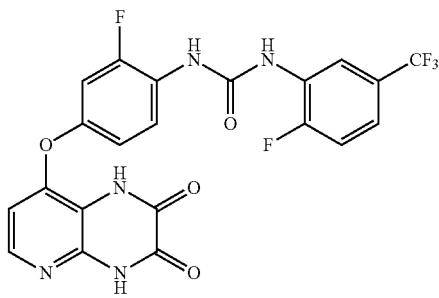 [SMILES: O=C(Nc1ccc(Oc2ccnc3[nH]c(=O)c(=O)[nH]c23)cc1F)Nc1cc(C(F)(F)F)ccc1F]

Method F2 was used with 8-(4-amino-3-fluorophenoxy)pyrido[3,2-b]pyrazine-2,3(1H,4H)-dione and 1-fluoro-2-isocyanato-4-(trifluoromethyl)benzene to give the title compound as a beige solid. Yield: 52 mg (51%).

$^1$H-NMR (DMSO-d$_6$), δ (ppm), J (Hz): 6.60 (d, J=5.4, 1H, H$_{Py}$), 7.04 (m, 2H, H$_{arom}$), 7.27 (m, 1H, H$_{arom}$), 7.41 (m, 1H, H$_{arom}$), 7.52 (m, 1H, H$_{arom}$), 7.98 (d, J=5.4, 1H, H$_{Py}$), 8.22 (m, 1H, H$_{arom}$), 8.64 (m, 1H, H$_{arom}$), 9.19 (s, 1H, NH), 9.35 (s, 1H, NH), 11.92 (s, 1H, NH), 12.40 (s, 1H, NH); $^{13}$C-NMR (DMSO-d$_6$), δ (Hz): 106.6, 108.2 (d, J$_{FC}$=22.5), 112.5, 116.0, 116.2, 116.6 (m), 119.5 (m), 120.6, 121.9 (d, J$_{FC}$=2.3), 123.9 (qua, J$_{FC}$=270), 124.3 (d, J$_{FC}$=10.6), 125.4 (m), 128.5 (d, J$_{FC}$=11.4), 140.6, 143.2, 149.0 (d, J$_{FC}$=10.4), 150.2, 152.0, 152.3 (d, J$_{FC}$=245), 153.4 (d, J$_{FC}$=249), 154.7, 156.0; $^{19}$F-NMR (DMSO-d$_6$), δ (ppm): −60.2, −123.5, −124.9; LC-MS (m/z): 494.0 (M+H, 100), rt=2.57 min; HRMS (3.06 min): m/z calcd. for C$_{21}$H$_{12}$F$_5$N$_5$NaO$_4$ [M+Na$^+$]: 516.07017; found: 516.06998.

Synthesis 132

1-(3-Tert-butyl-1-phenyl-1H-pyrazol-5-yl)-3-(2-fluoro-4-(3-morpholinopyrido[3,2-b]pyrazin-8-yloxy)phenyl)urea (AA-071)

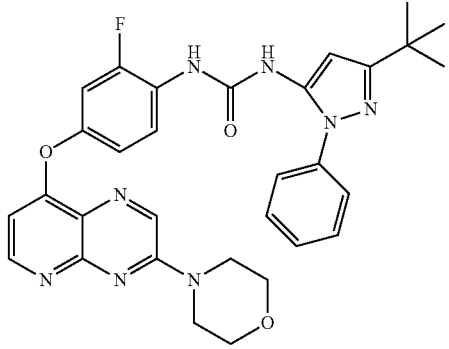 [SMILES: CC(C)(C)c1cc(NC(=O)Nc2ccc(Oc3ccnc4nc(N5CCOCC5)cnc34)cc2F)n(-c2ccccc2)n1]

A solution of 2-fluoro-4-(3-morpholinopyrido[2,3-b]pyrazin-8-yloxy)aniline (47 mg, 138 μmol) in dry THF (5 mL) was treated with a solution of 3-tert-butyl-5-isocyanato-1-phenyl-1H-pyrazole (1.1 mL of a 0.25 M solution in CH2Cl2, 275 μmol) at 0° C. A yellow precipitate started to form gradually and after 1 h at RT, hexane (20 mL) was added and the yellow precipitate was filtered off. It was redissolved in MeOH/CH$_2$Cl$_2$ (1:1), evaporated onto silica gel and the product was eluted with a gradient of 0% to 20% MeOH in EtOAc to give the product as a light yellow solid. Yield: 71 mg (89%).

1H-NMR (DMSO-d6), (ppm), J (Hz): 1.30 (s, 9H, tert-Bu), 3.77 (m, 4H, N(CH$_2$CH$_2$)$_2$O), 3.84 (m, 4H, N(CH$_2$CH$_2$)$_2$O), 6.41 (s, 1H, H$_{arom}$), 6.68 (d, 1H, J=5.2 Hz, H$_{Py}$), 7.02 (m, 1H, H$_{arom}$), 7.27 (m, 1H, H$_{arom}$), 7.44 (m, 1H, H$_{arom}$), 7.55 (m, 4H, H$_{arom}$), 8.15 (m, 1H, H$_{arom}$), 8.63 (d, 1H, J=5.2, H$_{arom}$), 8.84 (m, 2H, H$_{arom}$+H$_{urea}$), 8.98 (s, 1H, H$_{urea}$); $^{13}$C-NMR (DMSO-d6), (ppm), J (Hz): 30.2, 32.0, 44.4, 65.9, 95.1, 105.9, 108.3 (d, J$_{FH}$=22.3), 116.3, 121.8, 122.5, 124.4 (d, J$_{FH}$=10.7), 124.5, 127.4, 129.3, 136.3, 137.0, 138.3, 149.3 (d, J$_{FH}$=10.4), 151.4, 152.1, 152.4 (d, J$_{FH}$=245), 153.7, 153.9, 160.4, 160.8; $^{19}$F-NMR (DMSO-d6), (ppm): −125.3; LC-MS (m/z): 583.1 (M+H, 100), rt=2.33 min; HRMS (2.88 min): m/z calcd. for C31H32FN8O3 [M+H+]: 583.25759; found: 583.25719.

Synthesis 133

1-(3-tert-butyl-1-p-tolyl-1H-pyrazol-5-yl)-3-(2-fluoro-4-(3-morpholinopyrido[3,2-b]pyrazin-8-yloxy)phenyl)urea (AA-073)

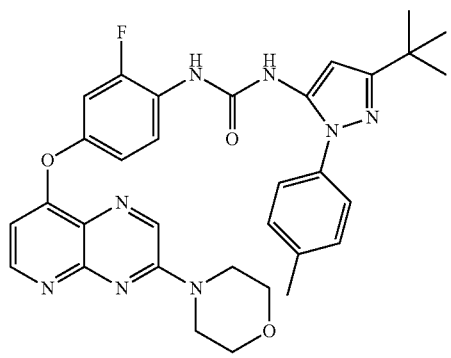 [SMILES: Cc1ccc(-n2nc(C(C)(C)C)cc2NC(=O)Nc2ccc(Oc3ccnc4nc(N5CCOCC5)cnc34)cc2F)cc1]

Method F2 was used with 2-fluoro-4-(3-morpholinopyrido[2,3-b]pyrazin-8-yloxy)aniline and 3-tert-butyl-5-isocyanato-1-phenyl-1H-pyrazole to give the product as a light yellow solid. Yield: 97 mg (90%).

$^1$H-NMR (DMSO-d$_6$), δ (ppm), J (Hz): 1.29 (s, 9H, tert-Bu), 2.39 (s, 3H, CH$_3$), 3.77 (m, 4H, N(CH$_2$CH$_2$)$_2$O), 3.84 (m, 4H, N(CH$_2$CH$_2$)$_2$O), 6.40 (s, 1H, H$_{Pyz}$), 6.67 (d, 1H, J=5.3, $_{Py}$rH), 7.03 (m, 1H, H$_{arom}$), 7.27 (m, 1H, H$_{arom}$), 7.35 (d, 2H, J=8.3, H$_{arom}$), 7.41 (d, 2H, J=8.3, H$_{arom}$), 8.17 (m, 1H, H$_{arom}$), 8.62 (d, 1H, J=5.3, H$_{Py}$), 8.80 (s, 1H, NH), 8.84 (s, 1H, H$_{arom}$), 9.00 (s, 1H, NH); $^{13}$C-NMR (DMSO-d$_6$), δ (ppm), J (Hz): 20.6, 30.2, 32.0, 44.4, 65.9, 94.6, 105.8, 108.3 (d, J$_{FC}$=22.4), 116.2, 121.7, 122.5, 124.5, 124.6 (d, J$_{FC}$=10.7), 129.7, 135.9, 136.3, 136.9 (d, J$_{FC}$=5.7), 149.2 (d, J$_{FC}$=10.4), 151.3, 152.1, 152.3 (d, J$_{FC}$=245), 153.7, 153.9, 160.4, 160.8; $^{19}$F-NMR (DMSO-d$_6$), δ (ppm): −124.8; LC-MS (m/z): 597.2 (M+H, 100), rt=2.43 min; HRMS (3.01 min): m/z calcd. for C$_{32}$H$_{34}$FN$_8$O$_3$ [M+H$^+$]: 597.27324; found: 597.27289.

Synthesis 134

1-(3-Tert-butyl-1-p-tolyl-1H-pyrazol-5-yl)-3-(4-(2,3-dioxo-1,2,3,4-tetrahydropyrido[3,2-b]pyrazin-8-yloxy)-2-fluorophenyl)urea (AA-074)

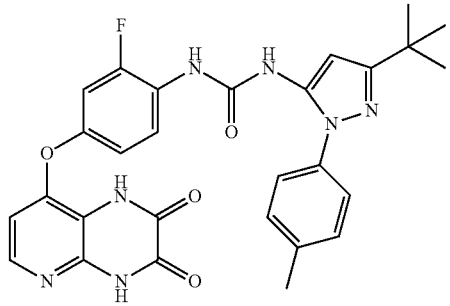 [SMILES: Cc1ccc(-n2nc(C(C)(C)C)cc2NC(=O)Nc2ccc(Oc3ccnc4[nH]c(=O)c(=O)[nH]c34)cc2F)cc1]

Method F2 was used with 8-(4-amino-3-fluorophenoxy)pyrido[3,2-b]pyrazine-2,3(1H,4H)-dione and 3-tert-butyl-5-isocyanato-1-p-tolyl-1H-pyrazole to give the title compound as a white solid. Yield: 33 mg (44%).

$^1$H-NMR (DMSO-d$_6$), δ (ppm), J (Hz): 1.28 (s, 9H, tert-Bu), 2.36 (s, 3H, CH$_3$), 6.37 (s, 1H, $_{Py}$razole H), 6.53 (d, 1H, J=5.3, H$_{Py}$), 6.91 (m, 1H, H$_{arom}$), 7.08 (m, 1H, H$_{arom}$), 7.29 (d, 2H, J=8.3, H$_{arom}$), 7.38 (d, 2H, J=8.3, H$_{arom}$), 7.90 (d, 1H, J=5.3, H$_{Py}$), 8.07 (m, 1H, H$_{arom}$), 9.14 (br s, 1H, NH), 9.24 (br s, 1H, H$_{arom}$), 12.00 (br s, 2H, NH); $^{13}$C-NMR (DMSO-d$_6$), δ (ppm), J (Hz): 20.6, 30.2, 32.0, 94.8, 106.6, 107.8 (d, J$_{FC}$=22.4), 115.8, 122.2, 124.3 (d, J$_{FC}$=10.7), 129.5, 136.0, 136.7, 137.2, 141.1, 142.3 (br), 149.2 (d, J$_{FC}$=9.8), 150.7, 151.5, 151.6, 152.3 (d, J$_{FC}$=245), 153.5, 156.3 (br), 156.4, 160.5; $^{19}$F-NMR (DMSO-d$_6$), δ (ppm): −124.4; LC-MS (m/z): 544.0 (M+H, 100), rt=2.62 min; HRMS (3.01 min): m/z calcd. for C$_{28}$H$_{27}$FN$_7$O$_4$ [M+H$^+$]: 544.21031; found: 544.21063.

Synthesis 135

1-(3-tert-butyl-1-phenyl-1H-pyrazol-5-yl)-3-(3-(3-oxo-3,4-dihydropyrido[2,3-b]pyrazin-8-yloxy)phenyl)urea (AA-075)

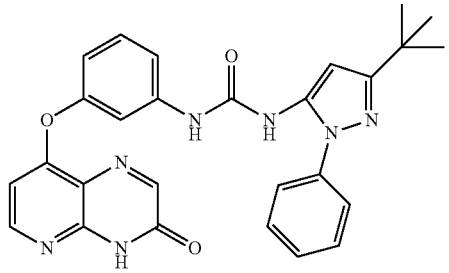 [SMILES: CC(C)(C)c1cc(NC(=O)Nc2cccc(Oc3ccnc4[nH]c(=O)cnc34)c2)n(-c2ccccc2)n1]

Method F2 was used with 8-(3-aminophenoxy)pyrido[2,3-b]pyrazin-3(4H)-one and 3-tert-butyl-5-isocyanato-1-phenyl-1H-pyrazole to afford the title compound as a slightly yellow solid (97 mg, 62%).

$^1$H-NMR (DMSO-d6), δ (ppm), J (Hz): 1.27 (s, 9H, tert-Bu), 6.35 (s, 1H, H$_{arom}$), 6.61 (d, 1H, H$_{Py}$, J=5.6 Hz), 6.84 (dd, 1H, H$_{arom}$, J=1.8 Hz, J=8.0 Hz), 7.20 (d, 1H, H$_{arom}$, J=1.2 Hz, J=8.1 Hz), 7.36-7.42 (m, 2H, H$_{arom}$), 7.44 (t, 1H, H$_{arom}$, J=2.1 Hz), 7.52-7.53 (m, 4H, H$_{arom}$), 8.18 (s, 1H, H$_{arom}$,), 8.36 (d, 1H, H$_{Py}$, J=5.6 Hz), 8.44 (s, 1H, NH$_{urea}$), 9.23 (s, 1H, NH$_{urea}$), 12.89 (s, 1H, NH$_{lactame}$). $^{13}$C-NMR (DMSO-d6), δ (ppm), J (Hz): 30.04 (tert-Bu), 31.89 (tert-Bu), 95.63, 106.54, 109.58, 113.54, 114.96, 118.38, 124.14 (2*C), 127.13, 129.14 (2*C), 130.46, 136.76, 138.40, 141.25, 145.42, 151.05, 151.42, 152.01, 154.34, 156.35, 160.40, 160.65.

Synthesis 136

1-(3-tert-butyl-1-phenyl-1H-pyrazol-5-yl)-3-(3-(2-oxo-1,2-dihydropyrido[2,3-b]pyrazin-8-yloxy)phenyl)urea (AA-076)

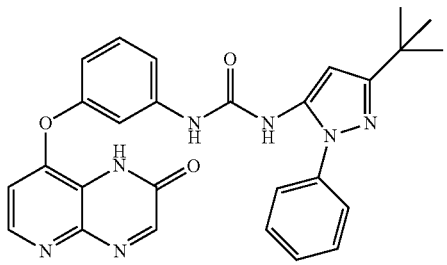 [SMILES: CC(C)(C)c1cc(NC(=O)Nc2cccc(Oc3ccnc4ncc(=O)[nH]c34)c2)n(-c2ccccc2)n1]

Method F2 was used with 8-(3-aminophenoxy)pyrido[2,3-b]pyrazin-2(1H)-one and 3-tert-butyl-5-isocyanato-1-phenyl-1H-pyrazole to afford the title compound as a yellow solid (57 mg, 29%).

$^{1}$H-NMR (DMSO-d6), δ (ppm), J (Hz): 1.27 (s, 9H, tert-Bu), 6.35 (s, 1H, H$_{arom}$,), 6.85 (dd, 1H, H$_{arom}$, J=8.1 Hz, J=1.9 Hz), 6.88 (d, 1H, H$_{Py}$, J=5.3 Hz), 7.20 (dd, 1H, H$_{arom}$, J=8.2 Hz, J=1.2 Hz), 7.37-7.42 (m, 2H, H$_{arom}$), 7.47 (t, 1H, H$_{arom}$, J=2.0 Hz), 7.52-7.53 (m, 4H, H$_{arom}$), 8.35-8.43 (m, 3H, H$_{arom}$), 9.23 (s, 1H, NH$_{urea}$), 12.54 (s, 1H, NH$_{lactame}$). $^{13}$C-NMR (DMSO-d6), δ (ppm), J (Hz): 30.04 (tert-Bu), 31.90 (tert-Bu), 105.11, 106.87, 109.67, 110.38, 111.17, 113.58, 115.00, 119.52, 124.14 (2*C), 127.35, 129.14 (2*C), 130.38, 136.77, 138.41, 141.21, 145.22, 151.42, 154.09, 154.55, 155.88, 160.66.

Synthesis 137

1-(4-(2-amino-3-oxo-3,4-dihydropyrido[2,3-b]pyrazin-8-yloxy)naphthalen-1-yl)-3-(3-tert-butyl-1-p-tolyl-1H-pyrazol-5-yl)urea (AA-077)

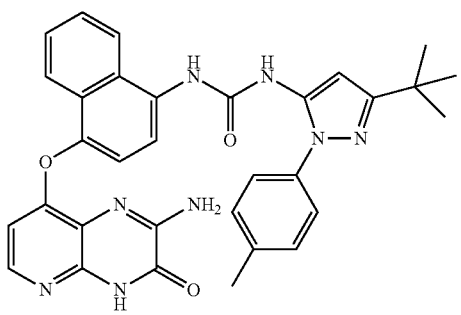 [SMILES: Cc1ccc(-n2nc(C(C)(C)C)cc2NC(=O)Nc2ccc(Oc3ccnc4[nH]c(=O)c(N)nc34)c3ccccc23)cc1]

Method F2 was used with 2-amino-8-(4-aminonaphthalen-1-yloxy)pyrido[2,3-b]pyrazin-3(4H)-one and 3-tert-butyl-5-isocyanato-1-tolyl-1H-pyrazole to afford the title compound as a beige solid (46 mg, 51%).

$^{1}$H-NMR (DMSO-d6), δ (ppm), J (Hz): 1.28 (s, 9H, tert-Bu), 2.40 (s, 3H, Me), 6.30 (d, 1H, H$_{arom}$, J=5.5 Hz), 6.39 (s, 1H, H$_{arom}$), 7.22 (d, 1H, H$_{arom}$, J=8.3 Hz), 7.37 (d, 2H, H$_{arom}$, J=8.2 Hz), 7.46 (d, 2H, H$_{arom}$, J=8.3 Hz), 7.56 (t, 1H, H$_{arom}$, J=7.5 Hz), 7.63 (t, 1H, H$_{arom}$, J=8.0 Hz), 7.86-7.91 (m, 3H, H$_{arom}$), 8.06 (d, 1H, H$_{arom}$, J=8.5 Hz), 8.72 (s, 1H, NHurea), 9.05 (s, 1H, NHurea), 12.58 (s, 1H, NH$_{lactame}$). $^{13}$C-NMR (DMSO-d6), δ (ppm), J (Hz): 20.50 (CH$_{3}$), 30.11 (tert-Bu), 31.90 (tert-Bu), 95.11, 106.44, 116.08, 118.75, 119.35, 121.56, 122.26, 124.22 (2*C), 126.33, 126.49, 126.55, 127.85, 129.58 (2*C), 131.26, 136.07, 136.67, 137.12, 142.95, 143.56, 146.12, 151.71, 152.21, 152.72, 157.14, 160.43. HRMS (EI): m/z [M+H] calcd for C$_{32}$H$_{30}$N$_{8}$O$_{3}$: 575.2514; found: 575.2519.

Synthesis 138

1-(3-tert-butyl-1-p-tolyl-1H-pyrazol-5-yl)-3-(3-(2-methyl-3-oxo-3,4-dihydropyrido[2,3-b]pyrazin-8-yloxy)phenyl)urea (AA-078)

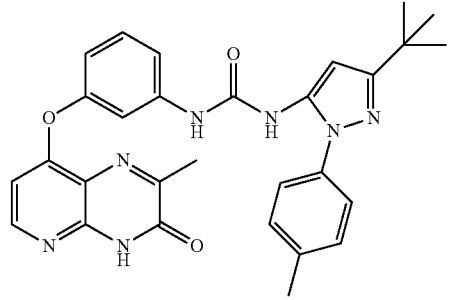 [SMILES: Cc1ccc(-n2nc(C(C)(C)C)cc2NC(=O)Nc2cccc(Oc3ccnc4[nH]c(=O)c(C)nc34)c2)cc1]

Method F2 was used with 8-(3-aminophenoxy)-2-methylpyrido[2,3-b]pyrazin-3(4H)-one and 3-tert-butyl-5-isocyanato-1-p-tolyl-1H-pyrazole to afford the title compound as a white solid (89 mg, 57%).

$^{1}$H-NMR (DMSO-d6), δ (ppm), J (Hz): 1.26 (s, 9H, tert-Bu), 2.36 (s, 3H, Me), 2.42 (s, 3H, Me), 6.32 (s, 1H, H$_{arom}$), 6.55 (d, 1H, H$_{Py}$, J=6.6 Hz), 6.83 (dd, 1H, H$_{arom}$, J=2.2 Hz, J=8.1 Hz), 7.21 (d, 1H, H$_{arom}$, J=7.9 Hz), 7.31 (d, 2H, H$_{arom}$, J=8.3 Hz), 7.36 (s, 1H, H$_{arom}$), 7.37 (d, 2H, H$_{arom}$, J=8.3 Hz), 7.44 (t, 1H, H$_{arom}$, J=2.1 Hz), 8.27 (d, 1H, H$_{Py}$, J=6.8 Hz), 8.48 (s, 1H, NH$_{urea}$), 9.30 (s, 1H, NH$_{urea}$), 12.75 (s, 1H, NH$_{lactame}$). $^{13}$C-NMR (DMSO-d6), δ (ppm), J (Hz): 20.42 (CH$_{3}$), 20.46 (CH$_{3}$), 30.08 (tert-Bu), 31.87 (tert-Bu), 95.67, 106.19, 109.72, 113.56, 114.91, 117.74, 124.08 (2*C), 129.49 (2*C), 130.38, 136.03, 136.51, 136.76, 141.44, 145.71, 150.40, 151.61, 154.30, 156.32, 158.98, 159.67, 160.33. HRMS (EI): m/z [M+H] calcd for C$_{29}$H$_{2}$N$_{7}$O$_{3}$: 524.2405; found: 524.2409.

Synthesis 139

1-(4-(3-amino-2-oxo-1,2-dihydropyrido[2,3-b]pyrazin-8-yloxy)naphthalen-1-yl)-3-(2-fluoro-5-(trifluoromethyl)phenyl)urea (AA-079)

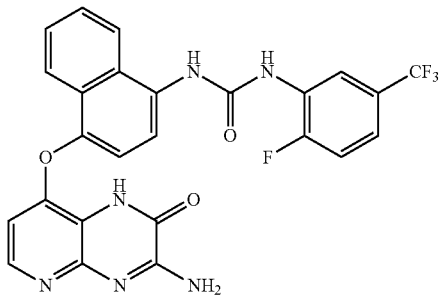 [SMILES: Nc1nc2nccc(Oc3ccc(NC(=O)Nc4cc(C(F)(F)F)ccc4F)c4ccccc34)c2[nH]c1=O]

Method F2 was used with 3-amino-8-(4-aminonaphthalen-1-yloxy)pyrido[2,3-b]pyrazin-2(1H)-one and 1-fluoro-2-isocyanato-4-(trifluoromethyl)benzene to afford the title compound as a yellow/orange solid (31 mg, 38%).

$^1$H-NMR (DMSO-d6), δ (ppm), J (Hz): 6.30 (d, 1H, H$_{arom}$, J=5.5 Hz), 7.34 (d, 1H, H$_{arom}$, J=8.3 Hz), 7.41 (s, 1H, H$_{arom}$), 7.54 (t, 1H, H$_{arom}$, J=8.7 Hz), 7.60 (t, 1H, H$_{arom}$, J=7.4 Hz), 7.71 (t, 1H, H$_{arom}$, J=7.2 Hz), 7.99 (d, 1H, H$_{arom}$, J=8.8 Hz), 8.01 (d, 1H, H$_{arom}$, J=5.6 Hz), 8.04 (d, 1H, H$_{arom}$, J=8.3 Hz), 8.24 (d, 1H, H$_{arom}$, J=8.6 Hz), 8.69 (d, 1H, H$_{arom}$, J=7.2 Hz), 9.32 (s, 1H, NH$_{urea}$), 9.38 (s, 1H, NH$_{urea}$), 12.39 (s, 1H, NH$_{lactame}$). $^{13}$C-NMR (DMSO-d6), δ (ppm), J (Hz): 104.61, 113.94, 116.00, 116.47, 118.03, 119.16, 121.96, 122.73, 124.89, 125.33, 126.53, 126.72, 127.44, 128.73, 131.24, 144.29, 145.44, 146.76, 151.08, 152.38, 152.60, 154.35, 154.77. HRMS (EI): m/z [M+H] calcd for C25H16F4N6O3: 525.1293; found: 525.1292.

Synthesis 140

1-(4-(2-amino-3-oxo-3,4-dihydropyrido[2,3-b]pyrazin-8-yloxy)naphthalen-1-yl)-3-(3-tert-butyl-1-phenyl-1H-pyrazol-5-yl)urea (AA-080)

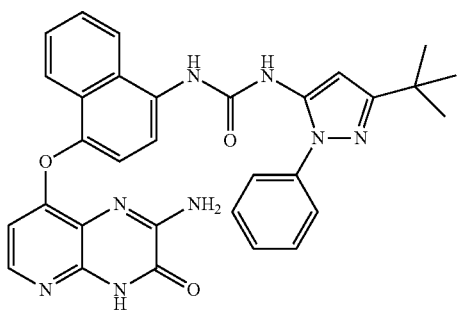 [SMILES: CC(C)(C)c1cc(NC(=O)Nc2ccc(Oc3ccnc4[nH]c(=O)c(N)nc34)c3ccccc23)n(-c2ccccc2)n1]

Method F2 was used with 2-amino-8-(4-aminonaphthalen-1-yloxy)pyrido[2,3-b]pyrazin-3(4H)-one and 3-tert-butyl-5-isocyanato-1-phenyl-1H-pyrazole to afford the title compound as a slightly pink solid (70 mg, 80%). $^1$H-NMR (DMSO-d6), δ (ppm), J (Hz): 1.29 (s, 9H, tert-Bu), 6.31 (d, 1H, H$_{arom}$, J=5.5 Hz), 6.41 (s, 1H, H$_{arom}$), 7.22 (d, 1H, H$_{arom}$, J=8.3 Hz), 7.44 (t, 1H, J=7.0 Hz), 7.54-7.65 (m, 6H, H$_{arom}$), 7.85 (d, 1H, H$_{arom}$, J=8.3 Hz), 7.88-7.91 (m, 2H, H$_{arom}$), 8.06 (d, 1H, H$_{arom}$, J=8.6 Hz), 8.76 (s, 1H, NH$_{urea}$), 9.04 (s, 1H, NH$_{urea}$), 12.58 (s, 1H, NH$_{lactame}$). $^{13}$C-NMR (DMSO-d6), δ (ppm), J (Hz): 30.08 (tert-Bu), 31.92 (tert-Bu), 95.69, 106.46, 116.05, 118.94, 119.36, 121.56, 122.27, 124.12 (2*C), 126.32, 126.52, 126.55, 127.11, 127.97, 129.17 (2*C), 131.22, 137.15, 138.59, 142.95, 143.56, 146.22, 151.71, 152.33, 152.72, 157.12, 160.68. HRMS (EI): m/z [M+H] calcd for C$_{31}$H$_{28}$N$_8$O$_3$: 561.2357; found: 561.2351.

Synthesis 141

1-(4-(3-amino-2-oxo-1,2-dihydropyrido[2,3-b]pyrazin-8-yloxy)naphthalen-1-yl)-3-(3-tert-butyl-1-phenyl-1H-pyrazol-5-yl)urea (AA-081)

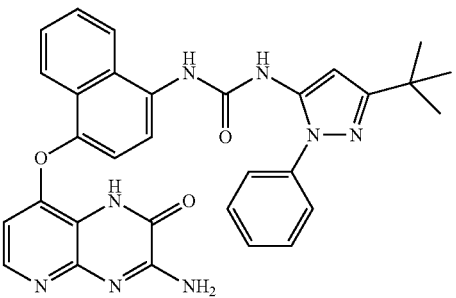 [SMILES: CC(C)(C)c1cc(NC(=O)Nc2ccc(Oc3ccnc4nc(N)c(=O)[nH]c34)c3ccccc23)n(-c2ccccc2)n1]

Method F2 was used with 3-amino-8-(4-aminonaphthalen-1-yloxy)pyrido[2,3-b]pyrazin-2(1H)-one and 3-tert-butyl-5-isocyanato-1-phenyl-1H-pyrazole to afford the title compound as a yellow/orange solid (46 mg, 44%). $^1$H-NMR (DMSO-d6), δ (ppm), J (Hz): 1.30 (s, 9H, tert-Bu), 6.28 (d, 1H, H$_{arom}$, J=5.5 Hz), 6.42 (s, 1H, H$_{arom}$), 7.31 (d, 1H, H$_{arom}$, J=8.3 Hz), 7.44 (t, 1H, J=7.1 Hz), 7.55-7.66 (m, 6H, H$_{arom}$), 7.89-7.96 (m, 2H, H$_{arom}$), 7.99 (d, 1H, H$_{arom}$, J=5.5 Hz), 8.08 (d, 1H, H$_{arom}$, J=8.6 Hz), 8.82 (s, 1H, NH$_{urea}$), 9.11 (s, 1H, NH$_{urea}$), 12.38 (s, 1H, NH$_{lactame}$). $^{13}$C-NMR (DMSO-d6), δ (ppm), J (Hz): 30.08 (tert-Bu), 31.93 (tert-Bu), 95.78, 104.61, 113.91, 116.44, 118.37, 121.92, 122.14, 124.09 (2*C), 126.45, 126.47, 126.54, 127.09, 127.73, 129.15 (2*C), 131.63, 137.13, 138.59, 144.28, 145.43, 146.74, 151.01, 151.12, 152.33, 154.75, 160.69. HRMS (EI): m/z [M+H] calcd for C$_{31}$H$_{28}$H$_8$O$_3$: 561.2357; found: 561.2350.

Synthesis 142

1-(2-fluoro-5-(trifluoromethyl)phenyl)-3-(4-(3-oxo-2-(trifluoromethyl)-3,4-dihydropyrido[2,3-b]pyrazin-8-yloxy)naphthalen-1-yl)urea (AA-082)

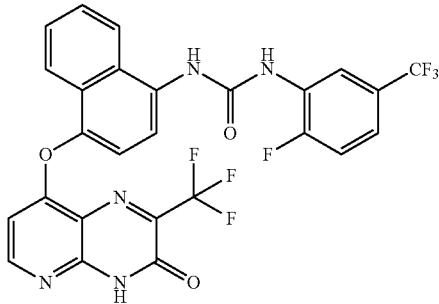 [SMILES: O=C(Nc1cc(C(F)(F)F)ccc1F)Nc1ccc(Oc2ccnc3[nH]c(=O)c(C(F)(F)F)nc23)c2ccccc12]

Method F2 was used with 8-(4-aminonaphthalen-1-yloxy)-2-(trifluoromethyl)pyrido[2,3-b]pyrazin-3(4H)-one and 1-fluoro-2-isocyanato-4-(trifluoromethyl)benzene to afford the title compound as a slightly yellow solid (31 mg, 45%).

$^1$H-NMR (DMSO-d6), δ (ppm), J (Hz): 6.40 (d, 1H, $H_{arom}$, J=5.7 Hz), 7.41-7.42 (m, 1H, $H_{arom}$), 7.49 (d, 1H, $H_{arom}$, J=8.3 Hz), 7.54 (t, 1H, $H_{arom}$, J=9.9 Hz), 7.60 (t, 1H, $H_{arom}$, J=7.6 Hz), 7.73 (t, 1H, $H_{arom}$, J=7.7 Hz), 7.85 (d, 1H, $H_{arom}$, J=8.4 Hz), 8.15 (d, 1H, $H_{arom}$, J=8.3 Hz), 8.29 (d, 1H, $H_{arom}$, J=8.6 Hz), 8.38 (d, 1H, $H_{arom}$, J=5.7 Hz), 8.71 (d, 1H, $H_{arom}$, J=6.0 Hz), 9.39 (s, 1H, NHurea), 9.42 (s, 1H, NHurea), 13.55 (s, 1H, $NH_{lactame}$). $^{13}$C-NMR (DMSO-d6), δ (ppm), J (Hz): 105.66, 116.02, 116.54, 117.64, 118.82, 119.29, 121.01, 121.40, 122.08, 122.72, 124.88, 125.35, 126.15, 126.86, 127.63, 128.65, 132.23, 143.10, 144.37, 146.85, 152.39, 152.48, 153.32, 154.36, 154.82, 162.35. HRMS (EI): m/z [M+H] calcd for $C_{26}H_{14}F_7N_5O_3$: 578.1058; found: 578.1064.

Synthesis 143

1-(2-fluoro-5-(trifluoromethyl)phenyl)-3-(4-(2-oxo-3-(trifluoromethyl)-1,2-dihydropyrido[2,3-b]pyrazin-8-yloxy)naphthalen-1-yl)urea (AA-083)

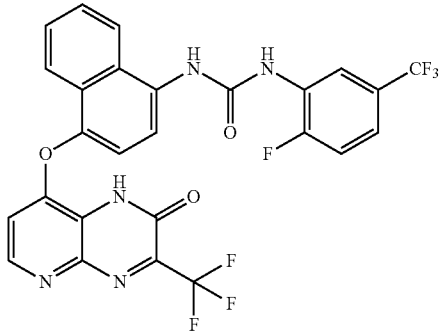 [SMILES: O=C(Nc1cc(C(F)(F)F)ccc1F)Nc1ccc(Oc2ccnc3nc(C(F)(F)F)c(=O)[nH]c23)c2ccccc12]

Method F2 was used with 8-(4-aminonaphthalen-1-yloxy)-3-(trifluoromethyl)pyrido[2,3-b]pyrazin-2(1H)-one and 1-fluoro-2-isocyanato-4-(trifluoromethyl)benzene to afford the title compound was obtained as a slightly yellow solid (5 mg, 5%).

$^1$H-NMR (DMSO-d6), δ (ppm), J (Hz): 6.79 (d, 1H, $H_{arom}$, J=5.3 Hz), 7.42-7.43 (m, 1H, $H_{arom}$), 7.47 (d, 1H, $H_{arom}$, J=8.3 Hz), 7.55 (t, 1H, $H_{arom}$, J=9.8 Hz), 7.62 (t, 1H, $H_{arom}$, J=7.6 Hz), 7.74 (t, 1H, $H_{arom}$, J=7.9 Hz), 7.97 (d, 1H, $H_{arom}$, J=8.5 Hz), 8.14 (d, 1H, $H_{arom}$, J=8.3 Hz), 8.28 (d, 1H, $H_{arom}$, J=8.6 Hz), 8.40 (d, 1H, $H_{arom}$, J=5.2 Hz), 9.71 (dd, 1H, $H_{arom}$, J=1.8, 7.2 Hz), 9.38 (s, 1H, $NH_{urea}$), 9.42 (s, 1H, $NH_{urea}$), 13.51 (s, 1H, $NH_{lactame}$).

$^{13}$C-NMR (DMSO-d6), δ (ppm), J (Hz): 110.67, 116.02, 116.48, 117.14, 117.76, 118.64, 119.21, 120.84, 121.88, 122.73, 123.05, 124.89, 125.40, 126.13, 126.87, 127.05, 127.37, 128.67, 131.99, 141.78, 144.58, 146.66, 151.64, 152.39, 152.53, 154.36. HRMS (EI): m/z [M+H] calcd for $C_{26}H_{14}F_7N_5O_3$: 578.1058; found: 578.1051.

(VII) Synthesis of Amides

1. Amides from Common Intermediates

Synthesis 144

N-(3-(3-oxo-3,4-dihydropyrido[2,3-b]pyrazin-8-yloxy)phenyl)-3-(trifluoro-methoxy)benzamide (AA-002)

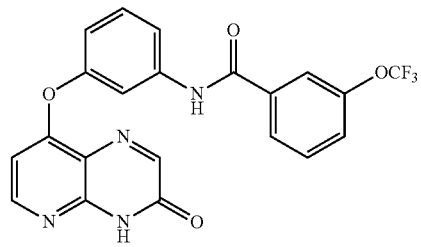 [SMILES: O=C(Nc1cccc(Oc2ccnc3[nH]c(=O)cnc23)c1)c1cccc(OC(F)(F)F)c1]

Method G1: 8-(3-aminophenoxy)pyrido[2,3-b]pyrazin-3(4H)-one (43 mg, 0.169 mmol) and diisopropylethylamine (44 μL, 0.254 mmol) were mixed in dry THF (5.0 mL) and 3-trifluoromethoxybenzoyl chloride (57 mg, 0.254 mmol) was added. This mixture was heated to reflux for 17 h. After cooling at RT, the solvent was removed in vacuo. The obtained oily residue was dissolved in DCM and washed with water and dried over MgSO$_4$. After evaporation of DCM, the residue was retaken in Et$_2$O, triturated and filtered off to afford the title compound as a white solid (45 mg, 60%).

$^1$H-NMR (DMSO-d6), δ (ppm), J (Hz): 6.68 (d, 1H, $H_{Py}$, J=5.6 Hz), 7.01 (ddd, 1H, $H_{arom}$, J=8.1 Hz, J=2.3 Hz, J=0.7 Hz), 7.50 (t, 1H, $H_{arom}$, J=8.2 Hz), 7.62 (d, 1H, $H_{arom}$, 8.3 Hz), 7.68-7.72 (m, 3H, $H_{arom}$), 7.89 (s, 1H, $H_{arom}$), 7.99 (d, 1H, $H_{arom}$, J=7.9 Hz), 8.19 (s, 1H, $H_{arom}$), 8.39 (d, 1H, $H_{Py}$, 6, J=5.6 Hz), 10.53 (s, 1H, $NH_{amide}$), 12.91 (s, 1H, $NH_{lactame}$). $^{13}$C-NMR (DMSO-d6), δ (ppm), J (Hz): 106.78, 111.77, 115.45, 117.10, 118.48, 120.08, 120.95, 124.07, 126.69, 130.39, 130.54, 136.68, 140.54, 145.47, 148.17, 151.16, 152.08, 154.21, 156.36, 160.28, 163.97. HRMS (EI): m/z [M+H] calcd for $C_{21}H_{13}F_3N_4O_4$: 443.0962; found: 443.0950.

Synthesis 145

3-tert-butyl-N-(3-(3-oxo-3,4-dihydropyrido[2,3-b]pyrazin-8-yloxy)phenyl)benzamide (AA-003)

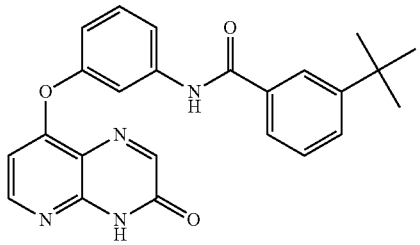 [SMILES: CC(C)(C)c1cccc(C(=O)Nc2cccc(Oc3ccnc4[nH]c(=O)cnc34)c2)c1]

Method G1 was used with 8-(3-aminophenoxy)pyrido[2,3-b]pyrazin-3(4H)-one and 3-tertbutylbenzoyl chloride to afford the title compound as a white solid (29 mg, 45%).

$^1$H-NMR (DMSO-d6), δ (ppm), J (Hz): 1.33 (s, 9H, tert-Bu), 6.67 (d, 1H, $H_{Py}$, 5, J=5.6 Hz), 6.98 (ddd, 1H, $H_{arom}$, J=8.1 Hz, J=2.4 Hz, J=0.8 Hz), 7.46 (t, 1H, $H_{arom}$, J=7.7 Hz), 7.48 (t, 1H, $H_{arom}$, J=8.2 Hz), 7.63 (d, 1H, $H_{arom}$, J=7.9 Hz), 7.70 (d, 1H, $H_{arom}$, J=8.2 Hz), 7.74-7.77 (m, 2H, $H_{arom}$), 7.90 (t, 1H, $H_{arom}$, J=1.7 Hz), 8.19 (s, 1H, $H_{arom}$,), 8.39 (d, 1H, $H_{Py}$, 6, J=5.6 Hz), 10.36 (s, 1H, $NH_{amide}$), 12.91 (s, 1H, $NH_{lactame}$). $^{13}$C-NMR (DMSO-d6), δ (ppm), J (Hz): 31.00 (tert-Bu), 34.56 (tert-Bu), 106.78, 111.84, 115.20, 117.18, 118.53, 124.30, 124.79, 128.11, 128.67, 130.37, 134.44, 141.05, 145.54, 150.95, 151.20, 152.16, 154.22, 156.45, 160.45, 166.45. HRMS (EI): m/z [M+H] calcd for $C_{24}H_{22}N_4O_3$: 415.1765; found: 415.1770.

Synthesis 146

3-tert-butyl-N-(3-(2-oxo-1,2-dihydropyrido[2,3-b]pyrazin-8-yloxy)phenyl)benzamide (AA-029)

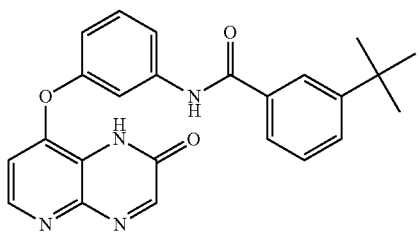 [SMILES: CC(C)(C)c1cccc(C(=O)Nc2cccc(Oc3ccnc4ncc(=O)[nH]c34)c2)c1]

Method G1 was used with 8-(3-aminophenoxy)pyrido[2,3-b]pyrazin-2(1H)-one and 3-tertbutylbenzoyl chloride to afford the title compound as a white solid (14 mg, 22%).

$^1$H-NMR (DMSO-d6), δ (ppm), J (Hz): 1.33 (s, 9H, tert-Bu), 6.94 (d, 1H, $H_{Py}$, J=5.3 Hz), 7.00 (dd, 1H, $H_{arom}$, J=8.1 Hz, J=2.4 Hz), 7.46 (t, 1H, $H_{arom}$, J=7.7 Hz), 7.49 (t, 1H, $H_{arom}$, J=8.1 Hz), 7.63 (d, 1H, $H_{arom}$, J=1.7 Hz), 7.71 (d, 1H, $H_{arom}$, J=8.2 Hz), 7.75-7.77 (m, 2H, $H_{arom}$), 7.91 (t, 1H, $H_{arom}$, J=7.9 Hz), 8.39 (d, 1H, $H_{Py}$, J=5.3 Hz), 8.43 (s, 1H, $H_{arom}$), 10.37 (s, 1H, $NH_{amide}$), 12.60 (s, 1H, $NH_{lactame}$). $^{13}$C-NMR (DMSO-d6), δ (ppm), J (Hz): 30.99 (tert-Bu), 34.55 (tert-Bu), 110.60, 111.94, 115.27, 117.23, 117.99, 124.29, 124.79, 128.11, 128.67, 130.27, 134.40, 134.96, 141.00, 150.94, 153.95, 154.77, 155.88, 166.10. HRMS (EI): m/z [M+H] calcd for $C_{24}H_{22}N_4O_3$: 415.1765; found: 415.1775.

Synthesis 147

N-(3-(2-oxo-1,2-dihydropyrido[2,3-b]pyrazin-8-yloxy)phenyl)-3-(trifluoro methoxy)benzamide (AA-030)

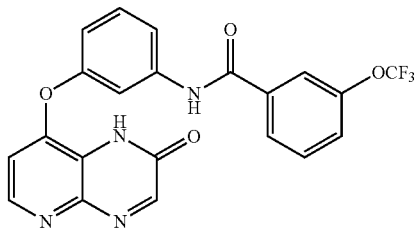 [SMILES: O=C(Nc1cccc(Oc2ccnc3ncc(=O)[nH]c23)c1)c1cccc(OC(F)(F)F)c1]

Method G1 was used with 8-(3-aminophenoxy)pyrido[2,3-b]pyrazin-2(1H)-one and 3-trifluoromethoxybenzoyl chloride to afford the title compound as a white solid (35 mg, 20%).

$^1$H-NMR (DMSO-d6), δ (ppm), J (Hz): 6.94 (d, 1H, $H_{Py}$, J=5.3 Hz), 7.03 (dd, 1H, $H_{arom}$, J=8.1 Hz, J=2.3 Hz), 7.50 (t, 1H, $H_{arom}$, J=8.2 Hz), 7.61-7.62 (m, 1H, $H_{arom}$), 7.68-7.71 (m, 2H, $H_{arom}$), 7.75 (t, 1H, $H_{arom}$, J=2.0 Hz), 7.90 (s, 1H, $H_{arom}$), 8.00 (d, 1H, $H_{arom}$, J=7.7 Hz), 8.39 (d, 1H, $H_{Py}$, J=5.3 Hz), 8.43 (s, 1H, $H_{arom}$,), 10.54 (s, 1H, NHamide), 12.61 (s, 1H, $NH_{lactame}$). $^{13}$C-NMR (DMSO-d6), δ (ppm), J (Hz): 110.64, 111.98, 115.65, 117.27, 119.00, 120.17, 121.04, 123.09, 124.18, 126.78, 130.40, 130.65, 136.75, 140.58, 145.36, 148.26, 154.01, 154.61, 164.05. HRMS (EI): m/z [M+H] calcd for $C_{21}H_{13}F_3N_4O_4$: 443.0962; found: 443.0966.

Synthesis 148

N-(3-(2-methyl-3-oxo-3,4-dihydropyrido[2,3-b]pyrazin-8-yloxy)phenyl)-3-(trifluoromethoxy)benzamide) (AA-004)

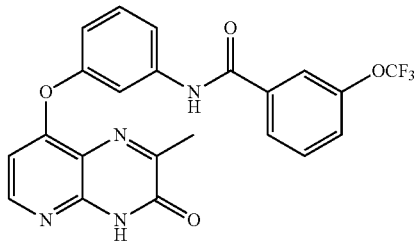 [SMILES: Cc1nc2c(Oc3cccc(NC(=O)c4cccc(OC(F)(F)F)c4)c3)ccnc2[nH]c1=O]

Method G1 was used with 8-(3-aminophenoxy)-2-methylpyrido[2,3-b]pyrazin-3(4H)-one and 3-trifluoromethoxybenzoyl chloride to afford the title compound as a slightly yellow solid (74 mg, 87%).

$^1$H-NMR (DMSO-d6), δ (ppm), J (Hz): 2.44 (s, 3H, Me), 6.62 (d, 1H, $H_{Py}$, J=5.6 Hz), 7.01 (dd, 1H, $H_{arom}$, J=8.1 Hz, J=2.3 Hz), 7.50 (t, 1H, $H_{arom}$, J=8.2 Hz), 7.61 (d, 1H, $H_{arom}$, J=8.4 Hz), 7.67-7.71 (m, 2H, $H_{arom}$), 7.73 (t, 1H, $H_{arom}$, J=2.1 Hz), 7.90 (s, 1H, $H_{arom}$), 8.01 (d, 1H, $H_{arom}$, J=7.9

Hz), 8.31 (d, 1H, $H_{Py}$, J=5.6 Hz), 10.55 (s, 1H, $NH_{amide}$), 12.77 (s, 1H, $NH_{lactame}$). $^{13}$C-NMR (DMSO-d6), δ (ppm), J (Hz): 20.52 (Me), 106.55, 112.11, 115.72, 117.24, 117.91, 120.03 (OCF$_3$), 120.23, 124.16, 126.85, 130.44, 130.62, 136.75, 140.66, 145.76, 148.26, 150.58, 154.25, 156.32, 159.24, 159.65, 164.08. HRMS (EI): m/z [M+H] calcd for $C_{22}H_{15}F_3N_4O_4$: 457.1124; found: 457.1118.

Synthesis 149

3-tert-butyl-N-(3-(2-methyl-3-oxo-3,4-dihydro-pyrido[2,3-b]pyrazin-8-yloxy)phenyl)benzamide (AA-005)

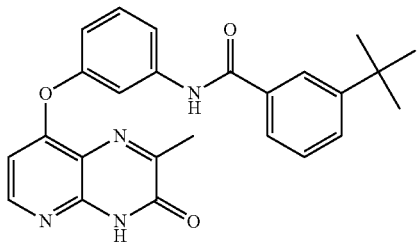 [SMILES: Cc1nc2c(Oc3cccc(NC(=O)c4cccc(C(C)(C)C)c4)c3)ccnc2[nH]c1=O]

Method G1 was used with 8-(3-aminophenoxy)-2-methylpyrido[2,3-b]pyrazin-3(4H)-one and 3-tertbutylbenzoyl chloride to afford the title compound as a slightly yellow solid (77 mg, 97%).

$^1$H-NMR (DMSO-d6), δ (ppm), J (Hz): 1.33 (s, 9H, tert-Bu), 2.44 (s, 3H, Me), 6.62 (d, 1H, $H_{Py}$, J=5.6 Hz), 6.98 (dd, 1H, $H_{arom}$, J=8.1 Hz, J=2.4 Hz), 7.44-7.50 (m, 2H, $H_{arom}$), 7.63 (d, 1H, $H_{arom}$, J=7.9 Hz), 7.70 (d, 1H, $H_{arom}$, J=8.2 Hz), 7.74-7.77 (m, 2H, $H_{arom}$), 7.91 (s, 1H, $H_{arom}$), 8.30 (d, 1H, $H_{Py}$, J=5.6 Hz), 10.37 (s, 1H, $NH_{amide}$), 12.77 (s, 1H, $NH_{lactame}$). $^{13}$C-NMR (DMSO-d6), δ (ppm), J (Hz): 20.52 (CH$_3$), 31.02 (tert-Bu), 34.57 (tert-Bu), 106.50, 112.06, 115.36, 117.20, 117.88, 124.36, 124.85, 128.11, 128.67, 130.34, 134.43, 141.07, 145.75, 150.58, 150.94, 154.19, 156.32, 159.20, 159.72, 166.14. HRMS (EI): m/z [M+H] calcd for $C_{25}H_{24}N_4O_3$: 429.1921; found: 429.1921.

(VIII) Synthesis of Reverse Amides
1. Reverse Amides from Common Intermediates

Synthesis 150

N-(3-tert-butyl-1-phenyl-1H-pyrazol-5-yl)-3-(3-oxo-3,4-dihydropyrido[2,3-b]pyrazin-8-yloxy)benzamide (AA-001)

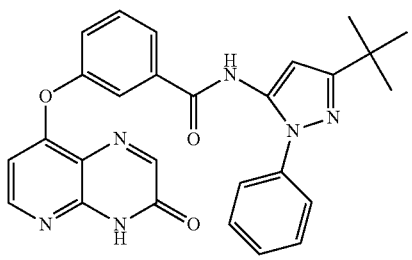 [SMILES: CC(C)(C)c1cc(NC(=O)c2cccc(Oc3ccnc4[nH]c(=O)cnc34)c2)n(-c2ccccc2)n1]

Method H1: A solution of AlMe$_3$ (solution in toluene 2M, 0.85 mL, 1.68 mmol,) was added dropwise to a cooled (0 C) solution of 3-tert-butyl-1-phenyl-1H-pyrazol-5-amine (362 mg, 1.68 mmol) in THF (5.0 mL). When the addition was complete, the mixture was allowed to warm to room temperature and stirring was continued for 30 minutes. Then methyl 3-(3-oxo-3,4-dihydropyrido[2,3-b]pyrazin-8-yloxy) benzoate (100 mg, 0.336 mmol) was added and the mixture was heated under reflux for 19 h. The mixture was cooled to room temperature and carefully quenched with 5% aq HCl (3.0 mL). After evaporation of solvent, the residue was retaken in CH$_2$Cl$_2$, washed with saturated solution of NaHCO$_3$ and dried over MgSO$_4$ and evaporated under vacuum. The obtained residue was chromatographed (eluent: CH$_2$Cl$_2$/EtOAc: 2/1 towards 1/3) and the title compound was obtained as a slightly yellow solid (29 mg, 18%).

$^1$H-NMR (DMSO-d6), δ (ppm), J (Hz): 1.31 (s, 9H, tert-Bu), 6.39 (s, 1H, $H_{Py}$), 6.71 (d, 1H, $H_{Py}$, J=5.6 Hz), 7.29-7.32 (m, 1H, $H_{arom}$), 7.41-7.44 (m, 2H, $H_{arom}$), 7.47 (dd, 1H, $H_{arom}$, J=8.1 Hz, J=2.4 Hz), 7.50-7.52 (m, 2H, $H_{arom}$), 7.61-7.64 (m, 2H, $H_{arom}$), 7.78 (d, 1H, $H_{arom}$, J=7.7 Hz), 8.17 (s, 1H, H-$_{arom}$), 8.42 (d, 1H, $H_{Py}$, J=5.6 Hz), 10.35 (s, 1H, $NH_{amide}$), 12.94 (s, 1H, $NH_{lactame}$). $^{13}$C-NMR (DMSO-d6), δ (ppm), J (Hz): 30.03 (tert-Bu), 32.00 (tert-Bu), 100.70, 107.39, 118.62, 118.67, 122.92, 122.98, 123.45, 124.39, 126.75, 128.87, 130.68, 135.32, 138.88, 145.58, 151.30, 152.17, 154.50, 156.35, 159.73, 160.71, 164.71. HRMS (EI): m/z [M+H] calcd for $C_{27}H_{24}N_6O_3$: 481.1983; found: 481.1983.

(IX) Synthesis of Ureas from Isocyanates and Nitro-Amino-Pyridine Intermediates

Synthesis 151

1-(4-(2-amino-3-nitropyridin-4-yloxy)-2-(methylthio)phenyl)-3-(4-chloro-3-(trifluoromethyl)phenyl) urea

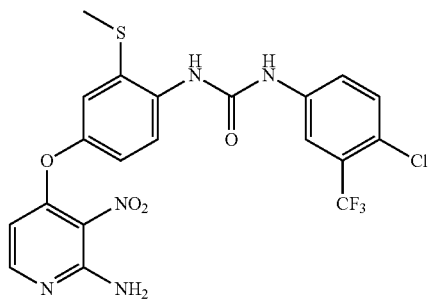 [SMILES: CSc1cc(Oc2ccnc(N)c2[N+](=O)[O-])ccc1NC(=O)Nc1ccc(Cl)c(C(F)(F)F)c1]

Using Method F2 with 4-(4-amino-3-(methylthio)phenoxy)-3-nitropyridin-2-amine (150 mg, 0.5 mmol) and 4-chloro-3-trifluoromethylisocyanate, the title compound (247 mg, 93%) was obtained as a orange powder.

$^1$H-NMR (DMSO-d6), δ (ppm), J (Hz): 2.47 (s, 3H, CH$_3$), 6.02 (d, 1H, $H_{Py}$, J=5.7 Hz), 7.04 (d, 1H, $H_{arom}$, J=8.8 Hz), 7.16 (5, 2H, $NH_{2,Py}$), 7.21 (m, 1H, $H_{arom}$, J=8.8 Hz), 7.62 (m, 2H, $H_{arom}$), 7.85 (m, 1H, $H_{arom}$), 8.01 (d, 1H, $H_{arom}$, J=8.8 Hz), 8.11 (d, 1H, $H_{Py}$, J=5.7 Hz), 8.20 (s, 1H, $NH_{urea1}$), 9.75 (s, 1H, $NH_{urea3}$). $^{13}$C-NMR (DMSO-d6), δ (ppm), J (Hz): 15.6, 100.4, 116.5, 118.0, 119.8, 121.6, 122.7, 123.8, 124.0, 126.5, 126.8, 131.7, 132.0, 133.9, 139.2, 149.3, 152.4, 153.1, 153.7, 158.9. LC-MS (m/z): 514 (M+H, 100), rt=8.37 min.

Synthesis 152

1-(4-(2-amino-3-nitropyridin-4-yloxy)-2-(methyl-thio)phenyl)-3-(2-fluoro-5-(trifluoromethyl)phenyl)urea

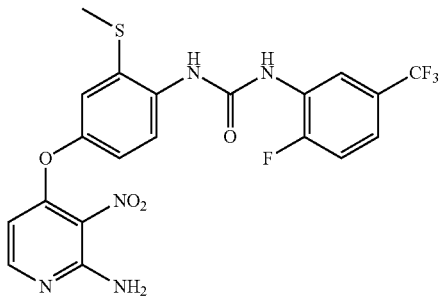 [SMILES: CSc1cc(Oc2ccnc(N)c2[N+](=O)[O-])ccc1NC(=O)Nc1cc(C(F)(F)F)ccc1F]

Using Method F2 with 4-(4-amino-3-(methylthio)phenoxy)-3-nitropyridin-2-amine (1.04 g, 3.57 mmol) and 2-fluoro-5-trifluoromethylphenyl isocyanate, the title compound (664 mg, 37%) was obtained as a yellow powder.

$^1$H-NMR (DMSO-d6), δ (ppm), J (Hz): 2.48 (s, 3H, CH$_3$), 6.02 (d, 1H, H$_{Py}$, J=5.7 Hz), 7.02 (dd, 1H, H$_{arom}$, J=8.7 Hz, J=2.7 Hz), 7.39 (m, 1H, H$_{arom}$), 7.50 (m, 1H, H$_{arom}$), 7.83 (d, 1H, H$_{arom}$, J=8.8 Hz), 8.01 (d, 1H, H$_{Py}$, J=5.7 Hz), 8.62 (dd, 1H, H$_{arom}$, J=7.1 Hz, J=1.6 Hz), 8.66 (s, 1H, H$_{arom}$), 9.69 (s, 1H, NH$_{urea1}$), 10.50 (s, 1H, NH$_{urea3}$). LC-MS (m/z): 498 (M+H, 100), rt=5.54 min.

Synthesis 153

1-(4-(2-amino-3-nitropyridin-4-yloxy)-2-fluorophenyl)-3-(2-fluoro-5-(trifluoro-methyl)phenyl)urea

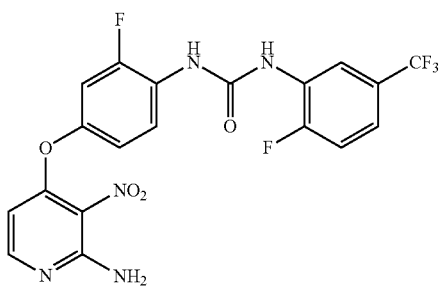 [SMILES: Nc1nccc(Oc2ccc(NC(=O)Nc3cc(C(F)(F)F)ccc3F)c(F)c2)c1[N+](=O)[O-]]

Using Method F2 with 4-(4-amino-3-fluorophenoxy)-3-nitropyridin-2-amine and 2-fluoro-5-trifluoromethylphenyl isocyanate, the title compound was obtained (yield 85%).

$^1$H-NMR (DMSO-d6), δ (ppm), J (Hz): 6.03 (d, 1H, J=5.7 Hz), 7.04 (dd, 1H, J=8.6, 2.2 Hz), 7.22 (bs, 2H), 7.33 (dd, 1H, J=8.6, 2.9 Hz), 8.60 (m, 1H), 9.22 (s, 1H), 9.37 (s, 1H). LC-MS (m/z): 470 (M+H, 100).

Synthesis 154

1-(4-(2-amino-3-nitropyridin-4-yloxy)-2-fluorophenyl)-3-(3-tert-butyl-1-phenyl-1H-pyrazol-5-yl)urea

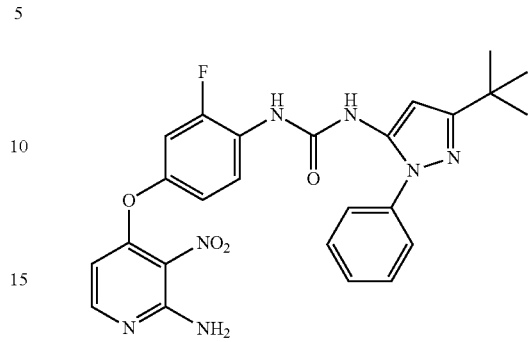

Using Method F3 with -tert-butyl-5-isocyanato-1-phenyl-1H-pyrazole (15 mL, 4.05 mmol) and 4-(4-amino-3-fluorophenoxy)-3-nitropyridin-2-amine (893 mg, 3.38 mmol) the title compound was obtained in quantitative yield (1.71 g) as a yellow solid after column chromatography with 5% to 50% EtOAc in CH$_2$Cl$_2$.

$^1$H-NMR (DMSO-d6), δ (ppm), J (Hz): 1.28 (s, 9H, tert-Bu), 6.03 (d, 1H, J=5.7, H$_{Py}$), 6.40 (s, 1H, H$_{Pyz}$), 7.01 (m, 1H, H$_{arom}$), 7.18 (br s, 2H, NH2), 7.26 (m, 1H, H$_{arom}$), 7.43 (m, 1H, H$_{arom}$), 7.54 (m, 4H, H$_{arom}$), 8.01 (d, 1H, J=5.7, H$_{Py}$), 8.16 (m, 1H, H$_{arom}$), 8.84 (s, 1H, NH), 8.98 (br s, 1H, NH); $^{13}$C-NMR (DMSO-d6), δ (ppm), J (Hz): 30.1, 32.0, 95.1, 100.6, 108.6 (d, J$_{FC}$=22.6), 116.6, 124.4, 125.2 (d, J$_{FC}$=10.8), 127.3, 129.3, 136.9, 138.4, 147.7 (d, J$_{FC}$=10.4), 151.1, 152.1 (d, J$_{FC}$=246), 153.2, 153.9, 158.8, 160.8, 170.3; $^{19}$F-NMR (DMSO-d6), δ (ppm): −124.7; LC-MS (m/z): 506.1 (M+H, 100), rt=2.73 min.

(X) Reduction of Nitro Group of Coupled Intermediates (According to Scheme 9)

Synthesis 155

1-(4-(2,3-Diaminopyridin-4-yloxy)-2-(methylthio)phenyl)-3-(4-chloro-3-(trifluoromethyl)phenyl)urea

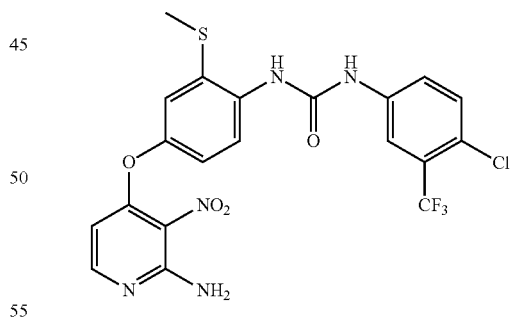

Method C4. A suspension of iron powder (4 equivalents, 78 mg, 1.4 mmol) and ammonium chloride (5.8 equivalents, 109 mg, 2 mmol) in ethanol (400 μL) and water (438 μL) was heated to reflux. The 1-(4-(2-amino-3-nitropyridin-4-yloxy)-2-(methylthio)phenyl)-3-(4-chloro-3-(trifluoromethyl)phenyl)urea compound (180 mg, 0.35 mmol) was added in portions and the mixture stirred at reflux for 24 hours. After cooling at RT, the slurry mixture was filtered and washed with ethanol. After removed the solvent, the crude powder is dissolved into EtOAc, filtered to removed the precipitate, and evaporated to provide the title compound (100 mg, 59%) as a sticky dark oil.

$^1$H-NMR (DMSO-d6), δ (ppm), J (Hz): 2.41 (s, 3H, CH$_3$), 5.61 (s, 2H, NH$_{2,Py}$), 6.06 (d, 1H, H$_{Py}$, J=5.6 Hz), 6.79 (d, 1H, H$_{arom}$, J=8.7 Hz), 7.01 (s, 1H, H$_{arom}$), 7.26 (d, 1H, H$_{Py}$, J=5.6 Hz), 7.58-7.69 (m, 4H, H$_{arom}$), 8.12 (s, 2H, NH$_{2,Py}$), 8.27 (s, 1H, NH$_{urea1}$), 10.02 (s, 1H, NH$_{urea3}$). $^{13}$C-NMR (DMSO-d6), δ (ppm), J (Hz): 15.6, 103.8, 115.6, 116.3, 117.6, 119.9, 122.5, 122.6, 124.9, 131.7, 131.9, 132.4, 134.7, 139.5, 139.6, 144.1, 147.0, 149.9, 152.3, 152.8. LC-MS (m/z): 484 (M+H, 100), rt=5.81 min.

Synthesis 156

1-(4-(2,3-diaminopyridin-4-yloxy)-2-(methylthio)phenyl)-3-(2-fluoro-5-(trifluoromethyl)phenyl)urea

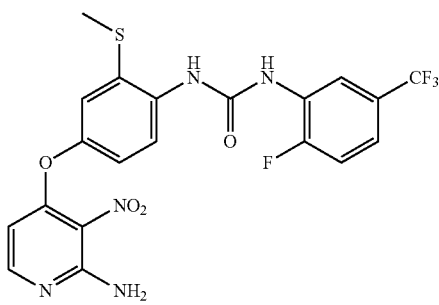 [SMILES: CSc1cc(Oc2ccnc(N)c2[N+](=O)[O-])ccc1NC(=O)Nc1cc(C(F)(F)F)ccc1F]

Using Method C4 with 1-(4-(2-amino-3-nitropyridin-4-yloxy)-2-(methylthio)phenyl)-3-(2-fluoro-5-(trifluoromethyl)phenyl)urea (664 mg, 1.3 mmol), the title compound (120 mg, 19%) was obtained as a dark powder after purification by chromatography on silica gel (EtOAc, then EtOAc-MeOH: 95-5)(R$_f$ 0.33, EtOAc-MeOH, 95:5).

$^1$H-NMR (DMSO-d6), δ (ppm), J (Hz): 2.43 (s, 3H, CH$_3$), 4.45 (s, 2H, NH$_{2,Py}$), 5.57 (s, 2H, NH$_{2,Py}$), 6.07 (d, 1H, H$_{Py}$, J=5.6 Hz), 6.79 (dd, 1H, H$_{arom}$, J=8.7 Hz, J=2.7 Hz), 7.01 (d, 1H, H$_{arom}$, J=2.7 Hz), 7.27 (d, 1H, H$_{Py}$, J=5.6 Hz), 7.37 (m, 1H, H$_{arom}$), 7.49 (m, 1H, H$_{arom}$), 7.67 (d, 1H, H$_{arom}$, J=8.8 Hz), 8.57 (s, 1H, NH$_{urea1}$), 8.62 (dd, 1H, H$_{arom}$, J=7.3 Hz, J=2.0 Hz), 9.43 (s, 1H, NH$_{urea3}$). $^{13}$C-NMR (DMSO-d6), δ (ppm), J (Hz): 15.4, 103.8, 115.4, 115.9, 116.0, 116.6, 117.3, 119.0, 119.8, 124.9, 128.6, 128.7, 131.3, 131.9, 135.5, 146.8, 150.2, 152.4, 152.5, 154.3. LC-MS (m/z): 468 (M+H, 100), rt=3.48 min.

Synthesis 157

1-(4-(2,3-diaminopyridin-4-yloxy)-2-fluorophenyl)-3-(2-fluoro-5-(trifluoromethyl)phenyl)urea

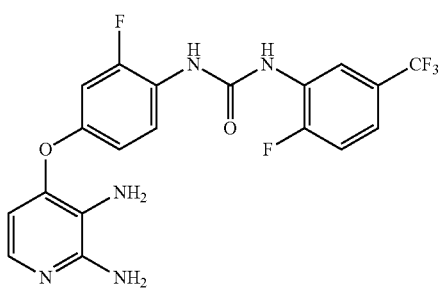 [SMILES: Nc1nccc(Oc2ccc(NC(=O)Nc3cc(C(F)(F)F)ccc3F)c(F)c2)c1N]

Method C2 was used with 1-(4-(2-amino-3-nitropyridin-4-yloxy)-2-fluorophenyl)-3-(2-fluoro-5-(trifluoromethyl)phenyl)urea (500 mg, 1.08 mmol) to yield the title compound (450 mg, 95%) as a yellow solid.

$^1$H-NMR (DMSO-d6), δ (ppm), J (Hz): 5.38 (bs, 2H), 6.05 (d, 1H, J=5.9 Hz), 6.75-6.86 (m, 2H), 7.21-7.33 (m, 4H) 8.07 (dd, 1H, J=18.0, 9.7 Hz), 8.94 (bs, 1H), 9.15 (bs, 1H). LC-MS (m/z): 440 (M+H, 100).

Synthesis 158

1-(3-tert-butyl-1-phenyl-1H-pyrazol-5-yl)-3-(4-(2,3-diaminopyridin-4-yloxy)-2-fluorophenyl)urea

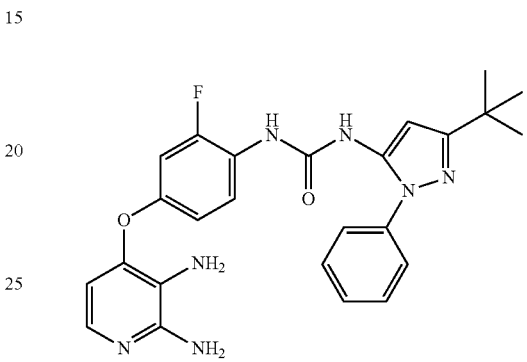

Method C2 was used with 1-(4-(2-amino-3-nitropyridin-4-yloxy)-2-fluorophenyl)-3-(3-tert-butyl-1-phenyl-1H-pyrazol-5-yl)urea (810 mg, 1.60 mmol) to give the title compound as a light pink solid (750 mg, 99% yield).

$^1$H-NMR (DMSO-d$_6$), δ (ppm), J (Hz): 1.28 (s, 9H, tert-Bu), 4.45 (br s, 2H, NH$_2$), 5.58 (br s, 2H, NH$_2$), 6.06 (d, 1H, J=5.6, H$_{Py}$), 6.38 (s, 1H, H$_{Pyz}$), 6.78 (m, 1H, H$_{arom}$), 6.92 (m, 1H, H$_{arom}$), 7.26 (d, 1H, J=5.6, H$_{Py}$), 7.41 (m, 1H, H$_{arom}$), 7.52 (m, 4H, H$_{arom}$), 7.98 (m, 1H, H$_{arom}$), 8.74 (s, 1H, NH), 8.82 (br s, 1H, NH); LC-MS (2.19 min): m/z 476.2 (M+H, 100).

(XI) Cyclisation of Coupled Intermediates

Synthesis 159

1-(4-chloro-3-(trifluoromethyl)phenyl)-3-(4-(2,3-dioxo-1,2,3,4-tetrahydropyrido[2,3-b]pyrazin-8-yloxy)-2-(methylthio)phenyl)urea (AA-051)

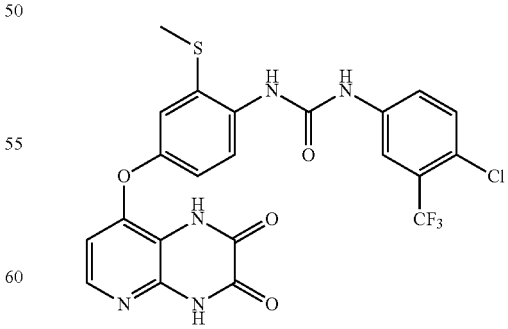

Method D3 was used with 1-(4-(2,3-diaminopyridin-4-yloxy)-2-(methylthio)phenyl)-3-(4-chloro-3-(trifluoromethyl)phenyl)urea (65 mg, 0.1 mmol) to provide the title compound (9 mg, 12%) as a pale white powder.

¹H-NMR (DMSO-d6), δ (ppm), J (Hz): 2.46 (s, 3H, CH₃); 6.55 (d, 1H, H$_{Py}$, J=5.5 Hz), 7.03 (dd, 1H, H$_{arom}$, J=8.7 Hz, J=2.5 Hz), 7.21 (d, 1H, H$_{arom}$, J=2.6 Hz), 7.62 (m, 2H, H$_{arom}$), 7.83 (d, 1H, H$_{arom}$, J=8.7 Hz), 7.95 (d, 1H, H$_{Py}$, J=5.0 Hz), 8.11 (m, 1H, H$_{arom}$), 8.22 (s, 1H, NH or CH), 9.81 (s, 1H, NH or CH), 11.89 (s, 1H, NH or CH), 12.38 (s, 1H, NH). ¹³C-NMR (DMSO-d6), δ (ppm), J (Hz): 15.7, 106.2, 112.2, 116.5, 117.7, 119.6, 122.2, 122.7, 122.8, 124.1, 129.6, 131.6, 131.9, 133.4, 139.2, 140.4, 143.1, 150.1, 150.4, 152.4, 15.5, 155.8. LC-MS (m/z): 538 (M+H, 100), rt=4.98 min.

Synthesis 160

1-(4-(2,3-dioxo-1,2,3,4-tetrahydropyrido[2,3-b]pyrazin-8-yloxy)-2-(methylthio)phenyl)-3-(2-fluoro-5-(trifluoromethyl)phenyl)urea (AA-052)

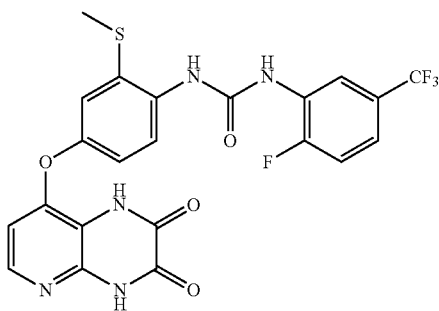 [SMILES: CSc1cc(Oc2ccnc3[nH]c(=O)c(=O)[nH]c23)ccc1NC(=O)Nc1cc(C(F)(F)F)ccc1F]

Method D3 was used with 1-(4-(2,3-diaminopyridin-4-yloxy)-2-(methylthio)phenyl)-3-(2-fluoro-5-(trifluoromethyl)phenyl)urea (87 mg, 0.18 mmol) to afford the title compound (34 mg, 35%) was obtained as a powder.

¹H-NMR (DMSO-d6), δ (ppm), J (Hz): 2.47 (s, 3H, CH₃), 6.56 (d, 1H, H$_{Py}$, J=5.6 Hz), 7.02 (dd, 1H, H$_{arom}$, J=8.7 Hz, J=1.7 Hz), 7.19 (d, 1H, H$_{arom}$, J=1.7 Hz), 7.39 (m, 1H, H$_{arom}$), 7.50 (m, 1H, H$_{arom}$), 7.82 (d, 1H, H$_{arom}$, J=8.7 Hz), 7.95 (dd, 1H, H$_{arom}$, J=5.6 Hz, J=0.9 Hz), 8.63 (d, 1H, H$_{Py}$, J=6.7 Hz), 8.67 (s, 1H, NH), 9.52 (s, 1H, NH), 11.90 (s, 1H, NH), 12.39 (s, 1H, NH). ¹³C-NMR (DMSO-d6), δ (ppm), J (Hz): 15.5, 106.2, 112.2, 115.9, 116.1, 116.7, 117.4, 119.2, 122.7, 124.6, 125.1, 128.6, 128.7, 131.9, 133.0, 140.4, 143.1, 150.3, 150.4, 152.4, 154.6, 155.8. LC-MS (m/z): 522 (M+H, 100), rt=4.82 min.

Synthesis 161

1-(4-(2-amino-3-oxo-3,4-dihydropyrido[2,3-b]pyrazin-8-yloxy)phenyl)-3-(4-chloro-3-(trifluoromethyl)phenyl)urea (AA-021)

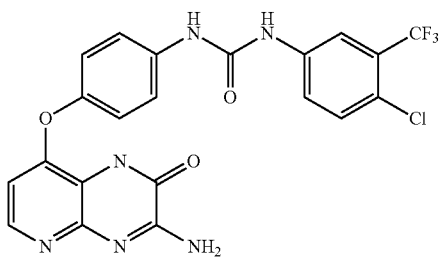 [SMILES: Nc1nc2nccc(Oc3ccc(NC(=O)Nc4ccc(Cl)c(C(F)(F)F)c4)cc3)c2[nH]c1=O]

Method D4 was used with 1-(4-chloro-3-(trifluoromethyl)phenyl)-3-(4-(2,3-diaminopyridin-4-yloxy)phenyl)urea (50 mg, 0.12 mmol) to afford the title compound (10 mg, 17% yield) as a white solid.

¹H-NMR (CD₃OD), δ (ppm), J (Hz): 8.03 (m, 2H), 8.68-8.73 (m, 4H), 8.94 (dd, 1H, J=8.8, 2.6 Hz), 9.58 (m, 2H), 10.86 (bs, 1H), 11.84 (bs, 1H). LC-MS (m/z): 491.0 (M+H, 100).

Synthesis 162

1-(2-fluoro-5-(trifluoromethyl)phenyl)-3-(4-(2-oxo-1,2-dihydropyrido[2,3-b]pyrazin-8-yloxy)phenyl)urea (AA-043)

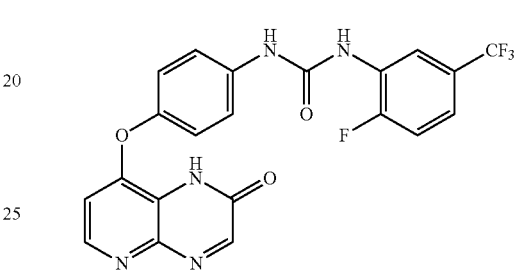

Method D1 was used with 1-(4-(2,3-diaminopyridin-4-yloxy)-2-fluorophenyl)-3-(2-fluoro-5-(trifluoromethyl)phenyl)urea to afford the title compound (yield 32%).

¹H-NMR (DMSO-d6), δ (ppm), J (Hz): 6.70 (d, 1H, J=5.4 Hz), 7.23 (d, 2H, J=9.6 Hz), 7.39 (m, 1H), 7.50 (m, 1H), 7.60 (d, 2H, J=9.6 Hz), 8.34 (d, 1H, J=5.4), 8.41 (s, 1H), 8.61 (dd, 1H, J=7.4, 1.6 Hz), 12.52 (bs, 1H). LC-MS (m/z): 492 (M+H, 100).

Synthesis 163

1-(4-(2-amino-3-oxo-3,4-dihydropyrido[2,3-b]pyrazin-8-yloxy)-2-fluorophenyl)-3-(2-fluoro-5-(trifluoromethyl)phenyl)urea (AA-044)

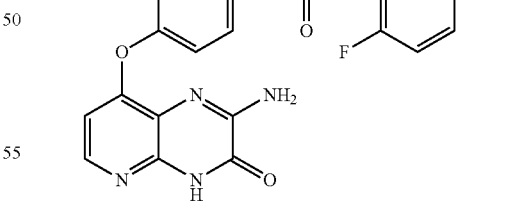

Method D4 was used with 1-(4-(2,3-diaminopyridin-4-yloxy)-2-fluorophenyl)-3-(2-fluoro-5-(trifluoromethyl)phenyl)urea to yield 40 mg (25%) of the title compound as a white solid.

¹H-NMR (DMSO), δ (ppm), J (Hz): 6.57 (d, 1H, 2H, J=5.6 Hz), 7.01 (dd, 1H, J=11.7, 2.8 Hz), 7.48-7.52 (m, 2H), 8.10 (d, 1H, J=5.6 HZ), 8.15 (d, 1H, 8.4 Hz), 8.60 (dd, 1H, J=8.4, 2.8 Hz), 9.34 (bs, 1H), 9.5 (bs, 1H). LC-MS (m/z): 493 (M+H, 100).

Synthesis 164

1-(4-(3-amino-2-oxo-1,2-dihydropyrido[2,3-b]pyrazin-8-yloxy)-2-fluorophenyl)-3-(2-fluoro-5-(trifluoromethyl)phenyl)urea (AA-022)

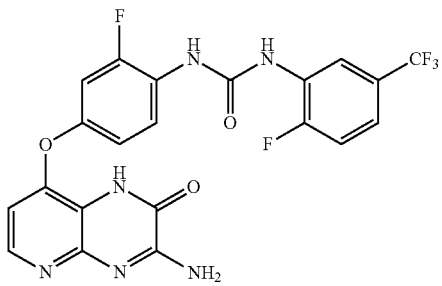

Method D4 was used with 1-(4-(2,3-diaminopyridin-4-yloxy)-2-fluorophenyl)-3-(2-fluoro-5-(trifluoromethyl)phenyl)urea to yield the title compound (yield 38%).

$^1$H-NMR (DMSO-d6), δ (ppm), J (Hz): 6.56 (d, 1H, J=5.4 Hz), 7.02 (dd, 1H, J=9.2, 2.7 Hz), 7.24 (dd, 1H, J=11.3, 2.6 Hz), 7.47-7.52 (m, 2H), 8.10 (d, 1H, 5.4 Hz), 8.15 (m, 1H), 8.61 (dd, 1H, J=7.3, 2.5 Hz), 9.35 (bs, 1H), 9.50 (bs, 1H). LC-MS (m/z): 493 (M+H, 100).

Synthesis 165

1-(3-tert-butyl-1-phenyl-1H-pyrazol-5-yl)-3-(2-fluoro-4-(3-oxo-3,4-dihydropyrido[3,2-b]pyrazin-8-yloxy)phenyl)urea and 1-(3-tert-butyl-1-phenyl-1H-pyrazol-5-yl)-3-(2-fluoro-4-(2-oxo-1,2-dihydropyrido[3,2-b]pyrazin-8-yloxy)phenyl)urea (AA-019 and AA-089)

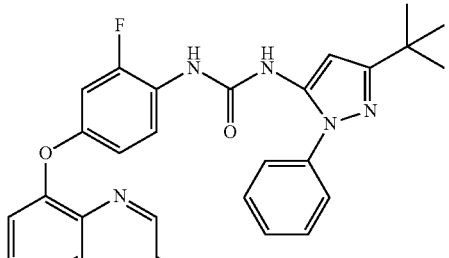

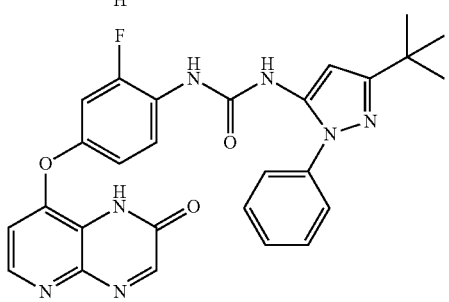

Method D1 was used with 1-(3-tert-butyl-1-phenyl-1H-pyrazol-5-yl)-3-(4-(2,3-diaminopyridin-4-yloxy)-2-fluorophenyl)urea (730 mg, 1.54 mmol) to give 1-(3-tert-butyl-1-phenyl-1H-pyrazol-5-yl)-3-(2-fluoro-4-(3-oxo-3,4-dihydropyrido[3,2-b]pyrazin-8-yloxy)phenyl)urea as the first fraction (412 mg, 52%) and 1-(3-tert-butyl-1-phenyl-1H-pyrazol-5-yl)-3-(2-fluoro-4-(2-oxo-1,2-dihydropyrido[3,2-b]pyrazin-8-yloxy)phenyl)urea as the second (300 mg, 38%).

1-(3-tert-butyl-1-phenyl-1H-pyrazol-5-yl)-3-(2-fluoro-4-(2-oxo-1,2-dihydropyrido[3,2-b]pyrazin-8-yloxy)phenyl)urea: $^1$H-NMR (DMSO-d$_6$), δ (ppm), J (Hz): 1.30 (s, 9H, tert-Bu), 6.41 (s, 1H, H$_{Pyrazole}$), 6.92 (d, 1H, J=5.4, H$_{Py}$), 7.08 (m, 1H, H$_{arom}$), 7.31 (m, 1H, H$_{arom}$), 7.44 (m, 1H, H$_{arom}$), 7.55 (m, 4H, H$_{arom}$), 8.18 (m, 1H, H$_{arom}$), 8.37 (d, 1H, J=5.4, H$_{Py}$), 8.43 (s, 1H, H$_{arom}$), 8.85 (s, 1H, NH), 9.01 (br s, 1H, NH); $^{13}$C-NMR (DMSO-d$_6$), δ (ppm), J (Hz): 30.2, 32.0, 95.1, 99.5, 108.6 (d, J$_{FC}$=22.5), 116.5, 121.7, 124.4, 124.9 (d, J$_{FC}$=10.8), 127.4, 129.3, 135.1, 136.9, 138.4, 139.5, 145.3 (br), 148.4 (d, J$_{FC}$=10.4), 149.7, 151.4, 152.2 (d, J$_{FC}$=248), 160.8; $^{19}$F-NMR (DMSO-d$_6$), δ (ppm): −124.7; LC-MS (m/z): 514.1 (M+H, 100), rt=2.54 min; HRMS (3.10 min): m/z calcd. for C$_{27}$H$_{25}$FN$_7$O$_3$ (M+H, 100)$^+$: 514.19974; found: 514.19856.

Synthesis 166

1-(4-(2-amino-3-oxo-3,4-dihydropyrido[2,3-b]pyrazin-8-yloxy)-2-fluorophenyl)-3-(3-tert-butyl-1-p-tolyl-1H-pyrazol-5-yl)urea (AA-057)

and 1-(3-tert-butyl-1-p-tolyl-1H-pyrazol-5-yl)-3-(2-fluoro-4-(2-oxo-1,2-dihydropyrido[3,2-b]pyrazin-8-yloxy)phenyl)urea (AA-085)

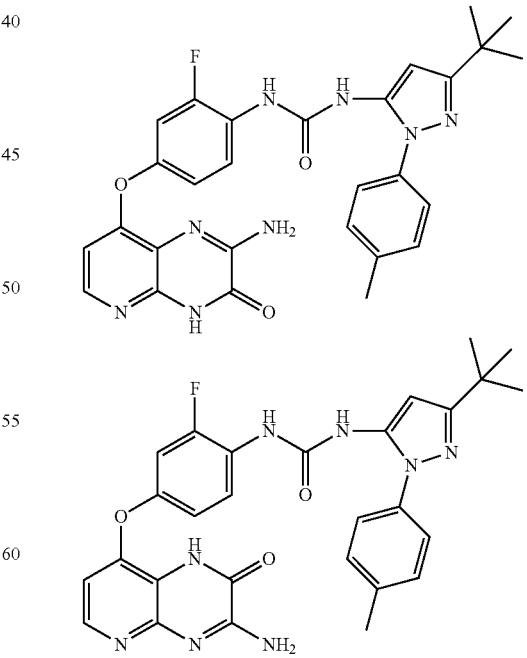

Method D4 was used with 1-(3-tert-butyl-1-p-tolyl-1H-pyrazol-5-yl)-3-(4-(2,3-diaminopyridin-4-yloxy)-2-fluorophenyl) urea (250 mg, 0.51 mmol) to afford after chromatography 1-(4-(2-amino-3-oxo-3,4-dihydropyrido[2,3-b]pyrazin-8-yloxy)-2-fluorophenyl)-3-(3-tert-butyl-1-p-tolyl-1H-pyrazol-5-yl)urea (AA-057)(25 mg, 9% yield) and 1H-pyrazol-5-yl)-3-(2-fluoro-4-(2-oxo-1,2-dihydropyrido[3,2-b]pyrazin-8-yloxy)phenyl) urea (AA-085) (15 mg, 6% yield).

1-(4-(2-amino-3-oxo-3,4-dihydropyrido[2,3-b]pyrazin-8-yloxy)-2-fluorophenyl)-3-(3-tert-butyl-1-p-tolyl-1H-pyrazol-5-yl)urea (AA-057): $^1$H-NMR (CD3OD), δ (ppm), J (Hz): 1.36 (s, 9H), 6.46 (s, 1H), 6.65 (d, 1H, J=5.7 Hz), 6.97 (d, 1H, J=9.0 Hz), 7.04 (dd, 1H, J=9.0, 2.6 Hz), 7.41 (AB system, 4H) 8.05 (d, 1H, J=5.7 Hz), 8.11 (t, 1H, J=9.0 Hz), 8.79 (bs, 1H), 9.00 (bs, 1H), 11.24 (bs, 1H), 12.26 (bs, 1H). LC-MS (m/z): 544 (M+H, 100).

1-(3-tert-butyl-1-p-tolyl-1H-pyrazol-5-yl)-3-(2-fluoro-4-(2-oxo-1,2-dihydropyrido[3,2-b]pyrazin-8-yloxy)phenyl) urea (AA-085): $^1$H-NMR (DMSO-d6), δ (ppm), J (Hz): 1.31-1.28 (m, 9H), 3.33 (s, 3H), 6.43 (s, 1H), 6.66 (d, 1H, J=5.6 Hz), 7.05 (dd, 1H, J=8.1, 2.0 Hz), 7.31 (dd, 1H, J=11.8, 2.0 Hz), 7.45 (d, 1H, J=8.3 Hz), 7.85 (dd, 1H, J=8.0, 3.3 Hz), 8.15 (t, 1H, J=9.2 Hz), 8.18 (s, 1H), 8.38 (d, 1H, J=6.0 Hz), 8.62 (d, 1H, J=3.3 Hz), 8.90 (s, 1H), 8.98 (s, 1H), 12.93 (bs, 1H). LC-MS: 544 (M+H, 100). HRMS: m/z calcd. for C27H25FN8O (M+H, 100): 543.2263; found: 543.2262.

Synthesis 167

1-(4-(3-(bromomethyl)-2-oxo-1,2-dihydropyrido[2,3-b]pyrazin-8-yloxy)-2-fluorophenyl)-3-(3-tert-butyl-1-p-tolyl-1H-pyrazol-5-yl)urea (AA-058)

and 1-(4-(2-(bromomethyl)-3-oxo-1,2,3,4-tetrahydropyrido[2,3-b]pyrazin-8-yloxy)-2-fluorophenyl)-3-(3-tert-butyl-1-p-tolyl-1H-pyrazol-5-yl)urea (AA-059)

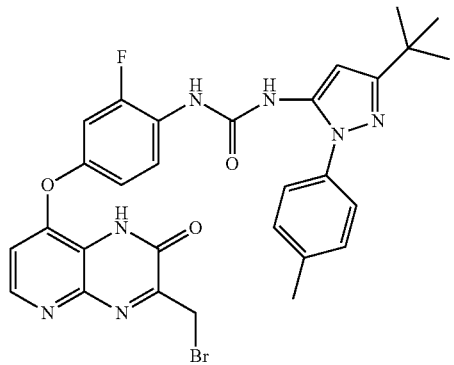

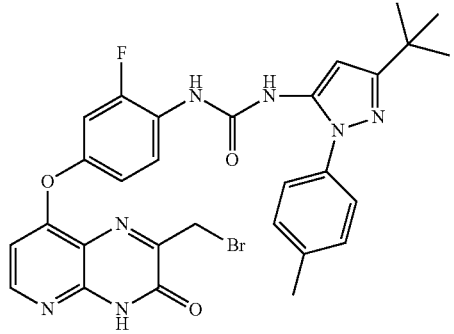

Method D8: To a solution of 1-(3-tert-butyl-1-p-tolyl-1H-pyrazol-5-yl)-3-(4-(2,3-diaminopyridin-4-yloxy)-2-fluorophenyl)urea (300 g, 0.61 mol) in dry ethanol (5 ml) ethyl 3-bromo-2-oxopropanoate (390 mg, 2 mmol) was added in one go. The resulting suspension was refluxed for 4 days. The solvent was then evaporated and chromatographed on a Biotage apparatus to afford 24 mg (6% yield) of 1-(4-(3-(bromomethyl)-2-oxo-1,2-dihydropyrido[2,3-b]pyrazin-8-yloxy)-2-fluorophenyl)-3-(3-tert-butyl-1-p-tolyl-1H-pyrazol-5-yl)urea and 13 mg (4% yield) of 1-(4-(2-(bromomethyl)-3-oxo-1,2,3,4-tetrahydropyrido[2,3-b]pyrazin-8-yloxy)-2-fluorophenyl)-3-(3-tert-butyl-1-p-tolyl-1H-pyrazol-5-yl)urea.

1-(4-(3-(bromomethyl)-2-oxo-1,2-dihydropyrido[2,3-b]pyrazin-8-yloxy)-2-fluorophenyl)-3-(3-tert-butyl-1-p-tolyl-1H-pyrazol-5-yl)urea (AA-058): $^1$H-NMR (CD3OD), δ (ppm), J (Hz): 1.34 (s, 9H), 2.42 (s, 3H), 4.63 (s, 2H), 6.46 (s, 1H), 6.66 (d, 1H, J=5.6 Hz), 7.05 (1H, dd, J=9.0, 2.5 Hz), 7.13 (1H, dd, J=9.0, 2.5 Hz), 7.37-7.35 (AB, 4H), 8.16 (t, 1H, J=9.0), 8.34 (d, 1H, J=5.6 Hz); LC-MS (m/z): 622-620 (M+H, 100).

1-(4-(2-(bromomethyl)-3-oxo-1,2,3,4-tetrahydropyrido[2,3-b]pyrazin-8-yloxy)-2-fluorophenyl)-3-(3-tert-butyl-1-p-tolyl-1H-pyrazol-5-yl)urea (AA-059): $^1$H-NMR (DMSO-d$_6$), δ (ppm), J (Hz): 1.27 (s, 9H), 2.08 (s, 3H), 2.39 (s, 2H), 6.92-6.90 (m, 2H), 7.12 (m, 1H), 7.13 (m, 1H), 7.38-7.35 (4H, AB), 7.92 (1H, d, J=5.7 Hz), 8.09 (1H, dd, J=4.7, 5.0 Hz), 8.74 (1H, s), 8.92 (1H, bs); LC-MS (m/z): 622-620 (M+H, 100).

(XII) Synthesis of Ureas from Activated Carbamates and Amino Intermediates

Synthesis 168

1-(2-fluoro-4-(3-oxo-3,4-dihydropyrido[2,3-b]pyrazin-8-yloxy)phenyl)-3-(5-(trifluoromethyl)pyridin-3-yl)urea (AA-069)

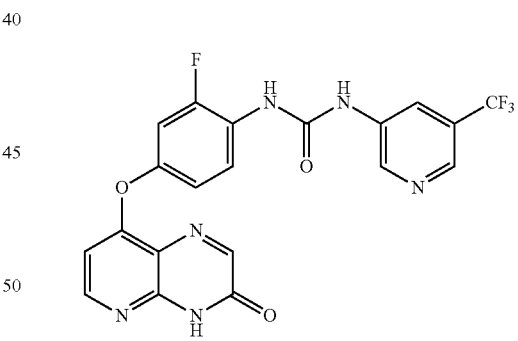

Method F5. w 8-(4-amino-3-fluorophenoxy)pyrido[2,3-b]pyrazin-3(4H)-one (26 mg, 96 μmol) and prop-1-en-2-yl 5-(trifluoromethyl)pyridin-3-ylcarbamate (45.8 mg, 186 μmol) were weighed into a 10 mL RBF, put under Ar and dry THF (3 mL) was added. To this mixture, N-methyl pyrrolidine (1 drop) was added and the mixture was heated to reflux for 48 h. The volatiles were evaporated and the resulting mixture was re-dissolved in MeOH (3 mL) and evaporated onto silica gel, which was loaded onto a silica gel column and purified with a 0-20% MeOH in EtOAc gradient. Yield: 5 mg (11%).

$^1$H-NMR (DMSO-d$_6$), δ (ppm), J (Hz): 6.66 (d, J=5.6, 1H, H$_{Py}$), 7.08 (m, 1H, H$_{arom}$), 7.35 (m, 1H, H$_{arom}$), 8.13 (m, 1H, H$_{arom}$), 8.18 (s, 1H, H$_{arom}$), 8.38 (d, J=5.6, 1H, H$_{Py}$), 8.46 (s, 1H, H$_{arom}$), 8.59 (s, 1H, H$_{arom}$), 8.77 (s, 1H, H$_{arom}$), 8.96 (s, 1H, NH), 9.67 (s, 1H, NH), 12.95 (s, 1H, NH); $^{19}$F-NMR (DMSO-d$_6$), δ (ppm): −60.6, −123.7; LC-MS (m/z): LC-MS: 461.1 (M+H, 100), rt=2.44 min; HRMS (7.17 min): m/z calcd. for C$_{20}$H$_{13}$F$_4$N$_6$O$_3$ [M+H$^+$]: 461.09798; found: 461.09771.

Synthesis 169 prop-1-en-2-yl 5-(trifluoromethyl)pyridin-3-ylcarbamate

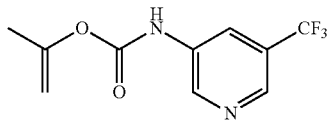 [SMILES: C=C(C)OC(=O)Nc1cncc(C(F)(F)F)c1]

5-(trifluoromethyl)pyridin-3-amine (883 mg, 5.45 mmol) was suspended in dry THF (20 mL) and N-methyl pyrrolidine (6804, 6.54 mmol) was added to give a brown suspension. The mixture was cooled to 0° C. and isopropenyl chloroformate (715 μL, 6.54 mmol) was added dropwise over 15 min. The suspension was allowed to reach RT and was stirred for 4 h. EtOAc (60 mL) and H$_2$O (10 mL) were added and the organic layer was isolated, washed with 50% brine (10 mL), dried (MgSO$_4$), filtered and evaporated to leave a brown oil, which solidified upon standing (1.05 g). The solid was taken up in CH$_2$Cl$_2$ (4 mL) and purified by column chromatography on silica gel, eluting with EtOAc in CH$_2$Cl$_2$ (6%→40%), to give a white solid. Yield: 600 mg (45%).

$^1$H-NMR (DMSO-d$_6$), δ (ppm), J (Hz): 1.96 (s, 3H, CH$_3$), 4.78 (m, 1H, CH), 4.80 (m, 1H, CFI), 8.27 (br, 1H, H$_{arom}$), 8.62 (br, 1H, H$_{arom}$), 8.86 (d, J=5.5, 1H, H$_{Py}$), 10.54 (s, 1H, NH); $^{13}$C-NMR (DMSO-d$_6$), δ (ppm), J (Hz): 19.3, 102.1, 121.2, 123.5 (q, J$_{FC}$=272), 125.1 (q, J$_{FC}$=31), 135.8, 139.8 (q, J$_{FC}$=3.8), 143.7, 151.3, 152.2; $^{19}$F-NMR (DMSO-d$_6$), δ (ppm): −61.2; LC-MS (m/z): m/z 247.0 (M+H, 100), rt=4.49 min.

Synthesis 170

Phenyl 2-fluoro-4-(3-oxo-3,4-dihydropyrido[3,2-b]pyrazin-8-yloxy)phenylcarbamate

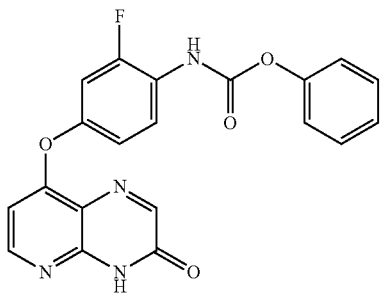 [SMILES: O=C(Nc1ccc(Oc2ccnc3[nH]c(=O)cnc23)cc1F)Oc1ccccc1]

Dry pyridine (125 μL, 1.55 mmol) was added to a suspension of 8-(4-amino-3-fluorophenoxy)pyrido[2,3-b]pyrazin-3(4H)-one (307 mg, 1.13 mmol) in dry THF (20 mL) under Ar and the mixture was cooled to 0° C. Phenyl chloroformate (170 μL, 1.35 mmol) was added dropwise over 5 min and the light brown mixture was stirred at 0° C. for an additional 5 min whereafter the mixture was allowed to warm up to RT and was stirred for 150 min. The brownish mixture was concentrated to dryness and the resulting residue was diluted with EtOAc (60 mL) and H$_2$O (30 mL). The organic layer was isolated and filtered (80 mg of impure product) and the filtrate was washed with aqueous saturated NaHCO$_3$ and brine. The organic layer was evaporated to dryness, re-dissolved in CH$_2$Cl$_2$ and chromatographed on a Biotage 25+M column, eluting with 20%→100% EtOAc in CH$_2$Cl$_2$ to give the title compound as a white solid. Yield: 280 mg (81%).

$^1$H-NMR (DMSO-d$_6$), δ (ppm), J (Hz): 6.71 (d, J=5.6, 1H, H$_{Py}$), 7.09 (m, 1H, H$_{arom}$), 7.23 (d, J=7.9, 2H, H$_{arom}$), 7.26 (t, J=7.9, 1H, H$_{arom}$), 7.33 (m, 1H, H$_{arom}$), 7.43 (d, J=7.9, 2H, H$_{arom}$), 7.75 (m, 1H, H$_{arom}$), 8.18 (s, 1H, H$_{arom}$), 8.39 (d, J=5.6, 1H, H$_{Py}$), 10.06 (s, 1H, NHBoc), 12.97 (s, 1H, NH); $^{13}$C-NMR (DMSO-d$_6$), δ (ppm), J (Hz): 107.1, 108.6 (d, J$_{FC}$=22.9), 116.1 (d, J$_{FC}$=3.3), 118.6, 121.8, 122.9 (d, J$_{FC}$=12.0), 125.5, 125.6 (br), 129.4, 145.6, 150.6, 151.3, 151.4 (br), 152.3, 152.4, 154.8 (d, J$_{FC}$=245), 156.4, 160.0; $^{19}$F-NMR (DMSO-d$_6$), δ (ppm): −119.2; LC-MS (m/z): 393.1 (M+H, 100), rt=2.44 min.

Synthesis 171

1-(2-nitro-4-(trifluoromethyl)phenyl)-1H-imidazole

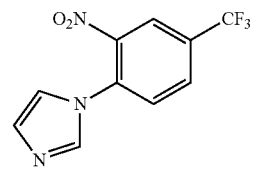 [SMILES: O=[N+]([O-])c1cc(C(F)(F)F)ccc1-n1ccnc1]

A mixture of imidazole (0.997 g, 14.65 mmol) and tert-BuOK (1.722 g, 15.35 mmol) was put under Ar in a 100 mL and dissolved in dry DMSO (15 mL) to give a colorless solution. After 5 min, 1-fluoro-2-nitro-4-(trifluoromethyl)benzene (2.04 mL, 14.58 mmol) was added within 30 s, immediately leading to a darkening of the rm to black. A temperature rise was also noted. The black solution was stirred at RT for 20 min. Ice water (60 mL) and EtOAc (50 mL) were added, the organic layer was isolated, and the aqueous phase was extracted twice with 20 mL EtOAc. The organic layer was washed with H$_2$O (2×30 mL), brine, dried, filtered and evaporated to give the title compound as an orange oil. Yield: 3.66 g (97%).

$^1$H-NMR (DMSO-d$_6$), δ (ppm), J (Hz): 7.14 (s, 1H, H$_{arom}$), 7.49 (s, 1H, H$_{arom}$), 7.97 (d, J=8.4, 1H, H$_{arom}$), 7.99 (s, 1H, H$_{arom}$), 8.28 (d, J=8.4, 1H, H$_{arom}$), 8.59 (s, 1H, H$_{arom}$); $^{13}$C-NMR (DMSO-d$_6$), δ (ppm), J (Hz): 120.4, 122.7 (d, J$_{FC}$=274), 122.9, 129.5 (d, J$_{FC}$=34), 129.9, 130.0, 130.9, 133.4, 137.4, 144.5; $^{19}$F-NMR (DMSO-d$_6$), δ (ppm): −60.8; LC-MS (m/z): 258.1 (M+H, 100), rt=1.37 min.

Synthesis 172

2-(1H-pyrazol-1-yl)-5-(trifluoromethyl)aniline

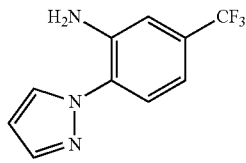 [SMILES: Nc1cc(C(F)(F)F)ccc1-n1cccn1]

Method C3 was used 1-(2-nitro-4-(trifluoromethyl)phenyl)-1H-pyrazole (1.80 g, 7.00 mmol) in EtOH (40 mL) to give 760 mg (48%) of the title compound as white crystals after crystallization from hexane.

$^1$H-NMR (DMSO-d$_6$), δ (ppm), J (Hz): 6.12 (s, 2H, NH$_2$), 6.56 (vt, J=2.1, 1H, H$_{arom}$), 6.95 (dd, J=8.3, $^4$J$_{FH}$=1.7, 1H, H$_{arom}$), 7.24 (d, $^4$J$_{FH}$=1.7, 1H, H$_{arom}$), 7.48 (d, J=8.3, 1H, H$_{arom}$), 7.82 (d, J=1.8, 1H, H$_{arom}$), 8.23 (d, J=2.5, 1H, H$_{arom}$); $^{13}$C-NMR (DMSO-d$_6$), δ (ppm), J (Hz): 106.9, 112.1, 112.9, 124.1 (d, J$_{FC}$=273), 124.2, 127.4, 128.3 (d, J$_{FC}$=31.7), 130.6, 140.5, 142.1; $^{19}$F-NMR (DMSO-d$_6$), δ (ppm): −60.8.

Synthesis 173

3-(2-nitro-4-(trifluoromethyl)phenoxy)pyridine

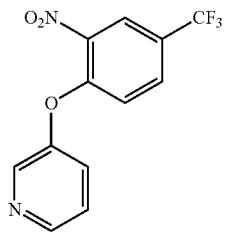 [SMILES: O=[N+]([O-])c1cc(C(F)(F)F)ccc1Oc1cccnc1]

A brown solution of 1-fluoro-2-nitro-4-(trifluoromethyl)benzene (2.01 g, 9.61 mmol) and 3-hydroxypyridine (0.923 g, 9.71 mmol) in dry DMF (15 ml) under Ar was treated with cesium carbonate (3.28 g, 10.07 mmol) at once and the brown mixture was stirred at RT for 2 h. H$_2$O (50 mL) and EtOAc (50 mL) were added and the organic layer was isolated. The water layer was extracted with EtOAc (2×30 mL). The combined organic layer was washed with H$_2$O (3×40 mL), brine (40 mL), dried (MgSO$_4$), filtered and concentrated to dryness to give a light yellow solid. Yield: 2.62 g (96%).

$^1$H-NMR (DMSO-d$_6$), δ (ppm), J (Hz): 7.33 (d, J=8.7, 1H, H$_{arom}$), 7.53 (m, 1H, H$_{arom}$), 7.71 (m, 1H, H$_{arom}$), 8.04 (dd, J=8.9, $^4$J$_{FH}$=2.3, 1H, H$_{arom}$), 8.49 (d, $^4$J$_{FH}$=2.2, 1H, H$_{arom}$), 8.52 (m, 1H, H$_{arom}$), 8.55 (d, J=2.9, 1H, H$_{arom}$); $^{13}$C-NMR (DMSO-d$_6$), δ (ppm), J (Hz): 120.7, 122.9 (d, J$_{FC}$=274), 123.4, 124.3 (d, J$_{FC}$=33.9), 125.0, 127.2, 131.7, 140.6, 141.6, 146.6, 151.3, 152.1; $^{19}$F-NMR (DMSO-d$_6$), δ (ppm): −60.4; LC-MS (m/z): 285.0 (M+H, 100), rt=2.40 min.

Synthesis 174

2-(pyridin-3-yloxy)-5-(trifluoromethyl)aniline

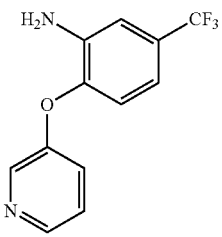 [SMILES: Nc1cc(C(F)(F)F)ccc1Oc1cccnc1]

Method C3 was used with 3-(2-nitro-4-(trifluoromethyl)phenoxy)pyridine (594 mg, 2.090 mmol) to give the title compound as a white crystalline solid. Yield: 501 mg (94%).

$^1$H-NMR (DMSO-d$_6$), δ (ppm), J (Hz): 5.55 (s, 2H, NH$_2$), 6.83 (d, J=8.2, 1H, H$_{arom}$), 6.94 (d, J=8.2, 1H, H$_{arom}$), 7.13 (s, 1H, H$_{arom}$), 7.33 (m, 1H, H$_{arom}$), 7.39 (m, 1H, H$_{arom}$), 8.33 (m, 1H, H$_{arom}$), 8.37 (m, 1H, H$_{arom}$); $^{13}$C-NMR (DMSO-d$_6$), δ (ppm), J (Hz): 111.7, 112.5, 119.7, 124.3 (d, J$_{FC}$=274), 124.4, 124.5, 125.8 (d, J$_{FC}$=33.9), 140.2, 141.0, 144.0, 144.1, 153.0; $^{19}$F-NMR (DMSO-d$_6$), δ (ppm): −60.3; LC-MS m/z: 255.0 (M+H, 100), rt=2.26 min.

Synthesis 175

Phenyl 2-(pyridin-3-yloxy)-5-(trifluoromethyl)phenylcarbamate

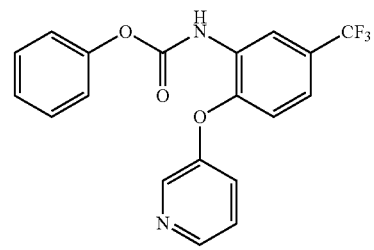 [SMILES: O=C(Nc1cc(C(F)(F)F)ccc1Oc1cccnc1)Oc1ccccc1]

A yellow solution of 2-(pyridin-3-yloxy)-5-(trifluoromethyl)aniline (263 mg, 1.035 mmol) and pyridine (108 μL, 1.341 mmol) in dry THF (8 mL) was treated dropwise with phenyl chloroformate (156 μL, 1.242 mmol) during 5 min at 0° C. The resulting suspension yellow suspension was stirred at 0° C. for an additional 5 min and then allowed to warm up to room temperature and stirred for 3 h. The yellow suspension was filtered over cotton, washed with Et$_2$O and diluted with EtOAc. The yellow solution was washed with sat. aqueous NaHCO$_3$ (30 mL) and H$_2$O (30 mL), dried and concentrated to dryness to give a yellow oil. Purification by column gave a tan solid. Yield: 300 mg (77%).

$^1$H-NMR (DMSO-d$_6$), δ (ppm), J (Hz): 6.90 (d, J=8.5, 1H, H$_{arom}$), 7.23 (m, 2H, H$_{arom}$), 7.30 (m, 2H, H$_{arom}$), 7.42 (m, 4H, H$_{arom}$), 7.76 (br s, 1H, H$_{arom}$), 8.55 (m, 1H, H$_{arom}$), 8.64 (br s, 1H, NH); LC-MS (m/z): 375.0 (M+H, 100), rt=2.62 min.

Synthesis 176

1-(2-fluoro-4-(3-oxo-3,4-dihydropyrido[3,2-b]pyrazin-8-yloxy)phenyl)-3-(2-(pyridin-3-yloxy)-5-(trifluoromethyl)phenyl)urea (AA-093)

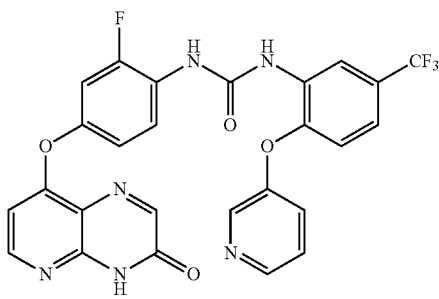 [SMILES: O=C(Nc1ccc(Oc2ccnc3[nH]c(=O)cnc23)cc1F)Nc1cc(C(F)(F)F)ccc1Oc1cccnc1]

Method F2 was used with 8-(4-amino-3-fluorophenoxy)pyrido[2,3-b]pyrazin-3(4H)-one (30.6 mg, 0.112 mmol) and a 60.6 mM solution of phenyl 2-(pyridin-3-yloxy)-5-(trifluoromethyl)phenylcarbamate (1.6 ml, 0.097 mmol). After 40 h, the mixture was evaporated onto silica gel, loaded onto a Biotage 12+M column, which was eluted with 40%-100% EtOAc in DCM. Yield: 4 mg (7%).

$^1$H-NMR (DMSO-d$_6$), δ (ppm), J (Hz): 6.64 (d, J=5.6, 1H, H$_{Py}$), 7.02 (d, J=8.5, 1H, H$_{arom}$), 7.07 (m, 1H, H$_{arom}$), 7.32 (m, 2H, H$_{arom}$), 7.53 (m, 1H, H$_{arom}$), 7.65 (m, 1H, H$_{arom}$), 8.15 (s, 1H, H$_{arom}$), 8.26 (m, 1H, H$_{arom}$), 8.38 (d, J=5.6, 1H, H$_{arom}$), 8.50 (m, 1H, H$_{arom}$), 8.58 (d, J=2.8, 1H, H$_{arom}$), 8.74 (d, J=2.8, 1H, H$_{arom}$), 9.36 (s, 1H, NH), 9.39 (s, 1H, NH), 12.88 (s, 1H, NH); LC-MS (m/z): 553.1 (M+H, 100), rt=2.63 min; HRMS (3.22 min): m/z calcd. for C$_{26}$H$_{16}$F$_4$N$_6$O$_4$ (M+H, 100)$^+$: 553.12419; found: 553.12312.

Synthesis 177

1-(2-(1H-pyrazol-1-yl)-5-(trifluoromethyl)phenyl)-3-(2-fluoro-4-(3-oxo-3,4-dihydropyrido[3,2-b]pyrazin-8-yloxy)phenyl)urea (AA-094)

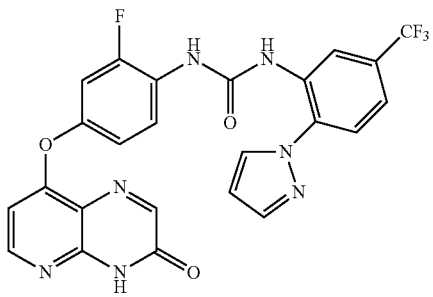 [SMILES: O=C(Nc1ccc(Oc2ccnc3[nH]c(=O)cnc23)cc1F)Nc1cc(C(F)(F)F)ccc1-n1cccn1]

Method F4: A mixture of phenyl 2-fluoro-4-(3-oxo-3,4-dihydropyrido[2,3-b]pyrazin-8-yloxy)phenylcarbamate (36.3 mg, 0.093 mmol) and 2-(1H-imidazol-1-yl)-5-(trifluoromethyl)aniline (21.1 mg, 0.093 mmol) was dissolved in dry DMSO (250 µL) the resulting orange solution was stirred at 60° C. for 7 h. The solution was diluted with H$_2$O, extracted with EtOAc and the organic layer was dried and evaporated to dryness. After a column (DCM/EtOAc) the resulting oil was triturated with EtOAc and the resulting white solid was collected. Yield: 11 mg (23%).

$^1$H-NMR (DMSO-d$_6$), δ (ppm), J (Hz): 6.67 (m, 2H, H$_{arom}$), 7.07 (m, 1H, H$_{arom}$), 7.31 (m, 1H, H$_{arom}$), 7.53 (m, 1H, H$_{arom}$), 7.69 (m, 1H, H$_{arom}$), 7.93 (s, 1H, H$_{arom}$), 8.04 (m, 1H, H$_{arom}$), 8.19 (s, 1H, H$_{arom}$), 8.35 (m, 1H, H$_{arom}$), 8.39 (m, 1H, H$_{arom}$), 8.59 (s, 1H, H$_{arom}$), 9.40 (s, 1H, H$_{arom}$), 9.52 (s, 1H, H$_{arom}$), 12.93 (s, 1H, H$_{arom}$); $^{19}$F-NMR (DMSO-d$_6$), δ (ppm): −60.3, −122.1; LC-MS (m/z): 526.1 (M+H, 100), rt=2.54 min; HRMS (3.10 min): m/z calcd. for C$_{24}$H$_{15}$F$_4$N$_7$O$_3$ (M+H, 100)$^+$: 526.12453; found: 526.12498.

Synthesis 178

1-(3-tert-butyl-1-(6-methylpyridin-3-yl)-1H-pyrazol-5-yl)-3-(2-fluoro-4-(3-oxo-3,4-dihydropyrido[3,2-b]pyrazin-8-yloxy)phenyl)urea (AA-084)

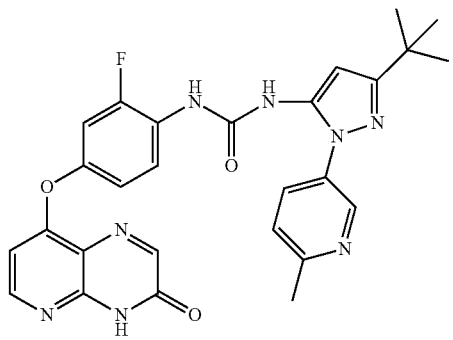

Method F4 was used with 65 mg (0.17 mmol) of phenyl 2-fluoro-4-(3-oxo-3,4-dihydropyrido[3,2-b]pyrazin-8-yloxy)phenylcarbamate and 45 mg (0.2 mmol) of 3-tert-butyl-1-(6-methylpyridin-3-yl)-1H-pyrazol-5-amine (Regan, J. et al., *J. Med. Chem.* 2002, 45, 2994-3008). Obtained 15 mg, 17% yield of the title compound.

$^1$H-NMR (CD3OD), δ (ppm), J (Hz): 1.31-1.28 (m, 9H), 3.33 (s, 3H), 6.43 (s, 1H), 6.66 (d, 1H, J=5.6 Hz), 7.05 (dd, 1H, J=8.1, 2.0 Hz), 7.31 (dd, 1H, J=11.8, 2.0 Hz), 7.45 (d, 1H, J=8.3 Hz), 7.85 (dd, 1H, J=8.0, 3.3 Hz), 8.15 (t, 1H, J=9.2 Hz), 8.18 (s, 1H), 8.38 (d, 1H, J=6.0 Hz), 8.62 (d, 1H, J=3.3 Hz), 8.90 (s, 1H), 8.98 (s, 1H), 12.93 (bs, 1H). LC-MS (m/z): 529.12 (M+H, 100). HRMS: m/z calcd. for C27H25FN8O (M+H, 100): 529.2106; found: 529.2095.

(XI) Urea Formation Via Curtius Rearrangement

Synthesis 179

Ethyl 3-tert-butyl-1-(cyclopropylmethyl)-1H-pyrazole-5-carboxylate

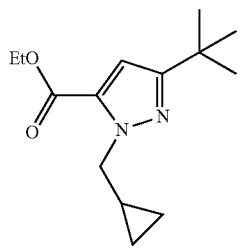 [SMILES: CCOC(=O)c1cc(C(C)(C)C)nn1CC1CC1]

Method I: A mixture of 3-tert-butyl-1H-pyrazole-5-carboxylate (993 mg, 5.06 mmol) caesium carbonate (2.71 g, 8.32 mmol) in dry DMF (10 mL) under Ar was treated dropwise over 15 min with bromomethylcyclopropane (500 μl, 5.16 mmol) at 0° C. The mixture was then allowed to warm up to RT and stirred for 5 h. The mixture was poured into water and extracted with Et$_2$O. The combined organic fraction was washed with H$_2$O, dried (MgSO$_4$), filtered and evaporated to give residue, which was subsequently Column eluent: 40→100% CH$_2$Cl$_2$ in hexane. Yield: 1.10 g (87%) of a colorless oil. Five hours reaction time. $^1$H-NMR (DMSO-d$_6$), δ (ppm), J (Hz): 0.32 (m, 2H, Hcyclopropyl), 0.44 (m, 2H, Hcyclopropyl), 1.25 (m, 10H, tert-Bu+Hcyclopropyl), 1.29 (t, J=7.1, 3H, CH$_3$), 4.28 (m, 4H, NCH$_2$+OCH$_2$), 6.71 (s, 1H, H$_{arom}$); $^{13}$C-NMR (DMSO-d$_6$), δ (ppm), J (Hz): 3.2, 11.7, 14.0, 30.2, 31.6, 54.8, 60.6, 107.1, 131.4, 159.3, 159.4; LC-MS (m/z): 251.1 (M+H, 100), rt=2.92 min.

Synthesis 180

Ethyl 3-tert-butyl-1-(methoxymethyl)-1H-pyrazole-5-carboxylate

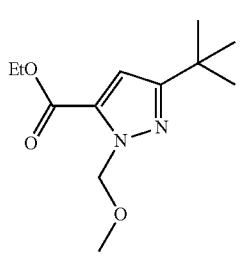

Method I was used with ethyl 3-tert-butyl-1H-pyrazole-5-carboxylate (1078 mg, 5.49 mmol), caesium carbonate (2.89 g, 8.87 mmol) and chloro(methoxy)methane (426 μl, 5.60 mmol). 16 hours reaction time. Column eluent: 0→10% EtOAc in CH$_2$Cl$_2$. Yield: 485 mg (37%) of a colorless oil.
$^1$H-NMR (DMSO-d$_6$), δ (ppm), J (Hz): 1.26 (s, 9H, tert-Bu), 1.30 (t, 3H, J=7.1, CH$_3$), 3.22 (s, 3H, OCH$_3$), 4.29 (q, 2H, J=7.1, OCH$_2$CH$_3$), 5.64 (s, 2H, OCH$_2$N), 6.69 (s, 1H, H$_{arom}$); $^{13}$C-NMR (DMSO-d$_6$), δ (ppm), J (Hz): 14.0, 30.0, 31.7, 56.0, 60.8, 80.0, 108.7, 132.7, 158.9, 160.5; LC-MS (m/z): 241.1 (M+H, 100), rt=2.67 min.

Synthesis 181

Ethyl 3-tert-butyl-1-(cyclobutylmethyl)-1H-pyrazole-5-carboxylate

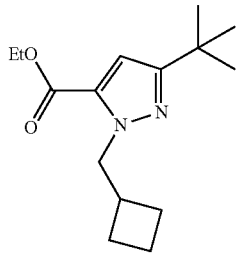 [SMILES: CC(C)(C)c1cc(C(=O)O)n(CC2CCC2)n1]

Method I: was used with ethyl 3-tert-butyl-1H-pyrazole-5-carboxylate (1085 mg, 5.53 mmol), caesium carbonate (2.89 g, 8.87 mmol) and (bromomethyl)cyclobutane (634 μl, 5.64 mmol). 16 hours reaction time. Column eluent: 40→100% CH$_2$Cl$_2$ in hexane. Yield: 0.98 g (67%) of a colorless oil.
$^1$H-NMR (DMSO-d$_6$), δ (ppm), J (Hz): 1.23 (s, 9H, tert-Bu), 1.29 (t, 3H, J=7.1, CH$_3$), 1.76 (m, 4H, CH$_2$), 1.89 (m, 2H, CH$_2$), 2.69 (sept, 1H, J=7.1, CH), 4.27 (q, 2H, J=7.1, OCH$_2$CH$_3$), 4.45 (d, 2H, J=7.1, NCH$_2$), 6.69 (s, 1H, H$_{arom}$); $^{13}$C-NMR (DMSO-d$_6$), δ (ppm), J (Hz): 14.0, 17.7, 24.9, 30.2, 31.6, 35.7, 54.9, 60.5, 106.9, 131.6, 159.3 (two coincident peaks); LC-MS (m/z): 265.1 (M+H, 100), rt=3.06 min.

Synthesis 182

Ethyl 3-tert-butyl-1-(2-(dimethylamino)ethyl)-1H-pyrazole-5-carboxylate

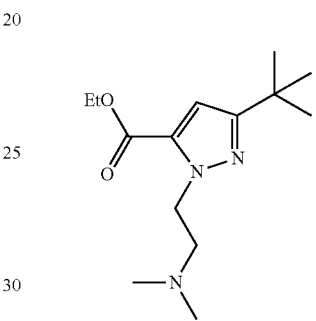

Method I was used with ethyl 3-tert-butyl-1H-pyrazole-5-carboxylate (124 mg, 0.632 mmol), caesium carbonate (624 mg, 1.915 mmol) and 2-chloro-N,N-dimethylethanamine hydrochloride (96.8 mg, 0.672 mmol). 48 hours reaction time. Column eluent: 50→100% EtOAc in CH$_2$Cl$_2$, followed by 0→10% MeOH in EtOAc. Yield: 103 mg (61%) of a colorless oil.
$^1$H-NMR (DMSO-d$_6$), δ (ppm), J (Hz): 1.25 (s, 9H, tert-Bu), 1.31 (t, 3H, J=7.1, CH$_3$), 2.15 (s, 6H, N(CH$_3$)$_2$), 2.60 (t, 2H, J=6.9, CH$_2$CH$_2$NMe$_2$), 4.29 (q, 2H, J=7.1, OCH$_2$CH$_3$), 4.51 (t, 2H, J=6.9, CH$_2$CH$_2$NMe$_2$), 6.70 (s, 1H, H$_{arom}$); $^{13}$C-NMR (DMSO-d$_6$), δ (ppm), J (Hz): 14.1, 30.2, 31.6, 45.1, 48.8, 58.7, 60.6, 107.0, 132.1, 159.2, 159.6; LC-MS (m/z): 268.2 (M+H, 100), 1.89 min.

Synthesis 183

3-Tert-butyl-1-(cyclopropylmethyl)-1H-pyrazole-5-carboxylic acid

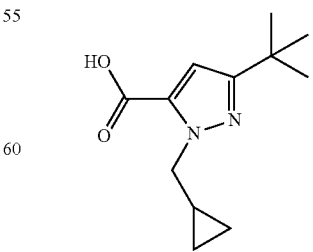

Method J: Ethyl 3-tert-butyl-1-(cyclopropylmethyl)-1H-pyrazole-5-carboxylate (1.1 g, 4.39 mmol) was dissolved in a 4:1:1 mixture of THF/MeOH/H₂O (total 25 mL M), lithium hydroxide monohydrate (200 mg, 4.7 mmol) was added and the colorless mixture was stirred for 16 h at RT. The volatiles were subsequently evaporated, the resulting solid was redissolved in H₂O and the pH of the solution was adjusted to 1 with 10% aqueous HCl. The resulting milky mixture was extracted with EtOAc and the combined organic fraction was washed with brine, dried and concentrated to dryness to give a white crystalline solid. Yield: 0.82 g (84%).

¹H-NMR (DMSO-d₆), δ (ppm), J (Hz): 0.32 (m, 2H, Hcyclopropyl), 0.42 (m, 2H, Hcyclopropyl), 1.24 (m, 10H, tert-Bu+Hcyclopropyl), 4.29 (d, 2H, J=7.0, NCH₂), 6.66 (s, 1H, H$_{arom}$), 13.10 (br s, 1H, COOH); ¹³C-NMR (DMSO-d₆), δ (ppm), J (Hz): 3.2, 11.8, 30.2, 31.6, 54.6, 107.1, 132.3, 159.2, 160.8; LC-MS (m/z): 223.1 (M+H, 100), rt=2.57 min.

Synthesis 184

3-Tert-butyl-1-(methoxymethyl)-1H-pyrazole-5-carboxylic acid

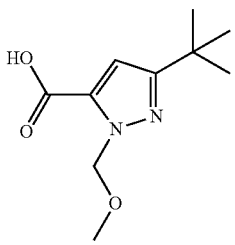

Method J was used with ethyl 3-tert-butyl-1-(methoxymethyl)-1H-pyrazole-5-carboxylate (485 mg, 2.02 mmol) as the starting material. Yield: 413 mg (96%) of a white, crystalline solid.

¹H-NMR (DMSO-d₆), δ (ppm), J (Hz): 1.25 (s, 9H, tert-Bu), 3.21 (s, 3H, OCH₃), 5.64 (s, 2H, OCH₂N), 6.79 (s, 1H, H$_{arom}$), 13.30 (br s, 1H, COOH); ¹³C-NMR (DMSO-d₆), δ (ppm), J (Hz): 30.1, 31.6, 56.0, 79.7, 108.7, 133.8, 160.3, 160.4; LC-MS (m/z): 213.1 (M+H, 100), rt=2.31 min.

Synthesis 185

3-Tert-butyl-1-(cyclobutylmethyl)-1H-pyrazole-5-carboxylic acid

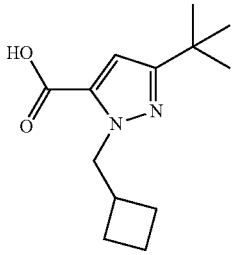

Method J was used with ethyl 3-tert-butyl-1-(cyclobutylmethyl)-1H-pyrazole-5-carboxylate (0.98 g, 3.71 mmol) as the starting material. Yield: 842 mg (95%) of a white, crystalline solid.

¹H-NMR (DMSO-d₆), δ (ppm), J (Hz): 1.23 (s, 9H, tert-Bu), 1.76 (m, 4H, CH₂), 1.89 (m, 2H, CH₂), 2.69 (sept, 1H, J=7.1, CH), 4.27 (q, 2H, J=7.1, OCH₂CH₃), 4.45 (d, 2H, J=7.1, NCH₂), 6.64 (s, 1H, H$_{arom}$), 13.07 (br s, 1H, COOH); ¹³C-NMR (DMSO-d₆), δ (ppm), J (Hz): 17.7, 24.9, 30.2, 31.5, 35.8, 54.7, 106.9, 132.6, 159.1, 160.8 LC-MS (m/z): 237.1 (M+H, 100), rt=2.74 min.

Synthesis 186

2-(3-Tert-butyl-5-carboxy-1H-pyrazol-1-yl)-N,N-dimethylethanaminium chloride

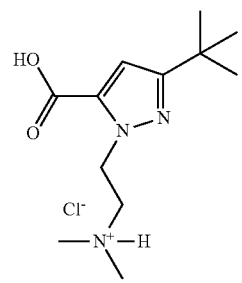 [SMILES: C[NH+](C)CCn1nc(C(C)(C)C)cc1C(=O)O ; [Cl-]]

Ethyl 3-tert-butyl-1-(2-(dimethylamino)ethyl)-1H-pyrazole-5-carboxylate (98 mg, 0.367 mmol) was dissolved in 6M aqueous HCl (4 mL, 24.00 mmol) and the colorless solution was heated to 80° C. for 72 h. The volatiles were evaporated in vacuo and the resulting white solid was coevaporated with Et₂O 10 mL) to give the title compound as a white solid. Yield: 100 mg (99%).

¹H-NMR (DMSO-d₆), δ (ppm), J (Hz): 1.26 (s, 9H, tert-Bu), 2.78 (d, 6H, J=4.8, CH₂CH₂N+H(CH₃)₂), 3.50 (q, 2H, J=5.3, CH₂CH₂NMe₂), 4.82 (t, 2H, J=6.6, CH₂CH₂NMe₂), 6.78 (s, 1H, H$_{arom}$), 10.66 (br s, 1H, COOH); LC-MS (m/z): 240.2 (M+H, 100), rt=1.56 min.

Synthesis 187

1-(3-Tert-butyl-1-(cyclopropylmethyl)-1H-pyrazol-5-yl)-3-(2-fluoro-4-(3-oxo-3,4-dihydropyrido[3,2-b]pyrazin-8-yloxy)phenyl)urea (AA-097)

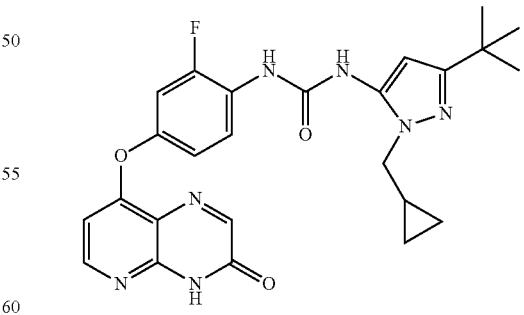

Method F5: 3-tert-butyl-1-(cyclopropylmethyl)-1H-pyrazole-5-carboxylic acid (51 mg, 0.229 mmol) was put under Ar and dry triethylamine (30 uL, 0.23 mmol) and dry DMF (1 mL) were subsequently added. The mixture was cooled to 0° C., DPPA (1 equiv) was added at once and the solution was stirred at 0° C. for an additional 30 min and then at RT for 1 h. Then, 8-(4-amino-3-fluorophenoxy)pyrido[2,3-b]pyrazin-3(4H)-one (31.9 mg, 0.117 mmol) was added at once and the solution was heated to 100° C. for 45 min. The resulting yellow solution was subsequently cooled to RT, diluted with EtOAc. The organic layer was washed with $H_2O$, 0.1 M citric acid, saturated aqueous $NaHCO_3$, brine, dried and concentrated to dryness to give a yellow solid. $Et_2O$ was added and the mixture was sonicated for 10 min and left to stand. The precipitate was filtered off and washed with $Et_2O$ to give the desired urea. Yield: 35 mg (62%) of a white solid.

$^1$H-NMR (DMSO-$d_6$), δ (ppm), J (Hz): 0.35 (m, 2H, Hcyclopropyl), 0.47 (m, 2H, Hcyclopropyl), 1.24 (m, 10H, tert-Bu+Hcyclopropyl), 3.84 (d, 2H, J=6.7, $NCH_2$), 6.12 (s, 1H, $H_{Pyrazole}$), 6.66 (d, J=5.6, 1H, $H_{Py}$), 7.07 (m, 1H, $H_{arom}$), 7.34 (m, 1H, $H_{arom}$), 8.20 (m, 2H, $H_{arom}$), 8.38 (d, J=5.6, 1H, $H_{Py}$), 8.80 (br s, 1H, NH), 8.85 (br s, 1H, NH), 12.93 (br s, 1H, NH); $^{19}$F-NMR (DMSO-$d_6$), δ (ppm): −125.0; LC-MS (m/z): 492.1 (M+H, 100), 2.54 min; HRMS (3.10 min): m/z calcd. for $C_{25}H_{27}FN_7O_3$ (M+H, 100)+: 492.21539; found: 492.21664.

Synthesis 188

1-(3-Tert-butyl-1-(methoxymethyl)-1H-pyrazol-5-yl)-3-(2-fluoro-4-(3-oxo-3,4-dihydropyrido[3,2-b]pyrazin-8-yloxy)phenyl)urea (AA-098)

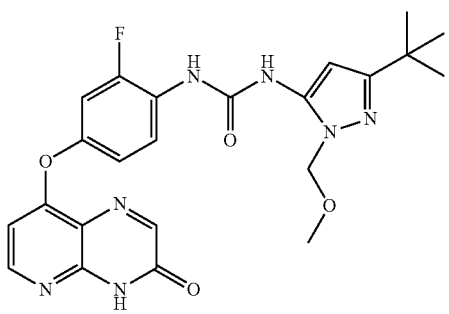 [SMILES: COCn1nc(C(C)(C)C)cc1NC(=O)Nc1ccc(Oc2ccnc3[nH]c(=O)cnc23)cc1F]

Method F5 was employed, using 3-tert-butyl-1-(methoxymethyl)-1H-pyrazole-5-carboxylic acid (49.5 mg, 0.233 mmol) and 8-(4-amino-3-fluorophenoxy)-pyrido[2,3-b]pyrazin-3(4H)-one (31.9 mg, 0.117 mmol). Yield: 45 mg (80%) of a white solid.

$^1$H-NMR (DMSO-$d_6$), δ (ppm), J (Hz): 1.24 (s, 9H, tert-Bu), 3.25 (s, 3H, $OCH_3$), 5.28 (s, 2H, $OCH_2N$), 6.26 (s, 1H, $H_{arom}$), 6.67 (d, J=5.6, 1H, Hp), 7.07 (M, 1H, $H_{arom}$), 7.34 (m, 1H, $H_{arom}$), 8.22 (m, 2H, $H_{arom}$), 8.38 (d, J=5.6, 1H, $H_{Py}$), 9.01 (br s, 1H, NH), 9.11 (br s, 1H, NH), 12.93 (br s, 1H, NH); $^{13}$C-NMR (DMSO-$d_6$), δ (ppm), J (Hz): 30.1, 31.8, 55.7, 77.5, 93.1, 106.5, 108.5 (d, $J_{FC}$=22.9), 116.5 (d, $J_{FC}$=3.3), 118.4, 121.5, 124.9 (d, $J_{FC}$=12.0), 137.6, 145.5, 148.5 (d, $J_{FC}$=10.4), 150.9, 151.2, 152.2, 152.3 (d, $J_{FC}$=245), 156.5, 159.9, 160.5; LC-MS (m/z): 482.1 (M+H, 100), 2.48 min; HRMS (3.05 min): m/z calcd. for $C_{23}H_{24}FN_7NaO_4$ [M+Na]$^+$: 504.17660; found: 504.17641.

Synthesis 189

1-(3-Tert-butyl-1-(cyclobutylmethyl)-1H-pyrazol-5-yl)-3-(2-fluoro-4-(3-oxo-3,4-dihydropyrido[3,2-b]pyrazin-8-yloxy)phenyl)urea (AA-099)

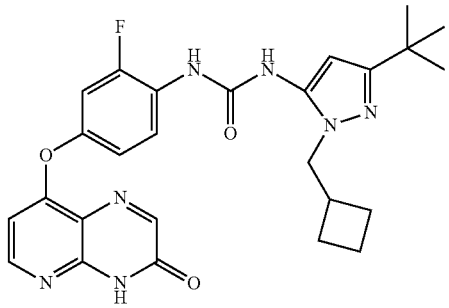 [SMILES: CC(C)(C)c1cc(NC(=O)Nc2ccc(Oc3ccnc4[nH]c(=O)cnc34)cc2F)n(CC2CCC2)n1]

Method F5 was employed, using 3-tert-butyl-1-(cyclobutylmethyl)-1H-pyrazole-5-carboxylic acid (78.5 mg, 0.332 mmol) and 8-(4-amino-3-fluorophenoxy)-pyrido[2,3-b]pyrazin-3(4H)-one (41 mg, 0.151 mmol). Yield: 50 mg (60%) of a white solid.

$^1$H-NMR (DMSO-$d_6$), δ (ppm), J (Hz): 1.22 (s, 9H, tert-Bu), 1.82 (m, 4H, $CH_2$), 1.98 (m, 2H, $CH_2$), 2.72 (sept, 1H, J=7.1, CH), 3.96 (d, 2H, J=7.1, $NCH_2$), 6.11 (s, 1H, $H_{arom}$), 6.66 (d, J=5.6, 1H, $H_{Py}$), 7.07 (m, 1H, $H_{arom}$), 7.33 (m, 1H, $H_{arom}$), 8.21 (m, 2H, $H_{arom}$), 8.38 (d, J=5.6, 1H, $H_{Py}$), 8.79 (br s, 1H, NH), 8.83 (br s, 1H, NH), 12.93 (br s, 1H, NH); $^{13}$C-NMR (DMSO-$d_6$), δ (ppm), J (Hz): 16.4, 23.9, 29.0, 30.4, 33.7, 50.5, 91.7, 105.2, 107.1 (d, $J_{FC}$=22.4), 115.2, 117.0, 120.2, 123.7 (d, $J_{FC}$=10.7), 134.8, 144.2, 147.1 (d, $J_{FC}$=10.3), 149.8, 150.0, 150.8, 150.9 (d, $J_{FC}$=245), 155.1, 157.3, 159.2 LC-MS (m/z): 507.1 (M+H, 100), 2.65 min; HRMS (3.24 min): m/z calcd. for $C_{26}H_{28}FN_7NaO_3$ [M+Na]$^+$: 528.21299; found: 528.21311.

Synthesis 190

1-(3-Tert-butyl-1-(2-(dimethylamino)ethyl)-1H-pyrazol-5-yl)-3-(2-fluoro-4-(3-oxo-3,4-dihydro-pyrido[3,2-b]pyrazin-8-yloxy)phenyl)urea (AA-100)

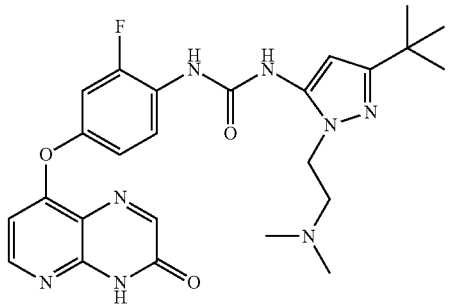 [SMILES: CN(C)CCn1nc(C(C)(C)C)cc1NC(=O)Nc1ccc(Oc2ccnc3[nH]c(=O)cnc23)cc1F]

Method F5 was employed, using 3-tert-butyl-1-(2-(dimethylamino)ethyl)-1H-pyrazole-5-carboxylic acid hydrochloride (89 mg, 0.323 mmol) and 8-(4-amino-3-fluorophenoxy)-pyrido[2,3-b]pyrazin-3(4H)-one (41 mg, 0.151 mmol). Two equiv of triethylamine were used and the citric acid wash was not performed. Yield: 34 mg (41%) of an orange solid.

$^1$H-NMR (DMSO-$d_6$), δ (ppm), J (Hz): 1.21 (s, 9H, tert-Bu), 2.24 (s, 6H, $CH_2CH_2N(CH_3)_2$), 2.68 (t, 2H, J=6.8, $CH_2CH_2NMe_2$), 4.04 (t, 2H, J=6.8, $CH_2CH_2NMe_2$), 6.10 (s, 1H, $_{Py}$zH), 6.64 (d, J=5.6, 1H, $_{Py}$rH), 7.06 (m, 1H, H$_{arom}$), 7.33 (m, 1H, H$_{arom}$), 8.16 (m, 2H, H$_{arom}$), 8.37 (d, J=5.6, 1H, $_{Py}$rH), 8.89 (br s, 1H, NH), 9.05 (br s, 1H, NH), 12.92 (br s, 1H, NH); $^{13}$C-NMR (DMSO-d$_6$), δ (ppm), J (Hz): 30.3, 31.8, 45.0, 45.5, 57.8, 93.7, 106.5, 108.5 (d, J$_{FC}$=22.4), 116.4, 118.4, 122.1, 124.9 (d, J$_{FC}$=10.7), 136.6, 145.5, 148.7 (d, J$_{FC}$=10.3), 151.2, 151.6, 152.2, 152.5 (d, J$_{FC}$=245), 156.5, 159.0, 160.5; $^{19}$F-NMR (DMSO-d$_6$), δ (ppm): −124.5; LC-MS (1.90 min): m/z 509.1 (M+H, 100); HRMS (3.24 min): m/z calcd. for C$_{25}$H$_{30}$FN$_8$O$_3$ (M+H, 100)$^+$: 509.24194; found: 509.24249.

Synthesis 191

5-[(4-amino-2-fluorophenyl-oxy)carbonylamino-5-(1-N-allyl-3-t-butyl-imidazolyl)]-pyridin-[2,3]-3-pyrazin-2-one (AA-095)

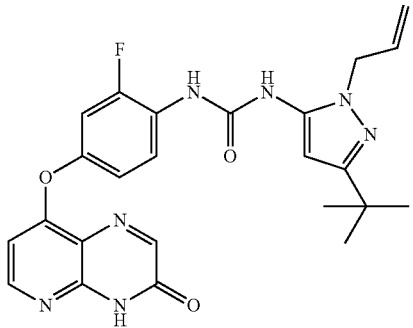 [SMILES: C=CCn1nc(C(C)(C)C)cc1NC(=O)Nc1ccc(Oc2ccnc3[nH]c(=O)cnc23)cc1F]

Method F2 was used with 34 mg (0.13 mmol) of 5-(4-amino-2-fluoro-phenyl-oxy)-pyridin-[2,3]-pyrazin-2-one, and 0.26 mmol of 1-N-allyl-3-t-butyl-imidazolyl-5-isocyanate, 38 mg (yield, 42%) of the desired product were obtained.

$^1$H-NMR (DMSO-d$_6$), δ (ppm), J (Hz): δ 4.59 (d, 2H, J=2.5 Hz), 4.90 (d, 1H, J=18.6 Hz), 5.15 (d, 1H, J=10.3 Hz), 5.92-6.00 (m, 1H), 6.15 (s, 1H$_{pyz}$), 6.64 (d, 1H, J=5.7 Hz), 7.05 (d, 1H, J=8.6 Hz), 7.34 (d, 2H, J=11.7 Hz), 8.18 (s, 1H$_{pyrazine}$), 8.20 (t, 1H, J=9.1 Hz), 8.37 (d, 1H, J=5.7 Hz), 8.81 (s, 1H, NH), 8.86 (s, 1H, NH), 12.95 (s, 1H, NH). LC-MS (m/z): m/z: 478.1 (M+H, 100)$^+$, rt=2.51 min; HRMS: (M+Na)$^+$ calcd for C$_{24}$H$_{24}$FN$_7$O$_3$Na, 500.1817; found: 500.1816.

Synthesis 192

5-[(4-amino-2-fluorophenyl-oxy)carbonylamino-5-(1-N-propargyl-3-t-butyl-imidazolyl)]-pyridin-[2,3]-3-pyrazin-2-one (AA-096)

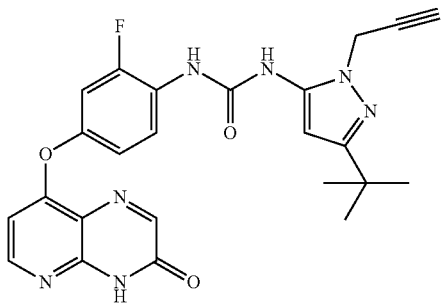 [SMILES: C#CCn1nc(C(C)(C)C)cc1NC(=O)Nc1ccc(Oc2ccnc3[nH]c(=O)cnc23)cc1F]

Method F2 was used with 35 mg (0.13 mmol) of 5-(4-amino-2-fluoro-phenyl-oxy)-pyridin-[2,3]-pyrazin-2-one, and 0.2 mmol of 1-N-propargyl-3-t-butyl-imidazolyl-5-isocyanate, 49 mg (yield, 80%) of the desired product were obtained.

$^1$H-NMR (DMSO-d$_6$), δ (ppm), J (Hz): δ 4.82 (s, 2H), 6.15 (s, 1H$_{pyrazole}$), 6.65 (d, 1H, J=5.7 Hz), 7.06 (d, 1H, J=8.7 Hz), 7.35 (d, 2H, J=11.7 Hz), 8.18 (s, 1H$_{pyrazine}$), 8.20 (t, 1H, J=9.1 Hz), 8.37 (d, 1H, J=5.7 Hz), 8.91 (s, 1H, NH), 9.02 (s, 1H, NH), 12.95 (s, 1H, NH). LC-MS (m/z): 476.1 (M+H, 100), rt=2.41 min; HRMS: (M+H, 100)+ calcd for C$_{24}$H$_{22}$FN$_7$O$_3$ 476.1841; found: 476.1844.

Biological Methods

Biological Methods—DELFIA Kinase Assay

Compounds were assessed by a kinase assay performed according to the following protocol.

The following reagents were prepared:
DELFIA Kinase Buffer (DKB):

| Reagent | Stock Concentration | Volume per mL (μL) | Volume per 10 mL plate (μL) |
|---|---|---|---|
| 20 mM MOPS pH 7.2 | 0.2M | 100 | 1000 |
| 0.5 M EGTA pH 8.0 | 0.5M | 10 | 100 |
| 10 mM MgCl$_2$ | 1M | 10 | 100 |
| 0.1% β-mercaptoethanol | — | 1 | 10 |
| 25 mM β-glycerophosphate | 0.5M | 50 | 500 |
| Water | 100% | 829 | 8290 |

MOPS = 3-[N-Morpholino] propanesulfonic acid (Sigma M3183).
EGTA = Ethylene glycol-bis(2-aminoethylether)-N,N,N',N'-tetraacetic acid (Sigma E3889).

DKB1 (DKB with B-RAF and MEK protein):
Combine 4950 μL of DKB and 50 μL of 2.5 mg/ml GST-MEK stock (to give 1 mg of MEK per 40 μL). Then add 22.5 μL of B-RAF to give ~0.2 μL of B-RAF per 40 μL.

DKB2 (DKB with MEK protein):
Combine 4950 μL of DKB and 50 μL of 2.5 mg/ml GST-MEK stock (to give 1 mg of MEK per 40 μL). Use 500 μL of this for the blow out (BO) and the empty vector (EV) control.

ATP:
100 mM stock, dilute to 500 μM to give 100 μM final concentration in assay.

Inhibitors (Test Compounds):
100 mM stock, dilute to 10, 3, 1, 0.3, 0.1, 0.03, 0.01, 0.003, 0.001, 0.0003, 0.0001 mM in DMSO in drug plate, resulting in concentration of 100, 30, 10, 3, 1, 0.3, 0.1, 0.03, 0.01, 0.003, 0.001 μM in the assay.

Primary Antibody:
Phospho-MEK1/2 CST #9121S diluted 1:1000 in DELFIA assay buffer (AB). Preincubate antibody in the AB for 30 minutes at room temperature prior to use.

Secondary Antibody:
Anti-rabbit-Eur labelled secondary Perkin Elmer #AD0105 diluted 1:1000 in DELFIA assay buffer (AB). Preincubate antibody in the AB for 30 minutes at room temperature prior to use. (Primary and secondary antibodies were incubated together.)

Tween:
0.1% Tween 20 in water.

Assay Buffer:
DELFIA assay buffer Perkin Elmer #4002-0010.

Enhancement Solution:
DELFIA enhancement solution Perkin Elmer #4001-0010.

Assay Plates:
96 well glutathione-coated black plate Perbio #15340.
Procedure:
1. Preblock wells with 5% milk in TBS for 1 hour.
2. Wash wells with 3× with 200 μL TBS.
3. Plate out 40 μL of DKB1 for all inhibitors (test compounds), DMSO control, and optionally other control compounds.
4. Plate out 40 μL of DKB2 for BO and EV wells.
5. Add inhibitors (test compounds) at 0.5 μL per well according to desired plate layout.
6. Add 0.5 μL DMSO to vehicle control wells.
7. Add 2 μL of B-RAF to BO and EV wells.
8. Pre-incubate with inhibitors (test compounds) for 10 minutes at room temperature with shaking.
9. Add 10 μL of 500 μM ATP stock, in DKB, to give 100 μM assay concentration.
10. Seal plates with TopSeal and incubate at room temperature with shaking for 45 minutes.
11. Wash plates 3× with 200 μL 0.1% Tween20/Water to terminate reaction.
12. Add 50 μL per well of antibody mix and incubate for 1 hour at room temperature with shaking.
13. Wash plates 3× with 200 μL 0.1% Tween20/Water.
14. Add 100 μL DELFIA enhancement solution per well, cover in foil, and incubate at room temperature for 30 minutes with shaking.
15. Read on Victor using Europium protocol.

Values for the blank (Empty Vector) are subtracted from all values. The DMSO controls are set as 100% activity and assay points (the response) are calculated as a percentage of the DMSO control. Data are plotted using Graphpad Prism software and a non-linear regression line is calculated using a variable slope sigmoidal dose-response equation (Y=Bottom+(Top−Bottom)/(1+10^((Log EC50−X)*Hill-Slope)) where X is the logarithm of concentration. Y is the response). The IC50 generated by this procedure is the concentration of the drug that produces a percentage control fluorescence value midway between the saturation, and zero-effect plateaus. Three independent assays are usually performed and the mean IC50 is reported.

Biological Methods—Cell Based Phosho-ERK Assay

Compounds were assessed using a cell-based assay which was performed according to the following protocol.
Day 0:
Plate out 16,000 cells/well in 99 μL medium in a 96-well plate.
Day 1:
1. Add 1 μL inhibitor to the cells (total 1 μL solution).
2. Incubate the cells with test compound for 6 hours at 37° C.
3. Aspirate off the solution from all of the wells.
4. Fixate the cells with 100 μL 4% formaldehyde/0.25% Triton X-100 PBS per well.
5. Incubate the plate for 1 hour at 4° C.
6. Aspirate off the fixing solution and add 300 μL TBS per well.
7. Leave the plate overnight at 4° C.
Day 2:
1. Wash the plate 2× with 200 μL PBS per well.
2. Block with 100 μL 5% dried milk in TBS.
3. Incubate the plate for 20 minutes at 37° C.
4. Wash the plate 2× with 0.1% tween/$H_2O$.
5. Add 50 μL of 3 μg/mL primary antibody pERK (Sigma M8159), diluted in 5% milk powder/TBS, to each well.
6. Incubate the plate for 2 hours at 37° C.
7. Wash the plate 3× with 0.1% tween/$H_2O$.
8. Add 50 μL of 0.45 μg/mL secondary Europium-labelled anti-mouse antibody (Perkin Elmer) to each well.
9. Incubate the plate for 1 hour at 37° C.
10. Wash the plate 3× with 0.1% tween/$H_2O$.
11. Add 100 μL enhancement solution (Perkin Elmer) to each well.
12. Leave the plate for approximately 10 minutes at room temperature before gently shaking the plate.
13. Read Europium Time Resolved Fluorescence in Victor2.
14. Wash the plate 2× with 0.1% tween/$H_2O$.
15. Measure the protein concentration with BCA (Sigma) by adding 200 μL of solution per well.
16. Incubate the plate for 30 minutes at 37° C.
17. Read absorbance levels at 570 nm in a plate reader.

Note that Europium counts are normalised for protein levels by dividing counts by absorbance.

Values for the blank (no cells) are subtracted from all values. The DMSO controls are set as 100% activity and assay points (the response) are calculated as a percentage of the DMSO control. Data are plotted using Graphpad Prism software and a non-linear regression line is calculated using a variable slope sigmoidal dose-response equation (Y=Bottom+(Top−Bottom)/(1+10^((Log EC50−X)*Hill-Slope)) where X is the logarithm of concentration. Y is the response). The IC50 generated by this procedure is the concentration of the drug that produces a percentage control fluorescence value midway between the saturation, and zero-effect plateaus. Three independent assays are usually performed and the mean IC50 is reported.

Biological Methods—SRB Cell Proliferation Assay (SRB $GI_{50}$)

Cultures of WM266.4 melanoma cells are routinely cultured in DMEM/10% foetal bovine serum, at 37° C., in 5% $CO_2$ water saturated atmosphere. Cultures are maintained in exponential growth phase by sub-culturing before having become confluent (3-5 day intervals). Single cell suspensions are prepared by harvesting an 80 $cm^2$ tissue culture flask with 5 mL commercial trypsin EDTA. After 5 minutes, the detached cells are mixed with 5 mL fully complemented culture medium and centrifugally pelleted (1000 rpm for 7 minutes). After aspirating the supernatant, the cell pellet is re-suspended in 10 mL fresh medium and the cells fully disaggregated by drawing the whole volume up/down 5 times through a 19-gauge needle. The concentration of the cells is determined using a haemocytometer (1/10 dilution). A suitable volume to give at least a 2-fold excess for the number of tests being conducted, typically 100-200 mL, is prepared by diluting the cell suspension to 10,000/mL, and 100 μL/well dispensed into 96 well plates using a programmable 8-channel peristaltic pump, giving 1000 cells/well, leaving column 12 blank. The plates are returned to the incubator for 24 hours to allow the cells to re-attach.

The compounds being tested are prepared at 20 mM in dimethylsulphoxide. Aliquots (200 μL) are diluted into 20 mL culture medium giving 200 μM, and 10 serial dilutions of 3× performed by transferring 5 mL to 10 mL. Aliquots (100 μL) of each dilution are added to the wells, using an 8-channel pipettor, thus performing a final further 2× dilution, and giving doses ranging from 100 μM to 0.005 μM. Column 11 receives plain culture medium only. Each compound is tested in quadruplicate, each replicate being the average of four wells, and two plates per compound.

After a further 6 days growth, the plates are emptied, and the cells are fixed in 10% trichloroacteic acid for 10 minutes on ice. After thorough rinsing in running tap water, the plates are dried, and stained by adding 50 μL of a solution of 0.1% sulphorhodamine-B in 1% acetic acid, for 10 minutes at room temperature. The stain is poured out and the plates thoroughly rinsed under a stream of 1% acetic acid, thus removing unbound stain, and dried. The bound stain is taken into solution by addition of 150 μL Tris buffer pH 8, followed by 10 minutes on a plate-shaker (approximately 500 rpm). The absorbance at 540 nm in each well (being proportional to the number of cells present) is determined using a plate reader.

After averaging the results in rows A-D and E-H, the blank value (row 12) is subtracted, and results expressed as percentage of the untreated value (row 11). The 10 values so derived (in quadruplicate) are plotted against the logarithm of the drug concentration, and analysed by non-linear regression to a four parameter logistic equation, setting constraints if suggested by inspection. The $GI_{50}$ generated by this procedure is the concentration of the drug that produces a percentage control $A_{540}$ midway between the saturation, and zero-effect plateaus.

Biological Results

The following compounds were tested in the "DELFIA Kinase Assay" described above: AA-001 through AA-056.

The following compounds have an IC50 BRAF of less than 1.0 μM:

AA-001, AA-002, AA-003, AA-004, AA-005, AA-006, AA-007, AA-008, AA-009, AA-010, AA-011, AA-012, AA-013, AA-014, AA-015, AA-016, AA-017, AA-018, AA-019, AA-020, AA-021, AA-022, AA-023, AA-024, AA-025, AA-026, AA-027, AA-028, AA-029, AA-030, AA-031, AA-032, AA-034, AA-037, AA-038, AA-039, AA-042, AA-044, AA-045, AA-046, AA-047, AA-048, AA-049, AA-050, AA-051, AA-052, AA-053, AA-054, AA-055, AA-056.

Additionally, the following compounds were tested in the "DELFIA Kinase Assay" described above: AA-001 through AA-098.

The following compounds have an IC50 BRAF of less than 0.1 μM:

AA-002, AA-003, AA-004, AA-005, AA-006, AA-007, AA-008, AA-009, AA-010, AA-011, AA-014, AA-015, AA-017, AA-018, AA-019, AA-020, AA-021, AA-023, AA-024, AA-025, AA-026, AA-027, AA-028, AA-029, AA-032, AA-044, AA-045, AA-047, AA-048, AA-050, AA-051, AA-052, AA-054, AA-060, AA-061, AA-062, AA-063, AA-064, AA-065, AA-067, AA-069, AA-072, AA-074, AA-075, AA-079, AA-080, AA-086, AA-087, AA-088, AA-093, AA-094, AA-095, AA-096, AA-097, AA-098.

The following compounds have an IC50 BRAF of at least 0.1 μM and less than 1.0 μM:

AA-001, AA-012, AA-013, AA-016, AA-022, AA-030, AA-031, AA-033, AA-034, AA-035, AA-037, AA-038, AA-039, AA-040, AA-041, AA-042, AA-043, AA-046, AA-049, AA-053, AA-055, AA-056, AA-057, AA-058, AA-059, AA-066, AA-068, AA-071, AA-076, AA-077, AA-078, AA-081, AA-082, AA-083, AA-084, AA-085, AA-089, AA-090, AA-091, AA-092.

One compound, compound AA-016, has an IC50 BRAF of 0.252 μM.

* * *

The following compounds were tested in the "Cell Based Phospho-ERK Assay" described above: AA-001 through AA-056.

The following compounds have an IC50 pERK of less than 10 μM:

AA-001, AA-002, AA-003, AA-004, AA-005, AA-006, AA-007, AA-008, AA-009, AA-010, AA-011, AA-013, AA-014, AA-015, AA-016, AA-017, AA-018, AA-019, AA-020, AA-021, AA-022, AA-023, AA-024, AA-025, AA-026, AA-027, AA-028, AA-029, AA-031, AA-033, AA-034, AA-035, AA-036, AA-037, AA-038, AA-039, AA-040, AA-041, AA-043, AA-044, AA-045, AA-046, AA-050, AA-051, AA-052, AA-053, AA-054.

Additionally, the following compounds were tested in the "Cell Based Phospho-ERK Assay" described above: AA-001 through AA-099.

The following compounds have an IC50 pERK of less than 1.0 μM:

AA-003, AA-006, AA-008, AA-009, AA-010, AA-011, AA-014, AA-015, AA-016, AA-017, AA-018, AA-019, AA-023, AA-024, AA-025, AA-026, AA-028, AA-031, AA-033, AA-034, AA-035, AA-036, AA-040, AA-041, AA-051, AA-052, AA-053, AA-057, AA-059, AA-060, AA-061, AA-062, AA-063, AA-064, AA-065, AA-066, AA-067, AA-071, AA-072, AA-073, AA-074, AA-075, AA-077, AA-078, AA-079, AA-080, AA-081, AA-084, AA-085, AA-087, AA-088, AA-089, AA-090, AA-091, AA-093, AA-094, AA-095, AA-096, AA-097, AA-099.

The following compounds have an IC50 pERK of at least 1.0 μM and less than 10 μM:

AA-001, AA-002, AA-004, AA-005, AA-007, AA-013, AA-020, AA-021, AA-022, AA-027, AA-029, AA-037, AA-038, AA-039, AA-043, AA-044, AA-045, AA-046, AA-050, AA-054, AA-058, AA-069, AA-070, AA-076, AA-083, AA-086, AA-092, AA-098.

One compound, compound AA-016, has an IC50 ppERK of 0.096 μM.

* * *

The following compounds were tested in the "SRB Cell Proliferation Assay" described above: AA-001 through AA-036 and AA-038 through AA-056.

The following compounds have a GI50 SRB of less than 10 μM:

AA-001, AA-002, AA-003, AA-004, AA-005, AA-006, AA-008, AA-009, AA-010, AA-011, AA-013, AA-014, AA-015, AA-016, AA-017, AA-018, AA-019, AA-020, AA-021, AA-022, AA-023, AA-024, AA-025, AA-026, AA-027, AA-028, AA-029, AA-030, AA-031, AA-032, AA-033, AA-034, AA-035, AA-036, AA-037, AA-038, AA-039, AA-040, AA-041, AA-042, AA-043, AA-044, AA-045, AA-046, AA-047, AA-048, AA-049, AA-050, AA-051, AA-052, AA-053, AA-054, AA-056.

Additionally, the following compounds were tested in the "SRB Cell Proliferation Assay" described above: AA-001 through AA-036 and AA-038 through AA-099.

The following compounds have an GI50 SRB of less than 1.0 μM:

AA-005, AA-006, AA-008, AA-009, AA-010, AA-011, AA-014, AA-015, AA-016, AA-017, AA-018, AA-019, AA-023, AA-024, AA-027, AA-028, AA-031, AA-033, AA-034, AA-035, AA-038, AA-040, AA-041, AA-051, AA-052, AA-053, AA-056, AA-057, AA-059, AA-060, AA-061, AA-062, AA-063, AA-064, AA-065, AA-066, AA-067, AA-071, AA-073, AA-074, AA-075, AA-077, AA-078, AA-079, AA-080, AA-081, AA-084, AA-085, AA-087, AA-088, AA-089, AA-090, AA-091.

The following compounds have an GI50 SRB of at least 1.0 μM and less than 10 μM:

AA-001, AA-002, AA-003, AA-004, AA-007, AA-012, AA-013, AA-020, AA-021, AA-022, AA-025, AA-026,

AA-029, AA-030, AA-032, AA-036, AA-039, AA-042, AA-043, AA-044, AA-045, AA-046, AA-047, AA-048, AA-049, AA-050, AA-054, AA-055, AA-058, AA-068, AA-069, AA-070, AA-072, AA-076, AA-083, AA-086, AA-092, AA-093, AA-094, AA-095, AA-096, AA-097, AA-098, AA-099.

One compound, compound AA-016, has a GI50 SRB of 0.062 µM.

In Vivo Study 1

AA-018 Non-Established 5 mg/kg/Day
Intraperitoneally

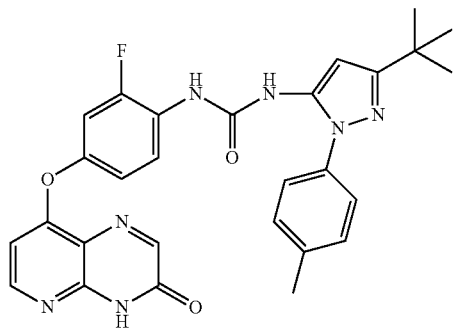 [SMILES: Cc1ccc(-n2nc(C(C)(C)C)cc2NC(=O)Nc2ccc(Oc3ccnc4[nH]c(=O)cnc34)cc2F)cc1]

$10^7$ A375M human melanoma cells were inoculated subcutaneously in 0.2 mL suspension into the right flank of female Crl:CD1-Foxn1nu athymic mice. The following day, treatment with test compound was begun. A suspension of test compound in DMSO:saline for injection 1:19 (v:v) was injected intraperitoneally at 10 mL/kg bodyweight. Treatment was continued daily for 24 doses. The results are shown in FIG. 1.

In Vivo Study 2

AA-018 Non-Established 10 mg/kg/Day
Intraperitoneally

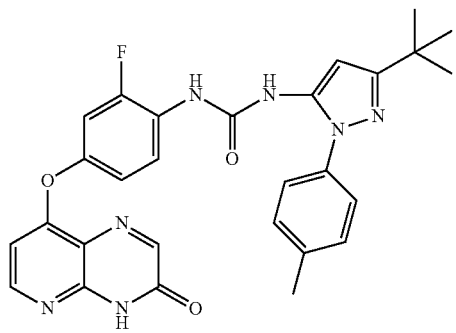 [SMILES: Cc1ccc(-n2nc(C(C)(C)C)cc2NC(=O)Nc2ccc(Oc3ccnc4[nH]c(=O)cnc34)cc2F)cc1]

Figure 2:
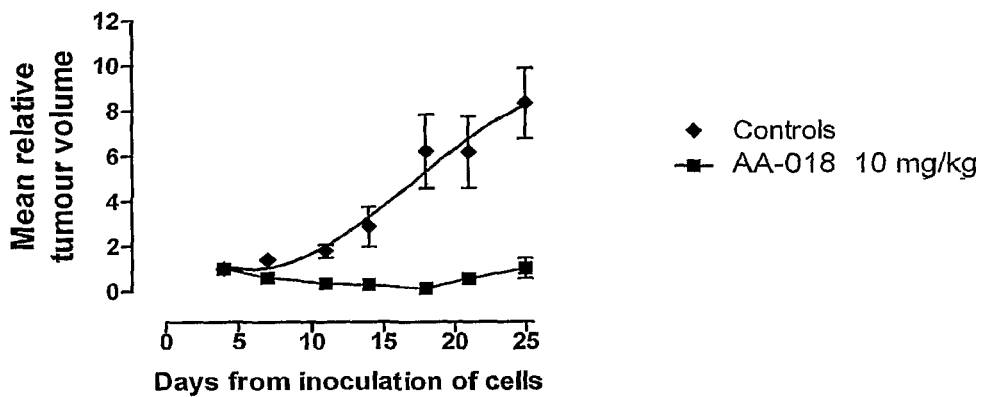
FIG. 2 is a graph of relative tumour volume as a function of days from inoculation for In Vivo Study 2 (AA-018) (non-established) (10 mg/kg/day) (intraperitoneally).

$10^7$ A375M human melanoma cells were inoculated subcutaneously in 0.2 mL suspension into the right flank of female Crl:CD1-Foxn1nu athymic mice. The following day, treatment with test compound was begun. A suspension in DMSO:saline for injection 1:19 (v:v) was injected intraperitoneally at 10 mL/kg bodyweight. Treatment was continued daily for 18 doses. The animals were then observed after the end of treatment. The results are shown in FIG. 2.

In Vivo Study 3

AA-019 Non-Established 5 mg/kg/Day
Intraperitoneally

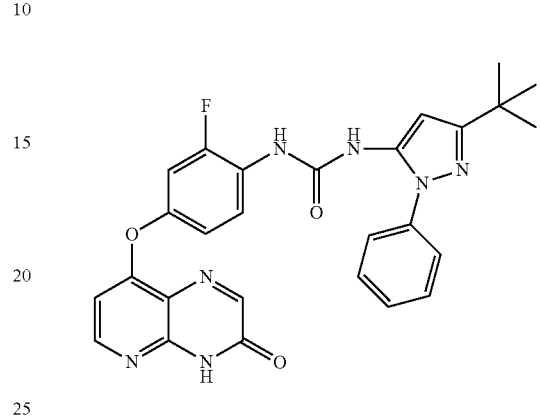

Figure 3:
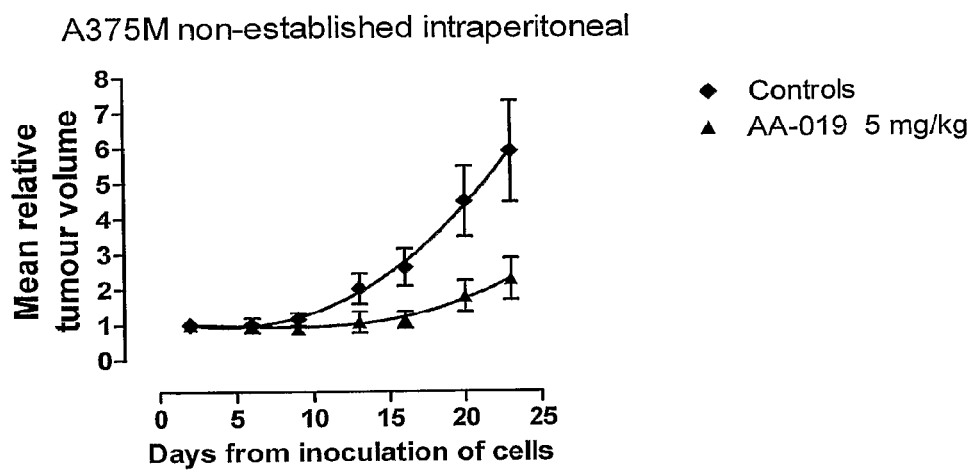
FIG. 3 is a graph of relative tumour volume as a function of days from inoculation for In Vivo Study 3 (AA-019) (non-established) (5 mg/kg/day) (intraperitoneally).

$10^7$ A375M human melanoma cells were inoculated subcutaneously in 0.2 mL suspension into the right flank of female Crl:CD1-Foxn1nu athymic mice. The following day, treatment with test compound was begun. A suspension in DMSO:saline for injection 1:19 (v:v) was injected intraperitoneally at 10 mL/kg bodyweight. Treatment was continued daily for 24 doses. The results are shown in FIG. 3.

In Vivo Study 4

AA-019 Non-Established 10 mg/kg/Day
Intraperitoneally

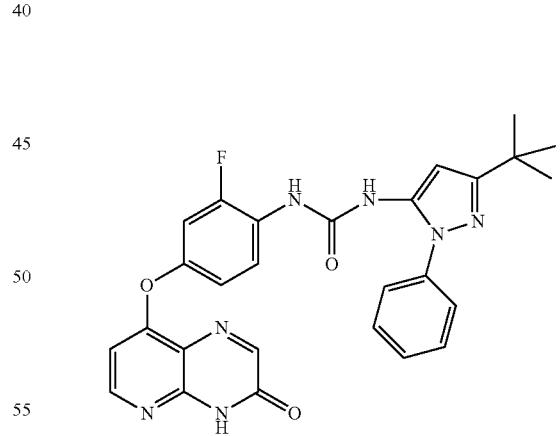

Figure 4:
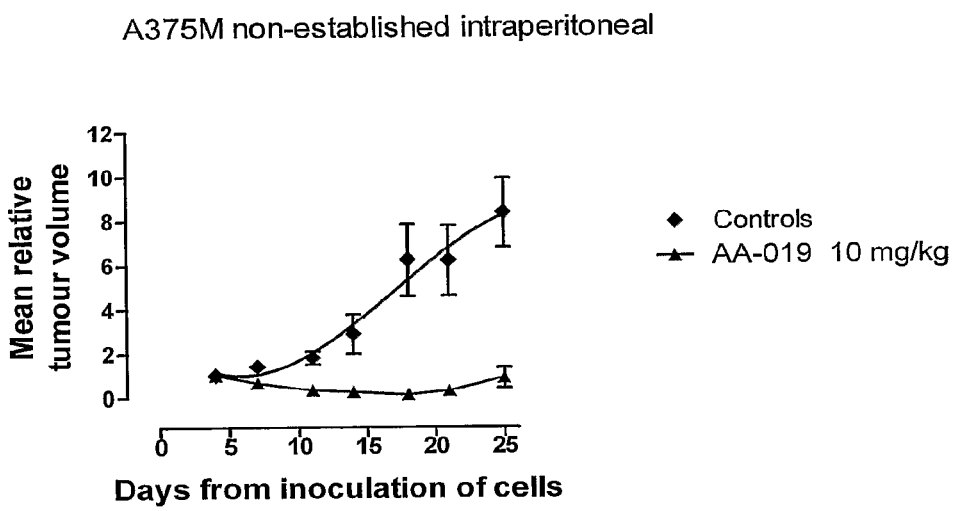
FIG. 4 is a graph of relative tumour volume as a function of days from inoculation for In Vivo Study 4 (AA-019) (non-established) (10 mg/kg/day) (intraperitoneally).

$10^7$ A375M human melanoma cells were inoculated subcutaneously in 0.2 mL suspension into the right flank of female Crl:CD1-Foxn1nu athymic mice. The following day, treatment with test compound was begun. A suspension in DMSO:saline for injection 1:19 (v:v) was injected intraperitoneally at 10 mL/kg bodyweight. Treatment was continued daily for 18 doses. The animals were then observed after the end of treatment. The results are shown in FIG. 4.

In Vivo Study 5

AA-019 Non-Established 15 mg/kg/Day Orally

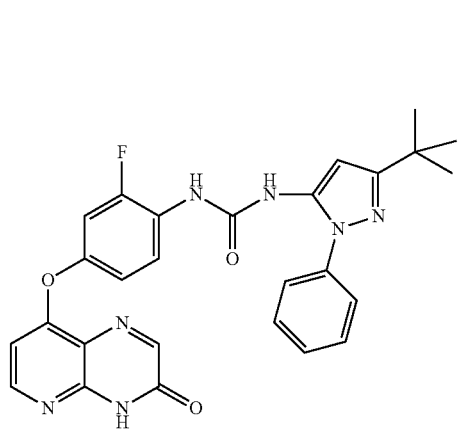

Figure 5:
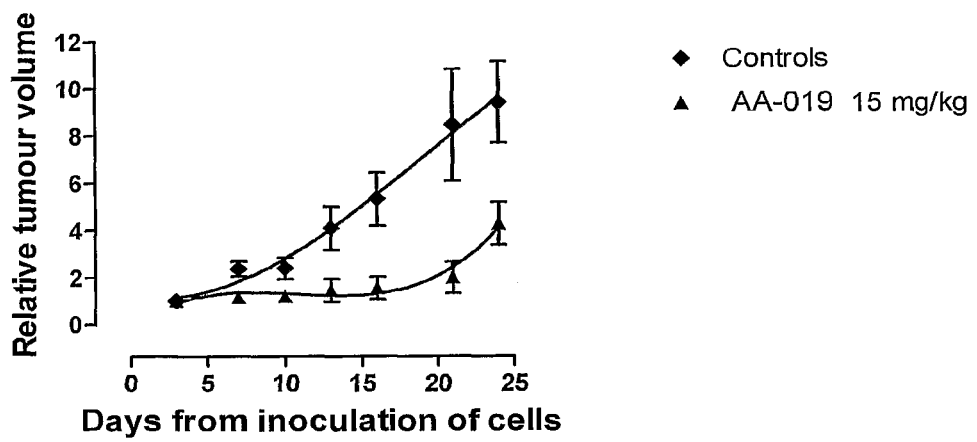
FIG. 5 is a graph of relative tumour volume as a function of days from inoculation for In Vivo Study 5 (AA-019) (non-established) (15 mg/kg/day) (orally).

$10^7$ A375M human melanoma cells were inoculated subcutaneously in 0.2 mL suspension into the right flank of female Crl:CD1-Foxn1nu athymic mice. The following day, treatment with test compound was begun. A suspension in DMSO:water 1:19 (v:v) was administered by gavage at 10 mL/kg bodyweight. Treatment was continued daily for 24 doses. The results are shown in FIG. 5.

In Vivo Study 6

AA-019 Established 10/5 mg/kg/Day Intraperitoneally

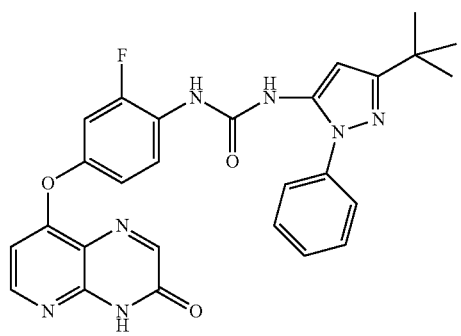 [SMILES: CC(C)(C)c1cc(NC(=O)Nc2ccc(Oc3ccnc4[nH]c(=O)cnc34)cc2F)n(-c2ccccc2)n1]

Figure 6:
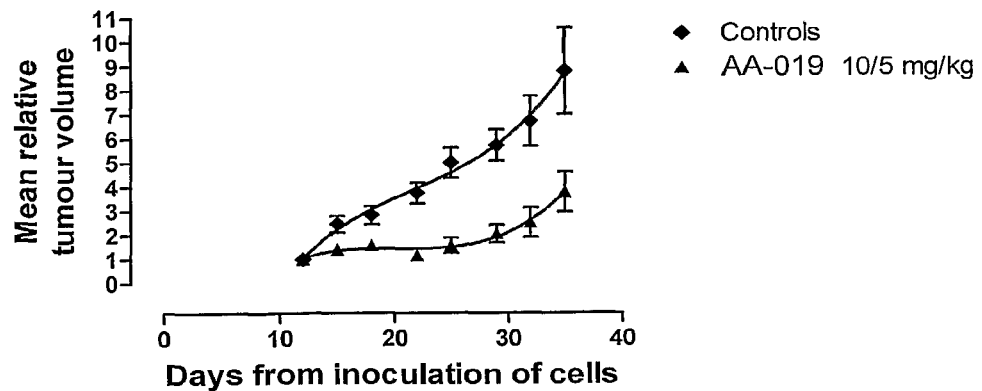
FIG. 6 is a graph of relative tumour volume as a function of days from inoculation for In Vivo Study 6 (AA-019) (established) (10/5 mg/kg/day) (intraperitoneally).

$10^7$ A375M human melanoma cells were inoculated subcutaneously in 0.2 mL suspension into the right flank of female Crl:CD1-Foxn1nu athymic mice. Groups of 8 from the middle range of tumour sizes were assigned to treatments by stratified allocation on tumour volume. Treatment with test compound at 10 mg/kg was begun on day 12 after giving cells. A suspension in DMSO:saline for injection 1:19 (v:v) was injected intraperitoneally at 10 mL/kg bodyweight. After 10 doses, the dosage was reduced to 5 mg/kg/day. Treatment was daily for a total of 24 doses. The results are shown in FIG. 6.

In Vivo Study 7

AA-019 Established 15 mg/kg/Day Orally

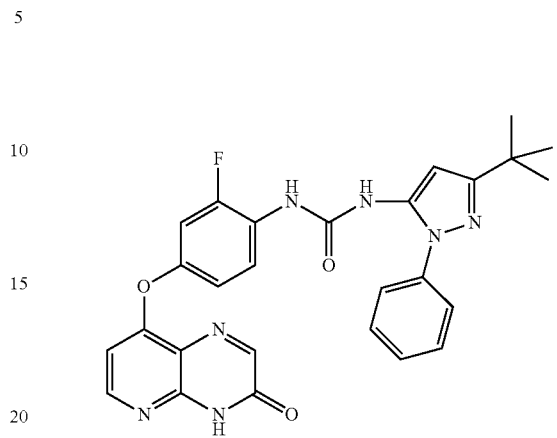

Figure 7:
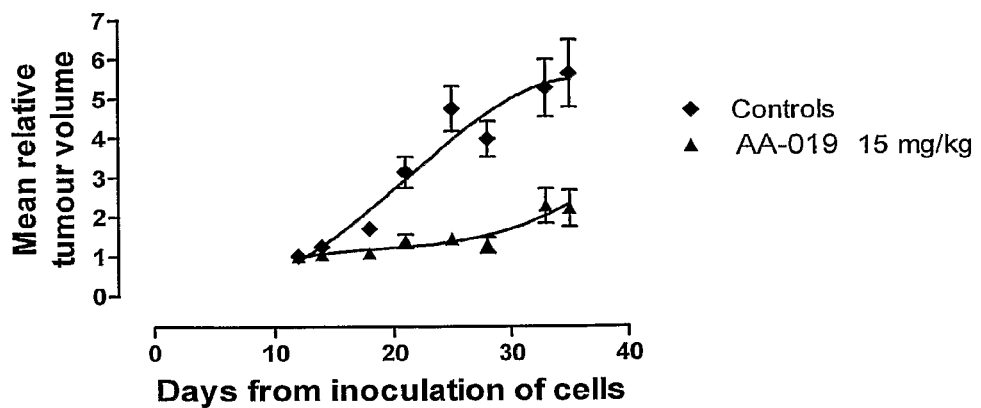
FIG. 7 is a graph of relative tumour volume as a function of days from inoculation for In Vivo Study 7 (AA-019) (established) (15 mg/kg/day) (orally).

$10^7$ A375M human melanoma cells were inoculated subcutaneously in 0.2 mL suspension into the right flank of female Crl:CD1-Foxn1nu athymic mice. Groups of 8 from the middle range of tumour sizes were assigned to treatments by stratified allocation on tumour volume. Treatment with test compound was begun on day 12 after giving cells. A suspension in DMSO:water 1:19 (v:v) was administered by gavage at 10 mL/kg bodyweight. Treatment was continued daily for 24 doses. The results are shown in FIG. 7.

In Vivo Study 8

AA-062 Established 50 mg/kg/Day Orally

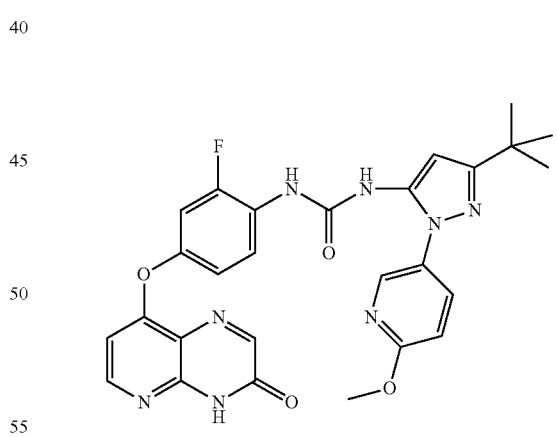

Figure 8:
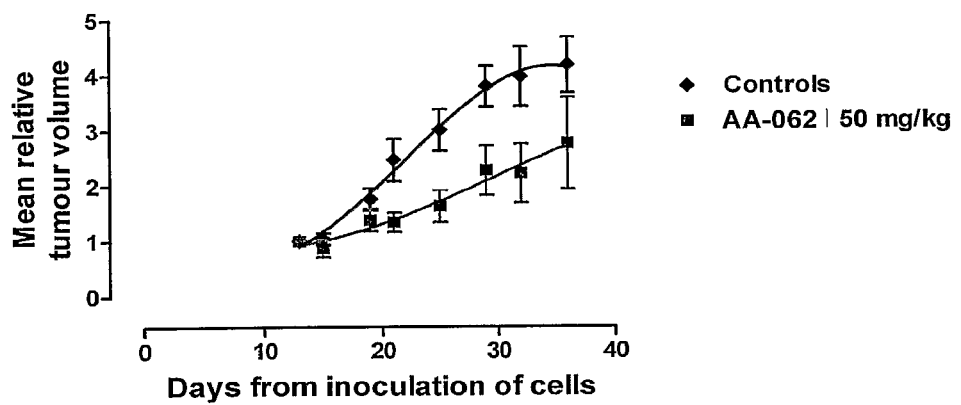
FIG. 8 is a graph of relative tumour volume as a function of days from inoculation for In Vivo Study 8 (AA-062) (established) (50 mg/kg/day) (orally).

$10^7$ A375M human melanoma cells were inoculated subcutaneously in 0.2 mL suspension into the right flank of female Crl:CD1-Foxn1nu athymic mice. Groups of 8 from the middle range of tumour sizes were assigned to treatments by stratified allocation on tumour volume. Treatment with test compound was begun on day 13 after giving cells. A suspension in DMSO:water 1:19 (v:v) was administered by gavage at 10 mL/kg bodyweight. Treatment was continued daily for 24 doses. The results are shown in FIG. 8.

In Vivo Study 9

AA-067 Established 10 mg/kg/Day Orally

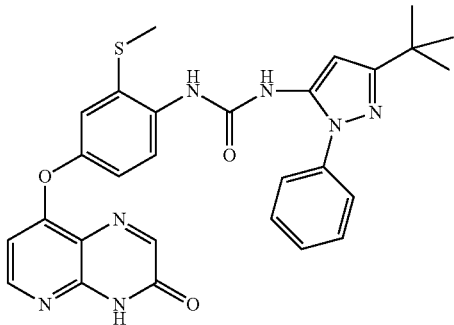 [SMILES: CSc1cc(Oc2ccnc3[nH]c(=O)cnc23)ccc1NC(=O)Nc1cc(C(C)(C)C)nn1-c1ccccc1]

Figure 9:
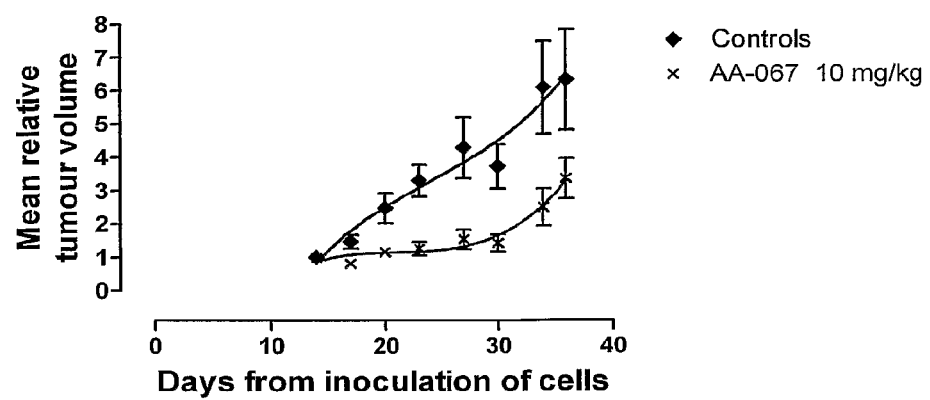
FIG. 9 is a graph of relative tumour volume as a function of days from inoculation for In Vivo Study 9 (AA-067) (established) (10 mg/kg/day) (orally).

$10^7$ A375M human melanoma cells were inoculated subcutaneously in 0.2 mL suspension into the right flank of female Crl:CD1-Foxn1nu athymic mice. Groups of 8 from the middle range of tumour sizes were assigned to treatments by stratified allocation on tumour volume. Treatment with test compound was begun on day 14 after giving cells. A suspension in DMSO:water 1:19 (v:v) was administered by gavage at 10 mL/kg bodyweight. Treatment was continued daily for 24 doses. The results are shown in FIG. 9.

In Vivo Study 10

AA-017 Established 20 mg/kg/Day Orally

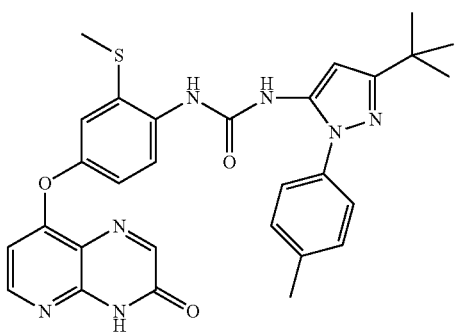 [SMILES: CSc1cc(Oc2ccnc3[nH]c(=O)cnc23)ccc1NC(=O)Nc1cc(C(C)(C)C)nn1-c1ccc(C)cc1]

Figure 10:
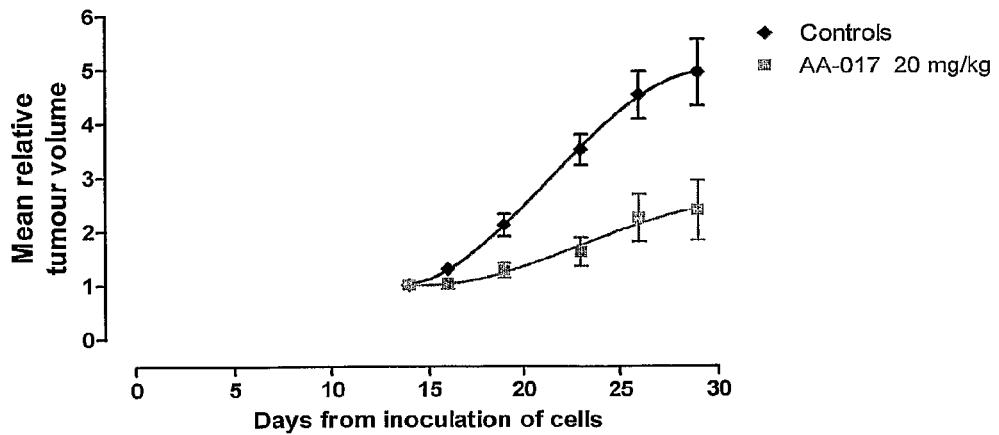
FIG. 10 is a graph of relative tumour volume as a function of days from inoculation for In Vivo Study 10 (AA-017) (established) (20 mg/kg/day) (orally).

$10^7$ A375M human melanoma cells were inoculated subcutaneously in 0.2 mL suspension into the right flank of female Crl:CD1-Foxn1nu athymic mice. Groups of 8 from the middle range of tumour sizes were assigned to treatments by stratified allocation on tumour volume. Treatment with test compound was begun on day 14 after giving cells. A suspension in DMSO:water 1:19 (v:v) was administered by gavage at 10 mL/kg bodyweight. Treatment is continuing daily for 24 doses (data for the first 16 days are provided). The results are shown in FIG. 10.

* * *

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention Claimed is:

1. A method of inhibiting the progress of, reducing the rate of progress of, alleviating a symptom of, or ameliorating cancer comprising administering to a subject in need of treatment a therapeutically-effective amount of a compound of the following formula, or a pharmaceutically acceptable salt thereof:

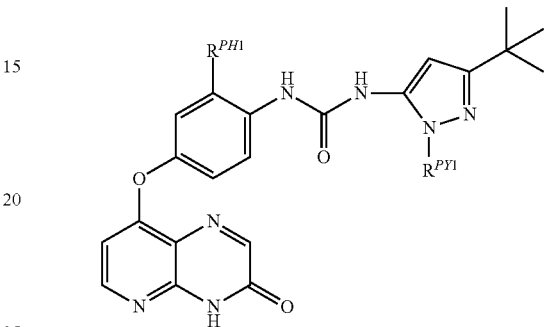

wherein:
—$R^{PH1}$ is independently —F or —SMe; and
—$R^{PY1}$ is independently phenyl or pyridyl, and is optionally substituted with one or more substituents selected from —F, —Cl, —Br, —I, —$R^5$, —OH, —$OR^5$, —CF3, —OCF3, wherein each —$R^5$ is independently saturated aliphatic $C_{1-4}$alkyl;
and wherein the cancer is:
 thyroid cancer;
 melanoma (including malignant melanoma);
 lung cancer (including non-small cell lung cancer and small cell lung cancer);
 colorectal cancer;
 pancreatic cancer;
 sarcoma;
 gastrointestinal cancer;
 ovarian cancer;
 lymphoma;
 leukemia;
 skin cancer;
 testicular cancer;
 prostate cancer;
 a carcinoma of the cervix;
 bladder cancer;
 breast cancer;
 liver cancer;
 kidney cancer;
 stomach cancer;
 endometrial cancer;
 seminoma;
 a hematopoietic tumor of myeloid lineage;
 myelodisplastic syndrome;
 a carcinoma of the oesophagus;
 brain cancer;
 glioma;
 bone cancer; or
 squamous cancer.

2. A method according to claim 1, wherein the cancer is:
 thyroid cancer;
 melanoma (including malignant melanoma);
 lung cancer (including non-small cell lung cancer and small cell lung cancer);
 colorectal cancer;

pancreatic cancer;
sarcoma;
gastrointestinal cancer;
ovarian cancer;
lymphoma;
leukemia;
skin cancer;
testicular cancer;
prostate cancer;
a carcinoma of the cervix;
bladder cancer;
breast cancer;
liver cancer;
kidney cancer;
stomach cancer;
endometrial cancer;
seminoma; or
a hematopoietic tumor of myeloid lineage.

3. A method according to claim 1, wherein the cancer is:
thyroid cancer;
melanoma (including malignant melanoma);
lung cancer (including non-small cell lung cancer and small cell lung cancer);
colorectal cancer;
pancreatic cancer;
sarcoma;
gastrointestinal cancer;
ovarian cancer;
lymphoma; or
leukemia.

4. A method according to claim 1, wherein the cancer is thyroid cancer.

5. A method according to claim 1, wherein the cancer is non-small cell lung cancer.

6. A method according to claim 1, wherein the cancer is characterized by activating mutant RAS or RAF.

7. A method according to claim 1, wherein $-R^{PH1}$ is $-F$.

8. A method according to claim 1, wherein $-R^{PH1}$ is $-SMe$.

9. A method according to claim 1, wherein $-R^{PY1}$ is phenyl, and is optionally substituted with one or more substituents selected from $-F$, $-Cl$, $-Br$, $-I$, $-R^5$, $-OH$, $-OR^5$, $-CF_3$, $-OCF_3$, wherein each $-R^5$ is independently saturated aliphatic $C_{1-4}$alkyl.

10. A method according to claim 7, wherein $-R^{PY1}$ is phenyl, and is optionally substituted with one or more substituents selected from $-F$, $-Cl$, $-Br$, $-I$, $-R^5$, $-OH$, $-OR^5$, $-CF_3$, $-OCF_3$, wherein each $-R^5$ is independently saturated aliphatic $C_{1-4}$alkyl.

11. A method according to claim 8, wherein $-R^{PY1}$ is phenyl, and is optionally substituted with one or more substituents selected from $-F$, $-Cl$, $-Br$, $-I$, $-R^5$, $-OH$, $-OR^5$, $-CF_3$, $-OCF_3$, wherein each $-R^5$ is independently saturated aliphatic $C_{1-4}$alkyl.

12. A method according to claim 1, wherein $-R^{PY1}$ is pyridyl, and is optionally substituted with one or more substituents selected from $-F$, $-Cl$, $-Br$, $-I$, $-R^5$, $-OH$, $-OR^5$, $-CF_3$, $-OCF_3$, wherein each $-R^5$ is independently saturated aliphatic $C_{1-4}$alkyl.

13. A method according to claim 7, wherein $-R^{PY1}$ is pyridyl, and is optionally substituted with one or more substituents selected from $-F$, $-Cl$, $-Br$, $-I$, $-R^5$, $-OH$, $-OR^5$, $-CF_3$, $-OCF_3$, wherein each $-R^5$ is independently saturated aliphatic $C_{1-4}$alkyl.

14. A method according to claim 8, wherein $-R^{PY1}$ is pyridyl, and is optionally substituted with one or more substituents selected from $-F$, $-Cl$, $-Br$, $-I$, $-R^5$, $-OH$, $-OR^5$, $-CF_3$, $-OCF_3$, wherein each $-R^5$ is independently saturated aliphatic $C_{1-4}$alkyl.

15. A method according to claim 1, wherein each $-R^5$, if present, is -Me.

16. A method according to claim 7, wherein each $-R^5$, if present, is -Me.

17. A method according to claim 8, wherein each $-R^5$, if present, is -Me.

18. A method according to claim 9, wherein each $-R^5$, if present, is -Me.

19. A method according to claim 10, wherein each $-R^5$, if present, is -Me.

20. A method according to claim 11, wherein each $-R^5$, if present, is -Me.

21. A method according to claim 12, wherein each $-R^5$, if present, is -Me.

22. A method according to claim 13, wherein each $-R^5$, if present, is -Me.

23. A method according to claim 14, wherein each $-R^5$, if present, is -Me.

24. A method according to claim 1, wherein the compound is a compound selected from the following compounds, or a pharmaceutically acceptable salt thereof:

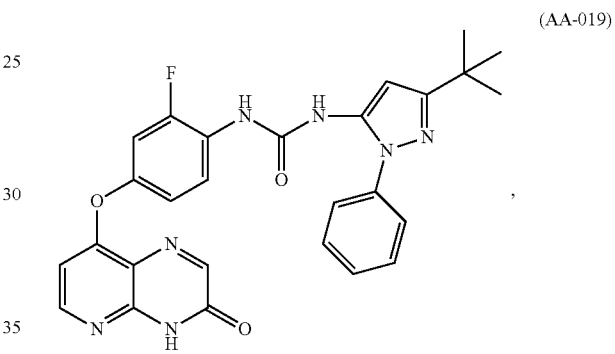
(AA-019)

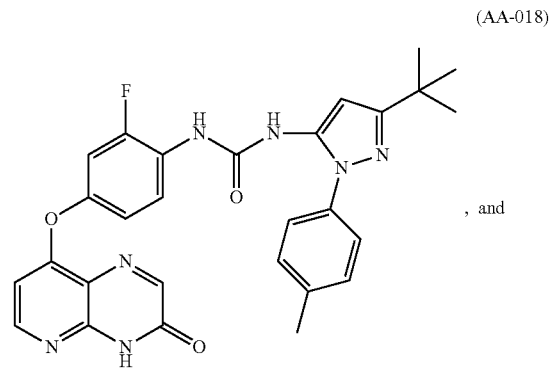
(AA-018)
, and

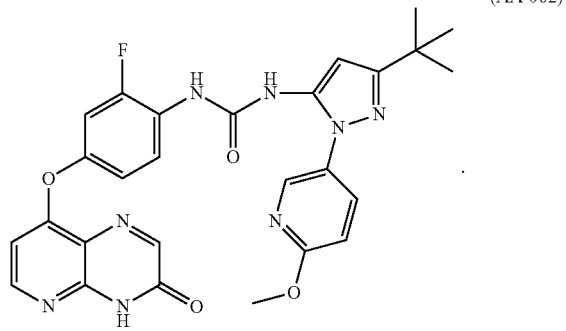
(AA-062)

25. A method according to claim 1, wherein the compound is a compound selected from the following compounds, or a pharmaceutically acceptable salt thereof:

(AA-067)

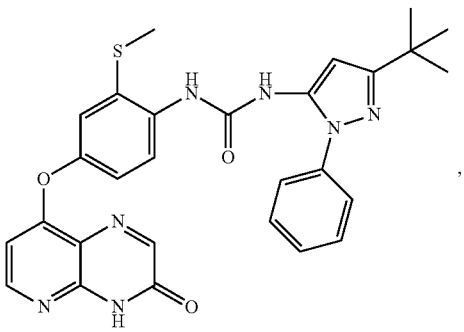

, (AA-017)

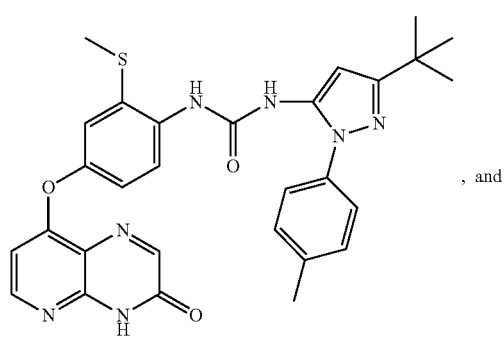

, and (AA-063)

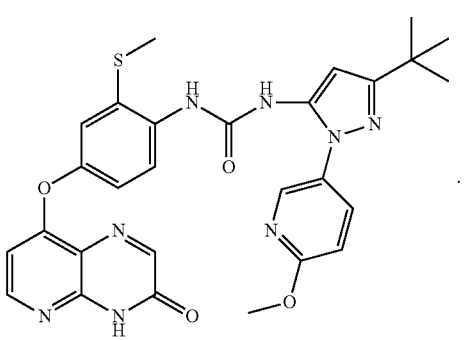

.

26. A method of inhibiting the progress of, reducing the rate of progress of, alleviating a symptom of, or ameliorating cancer comprising administering to a subject in need of treatment a therapeutically-effective amount of a compound of the following formula, or a pharmaceutically acceptable salt thereof:

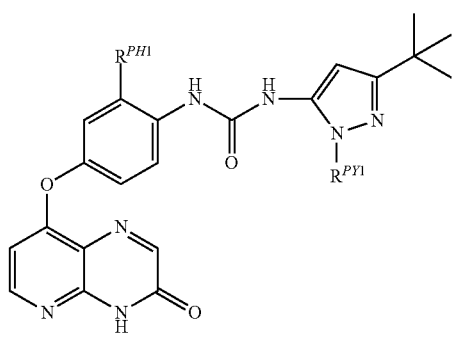

wherein:

—$R^{PH1}$ is —F or —SMe; and

—$R^{PY1}$ is phenyl, and is optionally substituted with one substituent selected from —F and Me;

and wherein the cancer is:

thyroid cancer;

melanoma (including malignant melanoma);

lung cancer (including non-small cell lung cancer and small cell lung cancer);

colorectal cancer;

pancreatic cancer;

sarcoma;

gastrointestinal cancer;

ovarian cancer;

lymphoma;

leukemia;

skin cancer;

testicular cancer;

prostate cancer;

a carcinoma of the cervix;

bladder cancer;

breast cancer;

liver cancer;

kidney cancer;

stomach cancer;

endometrial cancer;

seminoma; or a hematopoietic tumor of myeloid lineage.

27. A method according to claim 26, wherein the cancer is thyroid cancer.

28. A method according to claim 26, wherein the cancer is melanoma (including malignant melanoma).

29. A method according to claim 26, wherein the cancer is lung cancer (including non-small cell and small cell lung cancer).

30. A method according to claim 28, wherein the cancer is non-small cell lung cancer.

31. A method according to claim 26, wherein the cancer is colorectal cancer.

32. A method according to claim 26, wherein the cancer is pancreatic cancer.

33. A method according to claim 26, wherein the cancer is sarcoma.

34. A method according to claim 26, wherein the cancer is gastrointestinal cancer.

35. A method according to claim 26, wherein the cancer is ovarian cancer.

36. A method according to claim 26, wherein the cancer is lymphoma.

37. A method according to claim 26, wherein the cancer is leukemia.

* * * * *